United States Patent
Behnke et al.

(10) Patent No.: US 9,284,331 B2
(45) Date of Patent: Mar. 15, 2016

(54) DIAZEPINONE DERIVATIVES

(71) Applicants: Dirk Behnke, Grenzach-Wyhlen (DE); David Carcache, Binningen (CH); Peter Ertl, Munchenstein (CH); Manuel Koller, Schliern (CH); David Orain, Hesingue (FR)

(72) Inventors: Dirk Behnke, Grenzach-Wyhlen (DE); David Carcache, Binningen (CH); Peter Ertl, Munchenstein (CH); Manuel Koller, Schliern (CH); David Orain, Hesingue (FR)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 14/462,813

(22) Filed: Aug. 19, 2014

(65) Prior Publication Data

US 2014/0357625 A1 Dec. 4, 2014

Related U.S. Application Data

(63) Continuation of application No. 13/973,454, filed on Aug. 22, 2013.

(30) Foreign Application Priority Data

Aug. 23, 2012 (GB) .................................. 1215033.0

(51) Int. Cl.
*A61K 31/551* (2006.01)
*C07D 498/04* (2006.01)
*C07D 471/04* (2006.01)
*A61K 45/06* (2006.01)
*C07D 471/14* (2006.01)

(52) U.S. Cl.
CPC ............ *C07D 498/04* (2013.01); *A61K 31/551* (2013.01); *A61K 45/06* (2013.01); *C07D 471/04* (2013.01); *C07D 471/14* (2013.01)

(58) Field of Classification Search
CPC .................................................. A61K 31/551
USPC ........................................................ 514/220
See application file for complete search history.

(56) References Cited

U.S. PATENT DOCUMENTS

| 3,853,851 A | 12/1974 | Gschwend |
| 2014/0057902 A1 | 2/2014 | Behnke et al. |

FOREIGN PATENT DOCUMENTS

| WO | 03/047581 A | 6/2003 |
| WO | 2004/087048 A2 | 10/2004 |
| WO | 2005/123703 A3 | 12/2005 |
| WO | 2011041989 A2 | 4/2011 |
| WO | 2012153796 A1 | 11/2012 |

OTHER PUBLICATIONS

Backstrom et al.: "mGluR5 Antagonist MPEP Reduces Ethanol-Seeking and Relapse Behavior", Neuropyschopharmacology, (2004), vol. 29, pp. 921-928.
Bespalov et al.: "Metabotropic glutamate receptor (mGluR5) antagonist MPEP attenuated cue- and schedule-induced reinstatement of nicotine self-admininstration behavior in rats", Neuropharmacology, (2005), vol. 49, pp. 167-178.
Chiamulera et al.: "Reinforcing and locomotor stimulant effects of cocaine are absent in mGlur5 null mutant mice", Nature Neuroscience, vol. 4, No. 9, Sep. 2001, pp. 873-874.
Gass et al.: "mGluR5 Antagonism Attenuates Methamphetamine Reinforcement and Prevents Reinstatement of Methamphetamine-Seeking Behavior in Rats", Neuropsychopharmacology, (2009), vol. 34, pp. 820-833.
Tessari et al.: "Antagonism at metabotropic glutamate 5 receptors inhibits nicotine- and cocaine-taking behaviours and prevents nicotine-triggered relapse to nicotine-seeking", European Journal of Pharmacology (2004), vol. 499, pp. 121-133.
Donald Jr. et al., Applications of multicomponent Assembly Processes to the Facile Syntheses of Diversly Functionalized Nitrogen Heterocycles, Heterocycles, 84(2):1089-1112 (2012).
Granger Ba et al., Multicomponent assembly strategies for the synthesis of diverse tetrahydroisoquinoline scaffolds, Organic Letters, 13(17):4542-4545 (2011).
Tsizin et al., The structure and anthelmintic action of tricyclic analogs of praziquantel and 4-acylpiperazinones-2, Med. Parazitol (Mosk), Nov.-Dec. 1991; (6):50-2.
Shekter et al., Synthesis of Tricyclic Systems Incorporating the Azepine Ring, Khimiya Geterotsiklicheskikh Soedinenii, 12:1665-1669 (1990).
Stoker et al., "Involvement of metabotropic glutamate receptor 5 in brain reward deficits associated with cocaine and nicotine withdrawal and somatic signs of nicotine withdrawal", Pyschopharmacology (2012), vol. 221, pp. 317-327.

(Continued)

*Primary Examiner* — Bruck Kifle
(74) *Attorney, Agent, or Firm* — Laura K. Madden

(57) ABSTRACT

The invention relates to compound of the formula I

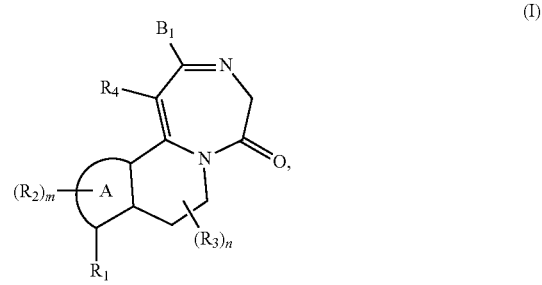

or a salt thereof, wherein the substituents are as defined in the specification; to its preparation, to its use as medicament and to medicaments comprising it.

19 Claims, No Drawings

(56) References Cited

OTHER PUBLICATIONS

Markou, Athina, "Metabotropic Glutamate Receptor Antagonists: Novel Therapeutics for Nicotine Dependence and Depression?", Biol. Psychiatry 2007; vol. 61, pp. 17-22.

Mitrano et al., "Comparative Analysis of the Subcellular and Subsynaptic Localization of mGluR1a and mGluR5 Metabotropic Glutamate Receptors in the Shell and Core of the Nucleus Accumbers in Rat and Monkey", The Journal of Comparative Neurology, vol. 500, pp. 788-806, (2007).

Wise, Roy A., "Neurobiology of addiction", Cognitive Neuroscience, Current Opinion in Neurobiology, (1996), vol. 6, pp. 243-251.

Olive, "Metabotropic glutamate receptor ligands as potential therapeutics for addiction", Curr Drug Abuse Rev. Jan. 2009; 2(1): 83-989.

Keck et al. "A novel mGluR5 antagonist, MFZ 10-7, inhibits cocaine-taking and cocaine-seeking behavior in rats", Addiction Biology, 19, 195-209, 2013.

DIAZEPINONE DERIVATIVES

The invention relates to diazepinone derivatives, to their preparation, to their use as medicaments and to medicaments comprising them.

Some mGluR5 antagonists are described e.g. in WO2003047581.

U.S. Pat. No. 3,853,851 describes 5-(oxo, thio or imino)-7,8-dihydro[1,4]diazepino[7.1a]isoquinolines and their use as neuroleptic agents.

mGluR5 antagonists are considered to be useful in the treatment of a wide range of disorders, in particular fragile X syndrome (FXS), L-dopa induced dyskinesias in Parkinsons Disease (PD-LID) and Gastro-Esophageal Reflux Disease (GERD).

There is a need to provide new mGluR5 antagonists that are good drug candidates. In particular, preferred compounds should bind potently to mGluR5 whilst showing little affinity for other mGluRs. They should exhibit a low binding to plasma proteins. They should be well absorbed from the gastrointestinal tract, be sufficiently metabolically stable and possess favorable pharmacokinetic properties. They should be non-toxic and demonstrate few side-effects. Furthermore, the ideal drug candidate will be able to exist in a physical form that is stable, non-hygroscopic and easily formulated.

The compounds of the invention are mGluR5 antagonists and are therefore potentially useful in the treatment of a wide range of disorders, particularly FXS, PD-LID and GERD.

In a first aspect, the invention relates to a compound of the formula I

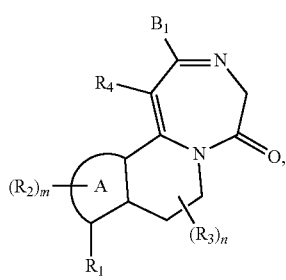

or a salt thereof, wherein

A is a fused five- to seven-membered monocyclic ring system which may be aromatic, saturated or unsaturated non-aromatic and which may contain from 1 to 4 hetero atoms selected from nitrogen, oxygen and sulfur;

$R_1$ is halogen; cyano; nitro; hydroxy; amino; —C(O)H; —C(O)NH$_2$; —X$_1$—R$_5$; or —X$_2$—B$_2$;

$X_1$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_5$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl;

$X_2$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$halogenalkyl, $C_{1-4}$alkoxy, or $C_{1-4}$halogenalkoxy; or two $R_6$ at the same ring atom together are oxo;

m is 0, 1, 2, 3 or 4;

each $R_2$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;

n is 0, 1, 2, 3 or 4;

each $R_3$ independently is halogen, cyano, hydroxy, amino, $C_{1-4}$alkyl; $C_{1-4}$halogenalkyl; $C_{1-4}$hydroxyalkyl; $C_{1-4}$-aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;

$R_4$ is hydrogen, halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;

$B_1$ is a five- to six-membered aromatic ring system, which may contain from 1 to 4 hetero atoms selected from nitrogen, oxygen and sulfur, wherein the ring system may in turn be substituted once or more than once by $R_7$;

each $R_7$ independently is halogen, cyano, hydroxy, amino,
$C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl;
$C_{2-4}$alkenyl; $C_{2-4}$halogenalkenyl; $C_{2-4}$alkinyl; $C_{2-4}$halogenalkinyl;
$C_{1-4}$alkoxy; $C_{1-4}$alkoxy-$C_{1-4}$alkoxy $C_{1-4}$halogenalkoxy;
$C_{1-4}$alkyl-amino; di-($C_{1-4}$alkyl)amino;
$C_{1-4}$alkoxycarbonyl;
or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$;

each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo;

or two $R_7$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_9$;

each $R_9$ independently is halogen, hydroxy, cyano, $C_{1-4}$alkyl, $C_{1-4}$halogenalkyl, $C_{1-4}$alkoxy, or $C_{1-4}$halogenalkoxy; or two $R_9$ at the same ring atom together are oxo.

In another aspect, the invention relates to a compound of the formula I-1

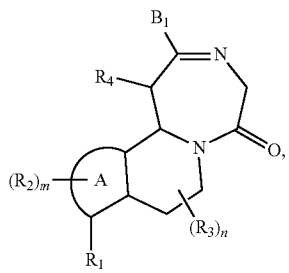

(I-1)

or a salt thereof, wherein

A is a fused five- to seven-membered monocyclic ring system which may be aromatic, saturated or unsaturated non-aromatic and which may contain from 1 to 4 hetero atoms selected from nitrogen, oxygen and sulfur;

$R_1$ is halogen; cyano; nitro; hydroxy; amino; —C(O)H; —C(O)NH$_2$; —X$_1$—R$_5$; or —X$_2$—B$_2$;

$X_1$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_5$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$-alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl;

$X_2$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 0, 1, 2, 3 or 4;

each $R_2$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;

n is 0, 1, 2, 3 or 4;

each $R_3$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;

$R_4$ is hydrogen, halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;

$B_1$ is a five- to six-membered aromatic ring system, which may contain from 1 to 4 hetero atoms selected from nitrogen, oxygen and sulfur, wherein the ring system may in turn be substituted once or more than once by $R_7$;

each $R_7$ independently is
halogen, cyano, hydroxy, amino,
$C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl;
$C_{2-4}$alkenyl; $C_{2-4}$halogenalkenyl; $C_{2-4}$alkinyl; $C_{2-4}$halogenalkinyl;
$C_{1-4}$alkoxy; $C_{1-4}$alkoxy-$C_{1-4}$alkoxy $C_{1-4}$halogenalkoxy;
$C_{1-4}$alkyl-amino; di-($C_{1-4}$alkyl)amino;
$C_{1-4}$alkoxycarbonyl;
or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$;

each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo;

or two $R_7$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_9$;

each $R_9$ independently is halogen, hydroxy, cyano, $C_{1-4}$alkyl, $C_{1-4}$halogenalkyl, $C_{1-4}$alkoxy, or $C_{1-4}$halogenalkoxy; or two $R_9$ at the same ring atom together are oxo.

Unless specified otherwise, the term "compounds of the invention" refers to compounds of formula (I) and subformulae thereof; salts of the compounds; hydrates or solvates of the compounds and/or salts; as well as all stereoisomers (including diastereoisomers), tautomers and isotopically labeled compounds (including deuterium substitutions); as well as inherently formed moieties (e.g. polymorphs, solvates and/or hydrates).

Unless indicated otherwise, the expressions used in this invention have the following meaning:

"Alkyl" represents a straight-chain or branched-chain alkyl group and, for example, may be methyl, ethyl, n- or iso-propyl, n-, iso-, sec- or tert-butyl; $C_{1-4}$alkyl typically represents a straight-chain or branched-chain $C_{1-3}$alkyl, e.g. methyl, ethyl, n-propyl or iso-propyl.

Each alkyl part of "alkoxy", "halogenalkyl" and so on shall have the same meaning as described in the above-mentioned definition of "alkyl", especially regarding linearity and size.

"$C_{3-6}$cycloalkyl" represents a saturated alicyclic moiety having from three to six carbon atoms. This term refers to groups such as cyclopropyl, cyclobutyl, cyclopentyl and cyclohexyl.

Halogen is generally fluorine, chlorine, bromine or iodine; e.g. fluorine, chlorine or bromine. Halogenalkyl groups typically have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl.

In the context of the invention, the definition of A as a "fused five- to seven-membered monocyclic ring system which may be aromatic, saturated or unsaturated non-aromatic and which may contain from 1 to 4 hetero atoms" encompasses phenyl, five- to six-membered monocyclic heterocyclic aromatic ring systems, five- to seven-membered monocyclic non-aromatic hydrocarbon/heterocyclic ring systems. In the context of the invention, $R_1$ is bound to a carbon atoms adjacent to a fusion carbon atom, as it is depicted for compounds of formula (I).

In the context of the invention, the definitions of $B_2$ and $R_7$ as a "three- to seven-membered monocyclic ring system which may be aromatic, saturated or unsaturated non-aromatic and which may contain from 1 to 4 hetero atoms" encompasses three- to seven-membered monocyclic aromatic or non-aromatic hydrocarbon groups and aromatic or non-aromatic heterocyclic ring systems of the same sizes.

In the context of the invention, the definition of $B_1$ as a "five- to six-membered aromatic ring system which may contain from 1 to 4 hetero atoms" encompasses phenyl or a five- to six-membered monocyclic heterocyclic aromatic ring system.

In the context of the invention, the definition of two $R_7$ as a "fused five- to seven-membered monocyclic unsaturated non-aromatic ring system which may contain from 1 to 4 hetero atoms" encompasses a five- to seven-membered monocyclic unsaturated non-aromatic hydrocarbon group or a five- to seven-membered monocyclic heterocyclic unsaturated non-aromatic ring system. All said groups/ring systems comprise at least one double-bond, which is shared with the aromatic ring system $B_1$ they are fused to.

Examples of heterocyclic ring systems are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, oxadiazole, dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine.

Compounds of formula I may exist in optically active form or in form of mixtures of optical isomers, e.g. in form of racemic mixtures or diastereomeric mixtures. In particular, asymmetrical carbon atom(s) may be present in the compounds of formula I and their salts. Unless otherwise provided herein, all optical isomers and their mixtures, including the racemic mixtures, are embraced by the invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. The compounds described herein may contain one or more asymmetric centers and may thus give rise to enantiomers, diastereomers, and other stereoisomeric forms that may be defined, in terms of absolute stereochemistry, as (R)- or (S)-. Unless otherwise provided herein, the invention is meant to include all such possible isomers, including racemic mixtures, optically pure forms and intermediate mixtures. Optically active (R)- and (S)-isomers may be prepared using chiral synthons or chiral reagents, or resolved using conventional techniques.

If the compound contains a double bond, the substituent may be E or Z configuration.

If the compound contains a disubstituted cycloalkyl, the cycloalkyl substituent may have a cis- or trans-configuration.

Any asymmetric atom (e.g. carbon or the like) of the compound(s) of the invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein, a compound of the invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on substituent definition, compounds of formula I may occur in various tautomeric forms. All tautomeric forms of the compounds of formula I are embraced by the invention.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. The compounds of the invention may be capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the invention may also form internal salts, e.g., zwitterionic molecules.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula (I).

The invention also envisages the use of pro-drugs of the compounds of the invention that convert in vivo to the compounds of the invention. A pro-drug is an active or inactive compound that is modified chemically through in vivo physiological action, such as hydrolysis, metabolism and the like, into a compound of the invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See The Practice of Medicinal Chemistry, Ch. 31-32 (Ed. Wermuth, Academic Press, San Diego, Calif., 2001).

Furthermore, the compounds of the invention, including their salts, can also be obtained in the form of their hydrates, or include other solvents used for their crystallization. The compounds of the invention may inherently or by design form solvates with pharmaceutically acceptable solvents (including water); therefore, it is intended that the invention embrace both solvated and unsolvated forms. The term "solvate" refers to a molecular complex of a compound of the invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the invention, including salts, hydrates and solvates thereof, may inherently or by design form polymorphs.

Preferred substituents, preferred ranges of numerical values or preferred ranges of the radicals present in compounds of the formula I and the corresponding intermediate compounds are defined below. The definition of the substituents applies to the end-products as well as to the corresponding intermediates. The definitions of the substituents may be combined at will, e.g. preferred substituents $R_1$ and particularly preferred substituents $R_2$.

The preferred substituents, preferred ranges of numerical values or preferred ranges of the radicals present in compounds of the formula I, which are described herein below, are also preferred for compounds of the formula I-1 or I0-1.

In one embodiment, the invention provides a compound of formula I or a salt thereof, wherein A is phenyl.

According to the invention, a compound the formula I or I-1, or salt thereof wherein A is phenyl means a compound of formula I wherein the cycle A, with substituents R1 and R2 as defined herein, is a moiety of the formula A0 wherein the two carbon atoms marked by asterisk denote the positions wherein the moiety is bound in formula I.

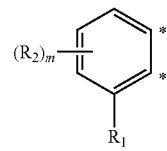

Thus, in an aspect, the invention relates to a compound of the formula I0

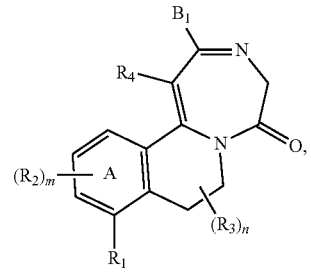

or a salt thereof, wherein R1, R2, R3, R4, B1, m and n are as defined herein.

Thus, in an aspect, the invention relates to a compound of the formula I0-1.

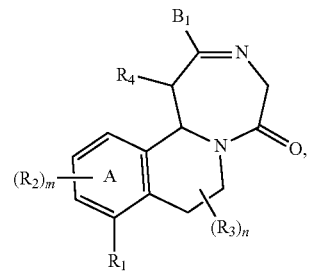

or a salt thereof, wherein R1, R2, R3, R4, B1, m and n are as defined herein.

In one embodiment, the invention provides a compound of formula I or a salt thereof, wherein A is pyridyl.

In one embodiment, the invention provides a compound of formula I or a salt thereof, wherein A is A1

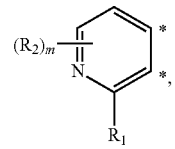

wherein A1 is fused via the two carbon atoms marked by asterisk.

In one embodiment, the invention provides a compound of formula I or a salt thereof, wherein A is A2

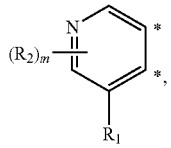

A2 wherein A2 is fused via the two carbon atoms marked by asterisk.

In one embodiment, the invention provides a compound of formula I or a salt thereof, wherein A is A3

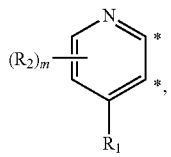

A3 wherein A3 is fused via the two carbon atoms marked by asterisk.

In one embodiment, the invention provides a compound of formula I or a salt thereof, wherein $R_1$ is —$X_1$—$R_5$; or —$X_2$—$B_2$.

In one embodiment, the invention provides a compound of formula I or a salt thereof, wherein $R_1$ is —$X_2$—$B_2$.

In one embodiment, the invention provides a compound of formula I or a salt thereof, wherein $R_1$ is —$X_2$—$B_2$, wherein $X_2$ is bond.

In one embodiment, the invention provides a compound of formula I or a salt thereof, wherein $R_1$ is —$X_2$—$B_2$, wherein $X_2$ is bond and $B_2$ is a three- to seven-membered saturated monocyclic ring system which may contain from 1 to 4 hetero atoms selected from nitrogen, oxygen and sulfur, wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo.

In one embodiment, the invention provides a compound of formula I or a salt thereof, wherein $R_1$ is —$X_2$—$B_2$, wherein $X_2$ is bond and $B_2$ is $C_{3-6}$cycloalkyl which may be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

In one embodiment, the invention provides a compound of formula I or a salt thereof, wherein $R_1$ is —$X_2$—$B_2$, wherein $X_2$ is bond and $B_2$ is a five- to six-membered aromatic ring system which may contain from 1 to 4 hetero atoms selected from nitrogen, oxygen and sulfur, wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

In one embodiment, the invention provides a compound of formula I or a salt thereof, wherein $R_1$ is —$X_2$—$B_2$, wherein $X_2$ is bond and $B_2$ is pyridyl, which may be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

In one embodiment, the invention provides a compound of formula I or a salt thereof, wherein m is 0, 1 or 2 and each $R_2$ independently is halogen, $C_{1-4}$alkyl; $C_{1-4}$halogenalkyl; $C_{1-4}$alkoxy; $C_{1-4}$halogenalkoxy or $C_{3-6}$cycloalkyl.

In one embodiment, the invention provides a compound of formula I or a salt thereof, wherein m is 0.

In one embodiment, the invention provides a compound of formula I or a salt thereof, wherein n is 0, 1 or 2 and each $R_3$ independently is halogen, $C_{1-4}$alkyl; $C_{1-4}$halogenalkyl; $C_{1-4}$alkoxy; $C_{1-4}$halogenalkoxy or $C_{3-6}$cycloalkyl.

In one embodiment, the invention provides a compound of formula I or a salt thereof, wherein n is 0.

In one embodiment, the invention provides a compound of formula I or a salt thereof, wherein $R_4$ is hydrogen, halogen, $C_{1-4}$alkyl; $C_{1-4}$halogenalkyl; $C_{1-4}$alkoxy; $C_{1-4}$halogenalkoxy or $C_{3-6}$cycloalkyl.

In one embodiment, the invention provides a compound of formula I or a salt thereof, wherein $R_4$ is hydrogen.

In one embodiment, the invention provides a compound of formula I or a salt thereof, wherein $B_1$ is phenyl, which may be substituted once or more than once by $R_7$.

In one embodiment, the invention provides a compound of formula I or a salt thereof, wherein $B_1$ is phenyl, which may be substituted once or more than once by $R_7$; and wherein each $R_7$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl, $C_{2-4}$alkenyl, $C_{2-4}$halogenalkenyl, $C_{2-4}$alkinyl, $C_{2-4}$halogenalkinyl, $C_{1-4}$alkoxy, $C_{1-4}$alkoxy-$C_{1-4}$alkoxy $C_{1-4}$halogenalkoxy, $C_{1-4}$alkylamino; di-($C_{1-4}$alkyl)amino, $C_{1-4}$alkoxycarbonyl, or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$; each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo.

In one embodiment, the invention provides a compound of formula I or a salt thereof, wherein $B_1$ is phenyl, which may be substituted once or more than once by $R_7$; and wherein each $R_7$ independently is halogen, $C_{1-4}$alkyl; $C_{1-4}$halogenalkyl; $C_{1-4}$alkoxy-$C_{1-4}$alkyl, $C_{1-4}$alkoxy, $C_{1-4}$alkoxy-$C_{1-4}$alkoxy or $C_{3-6}$cycloalkyl.

In one embodiment, the invention provides a compound of formula I or a salt thereof, wherein $B_1$ is a five- to six-membered aromatic ring system, which contains from 1 to 4 hetero atoms selected from nitrogen, oxygen and sulfur, wherein the ring system may in turn be substituted once or more than once by $R_7$.

In one embodiment, the invention provides a compound of formula I or a salt thereof, wherein $B_1$ is a five- to six-membered aromatic ring system, which contains from 1 to 4 hetero atoms selected from nitrogen, oxygen and sulfur, wherein the ring system may in turn be substituted once or more than once by $R_7$; and wherein each $R_7$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl, $C_{2-4}$alkenyl, $C_{2-4}$halogenalkenyl, $C_{2-4}$alkinyl, $C_{2-4}$halogenalkinyl, $C_{1-4}$alkoxy, $C_{1-4}$alkoxy-$C_{1-4}$alkoxy $C_{1-4}$halogenalkoxy, $C_{1-4}$alkyl-amino; di-($C_{1-4}$alkyl)amino, $C_{1-4}$alkoxycarbonyl, or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$; each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo.

In one embodiment, the invention provides a compound of formula I or a salt thereof, wherein $B_1$ is a five- to six-membered aromatic ring system, which contains from 1 to 4 hetero atoms selected from nitrogen, oxygen and sulfur, wherein the ring system may in turn be substituted once or more than once by $R_7$; and wherein each $R_7$ independently is halogen, $C_{1-4}$alkyl; $C_{1-4}$halogenalkyl; $C_{1-4}$alkoxy-$C_{1-4}$alkyl, $C_{1-4}$alkoxy, $C_{1-4}$alkoxy-$C_{1-4}$alkoxy or $C_{3-6}$cycloalkyl.

In one embodiment, the invention provides a compound of formula I or a salt thereof, wherein $B_1$ is a five-membered aromatic ring system, which contains from 1 to 4 hetero atoms selected from nitrogen, oxygen and sulfur, wherein the ring system may in turn be substituted once or more than once by $R_7$.

In one embodiment, the invention provides a compound of formula I or a salt thereof, wherein $B_1$ is a five-membered aromatic ring system, which contains from 1 to 2 nitrogen atoms, wherein the ring system may in turn be substituted once or more than once by $R_7$.

In one embodiment, the invention provides a compound of formula I or a salt thereof, wherein $B_1$ is imidazol-1-yl, which may be substituted once or more than once by $R_7$.

In one embodiment, the invention provides a compound of formula I or a salt thereof, wherein $B_1$ is imidazol-1-yl, which may be substituted once or more than once by $R_7$; and wherein each $R_7$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl, $C_{2-4}$alkenyl, $C_{2-4}$halogenalkenyl, $C_{2-4}$alkinyl, $C_{2-4}$halogenalkinyl, $C_{1-4}$alkoxy, $C_{1-4}$alkoxy-$C_{1-4}$alkoxy $C_{1-4}$halogenalkoxy, $C_{1-4}$alkylamino; di-($C_{1-4}$alkyl)amino, $C_{1-4}$alkoxycarbonyl, or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$; each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo.

In one embodiment, the invention provides a compound of formula I or a salt thereof, wherein $B_1$ is imidazol-1-yl, which may be substituted once or more than once by $R_7$; and wherein each $R_7$ independently is halogen, $C_{1-4}$alkyl; $C_{1-4}$halogenalkyl; $C_{1-4}$alkoxy, $C_{1-4}$alkoxy-$C_{1-4}$alkoxy or $C_{3-6}$cycloalkyl.

In embodiment E1, the invention provides a compound of formula I or a salt thereof, wherein
A is phenyl;
$R_1$ is —$X_2$—$B_2$, wherein $X_2$ is bond;
$B_2$ is $C_{3-6}$cycloalkyl which may be substituted once or more than once by $R_6$;
or $B_2$ is a five- to six-membered aromatic ring system which may contain from 1 to 4 hetero atoms selected from nitrogen, oxygen and sulfur, wherein the ring system may in turn be substituted once or more than once by $R_6$;
each $R_6$ independently is halogen, hydroxy, cyano, $C_{1-4}$alkyl, $C_{1-4}$halogenalkyl, $C_{1-4}$alkoxy, or $C_{1-4}$halogenalkoxy;
m is 0, 1 or 2;
each $R_2$ independently is halogen, $C_{1-4}$alkyl; $C_{1-4}$halogenalkyl; $C_{1-4}$alkoxy; $C_{1-4}$halogenalkoxy or $C_{3-6}$cycloalkyl;
n is 0, 1 or 2;
each $R_3$ independently is halogen, $C_{1-4}$alkyl; $C_{1-4}$halogenalkyl; $C_{1-4}$alkoxy; $C_{1-4}$halogenalkoxy or $C_{3-6}$cycloalkyl;

$R_4$ is hydrogen, halogen, $C_{1-4}$alkyl; $C_{1-4}$halogenalkyl; $C_{1-4}$alkoxy; $C_{1-4}$halogenalkoxy or $C_{3-6}$cycloalkyl;
$B_1$ is a five- to six-membered aromatic ring system, which contains from 1 to 4 hetero atoms selected from nitrogen, oxygen and sulfur, wherein the ring system may in turn be substituted once or more than once by $R_7$;
and wherein each $R_7$ independently is halogen, $C_{1-4}$alkyl; $C_{1-4}$halogenalkyl; $C_{1-4}$alkoxy-$C_{1-4}$alkyl, $C_{1-4}$alkoxy, $C_{1-4}$alkoxy-$C_{1-4}$alkoxy or $C_{3-6}$cycloalkyl.

In one embodiment of E1, the invention provides a compound of formula I or a salt thereof,
wherein $R_1$ is —$X_2$—$B_2$, wherein $X_2$ is bond;
$B_2$ is $C_{3-6}$cycloalkyl which may be substituted once or more than once by $R_6$;
each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

In one embodiment of E1, the invention provides a compound of formula I or a salt thereof, wherein $R_1$ is —$X_2$—$B_2$, wherein $X_2$ is bond;
$B_2$ is a five- to six-membered aromatic ring system which may contain from 1 to 4 hetero atoms selected from nitrogen, oxygen and sulfur, wherein the ring system may in turn be substituted once or more than once by $R_6$;
each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

In one embodiment of E1, the invention provides a compound of formula I or a salt thereof, wherein
m is 0, 1 or 2;
each $R_2$ independently is halogen, $C_{1-4}$alkyl; $C_{1-4}$halogenalkyl; $C_{1-4}$alkoxy; $C_{1-4}$halogenalkoxy or $C_{3-6}$cycloalkyl;
n is 0; and
$R_4$ is hydrogen.

In one embodiment of E1, the invention provides a compound of formula I or a salt thereof, wherein $B_1$ is imidazol-1-yl, which may be substituted once or more than once by $R_7$; and wherein each $R_7$ independently is halogen, $C_{1-4}$alkyl; $C_{1-4}$halogenalkyl; $C_{1-4}$alkoxy-$C_{1-4}$alkyl, $C_{1-4}$alkoxy, $C_{1-4}$alkoxy-$C_{1-4}$alkoxy or $C_{3-6}$cycloalkyl.

In embodiment E1-1, the invention provides a compound of formula I or I-1, as defined herein, wherein
A is phenyl;
$R_1$ is halogen; cyano; —$X_1$—$R_5$; or —$X_2$—$B_2$;
$X_1$ is selected from bond; carbonyl and oxygen; preferably bond;
$R_5$ is $C_{1-6}$alkyl; $C_{1-6}$halogenalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; di($C_{1-4}$alkyl)amino-$C_{1-6}$alkyl; aminocarbonyl-$C_{1-6}$alkyl; $C_{2-6}$alkenyl; $C_{2-6}$alkinyl;
$X_2$ is bond;
$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;
each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;
m is 0 or is 1 and $R_2$ is halogen or $C_{1-4}$alkoxy;
and
n is 0.

In embodiment E1-2, the invention provides a compound of formula I or I-1, as defined herein, wherein
A is phenyl;
$R_1$ is —$X_2$—$B_2$;
$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 0 or is 1 and $R_2$ is independently halogen or $C_{1-4}$alkoxy; and n is 0.

In embodiment E1-3, the invention provides a compound of formula I or I-1, as defined herein, wherein A is phenyl;

$R_1$ is halogen; cyano; —$X_1$—$R_5$; or —$X_2$—$B_2$;

$X_1$ is selected from bond; carbonyl and oxygen; preferably bond;

$R_5$ is $C_{1-6}$alkyl; $C_{1-6}$halogenalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; di($C_{1-4}$alkyl)amino-$C_{1-6}$alkyl; aminocarbonyl-$C_{1-6}$alkyl; $C_{2-6}$alkenyl; $C_{2-6}$alkinyl;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 0 or is 1 and $R_2$ is halogen; and n is 0.

In embodiment E1-4, the invention provides a compound of formula I or I-1, as defined herein, wherein A is phenyl;

$R_1$ is —$X_2$—$B_2$;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 0 or is 1 and $R_2$ is halogen; and n is 0.

In embodiment E2-1, the invention provides a compound of formula I or I-1, as defined herein, wherein A is phenyl;

$R_1$ is halogen; cyano; —$X_1$—$R_5$; or —$X_2$—$B_2$;

$X_1$ is selected from bond; carbonyl and oxygen; preferably bond;

$R_5$ is $C_{1-6}$alkyl; $C_{1-6}$halogenalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; di($C_{1-4}$alkyl)amino-$C_{1-6}$alkyl; aminocarbonyl-$C_{1-6}$alkyl; $C_{2-6}$alkenyl; $C_{2-6}$alkinyl;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 0; and n is 0.

In embodiment E2-2, the invention provides a compound of formula I or I-1, as defined herein, wherein A is phenyl;

$R_1$ is —$X_2$—$B_2$;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$halogenalkyl, $C_{1-4}$alkoxy, or $C_{1-4}$halogenalkoxy; or two $R_6$ at the same ring atom together are oxo;

m is 0; and n is 0.

In embodiment E3-1, the invention provides a compound of formula I or I-1, as defined herein, wherein A is phenyl;

$R_1$ is halogen; cyano; —$X_1$—$R_5$; or —$X_2$—$B_2$;

$X_1$ is selected from bond; carbonyl and oxygen; preferably bond;

$R_5$ is $C_{1-6}$alkyl; $C_{1-6}$halogenalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; di($C_{1-4}$alkyl)amino-$C_{1-6}$alkyl; aminocarbonyl-$C_{1-6}$alkyl; $C_{2-6}$alkenyl; $C_{2-6}$alkinyl;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 1;

$R_2$ is halogen or $C_{1-4}$alkoxy; and n is 0.

In embodiment E3-2, the invention provides a compound of formula I or I-1, as defined herein, wherein A is phenyl;

$R_1$ is —$X_2$—$B_2$;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 1;

$R_2$ is halogen or $C_{1-4}$alkoxy; and n is 0.

In embodiment E3-3, the invention provides a compound of formula I or I-1, as defined herein, wherein A is phenyl;

$R_1$ is halogen; cyano; —$X_1$—$R_5$; or —$X_2$—$B_2$;

$X_1$ is selected from bond; carbonyl and oxygen; preferably bond;

$R_5$ is $C_{1-6}$alkyl; $C_{1-6}$halogenalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; di($C_{1-4}$alkyl)amino-$C_{1-6}$alkyl; aminocarbonyl-$C_{1-6}$alkyl; $C_{2-6}$alkenyl; $C_{2-6}$alkinyl;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 1;

$R_2$ is halogen; and n is 0.

In embodiment E3-4, the invention provides a compound of formula I or I-1, as defined herein, wherein A is phenyl;

$R_1$ is —$X_2$—$B_2$;

$X_2$ is bond;

$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;

each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;

m is 1;

$R_2$ is halogen; and n is 0.

In one embodiment of E1-1, E1-2, E1-3, E1-4, E2-1, E2-2, E3-1, E3-2, E3-3 and E3-4, the invention provides a compound of formula I or I-1, or a salt thereof, wherein $R_4$ is hydrogen.

In one embodiment of E1-1, E1-2, E1-3, E1-4, E2-1, E2-2, E3-1, E3-2, E3-3 and E3-4, the invention provides a compound of formula I or I-1, or a salt thereof, wherein $B_1$ is a five- to six-membered aromatic ring system, which may contain from 1 to 4 hetero atoms selected from nitrogen, oxygen and sulfur, wherein the ring system may in turn be substituted once or more than once by $R_7$;

each $R_7$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl;

$C_{2-4}$alkenyl; $C_{2-4}$halogenalkenyl; $C_{2-4}$alkinyl; $C_{2-4}$halogenalkinyl;

$C_{1-4}$alkoxy; $C_{1-4}$alkoxy-$C_{1-4}$alkoxy $C_{1-4}$halogenalkoxy; $C_{1-4}$alkyl-amino; di-($C_{1-4}$alkyl)amino;

$C_{1-4}$alkoxycarbonyl;

or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$;

each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo;

or two $R_7$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_9$;

each $R_9$ independently is halogen, hydroxy, cyano, $C_{1-4}$alkyl, $C_{1-4}$halogenalkyl, $C_{1-4}$alkoxy, or $C_{1-4}$halogenalkoxy; or two $R_9$ at the same ring atom together are oxo.

In one embodiment of E1-1, E1-2, E1-3, E1-4, E2-1, E2-2, E3-1, E3-2, E3-3 and E3-4, the invention provides a compound of formula I or I-1, or a salt thereof, wherein $R_4$ is hydrogen and $B_1$ is a five- to six-membered aromatic ring system, which may contain from 1 to 4 hetero atoms selected from nitrogen, oxygen and sulfur, wherein the ring system may in turn be substituted once or more than once by $R_7$;

each $R_7$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl;

$C_{2-4}$alkenyl; $C_{2-4}$halogenalkenyl; $C_{2-4}$alkinyl; $C_{2-4}$halogenalkinyl;

$C_{1-4}$alkoxy; $C_{1-4}$alkoxy-$C_{1-4}$alkoxy $C_{1-4}$halogenalkoxy; $C_{1-4}$alkyl-amino; di-($C_{1-4}$alkyl)amino;

$C_{1-4}$alkoxycarbonyl;

or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$;

each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo;

or two $R_7$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_9$;

each $R_9$ independently is halogen, hydroxy, cyano, $C_{1-4}$alkyl, $C_{1-4}$halogenalkyl, $C_{1-4}$alkoxy, or $C_{1-4}$halogenalkoxy; or two $R_9$ at the same ring atom together are oxo.

In one embodiment of E1-1, E1-2, E1-3, E1-4, E2-1, E2-2, E3-1, E3-2, E3-3 and E3-4, the invention provides a compound of formula I or I-1, or a salt thereof, wherein $B_1$ is imidazol-1-yl, piridin-4-yl, pyrazol-4-yl or 1,2,4-triazol-1-yl which may be substituted once or more than once by $R_7$; and wherein each $R_7$ independently is halogen, cyano, hydroxyl, di($C_{1-4}$alkyl)amino, $C_{1-4}$alkyl; $C_{1-4}$halogenalkyl; $C_{1-4}$alkoxy-$C_{1-4}$alkyl, $C_{1-4}$alkoxy, $C_{1-4}$alkoxy-$C_{1-4}$-alkoxy, $C_{3-6}$cycloalkyl, $C_{3-6}$hydroxycycloalkyl or isoxazol-5-yl.

In one embodiment of E1-1, E1-2, E1-3, E1-4, E2-1, E2-2, E3-1, E3-2, E3-3 and E3-4, the invention provides a compound of formula I or I-1, or a salt thereof, wherein $R_4$ is hydrogen and $B_1$ is imidazol-1-yl, piridin-4-yl, pyrazol-4-yl or 1,2,4-triazol-1-yl which may be substituted once or more than once by $R_7$; and wherein each $R_7$ independently is halogen, cyano, hydroxyl, di($C_{1-4}$alkyl)amino, $C_{1-4}$alkyl; $C_{1-4}$halogenalkyl; $C_{1-4}$alkoxy-$C_{1-4}$alkyl, $C_{1-4}$alkoxy, $C_{1-4}$alkoxy-$C_{1-4}$alkoxy, $C_{3-6}$cycloalkyl, $C_{3-6}$hydroxycycloalkyl or isoxazol-5-yl.

In embodiment E2, the invention provides a compound of formula I or a salt thereof, wherein A is A1, A2 or A3;

$R_1$ is —$X_2$—$B_2$, wherein $X_2$ is bond;

$B_2$ is $C_{3-6}$cycloalkyl which may be substituted once or more than once by $R_6$;

or B$_2$ is a five- to six-membered aromatic ring system which may contain from 1 to 4 hetero atoms selected from nitrogen, oxygen and sulfur, wherein the ring system may in turn be substituted once or more than once by R$_6$;

each R$_6$ independently is halogen, hydroxy, cyano, C$_{1-4}$alkyl, C$_{1-4}$halogenalkyl, C$_{1-4}$alkoxy, or C$_{1-4}$halogenalkoxy;

m is 0, 1 or 2;

each R$_2$ independently is halogen, C$_{1-4}$alkyl; C$_{1-4}$halogenalkyl; C$_{1-4}$alkoxy; C$_{1-4}$halogenalkoxy or C$_{3-6}$cycloalkyl;

n is 0, 1 or 2;

each R$_3$ independently is halogen, C$_{1-4}$alkyl; C$_{1-4}$halogenalkyl; C$_{1-4}$alkoxy; C$_{1-4}$halogenalkoxy or C$_{3-6}$cycloalkyl;

R$_4$ is hydrogen, halogen, C$_{1-4}$alkyl; C$_{1-4}$halogenalkyl; C$_{1-4}$alkoxy; C$_{1-4}$halogenalkoxy or C$_{3-6}$cycloalkyl;

B$_1$ is a five- to six-membered aromatic ring system, which contains from 1 to 4 hetero atoms selected from nitrogen, oxygen and sulfur, wherein the ring system may in turn be substituted once or more than once by R$_7$;

and wherein each R$_7$ independently is halogen, C$_{1-4}$alkyl; C$_{1-4}$halogenalkyl; C$_{1-4}$alkoxy-C$_{1-4}$alkyl, C$_{1-4}$alkoxy, C$_{1-4}$alkoxy-C$_{1-4}$alkoxy or C$_{3-6}$cycloalkyl.

In one embodiment of E2, the invention provides a compound of formula I or a salt thereof, wherein R$_1$ is —X$_2$—B$_2$, wherein X$_2$ is bond;

B$_2$ is C$_{3-6}$cycloalkyl which may be substituted once or more than once by R$_6$;

each R$_6$ independently is halogen, hydroxy, cyano, C$_{1-4}$alkyl, C$_{1-4}$halogenalkyl, C$_{1-4}$alkoxy, or C$_{1-4}$halogenalkoxy.

In one embodiment of E2, the invention provides a compound of formula I or a salt thereof, wherein R$_1$ is —X$_2$—B$_2$, wherein X$_2$ is bond;

B$_2$ is a five- to six-membered aromatic ring system which may contain from 1 to 4 hetero atoms selected from nitrogen, oxygen and sulfur, wherein the ring system may in turn be substituted once or more than once by R$_6$;

each R$_6$ independently is halogen, hydroxy, cyano, C$_{1-4}$alkyl, C$_{1-4}$halogenalkyl, C$_{1-4}$alkoxy, or C$_{1-4}$halogenalkoxy.

In one embodiment of E2, the invention provides a compound of formula I or a salt thereof, wherein m is 0, 1 or 2;

each R$_2$ independently is halogen, C$_{1-4}$alkyl; C$_{1-4}$halogenalkyl; C$_{1-4}$alkoxy; C$_{1-4}$halogenalkoxy or C$_{3-6}$cycloalkyl;

n is 0; and

R$_4$ is hydrogen.

In one embodiment of E2, the invention provides a compound of formula I or a salt thereof, wherein B$_1$ is imidazol-1-yl, which may be substituted once or more than once by R$_7$; and wherein each R$_7$ independently is halogen, C$_{1-4}$alkyl; C$_{1-4}$halogenalkyl; C$_{1-4}$alkoxy-C$_{1-4}$alkyl, C$_{1-4}$alkoxy, C$_{1-4}$alkoxy-C$_{1-4}$alkoxy or C$_{3-6}$cycloalkyl.

Further examples of suitable compounds of the invention are compounds selected from the following group P:

Group P: Suitable Compounds of the Invention:

9-methoxy-2-(3-methoxyphenyl)-7,8-dihydro-[1,4]diazepino[7,1-a]isoquinolin-5(4H)-one;

9-chloro-2-(thiophen-2-yl)-7,8-dihydro-[1,4]diazepino[7,1-a]isoquinolin-5(4H)-one;

9-chloro-2-(3-methoxyphenyl)-7,8-dihydro-[1,4]diazepino[7,1-a]isoquinolin-5(4H)-one;

2-(thiophen-2-yl)-9-(trifluoromethyl)-7,8-dihydro-[1,4]diazepino[7,1-a]isoquinolin-5(4H)-one;

9-methoxy-2-(thiophen-2-yl)-7,8-dihydro-[1,4]diazepino[7,1-a]isoquinolin-5(4H)-one;

9-chloro-2-(2-methoxypyridin-4-yl)-7,8-dihydro-[1,4]diazepino[7,1-a]isoquinolin-5(4H)-one;

9-methoxy-2-(5-methylfuran-2-yl)-7,8-dihydro-[1,4]diazepino[7,1-a]isoquinolin-5(4H)-one;

9-methoxy-2-(2-methoxypyridin-4-yl)-7,8-dihydro-[1,4]diazepino[7,1-a]isoquinolin-5(4H)-one;

9-methoxy-2-(6-methoxypyridin-2-yl)-7,8-dihydro-[1,4]diazepino[7,1-a]isoquinolin-5(4H)-one;

2-(2-ethylpyridin-4-yl)-9-methoxy-7,8-dihydro-[1,4]diazepino[7,1-a]isoquinolin-5(4H)-one;

9-methoxy-2-(1-methyl-1H-pyrazol-3-yl)-7,8-dihydro-[1,4]diazepino[7,1-a]isoquinolin-5(4H)-one;

9-methoxy-2-(3-(2-methoxyethoxy)phenyl)-7,8-dihydro-[1,4]diazepino[7,1-a]isoquinolin-5(4H)-one;

10-chloro-9-methoxy-2-(3-methoxyphenyl)-7,8-dihydro-[1,4]diazepino[7,1-a]isoquinolin-5(4H)-one;

11-chloro-9-methoxy-2-(3-methoxyphenyl)-7,8-dihydro-[1,4]diazepino[7,1-a]isoquinolin-5(4H)-one;

2-(3-ethoxyphenyl)-9-methoxy-7-methyl-7,8-dihydro-[1,4]diazepino[7,1-a]isoquinolin-5(4H)-one;

9-methoxy-2-(3-(trifluoromethyl)phenyl)-7,8-dihydro-[1,4]diazepino[7,1-a]isoquinolin-5(4H)-one;

9-methoxy-2-(4-methoxyphenyl)-7,8-dihydro-[1,4]diazepino[7,1-a]isoquinolin-5(4H)-one;

9-methoxy-2-(5-methoxy-2-methylphenyl)-7,8-dihydro-[1,4]diazepino[7,1-a]isoquinolin-5(4H)-one;

9-fluoro-2-(thiophen-2-yl)-7,8-dihydro-[1,4]diazepino[7,1-a]isoquinolin-5(4H)-one;

9-bromo-2-(3-methoxyphenyl)-7,8-dihydro-[1,4]diazepino[7,1-a]isoquinolin-5(4H)-one;

2-(2-(dimethylamino)pyridin-4-yl)-9-methoxy-7,8-dihydro-[1,4]diazepino[7,1-a]isoquinolin-5(4H)-one;

2-(2-methoxypyridin-4-yl)-9-morpholino-7,8-dihydro-[1,4]diazepino[7,1-a]isoquinolin-5(4H)-one;

2-(5-methylfuran-2-yl)-9-morpholino-7,8-dihydro-[1,4]diazepino[7,1-a]isoquinolin-5(4H)-one;

2-(1-methyl-1H-pyrazol-3-yl)-9-morpholino-7,8-dihydro-[1,4]diazepino[7,1-a]isoquinolin-5(4H)-one;

2-(1-methyl-1H-pyrazol-4-yl)-9-morpholino-7,8-dihydro-[1,4]diazepino[7,1-a]isoquinolin-5(4H)-one;

9-(2-hydroxypropan-2-yl)-2-(3-methoxyphenyl)-7,8-dihydro-[1,4]diazepino[7,1-a]isoquinolin-5(4H)-one;

9-(2-hydroxypropan-2-yl)-2-(1-methyl-1H-pyrazol-3-yl)-7,8-dihydro-[1,4]diazepino[7,1-a]isoquinolin-5(4H)-one;

2-(furan-2-yl)-9-(pyridin-4-yl)-7,8-dihydro-[1,4]diazepino[7,1-a]isoquinolin-5(4H)-one;

9-bromo-2-(thiophen-2-yl)-7,8-dihydro-[1,4]diazepino[7,1-a]isoquinolin-5(4H)-one;

9-iodo-2-(3-methoxyphenyl)-7,8-dihydro-[1,4]diazepino[7,1-a]isoquinolin-5(4H)-one;

9-iodo-2-(1-methyl-1H-pyrazol-3-yl)-7,8-dihydro-[1,4]diazepino[7,1-a]isoquinolin-5(4H)-one;

9-iodo-2-(1-methyl-1H-pyrazol-4-yl)-7,8-dihydro-[1,4]diazepino[7,1-a]isoquinolin-5(4H)-one;

9-iodo-2-(2-methoxypyridin-4-yl)-7,8-dihydro-[1,4]diazepino[7,1-a]isoquinolin-5(4H)-one;

2-(furan-3-yl)-9-iodo-7,8-dihydro-[1,4]diazepino[7,1-a]isoquinolin-5(4H)-one;

9-iodo-2-(1-isopropyl-1H-pyrazol-4-yl)-7,8-dihydro-[1,4]diazepino[7,1-a]isoquinolin-5(4H)-one;

9-iodo-2-(1-methyl-1H-imidazol-4-yl)-7,8-dihydro-[1,4]diazepino[7,1-a]isoquinolin-5(4H)-one;

9-methoxy-2-(4-methyl-3,4-dihydro-2H-pyrido[3,2-b][1,4]oxazin-7-yl)-7,8-dihydro-[1,4]diazepino[7,1-a]isoquinolin-5(4H)-one;

9-ethyl-2-(3-methoxyphenyl)-7,8-dihydro-[1,4]diazepino[7,1-a]isoquinolin-5(4H)-one;

9-ethynyl-2-(thiophen-2-yl)-7,8-dihydro-[1,4]diazepino[7,1-a]isoquinolin-5(4H)-one;

5-oxo-2-(thiophen-2-yl)-4,5,7,8-tetrahydro-[1,4]diazepino[7,1-a]isoquinoline-9-carbonitrile;

2-(1-methyl-1H-pyrazol-3-yl)-5-oxo-4,5,7,8-tetrahydro-[1,4]diazepino[7,1-a]isoquinoline-9-carbonitrile;
2-(3-methoxyphenyl)-9-morpholino-7,8-dihydro-[1,4]diazepino[7,1-a]isoquinolin-5(4H)-one;
2-(1-isopropyl-1H-pyrazol-4-yl)-9-(1H-pyrazol-1-yl)-7,8-dihydro-[1,4]diazepino[7,1-a]isoquinolin-5(4H)-one;
9-((dimethylamino)methyl)-2-(3-methoxyphenyl)-7,8-dihydro-[1,4]diazepino[7,1-a]isoquinolin-5(4H)-one;
9-((2-methoxyethoxy)methyl)-2-(3-methoxyphenyl)-7,8-dihydro-[1,4]diazepino[7,1-a]isoquinolin-5(4H)-one;
9-(hydroxymethyl)-2-(1-methyl-1H-pyrazol-3-yl)-7,8-dihydro-[1,4]diazepino[7,1-a]isoquinolin-5(4H)-one;
9-(hydroxymethyl)-2-(1-methyl-1H-pyrazol-4-yl)-7,8-dihydro-[1,4]diazepino[7,1-a]isoquinolin-5(4H)-one;
9-(1-methoxyethyl)-2-(1-methyl-1H-pyrazol-3-yl)-7,8-dihydro-[1,4]diazepino[7,1-a]isoquinolin-5(4H)-one;
9-acetyl-2-(3-methoxyphenyl)-7,8-dihydro-[1,4]diazepino[7,1-a]isoquinolin-5(4H)-one;
2-(3-methoxyphenyl)-9-phenyl-7,8-dihydro-[1,4]diazepino[7,1-a]isoquinolin-5(4H)-one;
2-(2-methoxypyridin-4-yl)-9-(pyridin-2-yl)-7,8-dihydro-[1,4]diazepino[7,1-a]isoquinolin-5(4H)-one;
2-(furan-3-yl)-9-(pyridin-4-yl)-7,8-dihydro-[1,4]diazepino[7,1-a]isoquinolin-5(4H)-one;
2-(2-methoxypyridin-4-yl)-9-(pyrazin-2-yl)-7,8-dihydro-[1,4]diazepino[7,1-a]isoquinolin-5(4H)-one;
9-(6-fluoropyridin-3-yl)-2-(2-methoxypyridin-4-yl)-7,8-dihydro-[1,4]diazepino[7,1-a]isoquinolin-5(4H)-one;
9-(3-fluoropyridin-4-yl)-2-(2-methoxypyridin-4-yl)-7,8-dihydro-[1,4]diazepino[7,1-a]isoquinolin-5(4H)-one;
2-(1-methyl-1H-imidazol-4-yl)-9-(pyridin-4-yl)-7,8-dihydro-[1,4]diazepino[7,1-a]isoquinolin-5(4H)-one;
2-(1-methyl-1H-pyrazol-3-yl)-9-(2-methylpyridin-4-yl)-7,8-dihydro-[1,4]diazepino[7,1-a]isoquinolin-5(4H)-one;
2-(3-methoxyphenyl)-9-(tetrahydrofuran-2-yl)-7,8-dihydro-[1,4]diazepino[7,1-a]isoquinolin-5(4H)-one,
(R)-2-(3-methoxyphenyl)-9-(tetrahydrofuran-2-yl)-7,8-dihydro-[1,4]diazepino[7,1-a]isoquinolin-5(4H)-one;
(S)-2-(3-methoxyphenyl)-9-(tetrahydrofuran-2-yl)-7,8-dihydro-[1,4]diazepino[7,1-a]isoquinolin-5(4H)-one;
9-methoxy-2-(6-oxo-1,6-dihydropyridin-2-yl)-7,8-dihydro-[1,4]diazepino[7,1-a]isoquinolin-5(4H)-one;
9,10-dimethoxy-2-(3-methoxyphenyl)-7,8-dihydro-[1,4]diazepino[7,1-a]isoquinolin-5(4H)-one;
9-methoxy-2-(2-oxo-1,2-dihydropyridin-4-yl)-7,8-dihydro-[1,4]diazepino[7,1-a]isoquinolin-5(4H)-one;
2-(4-isopropyl-1H-imidazol-1-yl)-9-methoxy-7,8-dihydro-[1,4]diazepino[7,1-a]isoquinolin-5(4H)-one;
9-chloro-2-(4-methyl-1H-imidazol-1-yl)-7,8-dihydro-[1,4]diazepino[7,1-a]isoquinolin-5(4H)-one;
9-iodo-2-(4-(trifluoromethyl)-1H-imidazol-1-yl)-7,8-dihydro-[1,4]diazepino[7,1-a]isoquinolin-5(4H)-one;
1-(9-iodo-5-oxo-4,5,7,8-tetrahydro-[1,4]diazepino[7,1-a]isoquinolin-2-yl)-1H-imidazole-4-carbonitrile;
2-(4-(hydroxymethyl)-1H-imidazol-1-yl)-9-iodo-7,8-dihydro-[1,4]diazepino[7,1-a]isoquinolin-5(4H)-one;
methyl 1-(9-iodo-5-oxo-4,5,7,8-tetrahydro-[1,4]diazepino[7,1-a]isoquinolin-2-yl)-1H-imidazole-4-carboxylate;
2-(2,4-dimethyl-1H-imidazol-1-yl)-9-iodo-7,8-dihydro-[1,4]diazepino[7,1-a]isoquinolin-5(4H)-one;
ethyl 1-(9-iodo-5-oxo-4,5,7,8-tetrahydro-[1,4]diazepino[7,1-a]isoquinolin-2-yl)-1H-imidazole-4-carboxylate;
2-(4-cyclobutyl-1H-imidazol-1-yl)-9-(1H-pyrazol-1-yl)-7,8-dihydro-[1,4]diazepino[7,1-a]isoquinolin-5(4H)-one;
2-(4-cyclobutyl-1H-imidazol-1-yl)-9-morpholino-7,8-dihydro-[1,4]diazepino[7,1-a]isoquinolin-5(4H)-one;
2-(4-(methoxymethyl)-1H-imidazol-1-yl)-9-(thiazol-2-yl)-7,8-dihydro-[1,4]diazepino[7,1-a]isoquinolin-5(4H)-one;
2-(4-isopropyl-1H-imidazol-1-yl)-9-(1-methyl-1H-pyrazol-4-yl)-7,8-dihydro-[1,4]diazepino[7,1-a]isoquinolin-5(4H)-one;
2-(4-isopropyl-1H-imidazol-1-yl)-9-(1-methyl-1H-imidazol-2-yl)-7,8-dihydro-[1,4]diazepino[7,1-a]isoquinolin-5(4H)-one;
2-(4-ethyl-1H-imidazol-1-yl)-9-(oxazol-2-yl)-7,8-dihydro-[1,4]diazepino[7,1-a]isoquinolin-5(4H)-one;
2-(4-ethyl-1H-imidazol-1-yl)-9-(furan-2-yl)-7,8-dihydro-[1,4]diazepino[7,1-a]isoquinolin-5(4H)-one;
2-(4-(2-methoxyethyl)-1H-imidazol-1-yl)-9-(thiazol-4-yl)-7,8-dihydro-[1,4]diazepino[7,1-a]isoquinolin-5(4H)-one;
2-(4-(methoxymethyl)-1H-imidazol-1-yl)-9-(5-methylthiazol-2-yl)-7,8-dihydro-[1,4]diazepino[7,1-a]isoquinolin-5(4H)-one;
2-(4-methyl-1H-imidazol-1-yl)-9-(pyrimidin-5-yl)-7,8-dihydro-[1,4]diazepino[7,1-a]isoquinolin-5(4H)-one;
2-(4-methyl-1H-imidazol-1-yl)-9-(pyridin-3-yl)-7,8-dihydro-[1,4]diazepino[7,1-a]isoquinolin-5(4H)-one;
2-(4-methyl-1H-imidazol-1-yl)-9-(pyridin-4-yl)-7,8-dihydro-[1,4]diazepino[7,1-a]isoquinolin-5(4H)-one;
9-(6-fluoropyridin-3-yl)-2-(4-methyl-1H-imidazol-1-yl)-7,8-dihydro-[1,4]diazepino[7,1-a]isoquinolin-5(4H)-one;
2-(4-methyl-1H-imidazol-1-yl)-9-(thiazol-5-yl)-7,8-dihydro-[1,4]diazepino[7,1-a]isoquinolin-5(4H)-one;
2-(4-chloro-1H-imidazol-1-yl)-9-(5-fluoropyridin-3-yl)-7,8-dihydro-[1,4]diazepino[7,1-a]isoquinolin-5(4H)-one;
9-(6-fluoropyridin-3-yl)-2-(4-(2-methoxyethyl)-1H-imidazol-1-yl)-7,8-dihydro-[1,4]diazepino[7,1-a]isoquinolin-5(4H)-one;
2-(4-(methoxymethyl)-1H-imidazol-1-yl)-9-vinyl-7,8-dihydro-[1,4]diazepino[7,1-a]isoquinolin-5(4H)-one;
2-(4-ethyl-1H-imidazol-1-yl)-9-(4-fluorophenyl)-7,8-dihydro-[1,4]diazepino[7,1-a]isoquinolin-5(4H)-one;
2-(4-cyclopropyl-1H-imidazol-1-yl)-9-(4-methyloxazol-2-yl)-7,8-dihydro-[1,4]diazepino[7,1-a]isoquinolin-5(4H)-one;
2-(4-cyclopropyl-1H-imidazol-1-yl)-9-(5-methyloxazol-2-yl)-7,8-dihydro-[1,4]diazepino[7,1-a]isoquinolin-5(4H)-one;
2-(4-(oxazol-2-yl)-1H-imidazol-1-yl)-9-propyl-7,8-dihydro-[1,4]diazepino[7,1-a]isoquinolin-5(4H)-one;
9-ethyl-2-(4-isopropyl-1H-imidazol-1-yl)-7,8-dihydro-[1,4]diazepino[7,1-a]isoquinolin-5(4H)-one;
2-(4-methyl-1H-imidazol-1-yl)-9-propyl-7,8-dihydro-[1,4]diazepino[7,1-a]isoquinolin-5(4H)-one;
9-cyclobutyl-2-(4-(methoxymethyl)-1H-imidazol-1-yl)-7,8-dihydro-[1,4]diazepino[7,1-a]isoquinolin-5(4H)-one;
9-cyclobutyl-2-(3-methyl-1H-1,2,4-triazol-1-yl)-7,8-dihydro-[1,4]diazepino[7,1-a]isoquinolin-5(4H)-one;
9-cyclopropyl-2-(3-(methoxymethyl)-1H-1,2,4-triazol-1-yl)-7,8-dihydro-[1,4]diazepino[7,1-a]isoquinolin-5(4H)-one;
4-(6-fluoropyridin-3-yl)-11-(4-isopropyl-1H-imidazol-1-yl)-5,6-dihydro-[1,4]diazepino[1,7-h][1,7]naphthyridin-8(9H)-one;
2-(4-cyclopropyl-1H-imidazol-1-yl)-9-(6-fluoropyridin-3-yl)-7,8-dihydro-[1,4]diazepino[7,1-a]isoquinolin-5(4H)-one;
9-cyclopropyl-2-(4-(methoxymethyl)-1H-imidazol-1-yl)-7,8-dihydro-[1,4]diazepino[7,1-a]isoquinolin-5(4H)-one;
2-(4-cyclopropyl-1H-imidazol-1-yl)-9-(2-fluoropyridin-3-yl)-7,8-dihydro-[1,4]diazepino[7,1-a]isoquinolin-5(4H)-one;

2-(4-cyclobutyl-1H-imidazol-1-yl)-9-(2-fluoropyridin-3-yl)-7,8-dihydro-[1,4]diazepino[7,1-a]isoquinolin-5(4H)-one;
2-(4-cyclopropyl-1H-imidazol-1-yl)-9-(2,6-difluoropyridin-3-yl)-7,8-dihydro-[1,4]diazepino[7,1-a]isoquinolin-5(4H)-one;
2-(4-cyclopropyl-1H-imidazol-1-yl)-9-(isoxazol-5-yl)-7,8-dihydro-[1,4]diazepino[7,1-a]isoquinolin-5(4H)-one;
2-(4-(methoxymethyl)-1H-imidazol-1-yl)-9-(thiazol-4-yl)-7,8-dihydro-[1,4]diazepino[7,1-a]isoquinolin-5(4H)-one;
2-(3-ethyl-1H-1,2,4-triazol-1-yl)-9-(6-fluoropyridin-3-yl)-7,8-dihydro-[1,4]diazepino[7,1-a]isoquinolin-5(4H)-one;
2-(3-cyclopropyl-1H-1,2,4-triazol-1-yl)-9-(6-fluoropyridin-3-yl)-7,8-dihydro-[1,4]diazepino[7,1-a]isoquinolin-5(4H)-one;
2-(4-cyclopropyl-1H-imidazol-1-yl)-9-(3-methylisothiazol-5-yl)-7,8-dihydro-[1,4]diazepino[7,1-a]isoquinolin-5(4H)-one;
2-(4-cyclopropyl-1H-imidazol-1-yl)-9-(oxazol-2-yl)-7,8-dihydro-[1,4]diazepino[7,1-a]isoquinolin-5(4H)-one;
2-(4-ethynyl-1H-imidazol-1-yl)-9-(thiazol-4-yl)-7,8-dihydro-[1,4]diazepino[7,1-a]isoquinolin-5(4H)-one;
9-(2-fluoropyridin-3-yl)-2-(4-(oxazol-2-yl)-1H-imidazol-1-yl)-7,8-dihydro-[1,4]diazepino[7,1-a]isoquinolin-5(4H)-one;
2-(4-cyclopropyl-1H-imidazol-1-yl)-1-methyl-9-(3-methylisoxazol-5-yl)-7,8-dihydro-[1,4]diazepino[7,1-a]isoquinolin-5(4H)-one;
2-(4-cyclopropyl-1H-imidazol-1-yl)-9-(2-methyloxazol-4-yl)-7,8-dihydro-[1,4]diazepino[7,1-a]isoquinolin-5(4H)-one;
2-(4-cyclopropyl-1H-imidazol-1-yl)-9-(oxazol-5-yl)-7,8-dihydro-[1,4]diazepino[7,1-a]isoquinolin-5(4H)-one;
2-(4-cyclopropyl-1H-imidazol-1-yl)-9-(6-fluoropyridin-3-yl)-7,8-dihydro-[1,4]diazepino[7,1-a][2,6]naphthyridin-5(4H)-one;
2-(4-ethyl-1H-imidazol-1-yl)-9-(tetrahydrofuran-2-yl)-7,8-dihydro-[1,4]diazepino[7,1-a]isoquinolin-5(4H)-one;
(R)-2-(4-ethyl-1H-imidazol-1-yl)-9-(tetrahydrofuran-2-yl)-7,8-dihydro-[1,4]diazepino[7,1-a]isoquinolin-5(4H)-one;
(S)-2-(4-ethyl-1H-imidazol-1-yl)-9-(tetrahydrofuran-2-yl)-7,8-dihydro-[1,4]diazepino[7,1-a]isoquinolin-5(4H)-one;
2-(4-(tert-butyl)-1H-imidazol-1-yl)-9-(tetrahydrofuran-2-yl)-7,8-dihydro-[1,4]diazepino[7,1-a]isoquinolin-5(4H)-one;
(R)-2-(4-(tert-butyl)-1H-imidazol-1-yl)-9-(tetrahydrofuran-2-yl)-7,8-dihydro-[1,4]diazepino[7,1-a]isoquinolin-5(4H)-one;
(S)-2-(4-(tert-butyl)-1H-imidazol-1-yl)-9-(tetrahydrofuran-2-yl)-7,8-dihydro-[1,4]diazepino[7,1-a]isoquinolin-5(4H)-one;
2-(4-ethyl-1H-imidazol-1-yl)-9-(1-fluorocyclobutyl)-7,8-dihydro-[1,4]diazepino[7,1-a]isoquinolin-5(4H)-one;
2-(4-ethyl-1H-imidazol-1-yl)-9-(3-fluorooxetan-3-yl)-7,8-dihydro-[1,4]diazepino[7,1-a]isoquinolin-5(4H)-one;
2-(4-ethyl-1H-imidazol-1-yl)-9-(1-hydroxyethyl)-7,8-dihydro-[1,4]diazepino[7,1-a]isoquinolin-5(4H)-one;
(R)-2-(4-ethyl-1H-imidazol-1-yl)-9-(1-hydroxyethyl)-7,8-dihydro-[1,4]diazepino[7,1-a]isoquinolin-5(4H)-one;
(S)-2-(4-ethyl-1H-imidazol-1-yl)-9-(1-hydroxyethyl)-7,8-dihydro-[1,4]diazepino[7,1-a]isoquinolin-5(4H)-one;
9-acetyl-2-(4-methyl-1H-imidazol-1-yl)-7,8-dihydro-[1,4]diazepino[7,1-a]isoquinolin-5(4H)-one;
9-acetyl-2-(4-cyclobutyl-1H-imidazol-1-yl)-7,8-dihydro-[1,4]diazepino[7,1-a]isoquinolin-5(4H)-one;
2-(4-(1-methoxyethyl)-1H-imidazol-1-yl)-9-(prop-1-en-2-yl)-7,8-dihydro-[1,4]diazepino[7,1-a]isoquinolin-5(4H)-one;
(R)-2-(4-(1-methoxyethyl)-1H-imidazol-1-yl)-9-(prop-1-en-2-yl)-7,8-dihydro-[1,4]diazepino[7,1-a]isoquinolin-5(4H)-one;
(S)-2-(4-(1-methoxyethyl)-1H-imidazol-1-yl)-9-(prop-1-en-2-yl)-7,8-dihydro-[1,4]diazepino[7,1-a]isoquinolin-5(4H)-one;
9-(cyclopent-1-en-1-yl)-2-(4-(methoxymethyl)-1H-imidazol-1-yl)-7,8-dihydro-[1,4]diazepino[7,1-a]isoquinolin-5(4H)-one;
2-(4-(methoxymethyl)-1H-imidazol-1-yl)-9-(prop-1-en-2-yl)-7,8-dihydro-[1,4]diazepino[7,1-a]isoquinolin-5(4H)-one;
9-cyclopropyl-2-(4-(1-methoxyethyl)-1H-imidazol-1-yl)-7,8-dihydro-[1,4]diazepino[7,1-a]isoquinolin-5(4H)-one;
(S)-9-cyclopropyl-2-(4-(1-methoxyethyl)-1H-imidazol-1-yl)-7,8-dihydro-[1,4]diazepino[7,1-a]isoquinolin-5(4H)-one;
(R)-9-cyclopropyl-2-(4-(1-methoxyethyl)-1H-imidazol-1-yl)-7,8-dihydro-[1,4]diazepino[7,1-a]isoquinolin-5(4H)-one;
2-(4-cyclobutyl-1H-imidazol-1-yl)-9-propionyl-7,8-dihydro-[1,4]diazepino[7,1-a]isoquinolin-5(4H)-one; or
9-(tert-butyl)-2-(4-(methoxymethyl)-1H-imidazol-1-yl)-7,8-dihydro-[1,4]diazepino[7,1-a]isoquinolin-5(4H)-one;
2-(3-cyclopropyl-1H-1,2,4-triazol-1-yl)-9-(3-fluoropyrazin-2-yl)-7,8-dihydro-[1,4]diazepino[7,1-a]isoquinolin-5(4H)-one;
2-(3-cyclopropyl-1H-1,2,4-triazol-1-yl)-9-(3-fluoropyridin-2-yl)-7,8-dihydro-[1,4]diazepino[7,1-a]isoquinolin-5(4H)-one;
2-(4-cyclopropyl-1H-imidazol-1-yl)-9-(thiazol-5-yl)-7,8-dihydro-[1,4]diazepino[7,1-a]isoquinolin-5(4H)-one;
2-(4-cyclopropyl-1H-imidazol-1-yl)-9-(2-methylthiazol-5-yl)-7,8-dihydro-[1,4]diazepino[7,1-a]isoquinolin-5(4H)-one;
2-(4-cyclopropyl-1H-imidazol-1-yl)-9-(pyrazin-2-yl)-7,8-dihydro-[1,4]diazepino[7,1-a]isoquinolin-5(4H)-one;
2-(3-cyclopropyl-1H-1,2,4-triazol-1-yl)-9-(thiazol-2-yl)-7,8-dihydro-[1,4]diazepino[7,1-a]isoquinolin-5(4H)-one;
2-(4-(2-methoxyethyl)-1H-imidazol-1-yl)-9-(thiazol-2-yl)-7,8-dihydro-[1,4]diazepino[7,1-a]isoquinolin-5(4H)-one;
2-(4-(ethoxymethyl)-1H-imidazol-1-yl)-9-(4-methylthiazol-2-yl)-7,8-dihydro-[1,4]diazepino[7,1-a]isoquinolin-5(4H)-one;
2-(4-(ethoxymethyl)-1H-imidazol-1-yl)-9-(thiazol-2-yl)-7,8-dihydro-[1,4]diazepino[7,1-a]isoquinolin-5(4H)-one;
2-(4-cyclopropyl-1H-imidazol-1-yl)-9-(4-fluoropyridin-3-yl)-7,8-dihydro-[1,4]diazepino[7,1-a]isoquinolin-5(4H)-one;
9-cyclopropyl-10-fluoro-2-(4-(methoxymethyl)-1H-imidazol-1-yl)-7,8-dihydro-[1,4]diazepino[7,1-a]isoquinolin-5(4H)-one;
2-(4-methyl-1H-imidazol-1-yl)-9-(2-methyloxazol-5-yl)-7,8-dihydro-[1,4]diazepino[7,1-a]isoquinolin-5(4H)-one;
2-(4-cyclopropyl-1H-imidazol-1-yl)-9-(3-(trifluoromethyl)-1H-pyrazol-5-yl)-7,8-dihydro-[1,4]diazepino[7,1-a]isoquinolin-5(4H)-one;
2-(4-cyclopropyl-1H-imidazol-1-yl)-9-(6-hydroxypyridin-3-yl)-7,8-dihydro-[1,4]diazepino[7,1-a]isoquinolin-5(4H)-one;
2-(4-cyclopropyl-1H-imidazol-1-yl)-9-(6-methoxypyridin-3-yl)-7,8-dihydro-[1,4]diazepino[7,1-a]isoquinolin-5(4H)-one;

2-(4-cyclopropyl-1H-imidazol-1-yl)-9-(1H-pyrazol-3-yl)-7,8-dihydro-[1,4]diazepino[7,1-a]isoquinolin-5(4H)-one;

2-(4-cyclopropyl-1H-imidazol-1-yl)-9-(2-fluoropyrimidin-5-yl)-7,8-dihydro-[1,4]diazepino[7,1-a]isoquinolin-5(4H)-one;

2-(4-cyclopropyl-1H-imidazol-1-yl)-9-(2-fluoropyridin-4-yl)-7,8-dihydro-[1,4]diazepino[7,1-a]isoquinolin-5(4H)-one;

2-(3-cyclobutyl-1H-1,2,4-triazol-1-yl)-9-(6-fluoropyridin-3-yl)-7,8-dihydro-[1,4]diazepino[7,1-a]isoquinolin-5(4H)-one;

9-cyclopropyl-12-fluoro-2-(4-(methoxymethyl)-1H-imidazol-1-yl)-7,8-dihydro-[1,4]diazepino[7,1-a]isoquinolin-5(4H)-one;

(R)-9-cyclopropyl-12-fluoro-2-(4-(1-methoxyethyl)-1H-imidazol-1-yl)-7,8-dihydro-[1,4]diazepino[7,1-a]isoquinolin-5(4H)-one;

9-cyclopropyl-11-fluoro-2-(4-(methoxymethyl)-1H-imidazol-1-yl)-7,8-dihydro-[1,4]diazepino[7,1-a]isoquinolin-5(4H)-one;

9-cyclopropyl-2-(4-(difluoromethyl)-1H-imidazol-1-yl)-7,8-dihydro-[1,4]diazepino[7,1-a]isoquinolin-5(4H)-one;

9-cyclopropyl-2-(4-(fluoromethyl)-1H-imidazol-1-yl)-7,8-dihydro-[1,4]diazepino[7,1-a]isoquinolin-5(4H)-one;

(R)-9-cyclopropyl-10-fluoro-2-(4-(1-methoxyethyl)-1H-imidazol-1-yl)-7,8-dihydro-[1,4]diazepino[7,1-a]isoquinolin-5(4H)-one;

10-fluoro-9-(6-fluoropyridin-3-yl)-2-(3-methyl-1H-1,2,4-triazol-1-yl)-7,8-dihydro-[1,4]diazepino[7,1-a]isoquinolin-5(4H)-one;

9-cyclopropyl-10-fluoro-2-(3-(methoxymethyl)-1H-1,2,4-triazol-1-yl)-7,8-dihydro-[1,4]diazepino[7,1-a]isoquinolin-5(4H)-one;

2-(3-cyclopropyl-1H-1,2,4-triazol-1-yl)-10-fluoro-9-(2-fluoropyridin-3-yl)-7,8-dihydro-[1,4]diazepino[7,1-a]isoquinolin-5(4H)-one;

10-fluoro-9-(2-fluoropyridin-3-yl)-2-(3-methyl-1H-1,2,4-triazol-1-yl)-7,8-dihydro-[1,4]diazepino[7,1-a]isoquinolin-5(4H)-one;

10-fluoro-9-(2-fluoropyridin-3-yl)-2-(4-methyl-1H-imidazol-1-yl)-7,8-dihydro-[1,4]diazepino[7,1-a]isoquinolin-5(4H)-one;

9-(6-fluoropyridin-3-yl)-2-(4-(1-methoxycyclopropyl)-1H-imidazol-1-yl)-7,8-dihydro-[1,4]diazepino[7,1-a]isoquinolin-5(4H)-one;

2-(4-methyl-1H-imidazol-1-yl)-9-(pyrazin-2-yl)-7,8-dihydro-[1,4]diazepino[7,1-a]isoquinolin-5(4H)-one;

9-(6-fluoropyridin-3-yl)-2-(4-(3-hydroxyoxetan-3-yl)-1H-imidazol-1-yl)-7,8-dihydro-[1,4]diazepino[7,1-a]isoquinolin-5(4H)-one;

2-(3-cyclopropyl-1H-1,2,4-triazol-1-yl)-9-(2-methyloxazol-4-yl)-7,8-dihydro-[1,4]diazepino[7,1-a]isoquinolin-5(4H)-one;

2-(4-cyclobutyl-1H-imidazol-1-yl)-9-(2-methyloxazol-4-yl)-7,8-dihydro-[1,4]diazepino[7,1-a]isoquinolin-5(4H)-one;

2-(4-methyl-1H-imidazol-1-yl)-9-(2-methyloxazol-4-yl)-7,8-dihydro-[1,4]diazepino[7,1-a]isoquinolin-5(4H)-one;

9-cyclopropyl-2-(4-cyclopropyl-1H-imidazol-1-yl)-7,8-dihydro-[1,4]diazepino[7,1-a][2,6]naphthyridin-5(4H)-one;

9-cyclopropyl-2-(3-cyclopropyl-1H-1,2,4-triazol-1-yl)-7,8-dihydro-[1,4]diazepino[7,1-a][2,6]naphthyridin-5(4H)-one;

(R)-9-cyclopropyl-2-(4-(1-methoxyethyl)-1H-imidazol-1-yl)-7,8-dihydro-[1,4]diazepino[7,1-a][2,6]naphthyridin-5(4H)-one;

9-cyclopropyl-2-(4-(difluoromethyl)-1H-imidazol-1-yl)-7,8-dihydro-[1,4]diazepino[7,1-a][2,6]naphthyridin-5(4H)-one;

9-cyclopropyl-2-(4-(oxazol-5-yl)-1H-imidazol-1-yl)-7,8-dihydro-[1,4]diazepino[7,1-a]isoquinolin-5(4H)-one;

9-cyclopropyl-2-(4-(isoxazol-5-yl)-1H-imidazol-1-yl)-7,8-dihydro-[1,4]diazepino[7,1-a]isoquinolin-5(4H)-one;

9-cyclopropyl-2-(3-cyclopropyl-1H-1,2,4-triazol-1-yl)-7,8-dihydro-[1,4]diazepino[7,1-a]isoquinolin-5(4H)-one;

9-cyclopropyl-2-(4-methoxy-1H-imidazol-1-yl)-7,8-dihydro-[1,4]diazepino[7,1-a]isoquinolin-5(4H)-one;

9-cyclopropyl-2-(4-(trifluoromethyl)-1H-imidazol-1-yl)-7,8-dihydro-[1,4]diazepino[7,1-a]isoquinolin-5(4H)-one;

9-cyclopropyl-2-(4-(pyridin-4-yl)-1H-imidazol-1-yl)-7,8-dihydro-[1,4]diazepino[7,1-a]isoquinolin-5(4H)-one;

9-cyclopropyl-2-(4-((trifluoromethoxy)methyl)-1H-imidazol-1-yl)-7,8-dihydro-[1,4]diazepino[7,1-a]isoquinolin-5(4H)-one;

9-cyclopropyl-2-(4-(1-hydroxycyclopropyl)-1H-imidazol-1-yl)-7,8-dihydro-[1,4]diazepino[7,1-a]isoquinolin-5(4H)-one;

9-cyclopropyl-2-(4-(2-hydroxyethyl)-1H-imidazol-1-yl)-7,8-dihydro-[1,4]diazepino[7,1-a]isoquinolin-5(4H)-one;

9-cyclopropyl-2-(4-(1-hydroxyethyl)-1H-imidazol-1-yl)-7,8-dihydro-[1,4]diazepino[7,1-a]isoquinolin-5(4H)-one;

9-cyclopropyl-2-(4-(cyclopropyl(hydroxy)methyl)-1H-imidazol-1-yl)-7,8-dihydro-[1,4]diazepino[7,1-a]isoquinolin-5(4H)-one;

9-cyclopropyl-2-(4-((trifluoromethoxy)methyl)-1H-imidazol-1-yl)-7,8-dihydro-[1,4]diazepino[7,1-a]isoquinolin-5(4H)-one;

methyl 2-(4-cyclopropyl-1H-imidazol-1-yl)-5-oxo-4,5,7,8-tetrahydro-[1,4]diazepino[7,1-a]isoquinoline-9-carboxylate;

2-(3-cyclopropyl-1H-1,2,4-triazol-1-yl)-9-(5-fluoropyridin-2-yl)-7,8-dihydro-[1,4]diazepino[7,1-a]isoquinolin-5(4H)-one;

2-(3-cyclopropyl-1H-1,2,4-triazol-1-yl)-9-(6-fluoropyridin-2-yl)-7,8-dihydro-[1,4]diazepino[7,1-a]isoquinolin-5(4H)-one;

2-(3-cyclopropyl-1H-1,2,4-triazol-1-yl)-9-(4-fluoropyridin-2-yl)-7,8-dihydro-[1,4]diazepino[7,1-a]isoquinolin-5(4H)-one;

2-(3-cyclopropyl-1H-1,2,4-triazol-1-yl)-9-(5-fluoropyrazin-2-yl)-7,8-dihydro-[1,4]diazepino[7,1-a]isoquinolin-5(4H)-one;

9-(5-fluoropyrazin-2-yl)-2-(3-methyl-1H-1,2,4-triazol-1-yl)-7,8-dihydro-[1,4]diazepino[7,1-a]isoquinolin-5(4H)-one;

2-(4-cyclopropyl-1H-imidazol-1-yl)-9-(2H-1,2,3-triazol-2-yl)-7,8-dihydro-[1,4]diazepino[7,1-a]isoquinolin-5(4H)-one;

2-(4-cyclopropyl-1H-imidazol-1-yl)-9-(5-fluoropyrazin-2-yl)-7,8-dihydro-[1,4]diazepino[7,1-a]isoquinolin-5(4H)-one;

9-cyclopropyl-2-(4-(1-fluorocyclopropyl)-1H-imidazol-1-yl)-7,8-dihydro-[1,4]diazepino[7,1-a][2,6]naphthyridin-5(4H)-one;

2-(4-cyclopropyl-1H-imidazol-1-yl)-9-(6-fluoropyrazin-2-yl)-7,8-dihydro-[1,4]diazepino[7,1-a]isoquinolin-5(4H)-one;

9-isopropoxy-2-(4-(methoxymethyl)-1H-imidazol-1-yl)-7,8-dihydro-[1,4]diazepino[7,1-a]isoquinolin-5(4H)-one;

or salts of these compounds.

In a further aspect, the invention also provides a process for the production of compounds of the formula Ia and Ib. Said compounds are obtainable according to the following process as described in scheme 1:

Scheme 1:

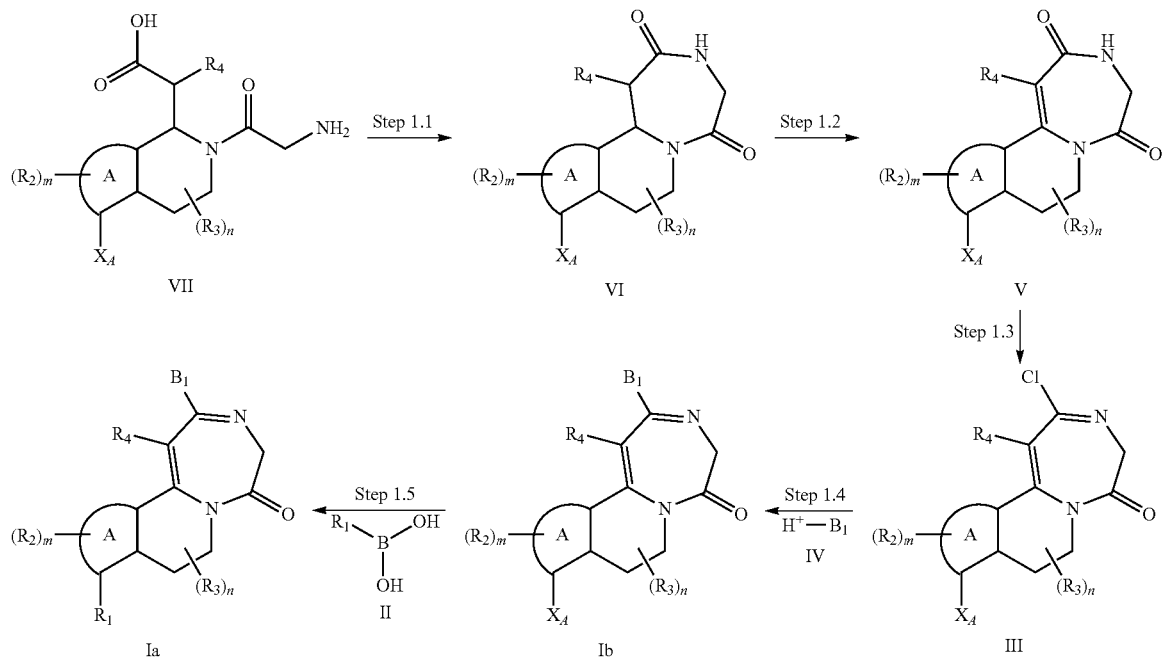

Step 1.1: A compound of formula VI, in which A, $R_2$, m, $R_3$, n and $R_4$ are as defined under formula I, and $X_A$ is halogen, may be obtained by reacting a compound of formula VII, in which A, $R_2$, m, $R_3$, n and $R_4$ are as defined under formula I, and $X_A$ is halogen, with propylphosphonic anhydride, in the presence of a suitable base, e.g. triethylamine, in the presence of a suitable solvent, e.g. dichloromethane.

Step 1.2: A compound of formula V, in which A, $R_2$, m, $R_3$, n and $R_4$ are as defined under formula I, and $X_A$ is halogen, may be obtained by oxidizing the compound of formula VI with an oxidizing agent, e.g. $SeO_2$, in the presence of a suitable solvent, e.g. pyridine.

Step 1.3: A compound of formula III, in which A, $R_2$, m, $R_3$, n and $R_4$ are as defined under formula I, and $X_A$ is halogen, may be obtained by chlorinating the compound of formula V with a chlorinating agent, e.g. $POCl_3$, in the presence of a suitable solvent, e.g. 1,2-dichloroethane.

Step 1.4: A compound of formula Ib, in which A, $R_2$, m, $R_3$, n and $R_4$ are as defined under formula I, $X_A$ is halogen, and $B_1$ is a five-membered aromatic ring system which contains 1 to 4 nitrogen atoms, wherein the ring system is bound via a nitrogen atom, and wherein the ring system may in turn be substituted once or more than once by $R_7$, each $R_7$ independently is as defined under formula I, may be obtained by reacting the compound of formula III with a compound of formula IV, in which $B_1$ is a five-membered aromatic ring system which contains 1 to 4 nitrogen atoms, wherein the ring system is bound to the hydrogen marked with an asterisk via a nitrogen atom, and wherein the ring system may be substituted once or more than once by $R_7$, each $R_7$ independently is as defined under formula I, in the presence of a suitable solvent, e.g. 1,2-dichloroethane.

Step 1.5: A compound of formula Ia, in which A, $R_2$, m, $R_3$, n and $R_4$ are as defined under formula I, $R_1$ is $C_{1-6}$alkyl; $C_{1-6}$halogenalkyl; $C_{1-6}$cyanoalkyl; $C_{1-6}$-carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$-aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and wherein the ring system may in turn be substituted once or more than once by $R_6$, each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo; and $B_1$ is a five-membered aromatic ring system which contains 1 to 4 nitrogen atoms, wherein the ring system is bound via a nitrogen atom, and wherein the ring system may in turn be substituted once or more than once by $R_7$, each $R_7$ independently is as defined under formula I, may be obtained by reacting the compound of formula Ib with a compound of formula II, in which $R_1$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino- $C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo, in the presence of a catalyst, e.g. Pd(PPh)$_3$, in the presence of a suitable base, e.g. Na$_2$CO$_3$, in the presence of a suitable solvent, e.g. 1,2-dimethoxyethane.

In a further aspect, the invention also provides a process for the production of compounds of the formula Ia. Said compounds are obtainable according to the following process as described in scheme 2:

wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo, may be obtained by reacting a compound of formula V, in which A, $R_2$, m, $R_3$, n and $R_4$ are as defined under formula I, and $X_A$ is halogen, with a compound of formula II, in which $R_1$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl;

Scheme 2:

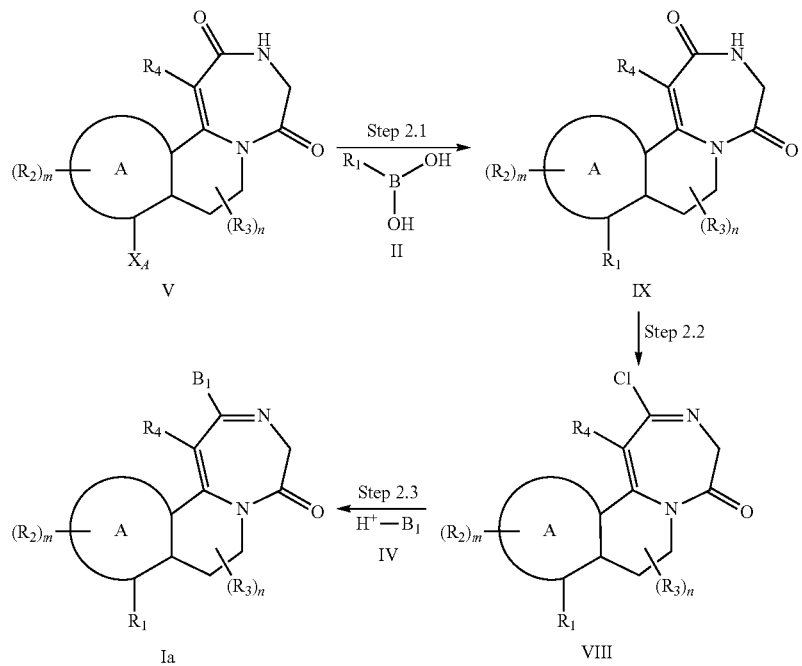

Step 2.1: A compound of formula IX, in which
A, $R_2$, m, $R_3$, n and $R_4$ are as defined under formula I, and
$R_1$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo, in the presence of a catalyst, e.g. Pd(PPh)$_3$, in the presence of a suitable base, e.g. Na$_2$CO$_3$, in the presence of a suitable solvent, e.g. 1,2-dimethoxyethane.

Step 2.2: A compound of formula VIII, in which
A, $R_2$, m, $R_3$, n and $R_4$ are as defined under formula I, $X_A$ is halogen, and $R_1$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy- $C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo, may be obtained by chlorinating the compound of formula IX with a chlorinating agent, e.g. $POCl_3$, in the presence of a suitable solvent, e.g. 1,2-dichloroethane.

Step 2.3: A compound of formula Ia, in which

A, $R_2$, m, $R_3$, n and $R_4$ are as defined under formula I, $R_1$ is $C_{1-6}$alkyl; $C_{1-6}$halogenalkyl; $C_{1-6}$cyanoalkyl; $C_{1-6}$-carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo; and $B_1$ is a five-membered aromatic ring system which contains 1 to 4 nitrogen atoms, wherein the ring system is bound via a nitrogen atom, and wherein the ring system may in turn be substituted once or more than once by $R_7$, each $R_7$ independently is as defined under formula I, may be obtained by reacting the compound of formula VIII with a compound of formula IV, in which $B_1$ is a five-membered aromatic ring system which contains 1 to 4 nitrogen atoms, wherein the ring system is bound to the hydrogen marked with an asterisk via a nitrogen atom, and wherein the ring system may be substituted once or more than once by $R_7$, each $R_7$ independently is as defined under formula I, in the presence of a suitable solvent, e.g. 1,2-dichloroethane.

Further compounds of formula I or their precursors may be obtainable from compounds of formula Ia and Ib or their precursors (e.g. compounds of formulae III)—prepared as described according to scheme 1 or scheme 2—by reduction, oxidation and/or other functionalization of resulting compounds and/or by cleavage of any protecting group(s) optionally present, and of recovering the so obtainable compound of the formula I.

Compounds of the formula I can also be prepared by further conventional processes, e.g. as described in the Examples, which processes are further aspects of the invention.

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Starting materials, e.g. compounds of the formulae VII, IV and II are known or may be prepared according to conventional procedures starting from known compounds, for example as described in the Examples.

In a further aspect, the invention also provides a novel compound of formula III

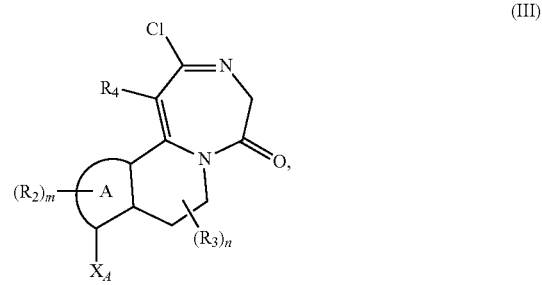

or a salt thereof, wherein A, $R_2$, m, $R_3$, n and $R_4$ are as defined under formula I, and $X_A$ is halogen.

In a further aspect, the invention also provides a novel compound of formula V

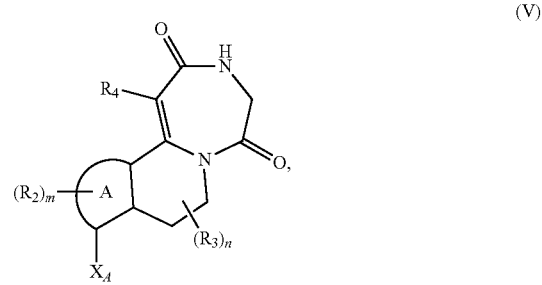

or a salt thereof, wherein A, $R_2$, m, $R_3$, n and $R_4$ are as defined under formula I, and $X_A$ is halogen.

In a further aspect, the invention also provides a novel compound of formula VI

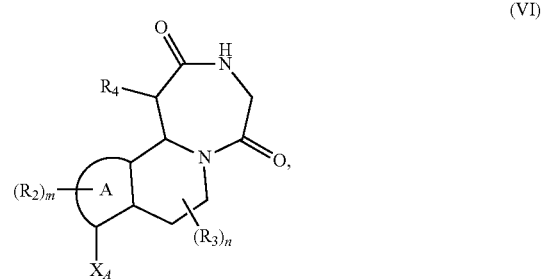

or a salt thereof, wherein A, $R_2$, m, $R_3$, n and $R_4$ are as defined under formula I, and $X_A$ is halogen.

In a further aspect, the invention also provides a novel compound of formula VIII

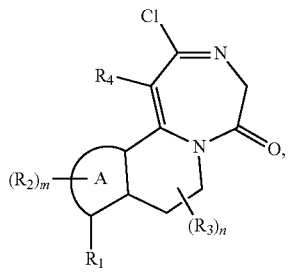

(VIII)

or a salt thereof, wherein A, $R_2$, m, $R_3$, n and $R_4$ are as defined under formula I, and $R_1$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo.

In one embodiment, the invention provides a compound of formula VIII, wherein A, $R_2$, m, $R_3$, n and $R_4$ are as defined under formula I, and $R_1$ is —$X_2$—$B_2$, wherein $X_2$ is bond; and $B_2$ is $C_{3-6}$cycloalkyl which may be substituted once or more than once by $R_6$;

or $B_2$ is a five- to six-membered aromatic ring system which may contain from 1 to 4 hetero atoms selected from nitrogen, oxygen and sulfur; wherein the ring system is bound via a carbon atom; and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

In a further aspect, the invention also provides a novel compound of formula IX

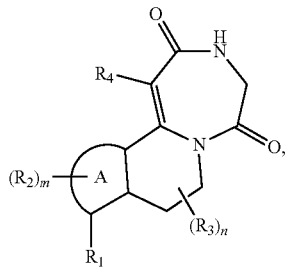

(IX)

or a salt thereof, wherein A, $R_2$, m, $R_3$, n and $R_4$ are as defined under formula I, and $R_1$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl; or a three- to seven-membered monocyclic ring system which may be aromatic, saturated or unsaturated non-aromatic and which may contain from 1 to 4 hetero atoms selected from nitrogen, oxygen and sulfur, wherein the ring system is bound via a carbon atom, and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo.

In one embodiment, the invention provides a compound of formula IX, wherein A, $R_2$, m, $R_3$, n and $R_4$ are as defined under formula I, and $R_1$ is —$X_2$—$B_2$, wherein $X_2$ is bond; and $B_2$ is $C_{3-6}$cycloalkyl which may be substituted once or more than once by $R_6$;

or $B_2$ is a five- to six-membered aromatic ring system which may contain from 1 to 4 hetero atoms selected from nitrogen, oxygen and sulfur; wherein the ring system is bound via a carbon atom; and wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

In another aspect, the invention provides a pharmaceutical composition comprising a compound of the invention and a pharmaceutically acceptable carrier. The pharmaceutical composition can be formulated for particular routes of administration such as oral administration, parenteral administration, and rectal administration, etc. In addition, the pharmaceutical compositions of the invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of formula I or pharmaceutical acceptable salts thereof exhibit valuable pharmacological properties and are therefore useful as pharmaceuticals.

Furthermore, compounds of formula I may be useful for research on mGluR5, e.g. as tool compounds.

In particular, compounds of formula I exhibit an antagonistic action at human metabotropic glutamate receptor 5 (human mGluR5). This can be determined in vitro, for example, at recombinant human mGluR5, using different procedures like, for example, measurement of the inhibition of the agonist induced elevation of intracellular $Ca^{2+}$ concentration in accordance with L. P. Daggett et al., Neuropharm. Vol. 34, pages 871-886 (1995), P. J. Flor et al., J. Neurochem. Vol. 67, pages 58-63 (1996) or by determination to what extent the agonist induced elevation of the inositol phosphate turnover is inhibited as described by T. Knoepfel et al., Eur. J. Pharmacol. Vol. 288, pages 389-392 (1994), L. P. Daggett et al., Neuropharm. Vol. 67, pages 58-63 (1996) and references cited therein. Isolation and expression of human mGluR subtypes are described in U.S. Pat. No. 5,521,297.

Selected compounds of formula (I) show $IC_{50}$ values for the inhibition of the agonist (e.g. glutamate or quisqualate) induced elevation of intracellular Ca2+ concentration or the agonist (e.g. glutamate or quisqualate) induced inositol phosphate turnover, measured in recombinant cells expressing hmGluR5a of about 1 nM to about 10 μM.

Preferred compounds of formula (I) show an inhibition of said inositol phosphate turnover in recombinant cells expressing hmGluR5a of at least 1 μM.

Further preferred compounds of formula (I) show an $IC_{50}$ value of said inositol phosphate turnover in recombinant cells expressing hmGluR5a of at least 500 nM.

Further preferred compounds of formula (I) show an $IC_{50}$ value of said inositol phosphate turnover in recombinant cells expressing hmGluR5a of at least 250 nM.

Further preferred compounds of formula (I) show an $IC_{50}$ value of said inositol phosphate turnover in recombinant cells expressing hmGluR5a of at least 100 nM.

The compounds of the invention may be therefore useful in the prevention, treatment or delay of progression of disorders associated with irregularities of the glutamatergic signal transmission, of the gastro-intestinal and urinary tract and of nervous system disorders mediated full or in part by mGluR5.

Disorders associated with irregularities of the glutamatergic signal transmission are for example epileptogenesis including neuronal protection after status epilepticus, cerebral ischemias, especially acute ischemias, ischemic diseases of the eye, muscle spasms such as local or general spasticity, skin disorders, obesity disorders and, in particular, convulsions or pain.

Disorders of the gastro-intestinal tract include Gastro-Esophageal Reflux Disease (GERD), Functional Gastro-intestinal Disorders and Post-operative Ileus.

Functional Gastro-intestinal Disorders (FGIDs) are defined as chronic or recurrent conditions associated with abdominal symptoms without organic cause using conventional diagnostic measures. A cardinal symptom present in many FGIDs is visceral pain and/or discomfort. FGIDs include functional dyspepsia (FD), functional heartburn (a subset of GERD), irritable bowel syndrome (IBS), functional bloating, functional diarrhea, chronic constipation, functional disturbancies of the biliary tract as well as other conditions according to Gut 1999; Vol. 45 Suppl. II. A disorder of particular interest is GERD.

Post-operative Ileus is defined as failure of aboral passage of intestinal contents due to transient impairment of GI motility following abdominal surgery.

Disorders of the Urinary Tract comprise conditions associated with functional disturbancies and/or discomfort/pain of the urinary tract. Examples of disorders of the urinary tract include but are not limited to incontinence, benign prostatic hyperplasia, prostatitis, detrusor hyperreflexia, outlet obstruction, urinary frequency, nocturia, urinary urgency, overactive bladder (OAB), pelvic hypersensitivity, urge incontinence, urethritis, prostatodynia, cystitis, idiopathic bladder hypersensitivity and the like. OAB is a syndrome characterized by urgency, with or without urinary incontinence, and usually with increased voiding frequency and nocturia.

Nervous system disorders mediated full or in part by mGluR5 are for example acute, traumatic and chronic degenerative processes of the nervous system, such as Parkinson's disease, Parkinson's dyskinesia (e.g. L-dopa induced dyskinesia), dyskinesias induced by neuroleptics (e.g. tardive dyskenisia), Tic disorders, Tourette Syndrome, Restless Leg Syndrome, Periodic Limb Movement Syndromes, senile dementia, Alzheimer's disease, Huntington's chorea, amyotrophic lateral sclerosis, multiple sclerosis and fragile X syndrome, substance-related disorders, psychiatric diseases such as schizophrenia, affective and anxiety disorders, attention deficit disorders and cognitive dysfunction associated with these and other CNS disorders. Substance-related disorders include substance abuse, substance dependence and substance withdrawal disorders, e.g. nicotine withdrawal. Anxiety disorders includes panic disorder, social and specific phobias, anxiety, obsessive compulsive disorder (OCD), post traumatic stress disorder (PTSD) and generalized anxiety disorder (GAD). Affective disorders include depressive (major depression, dysthymia, depressive disorders NOS) and bipolar disorders (bipolar I and II disorders). Cognitive dysfunction associated with these and other CNS disorders include deficits and abnormalities in attention and vigilance, executive functions and memory (for instance working memory and episodic memory). Other disorders which are mediated fully or in part by mGluR5 are pain and itch.

A disorder of particular interest is L-dopa induced dyskinesia in Parkinsons Disease.

The compounds of the invention, especially the compounds as defined in group P under Embodiment 8, are useful in the treatment, prevention or delay of progression of dyskinesias in Parkinsons Disease, especially L-dopa induced dyskinesia in Parkinsons Disease. Dyskinesia in Parkinsons Disease often, although not exclusively, occurs as a side-effect of treatment of Parkinson's Disease with levodopa (L-dopa), a precursor of dopamine. Characteristics of such dyskinesia include motor impairment, e.g. the appearance of slow and uncoordinated involuntary movements, shaking, stiffness and problems walking. Patients treated with L-dopa often have reduced symptoms of Parkinson's Disease but they experience increasing difficulties to remain standing or even sitting. After prolonged use of L-dopa, a majority of patients develop dyskinesia.

Dyskinesia can occur at any time during the cycle of treatment with L-dopa. In one embodiment, the compounds of the invention are for the treatment of dyskinesia which occurs at the time of peak L-dopa plasma concentrations in the patient. In one embodiment, the compounds of the invention are for the treatment of dyskinesia which occurs when the L-dopa plasma concentrations in a patient rise or fall (diphasic dyskinesia).

Dyskinesia can also develop in Parkinson's disease sufferers who do not take L-dopa. In one embodiment, the compounds of the invention are for the treatment of non-L-dopa induced Parkinson's dyskinesia.

Treatment with a compound of the invention, especially with a compound as defined in group P, may comprise a reduction in the characteristics associated with Parkinson's dyskinesia, including for example, although not limited to, a reduction in the scale of involuntary movements, a reduction in the number of involuntary movements, an improvement in the ability to carry out normal tasks, an improved ability to walk, increased period of time between episodes of dyskinesia.

In the case of prophylactic treatment, the compounds of the invention, especially the compounds as defined in group P may be used to delay or prevent the onset of Parkinson's dyskinesia.

For the above-mentioned indications (the conditions and disorders) the appropriate dosage will vary depending upon, for example, the compound employed, the host, the mode of administration and the nature and severity of the condition being treated. However, in general, satisfactory results in animals are indicated to be obtained at a daily dosage of from about 0.01 to about 100 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 1 to about 400 mg, most preferably from about 10 to about 100 mg of the compound of the invention conveniently administered, for example, in divided doses up to four times a day.

For use according to the invention, a compound of the invention, especially a compound as defined in group P, may be administered as single active agent or in combination with other active agents, in any usual manner, e.g. orally, for example in the form of tablets or capsules, or parenterally, for example in the form of injection solutions or suspensions. A combination comprising a compound of the invention and another active agent will be referred to as "combination of the invention".

In the case of Parkinson's dyskinesia induced by L-dopa, the compound of the invention, especially being a compound as defined in group P, will be combined with L-dopa and optionally with at least one active agent selected from the group consisting of a dopa decarboxylase inhibitor, a catechol-O-methyl transferase inhibitor, a dopamine agonist, a monoamine oxidase-B inhibitor, an adrenergic drug, a drug for obstructed airway disorders, a beta blocking agent, an alpha-adrenoreceptor antagonist, an angiotensin II antagonist, an anticholinergic, an anticholinesterase, an antidepressant, an anti-inflammatory agent, an anti-rheumatic agent, an antimigraine agent, an anxiolytic, a barbiturate, a barbiturate derivate, a belladonna alkaloid, a tertiary amine and a benzothiazepine derivative.

Dopa decarboxylase inhibitors are, for example, carbidopa or benserazide. Catechol-O-methyl transferase inhibitors are, for example, tolcapone or entacapone. Dopamine agonists are, for example, bromocriptine, pergolide, pramipexole, ropinirole, cabergoline, apomorphine or lisuride.

Monoamine oxidase-B inhibitors are, for example, selegiline, rasagiline.

Adrenergics and/or drugs for obstructed airway disorders are, for example, Budesonide with formoterol fumarate, Combivent, Sertide mite or Salbutamol.

Beta blocking agents are, for example, Acebutolol, Acebutolol hydrochloride, Atenolol, Betaxolol, Betaxolol hydrochloride, Bisoprolol, Bisoprolol fumarate, Bisoprolol hemifumarate, Carvedilol, Cosopt, Levobunolol hydrochloride, Metoprolol, Metoprolol succinate, Metoprolol tartrate, Propranolol, Propranolol hydrochloride, Sotalol, Sotalol hydrochloride, Tenoretic, Timolol, Timolol maleate or Timpilo.

Alpha-adrenoreceptor antagonists are, for example, Alfuzosin, Alfuzosin hydrochloride, Doxazosin, Doxazosin mesilate, Tamsulosin, Tamsulosin hydrochloride, Terazosin or Terazosin hydrochloride.

Angiotensin II antagonists are, for example, Candesartan cilexetil, Irbesartan, Losartan, Losartan potassium, Olmesartan medoxomil, Telmisartan or Valsartan.

Combinations of Angiotensin II antagonists are, for example, Blopress plus, Co-diovan, Hyzaar or Karvea hct.

Anticholinergics are, for example, Ibratropium bromide or Tiotropium bromide.

Anticholinesterases are, for example, Donepezil hydrochloride.

Antidepressants are, for example, Amitriptyline, Amitriptyline hydrochloride, Bupropion hydrochloride, Citalopram, Citalopram hydrobromide, Cyclobenzaprine, Cyclobenzaprine hydrochloride, Escitalopram, Escitalopram oxalate, Fluoxetine, Fluvoxamine maleate, Imipramine hydrochloride, Mirtazapine, Paroxetine, Paroxetine hydrochloride, Sertraline, Sertraline hydrochloride, Trazodone, Trazodone hydrochloride, Venlafaxine or Venlafaxine hydrochloride.

Antiepileptics are, for example, Carbamazepine, Clonazepam, Gabapentin, Phenobarbital, Phenyloin, Pregabalin or Topiramate.

Anti-inflammatory and/or anti-rheumatic agents are, for example, Betamethasone, Betamethasone valerate, Cortisone, Cortisone acetate, Desonide, Diclofenac, Diclofenac sodium, Flurbiprofen, Hydrocortisone, Indometacin, Salicylic acid, Triamcinolone acetonide, Aceclofenac, Aflexa, Arthrotec, Carbager-plus, Celecoxib, Glucosamine, Glucosamine sulfate, Glucosamine with chondroitin, Ibuprofen, Ketoprofen, Meloxicam, Naproxen, Naproxen sodium, Nimesulide, Osteo bi-flex or Sulindac.

Antimigraine preparations are, for example, Naratriptan hydrochloride, Rizatriptan or Sumatriptan.

Anxiolytics are, for example, Alprazolam, Bromazepam, Clonazepam, Clorazepate dipotassium, Diazepam, Ethyl loflazepate, Hydroxyzine, Hydroxyzine hydrochloride, Lorazepam, Oxazepam or Tetrazepam.

Barbiturates and/or barbiturate derivates are, for example, Phenobarbital or Phenobarbital.

Belladonna alkaloids and/or tertiary amines are, for example, Hyoscyamine sulfate Benzodiazepine derivatives and related drugs are, for example, Alprazolam, Bromazepam, Clonazepam, Clorazepate dipotassium, Diazepam, Ethyl loflazepate, Lorazepam, Lormetazepam, Oxazepam, Temazepam, Tetrazepam, Triazolam, Eszopiclone, Zolpidem, Zolpidem tartrate or Zopiclone.

Benzothiazepine derivatives are, for example, Diltiazem or Diltriazem hydrochloride.

In one embodiment of the invention a specific combination of the invention is used. Said combination comprises:
A compound of the invention, especially a compound as defined in group P; and L-dopa.

In one embodiment of the invention a specific combination of the invention is used. Said combination comprises:
A compound of the invention, especially a compound as defined in group P;
L-dopa; and
at least one active agent selected from the group consisting of: carbidopa, benserazide, tolcapone, entacapone, bromocriptine, pergolide, pramipexole, ropinirole, cabergoline, apomorphine, lisuride, selegiline, rasagiline, Budesonide with formoterol fumarate, Combivent, Sertide mite, Salbutamol, Acebutolol, Acebutolol hydrochloride, Atenolol, Betaxolol, Betaxolol hydrochloride, Bisoprolol, Bisoprolol fumarate, Bisoprolol hemifumarate, Carvedilol, Cosopt, Levobunolol hydrochloride, Metoprolol, Metoprolol succinate, Metoprolol tartrate, Propranolol, Propranolol hydrochloride, Sotalol, Sotalol hydrochloride, Tenoretic, Timolol, Timolol maleate, Timpilo, Alfuzosin, Alfuzosin hydrochloride, Doxazosin, Doxazosin mesilate, Tamsulosin, Tamsulosin hydrochloride, Terazosin, Terazosin hydrochloride, Candesartan cilexetil, Irbesartan, Losartan, Losartan potassium, Olmesartan medoxomil, Telmisartan, Valsartan, Blopress plus, Co-diovan, Hyzaar, Karvea hct, Ibratropium bromide, Tiotropium bromide, Donepezil hydrochloride, Amitriptyline, Amitriptyline hydrochloride, Bupropion hydrochloride, Citalopram, Citalopram hydrobromide, Cyclobenzaprine, Cyclobenzaprine hydrochloride, Escitalopram, Escitalopram oxalate, Fluoxetine, Fluvoxamine maleate, Imipramine hydrochloride, Mirtazapine, Paroxetine, Paroxetine hydrochloride, Sertraline, Sertraline hydrochloride, Trazodone, Trazodone hydrochloride, Venlafaxine, Venlafaxine hydrochloride, Carbamazepine, Clonazepam, Gabapentin, Phenobarbital, Phenyloin, Pregabalin, Topiramate, Betamethasone, Betamethasone valerate, Cortisone, Cortisone acetate, Desonide, Diclofenac, Diclofenac sodium, Flurbiprofen, Hydrocortisone, Indometacin, Salicylic acid, Triamcinolone acetonide, Aceclofenac, Aflexa, Arthrotec, Carbager-plus, Celecoxib, Glucosamine, Glucosamine sulfate, Glucosamine with chondroitin, Ibuprofen, Ketoprofen, Meloxicam, Naproxen, Naproxen sodium, Nimesulide, Osteo bi-flex or Sulindac. Antimigraine preparations are, for example, Naratriptan hydrochloride, Rizatriptan, Sumatriptan, Alprazolam, Bromazepam, Clonazepam, Clorazepate dipotassium, Diazepam, Ethyl loflazepate, Hydroxyzine, Hydroxyzine hydrochloride, Lorazepam, Oxazepam, Tetrazepam, Phenobarbital, Phenobarbital, Hyoscyamine sulfate, Alprazolam, Bromazepam, Clonazepam, Clorazepate dipotassium, Diazepam, Ethyl loflazepate, Lorazepam, Lormetazepam, Oxazepam, Temazepam, Tetrazepam, Triazolam, Eszopiclone, Zolpidem, Zolpidem tartrate, Zopiclone, Diltiazem and Diltriazem hydrochloride.

An example of a combination is a compound as defined in group P, L-dopa, and the dopa decarboxylase inhibitor carbidopa.

Another example of a combination is a compound as defined in group P, L-dopa, and entacapone.

Another example of a combination is a compound as defined in group P, L-dopa, entacapone, and carbidopa; an example of such a combination is a combination of a compound as defined in group P and Stalevo®.

An example of a combination is the first compound as defined in group P, i.e. 9-methoxy-2-(3-methoxyphenyl)-7,8-dihydro-[1,4]diazepino[7,1-a]isoquinolin-5(4H)-one, L-dopa, and the dopa decarboxylase inhibitor carbidopa.

Another example of a combination is the first compound as defined in group P, i.e. 9-methoxy-2-(3-methoxyphenyl)-7,8-dihydro-[1,4]diazepino[7,1-a]isoquinolin-5(4H)-one, L-dopa, and entacapone.

Another example of a combination is the first compound as defined in group P, i.e. 9-methoxy-2-(3-methoxyphenyl)-7,8-dihydro-[1,4]diazepino[7,1-a]isoquinolin-5(4H)-one, L-dopa, entacapone, and carbidopa; an example of such a combination is a combination of the first compound as defined in group P, i.e. 9-methoxy-2-(3-methoxyphenyl)-7,8-dihydro-[1,4]diazepino[7,1-a]isoquinolin-5(4H)-one, and Stalevo®.

The agents of the present invention may also be useful for treating or preventing migraine.

The agents of the present invention may also be useful for inflammatory diseases, such as pain, inflammation and/or oedema consequential to trauma, for example associated with burns, sprains, fractures or the like, inflammatory airways diseases, such as COPD, asthma, rhinitis, inflammatory bowel disease, cystitis, uveitis, inflammatory skin disorders, such as psoriasis or eczema, rheumatoid arthritis, use as a smooth muscle relaxant, for example for the treatment of spasms of the gastro-intestinal tract or uterus, for example in the therapy of Crohn's disease, ulcerative colitis or pancreatitis, or for the treatment of muscle spasticity and tremor, for example in multiple sclerosis, teno-synovitis, gout, ocular disorders, for example glaucoma, cough.

The agents of the present invention may also be useful for treating cognitive impairment and/or attention deficit disorder.

Cognitive dysfunction include deficits and abnormalities in attention and vigilance, executive functions and memory (for instance working memory and episodic memory). Other disorders relating to cognitive dysfunction include sleep related breathing disorders (SRBD), behavioral impairments, information processing deficits and age-related disorders.

Further examples falling of cognitive impairment and/or attention deficit disorders include: Attention-deficit hyperactivity disorder (ADHD), childhood ADHD, adult ADHD, excess daytime somnolence, sleep apnea, shift-worker's sleep-wake cycle disruption, traumatic brain injury, neurodegenerative disorders with associated memory and cognitive problems (such as Alzheimer's disease, Lewy body dementia, senile dementia, vascular dementia, Parkinson's disease), chronic fatigue syndrome, fatigue associated with sleep deprivation or prolonged wakefulness, age-related decline in memory and cognitive function (such as mild cognitive impairment), cognitive impairment associated with mood disorders (such as depression) and anxiety, schizophrenia, day time sleepiness associated with narcolepsy.

Furthermore, the agents of the present invention may provide treatment for or improve of the cognitive enhancement of a subject. The term "cognitive enhancement" includes, but is not limited to, cognition enhancement, vigilance, counteracting effects of fatigue, enhancing alertness, attention, memory (working, episodic), learning ability, reaction time, cognitive performance enhancement, excess daytime somnolence, reversal of information processing deficits, improvement of disorganization, i.e. improving organizational skills/level of organizational ability.

The agents of the present invention may also be useful for treating pervasive developmental disorders (PDD). PDD is a group of diseases characterized by a delay in the development of socialization and communications skills. The following diseases are part of the PDD: Autism, Asperger's syndrome, childhood disintegrative disorder, and Rett's syndrome, and fragile X. The main symptomatology are: Autistic-like behavior, repetitive behavior (OCD), in some cases irritability, and ADHS. Fragile X Syndrome have two different genotype-phenotype: Full mutation (mental retardation, ADHD, autism, and anxiety), partial mutation (tremor-ataxia, parkinsonism, anxiety). A disorder of particular interest is fragile X syndrome.

The compounds of the invention may be useful for the prevention of the above-mentioned conditions and disorders.

The compounds of the invention may be useful for the treatment of the above-mentioned conditions and disorders.

The compounds of the invention may be useful for the delay of progression of the above-mentioned conditions and disorders.

Compounds of the invention may be especially useful in the treatment of an indication selected from: L-dopa induced dyskinesias in Parkinsons Disease and fragile X syndrome.

Thus, as a further embodiment, the invention provides the use of a compound of formula (I) or a pharmaceutically acceptable salt thereof as a medicament.

As a further embodiment, the invention provides the use of a compound of formula (I) or a pharmaceutically acceptable salt thereof in therapy.

In a further embodiment, the therapy is selected from a disease which is ameliorated by inhibition of mGluR5. In another embodiment, the disease is selected from the aforementioned list, e.g. L-dopa induced dyskinesias in Parkinsons Disease and fragile X syndrome.

In another embodiment, the invention provides a method of treating a disease which is ameliorated by inhibition of mGluR5 comprising administration of a therapeutically acceptable amount of a compound of formula (I) or a pharmaceutically acceptable salt thereof. In a further embodiment, the disease is selected from the afore-mentioned list, suitably L-dopa induced dyskinesias in Parkinsons Disease and fragile X syndrome.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by mGluR5, or (ii) associated with mGluR5 activity, or (iii) characterized by abnormal activity of mGluR5; or (2) reducing or inhibiting the activity of mGluR5; or (3) reducing or inhibiting the expression of mGluR5. In another non-limiting embodiment, the term "a therapeutically effective amount" refers to the amount of the compound of the invention that, when administered to a cell, or a tissue, or a non-cellular biological material, or a medium, is effective to at least partially reducing or inhibiting the activity of mGluR5; or at least partially reducing or inhibiting the expression of mGluR5.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound of the invention can be assessed by in vitro & in vivo methods described herein.

The compound of the invention may be administered either simultaneously with, or before or after, at least one other therapeutic agent. The compound of the invention may be administered separately, by the same or different route of administration, or together in the same pharmaceutical composition.

The following Examples illustrate the invention, but do not limit it.

EXPERIMENTAL PART

General:

For reactions run in a microwave reactor, the model Initiator® from Biotage, heating with high-frequency microwaves of 2.45 GHz, was used.

Analytical UPLC/MS conditions (%=percent by volume): Waters Acquity UPLC system, column Acquity HSS-T3 1.8 µm; 2.1×50 mm; T=50° C.; gradient: A, water+0.05% HCOOH+0.05% ammonium acetate; B, acetonitrile+0.4% HCOOH; from A/B 98/2 to 2/98 in 1.4 min+0.57 min isocratic; flow rate 1.2 mL/min.

1H NMR spectra were acquired on a Bruker spectrometer (360, 400 or 600 MHz). Chemical shifts are given in parts per million (ppm) relative to the residual solvent peak.

Abbreviations:

AcOEt ethyl acetate

AcOH acetic acid cHex cyclohexane

CO carbon monoxide

DCM dichloromethane

DMA dimethylacetamide

DME 1,2-dimethoxyethane

DMF dimethylformamide

DMF-DMA N,N-Dimethylformamide dimethyl acetal dppf 1,1'-bis(diphenylphosphino)ferrocene eq equivalent h hour HATU O-(7-azabenzotriazol-1-yl)-N,N,N',N'-tetramethyluronium hexafluorophosphate MeOH methanol mg milligram min minute mL milliliter MPLC medium pressure chromatography MS mass spectrometry NMM N-methyl morpholine NMP N-methylpyrrolidone PEPPSI-iPr [1,3-Bis(2,6-Diisopropylphenyl)imidazol-2-ylidene](3-chloropyridyl)palladium(II) dichloride rt retention time RT room temperature T3P propylphosphonic anhydride solution TBME tert-butylmethylether TBTU O-(benzotriazol-1-yl)-N,N,N'N'-tetramethyluronium tetrafluoroborate TEA triethylamine TFA trifluoroacetic acid THF tetrahydrofuran UPLC ultra pressure liquid chromatography

Preparations 1-27

Preparation 1

5-iodo-1-methyl-3,4-dihydroisoquinoline

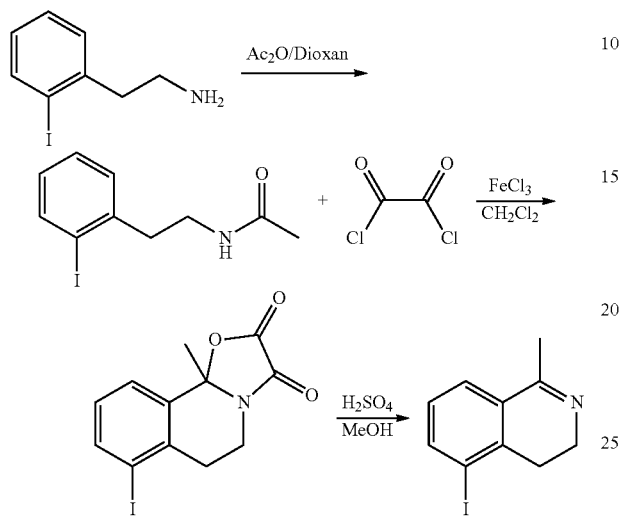

Step 1. N-(2-iodophenethyl)acetamide. A solution of 2-(2-iodophenyl)ethanamine (13.5 g, 54.6 mmol) and Ac$_2$O (10.3 mL, 109 mmol) in 1,4-dioxane (200 mL) was heated to 100° C. for 45 min. The reaction was then allowed to cool to RT and concentrated in vacuo. The resulting residue was taken up in DCM and washed with a saturated aq. solution of NaHCO$_3$— gas formation! The organic phase was separated, dried over Na$_2$SO$_4$, filtered and concentrated in vacuo to give the title compound as a yellow oil (16.2 g) which was used as it is in the next step. UPLC-MS: MS 290.3 (M+H$^+$); UPLC rt 0.96 min.

Step 2. 7-iodo-10b-methyl-5,6-dihydro-2H-oxazolo[2,3-a]isoquinoline-2,3(10bH)-dione. A solution of N-(2-iodophenethyl)acetamide (16.0 g, 55.3 mmol) in DCM (600 mL) under N2, was treated dropwise with (COCl)$_2$ (5.33 mL, 60.9 mmol). The reaction was stirred at RT for 45 min and then cooled to 0° C. FeCl$_3$ (10.8 g, 66.4 mmol) was then added and the mixture was allowed to slowly warm to RT and stirred at RT for 18 h. An aq. solution of 2N HCl (50 mL) was added and the mixture was stirred for 2 h. The organic phase was separated, dried over Na$_2$SO$_4$, filtered and concentrated in vacuo to provide the title compound as a brown solid (20.8 g) that was used as it is in the next step. UPLC-MS: MS 344.3 (M+H$^+$); UPLC rt 1.10 min.

Step 3. 5-iodo-1-methyl-3,4-dihydroisoquinoline. A suspension of 7-iodo-10b-methyl-5,6-dihydro-2H-oxazolo[2,3-a]isoquinoline-2,3(10bH)-dione (20.7 g; 60.3 mmol) in MeOH/H$_2$SO$_4$ (19:1, 750 mL) was heated to reflux for 5 h. The mixture was cooled to RT and concentrated in vacuo. The resulting residue was taken up in H2O (200 mL) and extracted with AcOEt. The org. phases was separated and extracted twice with a 1 N aqueous HCl solution. The aqueous phases were combined, cooled with ice and rendered basic with a concentrated aqueous solution of ammonia. This mixture was extracted with DCM, and the combined org. layers were dried over Na$_2$SO$_4$, filtered and concentrated in vacuo. The crude product was purified by flash chromatography (SiO2, DCM to DCM/MeOH 95:5) to give the title compound as a brown solid (8.6 g). UPLC-MS: MS 272.3 (M+H$^+$); UPLC rt 0.606 min. $^1$H NMR (400 MHz, CHLOROFORM-d): δ ppm 2.37 (s, 3 H); 2.68-2.78 (m, 2 H); 3.68 (td, J=7.62, 1.56 Hz, 2 H); 7.04 (t, J=7.82 Hz, 1 H); 7.46 (d, J=7.43 Hz, 1 H); 7.84 (d, J=7.82 Hz, 1 H).

Following the procedure described above for Preparation 1 and substituting the appropriate reagents, starting materials and purification methods known to those skilled in the art, the following building block of the present invention were prepared:

Preparation 2

5-fluoro-1-methyl-3,4-dihydroisoquinoline

MS 164.0 (M+H$^+$). UPLC (2 min) rt 0.616 min.

Preparation 3

5-chloro-1-methyl-3,4-dihydroisoquinoline

UPLC-MS: MS 180.1 (M+H$^+$); UPLC rt 0.25 min.

Preparation 4

5-bromo-1-methyl-3,4-dihydroisoquinoline

MS 224.0 (M+H$^+$). UPLC (2 min) rt 0.743 min.

Preparation 5

1-methyl-5-(trifluoromethyl)-3,4-dihydroisoquinoline

MS 214.0 (M+H$^+$). UPLC (2 min) rt 0.805 min.

Preparation 6

5-methoxy-1,3-dimethyl-3,4-dihydroisoquinoline

UPLC-MS: MS 190.0 (M+H$^+$); UPLC rt 0.58 min.

Preparation 7

6-chloro-5-methoxy-1-methyl-3,4-dihydroisoquinoline

UPLC-MS: MS 210.0 (M+H$^+$); UPLC rt 0.41 min.

Preparation 8

7-chloro-5-methoxy-1-methyl-3,4-dihydroisoquinoline

UPLC-MS: MS 210.0 (M+H$^+$); UPLC rt 0.59 min.

The following examples provide synthetic route to starting material useful for the preparation of compounds described in this invention:

Preparation 9

2-(3-chloro-2-methoxyphenyl)ethanamine

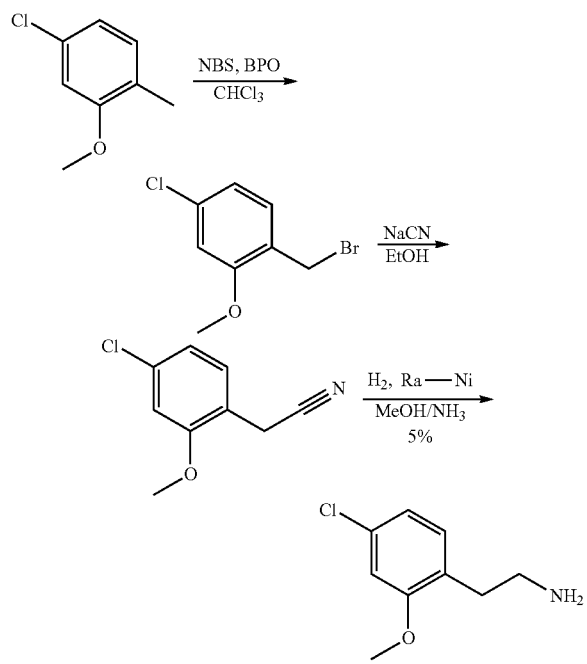

Step 1. 1-(bromomethyl)-3-chloro-2-methoxybenzene. A mixture of 4-chloro-2-methoxy-1-methylbenzene (26.5 g, 169 mmol), NBS (33.1 g, 186 mmol) and benzoyl peroxide (200 mg, 0.826 mmol) in CHCl₃ was heated to reflux for 24 h. The reaction was allowed to cool to RT and then concentrated in vacuo. The residue was stirred with petroleum ether and the resulting suspension was filtered off and the filtrate was concentrated in vacuo to give the title compound (30.9 g) as brown oil, which was used as it is in the next step. UPLC (2 min) rt 1.708 min.

Step 2. 2-(3-chloro-2-methoxyphenyl)acetonitrile. A solution of 1-(bromomethyl)-3-chloro-2-methoxybenzene (30.8 g, 131 mmol) in EtOH (150 mL) at RT and under $N_2$ was treated with an aq. solution of NaCN (12.8 g, 262 mmol in 50 mL $H_2O$) and the mixture was heated to 100° C. for 3 h. The reaction was then cooled to RT and taken up in $Et_2O$. The mixture was washed with $H_2O$ and brine, and the aq. phase was extracted again with $Et_2O$. The combined org. layers dried over $Na_2SO_4$, filtered and concentrated in vacuo. The crude product was purified by flash chromatography ($SiO_2$, Hexane to Hexane/AcOEt 4:1) to afford the title compound (15.8 g) as brown oil. UPLC (2 min) rt 1.383.

Step 3. 2-(3-chloro-2-methoxyphenyl)ethanamine. A suspension of 2-(3-chloro-2-methoxyphenyl)acetonitrile (15.8 g, 87 mmol) and Ra—Ni (87 mmol) in MeOH/NH₃ (96:4, 200 mL) was stirred at RT under an atmosphere of $H_2$ for 33 h. The mixture was then filtered and the filtrate was concentrated in vacuo to give the title compound (15.8 g) as a brownish liquid that was used as it is in the next step. UPLC-MS: MS 186.0 (M+H⁺); UPLC rt 0.43 min.

Following the procedure described above for 2-(3-chloro-2-methoxyphenyl)ethanamine and substituting the appropriate reagents, starting materials and purification methods known to those skilled in the art, the following intermediate was prepared:

Preparation 10

2-(4-chloro-2-methoxyphenyl)ethanamine

UPLC-MS: MS 186.0 (M+H⁺); UPLC rt 0.62 min.

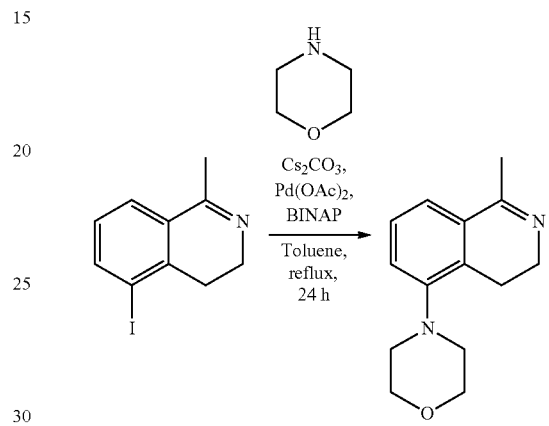

Preparation 11

4-(1-methyl-3,4-dihydroisoquinolin-5-yl)morpholine

A flask under Ar was charged with 5-iodo-1-methyl-3,4-dihydroisoquinoline (8.0 g, 29.5 mmol), morpholine (3.1 g, 35.4 mmol) and $Cs_2CO_3$ (13.5 g, 41.3 mmol) and a mixture of $Pd(OAc)_2$ (0.33 g, 1.48 mmol) and BINAP (0.92 g, 1.48 mmol) in toluene (150 mL) was added. The reaction was stirred at RT for 5 min and then heated to reflux for 24 h. The reaction was allowed to cool to RT, and then filtered over celite. The filtrate was concentrated in vacuo and the crude product was purified by flash chromatography ($SiO_2$, DCM to DCM/MeOH 9:1) to provide the title compound (3.05 g). UPLC-MS: MS 231.1 (M+H⁺); UPLC rt 0.40 min.

Preparation 12

2-(1-methyl-3,4-dihydroisoquinolin-5-yl)propan-2-ol

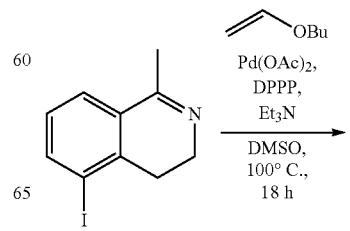

-continued

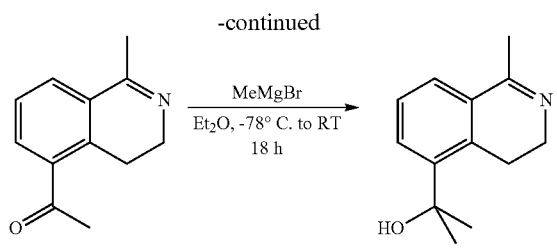

Step 1. 1-(1-methyl-3,4-dihydroisoquinolin-5-yl)ethanone. A solution of 5-iodo-1-methyl-3,4-dihydroisoquinoline (2.0 g, 7.38 mmol), Pd(OAc)$_2$ (41 mg, 0.184 mmol) and DPPP (85 mg, 0.207 mmol) in dry DMSO (15 mL) was degassed, and butylvinyl ether (4.80 mL, 36.9 mmol) and Et$_3$N (1.24 mL, 8.85 mmol) were then added in succession. The reaction was heated to 100° C. for 18 h, and then allowed to cool to RT. The mixture was diluted with Et$_2$O and washed with H$_2$O. The organic phase was then dried over Na$_2$SO$_4$, filtered and concentrated in vacuo to give a brown oil that was taken up in THF (50 mL) and treated with a 2N aq. solution of HCl (25 mL). The mixture was stirred at RT for 4 h, and then diluted with AcOEt and washed with H$_2$O. The aq. phase was then neutralized and rendered basic by adding Na$_2$CO$_3$, and then extracted with AcOEt. The combined org. layers were then dried over Na$_2$SO$_4$, filtered and concentrated in vacuo. The crude product was purified by flash chromatography (SiO$_2$, DCM to DCM/MeOH 9:1) to provide the title compound (1.06 g) as a brown oil, which was used as it is in the next step. UPLC-MS: MS 188.0 (M+H$^+$); UPLC rt 0.45 min.

Step 2. 2-(1-methyl-3,4-dihydroisoquinolin-5-yl)propan-2-ol. A solution of 1-(1-methyl-3,4-dihydroisoquinolin-5-yl)ethanone (800 mg, 4.27 mmol) in dry Et$_2$O (10 mL) under Ar was cooled to −78° C., and then treated dropwise with a 3M solution of MeMgBr (1.42 mL, 4.27 mmol). The mixture was stirred at −78° C. for another 30 min. It was then allowed to warm to RT and stirred for 18 h at RT. The reaction was then diluted with AcOEt and washed with H$_2$O. The organic phase was dried over Na$_2$SO$_4$, filtered and concentrated in vacuo. Purification by flash chromatography (SiO$_2$, DCM to DCM/MeOH 9:1) afforded 2-(1-methyl-3,4-dihydroisoquinolin-5-yl)propan-2-ol (166 mg) as a brown oil. UPLC-MS: MS 204.2 (M+H$^+$); UPLC rt 0.47 min.

Preparation 13

1-methyl-5-(pyridin-4-yl)-3,4-dihydroisoquinoline

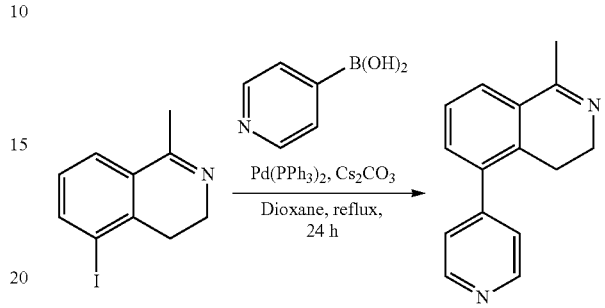

A mixture of 5-iodo-1-methyl-3,4-dihydroisoquinoline (3.0 g, 11.1 mmol), pyridin-4-ylboronic acid (2.04 g, 16.6 mmol), Pd(PPh$_3$)$_2$Cl$_2$ (3.88 g, 5.53 mmol) and Cs$_2$CO$_3$ (10.8 g, 33.2 mmol) in 1,4-dioxane (45 mL) was heated to reflux for 24 h. The mixture was allowed to cool to RT, and then filtered. The filter cake was washed with AcOEt, and the filtrate was then concentrated in vacuo. The crude product was purified by flash chromatography (SiO$_2$, DCM to DCM/MeOH 9:1) to afford the title compound (1.82 g) as a grey solid. UPLC-MS: MS 223.0 (M+H$^+$); UPLC rt 0.38 min.

Preparation 14

9-iodo-3,4,7,8-tetrahydro-[1,4]diazepino[7,1-a]isoquinoline-2,5-dione

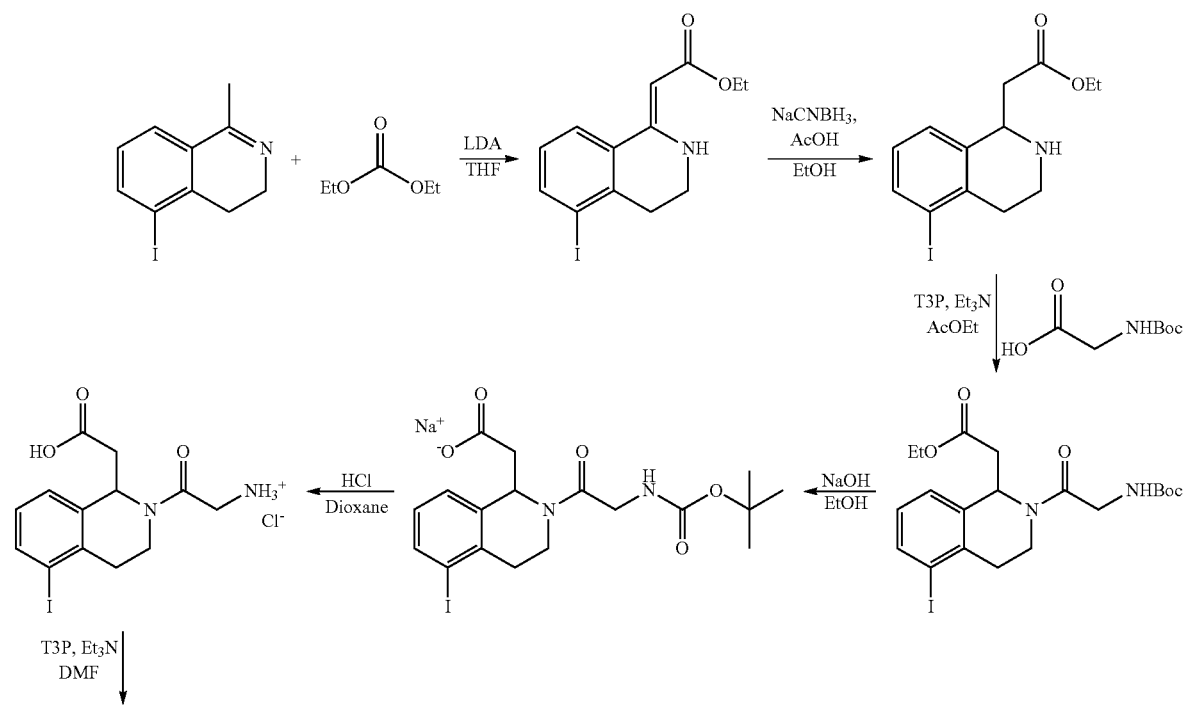

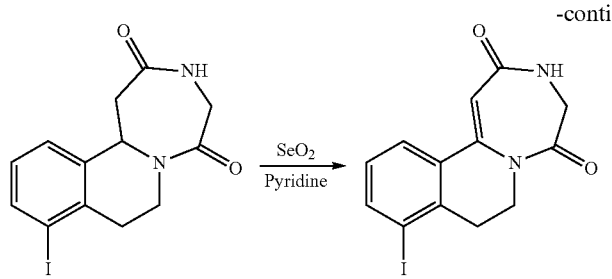

Step 1. (Z)-ethyl 2-(5-iodo-3,4-dihydroisoquinolin-1(2H)-ylidene)acetate. To a yellow cooled solution of 5-iodo-1-methyl-3,4-dihydroisoquinoline (30.1 g, 111 mmol) in dry THF (900 mL) was added dropwise a solution of LDA (2M in THF, 111 mL, 222 mmol) at −78° C. The resulting brown solution was stirred for at −78° C. for 45 min and a solution of diethyl carbonate (14 mL, 116 mmol) in THF (80 mL) was then added dropwise. The mixture was stirred at −78° C. for another 45 min, and then poured onto brine. The resulting yellow suspension was filtered and the filter cake was washed with AcOEt. The filtrate was extracted with AcOEt, and the combined org. phases were dried over $Na_2SO_4$, filtered and concentrated in vacuo to give the title compound (40.0 g) as a brown oil that was used as it is in the next step. UPLC-MS: MS 344.1 (M+H$^+$); UPLC rt 1.28 min.

Step 2. ethyl 2-(5-iodo-1,2,3,4-tetrahydroisoquinolin-1-yl)acetate. A solution of (Z)-ethyl 2-(5-iodo-3,4-dihydroisoquinolin-1(2H)-ylidene)acetate (40.0 g, 116 mmol) in dry EtOH (430 mL) was treated with AcOH (33 mL) and $NaBH_3CN$ (9.63 g, 146 mmol) portionwise at RT under Ar. The mixture was stirred at RT for 1.5 h, and another load of $NaBH_3CN$ (3.85 g, 58 mmol) was then added portionwise. The mixture was stirred for another 1.5 h, and then poured onto a saturated aq. solution of $NaHCO_3$. The pH was adjusted to 8, and the mixture was then extracted with AcOEt. The combined org. layers were dried over $Na_2SO_4$, filtered and concentrated in vacuo to give the title compound (39.5 g) as an orange oil that was used as it is in the next step. UPLC-MS: MS 346.1 (M+H$^+$); UPLC rt 0.66 min.

Step 3. ethyl 2-(2-(2-((tert-butoxycarbonyl)amino)acetyl)-5-iodo-1,2,3,4-tetrahydroisoquinolin-1-yl)acetate. A mixture of ethyl 2-(5-iodo-1,2,3,4-tetrahydroisoquinolin-1-yl)acetate (39.5 g, 114 mmol), Boc-Gly-OH (20.1 g, 114 mmol) and $Et_3N$ (32 mL, 230 mmol) in AcOEt (570 mL) was treated with a solution of T3P in DMF (80 mL, 137 mmol)—exothermic. The mixture was stirred at RT for 15 h and $H_2O$ (200 mL) was then added. The pH was adjusted to 8 by addition of saturated aq. solution of $NaHCO_3$, and the aq. phase was extracted with AcOEt. The combined org. phases were washed with brine, dried over $Na_2SO_4$, filtered and concentrated in vacuo to give the title compound (57.4 g) that was used as it is in the next step. UPLC-MS: MS 503.2 (M+H$^+$); UPLC rt 1.20 min.

Step 4. sodium 2-(2-(2-((tert-butoxycarbonyl)amino)acetyl)-5-iodo-1,2,3,4-tetrahydroisoquinolin-1-yl)acetate. To an orange solution of ethyl 2-(2-(2-((tert-butoxycarbonyl)amino)acetyl)-5-iodo-1,2,3,4-tetrahydroisoquinolin-1-yl)acetate (57.4 mmol, 114 mmol) in EtOH (800 mL) was added an aqueous solution of NaOH (4M, 33 mL, 132 mmol) and the mixture was stirred at RT for 60 h. The mixture was then filtered and the filter cake was washed with $Et_2O$. The filtrate was then concentrated down in vacuo until the formation of another precipitate. The mixture was then filtered again and the filter cake washed with $Et_2O$. The combined filter cakes were then dried in vacuo to give the title compound (49.8 g) as a beige powder that was used as it is in the next step. UPLC-MS: MS 475.2 (M+H$^+$); UPLC rt 1.00 min.

Step 5. 2-(1-(carboxymethyl)-5-iodo-3,4-dihydroisoquinolin-2(1H)-yl)-2-oxoethanaminium chloride. A suspension of sodium 2-(2-(2-((tert-butoxycarbonyl)amino)acetyl)-5-iodo-1,2,3,4-tetrahydroisoquinolin-1-yl)acetate (49.8 g, 100 mmol) in dry dioxane (1 L) was treated with an aqueous solution of HCl (4M, 280 ml, 1.12 mol) and the mixture was stirred at RT for 18 h. The reaction mixture was then concentrated in vacuo to give the title compound (46.1 g) as a beige powder that was used as it is in the next step. UPLC-MS: MS 375.1 (M+H$^+$); UPLC rt 0.60 min.

Step 6. 9-iodo-1,3,4,7,8,12b-hexahydro-[1,4]diazepino[7,1-a]isoquinoline-2,5-dione. A suspension of 2-(1-(carboxymethyl)-5-iodo-3,4-dihydroisoquinolin-2(1H)-yl)-2-oxoethanaminium chloride (46.1 g, 112 mmol) and $Et_3N$ (95 mL, 682 mmol) in dry DMF (1.1 L) was treated with a solution of T3P in DMF (98 mL, 169 mmol) exothermic. The mixture was stirred at RT overnight. The mixture was then concentrated in vacuo and the residue obtained was taken up in AcOEt and diluted with an saturated aq. solution of $NaHCO_3$. The aqueous phase was extracted with AcOEt and the combined org. layers were then washed with brine, dried over $Na_2SO_4$, filtered and concentrated in vacuo to give a brown solid. The crude product obtained was suspended in MeOH and filtered. The filter cake was washed with MeOH and DCM, and then dried in vacuo to give the title compound (12.4 g) as a beige powder that was used as it is in the next step. UPLC-MS: MS 357.1 (M+H$^+$); UPLC rt 0.73 min.

Step 7. 9-iodo-3,4,7,8-tetrahydro-[1,4]diazepino[7,1-a]isoquinoline-2,5-dione. A mixture of 9-iodo-1,3,4,7,8,12b-hexahydro-[1,4]diazepino[7,1-a]isoquinoline-2,5-dione (15.5 g, 43 mmol), $SeO_2$ (9.63 g, 87 mmol) in pyridine (650 mL) was heated to 160° C. for 20 min in a microwave reactor. The mixture was then concentrated in vacuo and the residue obtained was taken up in AcOEt (10 and diluted with $H_2O$ (1 L). The org. layer was separated and the aqueous layer was extracted with AcOEt. The combined AcOEt phases were then dried over $Na_2SO_4$, filtered and concentrated in vacuo. Purification by flash chromatography ($SiO_2$, Heptane to AcOEt to DCM/MeOH 9:1) gave 7.25 g of beige solid. The aqueous phase was then extracted again with DCM and the combined org. layers were dried over $Na_2SO_4$, filtered and concentrated in vacuo. Purification of the residue obtained by flash chromatography ($SiO_2$, Heptane to AcOEt to AcOEt/MeOH 50:1) gave 1.15 g of brownish solid. The two solids obtained were then combined and crystallize form $Et_2O$ to provide the title compound (8.15 g) as a beige solid. UPLC-MS: MS 355.0 (M+H$^+$); UPLC rt 0.78 min. $^1$H NMR (400 MHz, DMSO-$d_6$) δ ppm 2.83 (t, J=6.06 Hz, 2 H); 3.76 (d, J=5.47 Hz, 4 H); 6.36 (s, 1 H); 7.07 (t, J=7.82 Hz, 1 H); 7.90 (d, J=7.43 Hz, 2 H); 8.28 (br. s., 1 H).

Following the procedure described above for Preparation 14 and substituting the appropriate reagents, starting materials and purification methods known to those skilled in the art, the following intermediates of the present invention were prepared:

Preparation 15

9-chloro-3,4,7,8-tetrahydro-[1,4]diazepino[7,1-a]isoquinoline-2,5-dione

UPLC-MS: MS 263.0 (M+H$^+$); UPLC rt 0.75 min.

Preparation 16

9-methoxy-3,4,7,8-tetrahydro-[1,4]diazepino[7,1-a]isoquinoline-2,5-dione

UPLC-MS: MS 259.2 (M+H$^+$); UPLC rt 0.67 min.

Preparation 17

9-bromo-3,4,7,8-tetrahydro-[1,4]diazepino[7,1-a]isoquinoline-2,5-dione

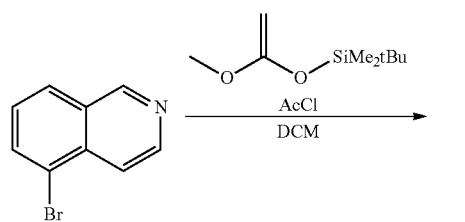

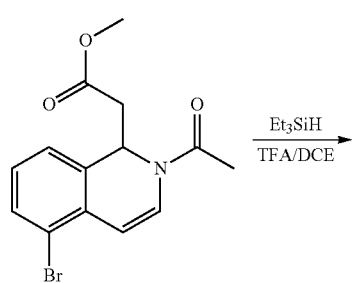

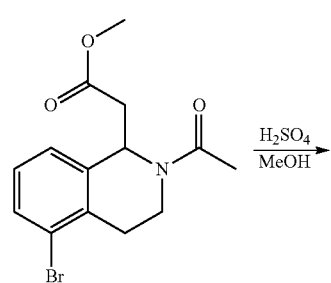

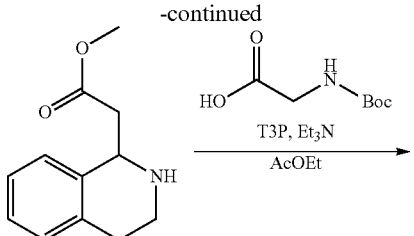

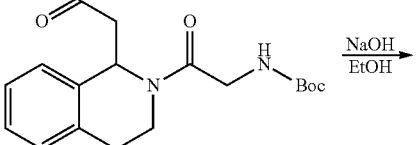

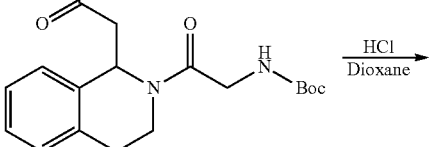

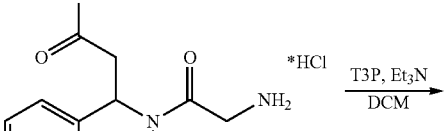

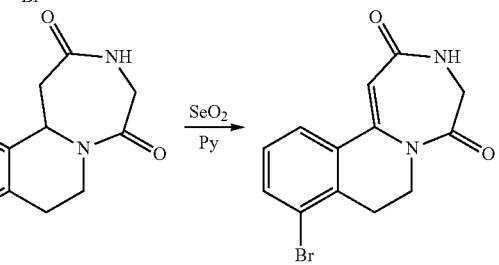

Step 1. methyl 2-(2-acetyl-5-bromo-1,2-dihydroisoquinolin-1-yl)acetate. To a stirred solution of 5-bromoisoquinoline (100 g, 481 mmol) in DCM (1900 mL) acetyl chloride (35.9 mL, 505 mmol) was dropped at RT and the solution was stirred for 60 min. The solution was cooled to −78° C. (yellow suspension) and then a solution of tert-butyl((1-methoxyvinyl)oxy)dimethylsilane (95 g, 505 mmol) in DCM (500 mL) was added in one portion. The resulting yellow solution was stirred at −78° C. for 1 h and then allowed to warm to rt overnight. 2N aqueous HCl (400 mL) was added and the reaction mixture was stirred for 10 min. The organic layer was separated and washed with brine (2×). The combined organic layers were dried with sodium sulfate, filtered and the solvent was removed under reduced pressure. The residue was dissolved in diethyl ether (1000 mL), charcoal was added and the mixture was filtrated through a pad of celite. The solvent was evaporated and the crude product was dried under high vacuo overnight to yield the title compound (147 g) which was used without further purification. UPLC-MS: MS 324.0/326.0 (M+H+); UPLC rt 1.03 min.

Step 2. methyl 2-(2-acetyl-5-bromo-1,2,3,4-tetrahydroisoquinolin-1-yl)acetate. A stirred solution of methyl 2-(2-acetyl-5-bromo-1,2-dihydroisoquinolin-1-yl)acetate (147 g, 453 mmol), triethylsilane (388 g, 3333 mmol) and trifluoroacetic acid (266 mL, 3446 mmol) in 1,2-dichloroethane (1100 mL) was stirred at 80° C. for 3 h. The reaction mixture was cooled to rt and the solvent was evaporated under reduced pressure. The remaining volatile components were evaporated under high vacuo and 40° C. bath temperature. To the resulting yellow residue saturated aqueous NaHCO$_3$ (500 mL) was added while stirring and the mixture was extracted with DCM (3×400 mL). The organic layer was washed with saturated aqueous NaHCO$_3$ (300 mL) and brine (300 mL). The organic layer was treated with charcoal, then dried with sodium sulfate, filtered through a pad of Hyflo and the solvent was removed under reduced pressure. The crude product was crystallized from diethyl ether (300 mL) to yield the title compound as white crystals (90 g). UPLC-MS: MS 326.0/328.0 (M+H+); UPLC rt 0.94 min.

Step 3. methyl 2-(5-bromo-1,2,3,4-tetrahydroisoquinolin-1-yl)acetate. MeOH (1280 mL) was cooled to −15° C. and conc. Sulfuric acid (147 mL, 2759 mmol) was added slowly (exotherm) under cooling. To this solution, methyl 2-(2-acetyl-5-bromo-1,2,3,4-tetrahydroisoquinolin-1-yl)acetate (90 g, 276 mmol) was added and the reaction mixture was stirred under reflux for 96 h. The reaction mixture was cooled to RT and slowly added to a solution of NaHCO$_3$ (540 g) in water (1.35 L). The slightly basic aqueous solution was extracted with AcOEt (3×500 mL). The combined organic layers were washed with saturated aqueous NaHCO$_3$ (300 mL) and brine (300 mL). The organic layer was dried with sodium sulfate, filtered and the solvent was removed under reduced pressure. The crude product was dried under high vacuo to yield the title compound as yellow foam (76 g) which was used without further purification. UPLC-MS: MS 284.1/286.1 (M+H+); UPLC rt 0.50 min.

Step 4. methyl 2-(5-bromo-2-(2-((tert-butoxycarbonyl)amino)acetyl)-1,2,3,4-tetrahydroisoquinolin-1-yl)acetate. To a stirred solution of methyl 2-(5-bromo-1,2,3,4-tetrahydroisoquinolin-1-yl)acetate (76 g, 267 mmol), Boc-glycine (51.5 g, 294 mmol) and triethylamine (74.6 mL, 535 mmol) in AcOEt (1350 mL), T3P (191 mL, 321 mmol, 50% m/m in AcOEt) was added and the solution was stirred at RT for 90 min. 0.2N aqueous HCl (400 mL) was added and the reaction mixture was stirred for 5 min. The organic layer was separated and washed with 0.2 N aqueous HCl (1×250 mL), saturated aqueous NaHCO$_3$ (2×250 mL) and brine (1×250 mL). The combined organic layers were dried with sodium sulfate, filtered and the solvent was removed under reduced pressure. The residue was dried under high vacuo overnight to yield the title compound as white foam (113 g) which was used without further purification. UPLC-MS: MS 441.2/443.2 (M+H+); UPLC rt 1.12 min.

Step 5. 2-(5-bromo-2-(2-((tert-butoxycarbonyl)amino)acetyl)-1,2,3,4-tetrahydroisoquinolin-1-yl)acetic acid. To a stirred solution of methyl 2-(5-bromo-2-(2-((tert-butoxycarbonyl)amino)acetyl)-1,2,3,4-tetrahydroisoquinolin-1-yl)acetate (113 g, 257 mmol) in EtOH (1000 mL), 4N aqueous NaOH (74.5 mL, 298 mmol) was added and the solution was stirred at RT for 2 h. The white precipitate was filtered off and the white solid was washed with a small amount of EtOH (1×) and diethyl ether (2×). The sodium salt was partitioned between 0.5N aqueous HCl and DCM, the organic layer was separated and washed with 0.5N aqueous HCl (1×) and brine (1×). The combined organic layers were dried with sodium sulfate, filtered and the solvent was removed under reduced pressure. The residue was dried under high vacuo overnight to yield the title compound as white foam (110 g). UPLC-MS: MS 427.2/429.2 (M+H+); UPLC rt 0.98 min.

Step 6. 2-(5-bromo-1-(carboxymethyl)-3,4-dihydroisoquinolin-2(1H)-yl)-2-oxoethanaminium chloride. To a stirred solution of 2-(5-bromo-2-(2-((tert-butoxycarbonyl)amino)acetyl)-1,2,3,4-tetrahydroisoquinolin-1-yl)acetic acid (110 g, 257 mmol) in dioxane (1290 mL), 4N HCl in dioxane (644 mL, 2574 mmol) was added and the reaction mixture was stirred at RT for 24 h. The white precipitate was filtered off and the white solid was washed with a small amount of diethyl ether (2×). The HCl salt was dried under high vacuo overnight to yield the title compound as white solid (88 g). UPLC-MS: MS 327.1/329.1 (M+H+); UPLC rt 0.56 min.

Step 7. 9-bromo-1,3,4,7,8,12b-hexahydro-[1,4]diazepino[7,1-a]isoquinoline-2,5-dione. To a stirred solution of 2-(5-bromo-1-(carboxymethyl)-3,4-dihydroisoquinolin-2(1H)-yl)-2-oxoethanaminium chloride (88 g, 242 mmol) and triethylamine (169 mL, 1210 mmol) in DCM (960 mL), T3P (212 mL, 363 mmol, 50% m/m in AcOEt) was added slowly (exotherm) and the suspension was stirred at rt for 1 h. The solvent was reduced to a small amount under reduced pressure and the thick suspension was treated with 2N aqueous HCl (500 mL). The white suspension was stirred at RT for 15 min and the solid was filtered off. The solid was again treated with 2N aqueous HCl (300 mL), stirred for 10 min and filtered of. The slightly yellow solid was washed with water (1×) and with diethyl ether (2×). The resulting solid was dried at 50° C. under high vacuo overnight to yield the title compound as beige solid (71 g). UPLC-MS: MS 309.1/311.1 (M+H+); UPLC rt 0.72 min.

Step 8. 9-bromo-3,4,7,8-tetrahydro-[1,4]diazepino[7,1-a]isoquinoline-2,5-dione. A mixture of 9-bromo-1,3,4,7,8,12b-hexahydro-[1,4]diazepino[7,1-a]isoquinoline-2,5-dione (84.4 g, 273 mmol) and SeO$_2$ (53 g, 476 mmol) in pyridine (2400 mL), partitioned in 4 large scale microwave reactors, was stirred at 160° C. for 30 min under microwave conditions. The reaction mixture was allowed to warm to RT, filtered through a pad of celite and the solvent was evaporated under reduced pressure. The residue was taken up in DCM and extracted with 0.25N aqueous HCl (2×) and brine (1×). The combined organic layers were dried with sodium sulfate, filtered and the solvent was removed under reduced pressure. The crude product was purified by flash-column chromatography over silicagel (1$^{st}$ chromatography: 100% AcOEt; 2$^{nd}$ chromatography: DCM/MeOH 95:5) to yield a yellow solid. The residue was triturated with diethyl ether to yield the title compound as slightly yellow crystals (25 g). UPLC-MS: MS 307.1/309.1 (M+H+); UPLC rt 0.77 min.

Preparation 17a 9-bromo-10-fluoro-3,4,7,8-tetrahydro-[1,4]diazepino[7,1-a]isoquinoline-2,5-dione

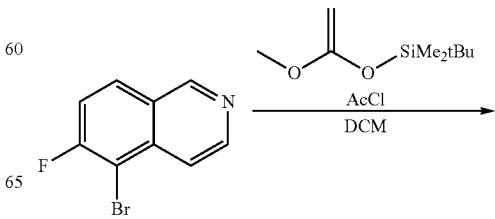

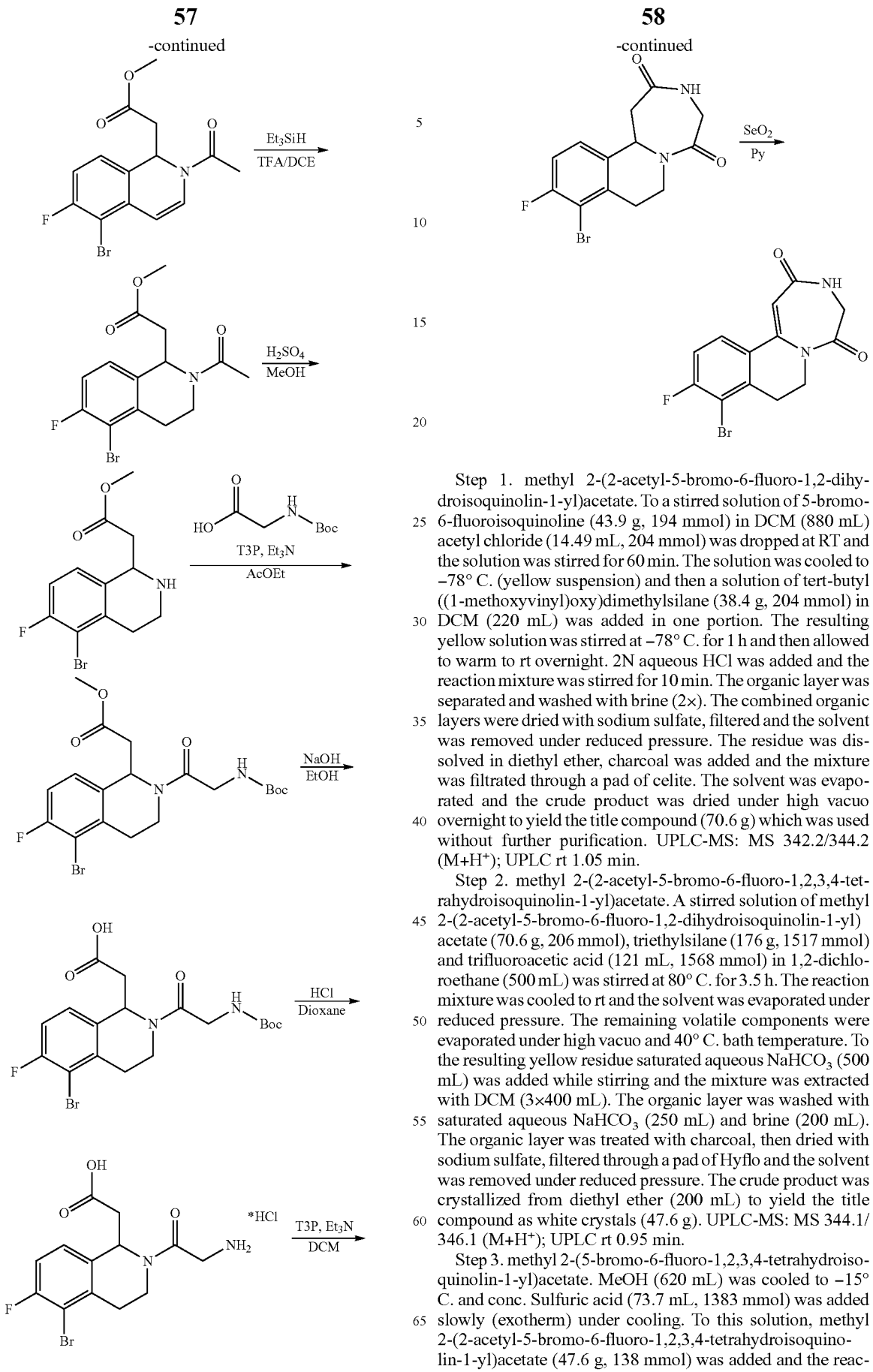

Step 1. methyl 2-(2-acetyl-5-bromo-6-fluoro-1,2-dihydroisoquinolin-1-yl)acetate. To a stirred solution of 5-bromo-6-fluoroisoquinoline (43.9 g, 194 mmol) in DCM (880 mL) acetyl chloride (14.49 mL, 204 mmol) was dropped at RT and the solution was stirred for 60 min. The solution was cooled to −78° C. (yellow suspension) and then a solution of tert-butyl ((1-methoxyvinyl)oxy)dimethylsilane (38.4 g, 204 mmol) in DCM (220 mL) was added in one portion. The resulting yellow solution was stirred at −78° C. for 1 h and then allowed to warm to rt overnight. 2N aqueous HCl was added and the reaction mixture was stirred for 10 min. The organic layer was separated and washed with brine (2×). The combined organic layers were dried with sodium sulfate, filtered and the solvent was removed under reduced pressure. The residue was dissolved in diethyl ether, charcoal was added and the mixture was filtrated through a pad of celite. The solvent was evaporated and the crude product was dried under high vacuo overnight to yield the title compound (70.6 g) which was used without further purification. UPLC-MS: MS 342.2/344.2 (M+H$^+$); UPLC rt 1.05 min.

Step 2. methyl 2-(2-acetyl-5-bromo-6-fluoro-1,2,3,4-tetrahydroisoquinolin-1-yl)acetate. A stirred solution of methyl 2-(2-acetyl-5-bromo-6-fluoro-1,2-dihydroisoquinolin-1-yl)acetate (70.6 g, 206 mmol), triethylsilane (176 g, 1517 mmol) and trifluoroacetic acid (121 mL, 1568 mmol) in 1,2-dichloroethane (500 mL) was stirred at 80° C. for 3.5 h. The reaction mixture was cooled to rt and the solvent was evaporated under reduced pressure. The remaining volatile components were evaporated under high vacuo and 40° C. bath temperature. To the resulting yellow residue saturated aqueous NaHCO$_3$ (500 mL) was added while stirring and the mixture was extracted with DCM (3×400 mL). The organic layer was washed with saturated aqueous NaHCO$_3$ (250 mL) and brine (200 mL). The organic layer was treated with charcoal, then dried with sodium sulfate, filtered through a pad of Hyflo and the solvent was removed under reduced pressure. The crude product was crystallized from diethyl ether (200 mL) to yield the title compound as white crystals (47.6 g). UPLC-MS: MS 344.1/346.1 (M+H$^+$); UPLC rt 0.95 min.

Step 3. methyl 2-(5-bromo-6-fluoro-1,2,3,4-tetrahydroisoquinolin-1-yl)acetate. MeOH (620 mL) was cooled to −15° C. and conc. Sulfuric acid (73.7 mL, 1383 mmol) was added slowly (exotherm) under cooling. To this solution, methyl 2-(2-acetyl-5-bromo-6-fluoro-1,2,3,4-tetrahydroisoquinolin-1-yl)acetate (47.6 g, 138 mmol) was added and the reaction mixture was stirred under reflux for 96 h. The reaction mixture was cooled to RT and slowly added to a solution of NaHCO₃ (244 g) in water (500 mL). The slightly basic aqueous solution was extracted with AcOEt (3×). The combined organic layers were washed with saturated aqueous NaHCO₃ and brine. The organic layer was dried with sodium sulfate, filtered and the solvent was removed under reduced pressure. The crude product was dried under high vacuo to yield the title compound as yellow foam (41.58 g) which was used without further purification. UPLC-MS: MS 302.1/304.1 (M+H⁺); UPLC rt 0.51 min.

Step 4. methyl 2-(5-bromo-2-(2-((tert-butoxycarbonyl)amino)acetyl)-6-fluoro-1,2,3,4-tetrahydroisoquinolin-1-yl)acetate. To a stirred solution of methyl 2-(5-bromo-6-fluoro-1,2,3,4-tetrahydroisoquinolin-1-yl)acetate (41.58 g, 138 mmol), Boc-glycine (26.5 g, 151 mmol) and triethylamine (38.4 mL, 275 mmol) in AcOEt (690 mL), T3P (98 mL, 165 mmol, 50% m/m in AcOEt) was added and the solution was stirred at RT for 1 h. 0.2N aqueous HCl (200 mL) was added and the reaction mixture was stirred for 5 min. The organic layer was separated and washed with 0.2N aqueous HCl (1×200 mL), saturated aqueous NaHCO₃ (2×200 mL) and brine (1×200 mL). The combined organic layers were dried with sodium sulfate, filtered and the solvent was removed under reduced pressure. The residue was dried under high vacuo overnight to yield the title compound as white foam (62.6 g) which was used without further purification. UPLC-MS: MS 459.3/461.3 (M+H⁺); UPLC rt 1.13 min.

Step 5. 2-(5-bromo-2-(2-((tert-butoxycarbonyl)amino)acetyl)-6-fluoro-1,2,3,4-tetrahydroisoquinolin-1-yl)acetic acid. To a stirred solution of methyl 2-(5-bromo-2-(2-((tert-butoxycarbonyl)amino)acetyl)-6-fluoro-1,2,3,4-tetrahydroisoquinolin-1-yl)acetate (62.6 g, 136 mmol) in EtOH (500 mL), 4N aqueous NaOH (39.5 mL, 158 mmol) was added and the solution was stirred at RT for 2 h. The white precipitate was filtered off and the white solid was washed with a small amount of EtOH (1×) and diethyl ether (2×). The sodium salt was partitioned between 0.5N aqueous HCl and DCM, the organic layer was separated and washed with 0.5N aqueous HCl (1×) and brine (1×). The combined organic layers were dried with sodium sulfate, filtered and the solvent was removed under reduced pressure. The residue was dried under high vacuo overnight to yield the title compound as white foam (58.45 g). UPLC-MS: MS 445.2/447.2 (M+H⁺); UPLC rt 0.99 min.

Step 6. 2-(2-(2-aminoacetyl)-5-bromo-6-fluoro-1,2,3,4-tetrahydroisoquinolin-1-yl)acetic acid (HCl salt). To a stirred solution of 2-(5-bromo-2-(2-((tert-butoxycarbonyl)amino)acetyl)-6-fluoro-1,2,3,4-tetrahydroisoquinolin-1-yl)acetic acid (58.45 g, 131 mmol) in dioxane (600 mL), 4N HCl in dioxane (328 mL, 1313 mmol) was added and the reaction mixture was stirred at RT for 24 h. The solvent was evaporated under reduced pressure and the HCl salt was dried under high vacuo overnight to yield the title compound as yellow foam (54.6 g). UPLC-MS: MS 345.2/347.2 (M+H⁺); UPLC rt 0.56 min.

Step 7. 9-bromo-10-fluoro-1,3,4,7,8,12b-hexahydro-[1,4]diazepino[7,1-a]isoquinoline-2,5-dione. To a stirred solution of 2-(2-(2-aminoacetyl)-5-bromo-6-fluoro-1,2,3,4-tetrahydroisoquinolin-1-yl)acetic acid (HCl salt) (54.6 g, 143 mmol) and triethylamine (100 mL, 715 mmol) in DCM (570 mL), T3P (125 mL, 215 mmol, 50% m/m in AcOEt) was added slowly (exotherm) and the suspension was stirred at rt for 1 h. The solvent was reduced to a small amount under reduced pressure and the thick suspension was treated with water (500 mL) and the suspension was stirred overnight. The suspension was filtered off and the solid was again treated with water (200 mL), stirred for 10 min and filtered off. The slightly yellow solid was washed with water (1×) and with diethyl ether (2×). The resulting solid was dried at rt under high vacuo overnight to yield the title compound as slightly yellow solid (40.5 g). UPLC-MS: MS 327.1/329.1 (M+H⁺); UPLC rt 0.73 min.

Step 8. 9-bromo-10-fluoro-3,4,7,8-tetrahydro-[1,4]diazepino[7,1-a]isoquinoline-2,5-dione. A mixture of 9-bromo-10-fluoro-1,3,4,7,8,12b-hexahydro-[1,4]diazepino[7,1-a]isoquinoline-2,5-dione (40.5 g, 124 mmol) and SeO₂ (24.1 g, 217 mmol) in pyridine (1240 mL) was stirred at 130° C. for 4 h. The reaction mixture was allowed to warm to RT, filtered through a pad of celite and the solvent was evaporated under reduced pressure. The residue was taken up in DCM and extracted with 1N aqueous HCl (2×) and brine (1×). The combined organic layers were dried with sodium sulfate, filtered and the solvent was removed under reduced pressure. The crude product was purified by flash-column chromatography over silicagel (Biotage Isolera Four, eluent: 90% AcOEt in DCM for 40 min, then from 0% MeOH in DCM to 5% MeOH in DCM in 50 min, followed by 5% MeOH in DCM for 15 min). During evaporation the compound crystallized and yielded slightly orange crystals (9.3 g). UPLC-MS: MS 325.2/327.2 (M+H⁺); UPLC rt 0.78 min.

Following the procedure described above for Preparation 17a and substituting the appropriate reagents, starting materials and purification methods known to those skilled in the art, the following intermediates of the present invention were prepared:

Preparation 17b (from
5-bromo-8-fluoroisoquinoline)

9-bromo-12-fluoro-3,4,7,8-tetrahydro-[1,4]diazepino[7,1-a]isoquinoline-2,5-dione UPLC-MS: MS 325.1/327.1 (M+H⁺); UPLC rt 0.77 min.

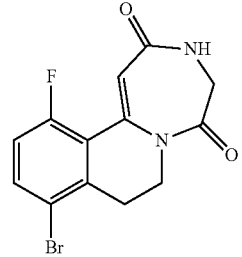 [SMILES: O=C1C=C2c3c(F)ccc(Br)c3CCN2C(=O)CN1]

Preparation 17c (from
5-bromo-7-fluoroisoquinoline)

9-bromo-11-fluoro-3,4,7,8-tetrahydro-[1,4]diazepino[7,1-a]isoquinoline-2,5-dione UPLC-MS: MS 325.0/327.0 (M+H⁺); UPLC rt 0.79 min.

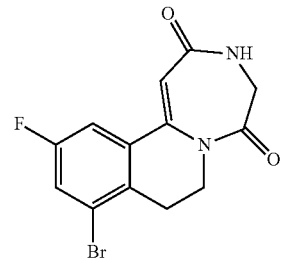 [SMILES: O=C1C=C2c3cc(F)cc(Br)c3CCN2C(=O)CN1]

Following the procedure described above for Preparation 17 and substituting the appropriate reagents, starting materials and purification methods known to those skilled in the art, the following intermediates of the present invention were prepared:

Preparation 18

9-(1H-pyrazol-1-yl)-3,4,7,8-tetrahydro-[1,4]diazepino[7,1-a]isoquinoline-2,5-dione UPLC-MS: MS 295.1 (M+H$^+$); UPLC rt 0.62 min.

Preparation 19

9-morpholino-3,4,7,8-tetrahydro-[1,4]diazepino[7,1-a]isoquinoline-2,5-dione

UPLC-MS: MS 314.0 (M+H$^+$); UPLC rt 0.67 min.

Preparation 20

9-iodo-1-methyl-3,4,7,8-tetrahydro-[1,4]diazepino[7,1-a]isoquinoline-2,5-dione

UPLC-MS: MS 369.1 (M+H$^+$); UPLC rt 0.84 min.

The following examples provide synthetic route to useful building blocks for the preparation of compounds of the present invention.

Preparation 21

5-(1H-pyrazol-1-yl)isoquinoline

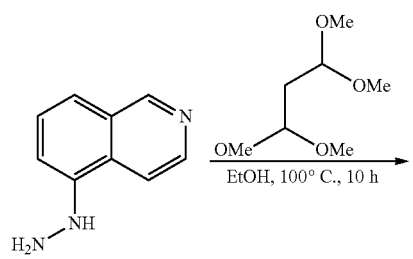

A suspension of 5-hydrazinylisoquinoline (22.0 g, 112 mmol) in EtOH (300 mL) was treated with 1,1,3,3-tetramethoxypropane (27.7 g, 169 mmol) and the mixture was heated to 100° C. for 10 h. The reaction mixture was then concentrated in vacuo and the residue obtained taken up in DCM (500 mL) and washed with a saturated aqueous solution of NaHCO$_3$—gas formation. The aqueous layer was extracted twice with DCM and the combined org. layers were then dried over Na$_2$SO$_4$, filtered and concentrated in vacuo. The crude product was purified by flash chromatography (SiO$_2$, DCM/MeOH 95:5 to DCM/MeOH 9:1) to give the title compound (16.1 g). UPLC-MS: MS 196.1 (M+H$^+$); UPLC rt 0.62 min.

Preparation 22

4-(isoquinolin-5-yl)morpholine

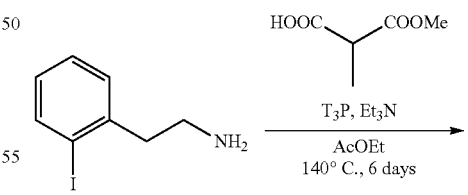

A mixture of 5-bromoisoquinoline (4.07 g, 19.6 mmol), morpholine (3.41 mL, 39.1 mmol), Cs$_2$CO$_3$ (12.75 g, 39.1 mmol), Pd(OAc)$_2$ (220 mg, 0.98 mmol) and BINAP (609 mg, 0.98 mmol) in toluene (160 mL) was heated at 110° C. for 6 h under N$_2$. The mixture was then concentrated in vacuo and the black residue obtained was taken up in DCM and filtered over Celite. The filtrate was concentrated in vacuo and the brown oil obtained was purified by flash chromatography (SiO$_2$, cHex to AcOEt) to give the title compound (4.17 g) as a brown oil. UPLC-MS: MS 215.1 (M+H$^+$); UPLC rt 0.57 min.

Preparation 23 methyl 2-(5-iodo-1,2,3,4-tetrahydroisoquinolin-1-yl)propanoate

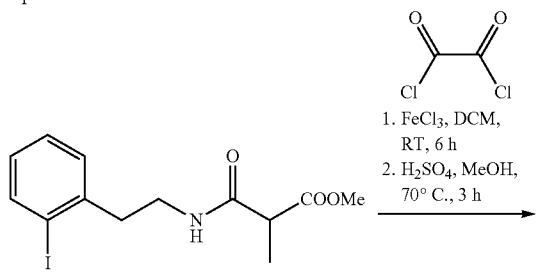

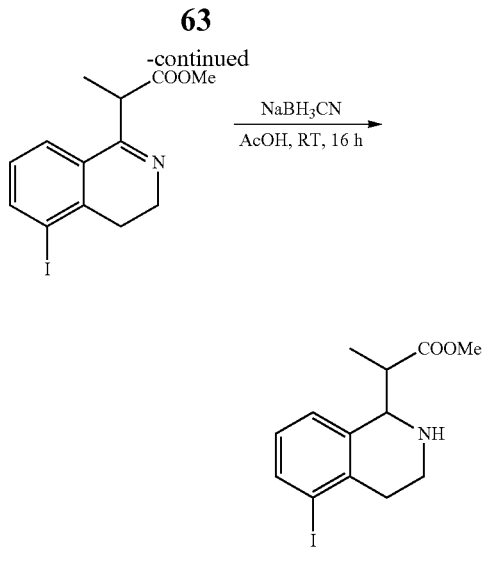

Step 1: methyl 3-((2-iodophenethyl)amino)-2-methyl-3-oxopropanoate. A solution of T3P in AcOEt (50%, 26.2 mL, 44.0 mmol) was added dropwise at 0° C. under N₂ to a clear solution of 2-(2-iodophenyl)ethanamine (9.45 g, 38.2 mmol), 3-methoxy-2-methyl-3-oxopropanoic acid (5.05 g, 38.2 mmol) and Et₃N (10.7 mL, 76.0 mmol) in AcOEt (350 mL). The mixture was stirred at RT for 6 days. A 2N aqueous solution of NaOH (50 mL) was then added to the reaction and the mixture was extracted with AcOEt. The combined org. layers were then dried over Na₂SO₄, filtered and concentrated in vacuo. The yellow oil obtained was purified by flash chromatography (SiO₂, cHEx/AcOEt 100:0 to 50:50) to afford the title compound (10.83 g) as a clear oil. UPLC-MS: MS 362.2 (M+H⁺); UPLC rt 0.95 min.

Step 2: methyl 2-(5-iodo-3,4-dihydroisoquinolin-1-yl)propanoate. A solution of methyl 3-((2-iodophenethyl)amino)-2-methyl-3-oxopropanoate (9.9 g, 27.4 mmol) in DCM (120 mL) was treated with oxalyl chloride (2.59 mL, 30.2 mmol) and the mixture was stirred at RT for 30 min. FeCl₃ (5.34 g, 32.9 mmol) was then added portionwise at 0° C. and the resulting brown mixture was stirred at RT for 4 h. A 2N aqueous solution of HCl (35 mL) was then added and the mixture was stirred at RT for another 2 h. The mixture was then diluted with H₂O and extracted with DCM. The combined org. phases were then dried over Na₂SO₄, filtered and concentrated in vacuo. The brown residue obtained was taken up in a 19:1 mixture of MeOH/H₂SO₄ (120 mL) and stirred at reflux for 3 h. The mixture was then concentrated in vacuo and the brown reside obtained was taken up in H₂O. The mixture was rendered basic with ammonia and then extracted with AcOEt. The combined org. phases were dried over Na₂SO₄, filtered and concentrated in vacuo. Purification by flash chromatography (SiO₂, cHex/AcOEt 100:0 to 70:30) gave the title compound (1.15 g) as yellow oil. UPLC-MS: MS 344.1 (M+H⁺); UPLC rt 0.96 min.

Step 3: methyl 2-(5-iodo-1,2,3,4-tetrahydroisoquinolin-1-yl)propanoate. A mixture of methyl 2-(5-iodo-3,4-dihydroisoquinolin-1-yl)propanoate (1.15 g, 3.35 mmol) in glacial AcOH (12 mL) was treated with NaBH₃CN (421 mg, 6.70 mmol) at RT under N₂. The mixture was stirred at RT for 16 h, and then poured onto H₂O. The mixture was rendered basic with a 50% aqueous solution of NaOH and extracted with AcOEt. The combined org. phases were then dried over Na₂SO₄, filtered and concentrated in vacuo to give the title compound (1.17 g) that was used as it is. UPLC-MS: MS 346.1 (M+H⁺); UPLC rt 0.65 min.

Preparation 24

(S)-4-(1-methoxyethyl)-1H-imidazole; Preparation 25: (R)-4-(1-methoxyethyl)-1H-imidazole

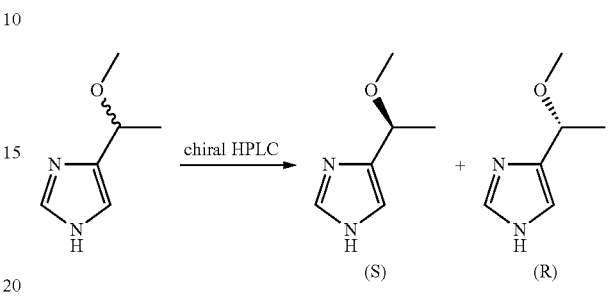

Chiral resolution of racemic 4-(1-methoxyethyl)-1H-imidazole (17.3 g, 137 mmol) by preparative HPLC (column: Chiralpak AD 20 µm, 5×50 cm; eluent: n-heptane:1-propanol:MeOH 90:6:4; flow 50 mL/min; UV detection at 220 nm) yielded the title compounds.

Peak 1 (first eluted): 8.2 g (>98% ee) of (S)-4-(1-methoxyethyl)-1H-imidazole

UPLC-MS: MS127.1 (M+H⁺); UPLC rt 0.25 min.

chiral LC: instrument Shimadzu SCL 10A, injection volume 5 µL, flow rate 1 mL/min, column AD 10 µM 4.6×250 mm, UV detection at 220 nm, eluent: n-heptane/n-propanol/MeOH 90:6:4, rt 5.39 min.

Peak 2 (second eluted): 7.8 g (>98% ee) of (R)-4-(1-methoxyethyl)-1H-imidazole

UPLC-MS: MS127.1 (M+H⁺); UPLC rt 0.25 min.

chiral LC: instrument Shimadzu SCL 10A, injection volume 5 µL, flow rate 1 mL/min, column AD 10 µM 4.6×250 mm, UV detection at 220 nm, eluent: n-heptane/n-propanol/MeOH 90:6:4, rt 6.43 min.

The absolute configuration of both enantiomers were determined by X-ray analysis.

Preparation 26

4-cyclobutyl-1H-imidazole

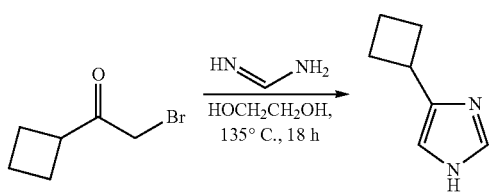

A mixture of 2-bromo-1-cyclobutylethanone (27.2 g, 154 mmol) and formamidine acetate (80.0 g, 768 mmol) in ethyleneglycol (150 mL) was heated to 135° C. for 18 h. The mixture was then diluted with H₂O and then continuously extracted with Et₂O for 18 h. The org. phase was then dried over Na₂SO₄, filtered and concentrated in vacuo. Purification by distillation in a Kugelrohr oven and flash chromatography (SiO₂, DCM to DCM/MeOH 9:1) afforded the title compound (3.5 g). UPLC-MS: MS 123.1 (M+H⁺); UPLC rt 0.36 min.

Preparation 27

5-methyl-2-(tributylstannyl)oxazole

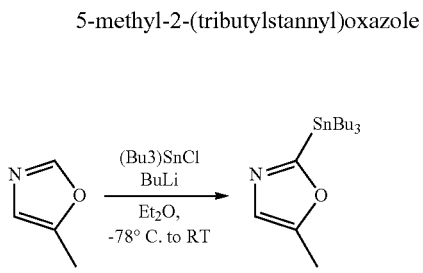

A solution of 5-methyloxazole (5.0 g, 60.2 mmol) in Et₂O (100 mL) was cooled to −78° C. under N₂ and treated with a 1.6 M solution of BuLi in hexane (41.4 mL, 66.2 mmol) dropwise. The mixture was stirred at −78° C. for 30 min and a solution of Bu₃SnCl (16.31 mL, 60.2 mmol) in Et₂O (50 mL) was then added dropwise. The mixture was stirred at −78° C. for another 30 min and then allowed to warm to RT. The reaction mixture was filtered on celite, and the filtrate concentrated in vacuo. Purification by distillation (0.1 Torr, 128-130° C.) afforded the title compound (3.5 g) as a yellow liquid. ¹H NMR (400 MHz, CHLOROFORM-d) δ ppm 0.88 (m, 12 H) 1.14-1.22 (m, 6 H) 1.27-1.38 (m, 6 H) 1.52-1.61 (m, 6 H) 2.17-2.21 (m, 3 H) 7.49-7.54 (m, 1 H).

Preparation 28

4-(((tert-butyldiphenylsilynoxy)methyl)-1H-imidazole

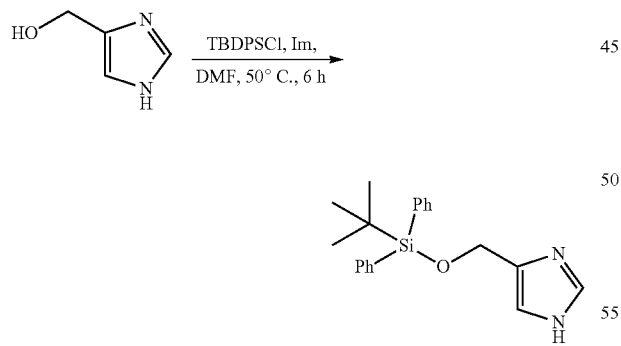

A solution of (1H-imidazol-4-yl)methanol (14.6 g, 108 mmol) in DMF (100 mL) was treated with imidazole (22.16 g, 325 mmol) and TBDPSCl (29.8 g, 108 mmol) and the mixture was stirred and heated to 50° C. for 6 h. It was then allowed to cool to RT, poured onto H₂O and extracted with DCM. The combined org. layers were dried over Na₂SO₄, filtered and concentrated in vacuo. Purification by flash chromatography (SiO2, DCM/MeOH 100:0 to 90:10) afforded the title compound (35.3 g). UPLC-MS: MS 337.2 (M+H+); UPLC rt 1.04 min.

Preparation 29

5-(1H-imidazol-4-yl)oxazole

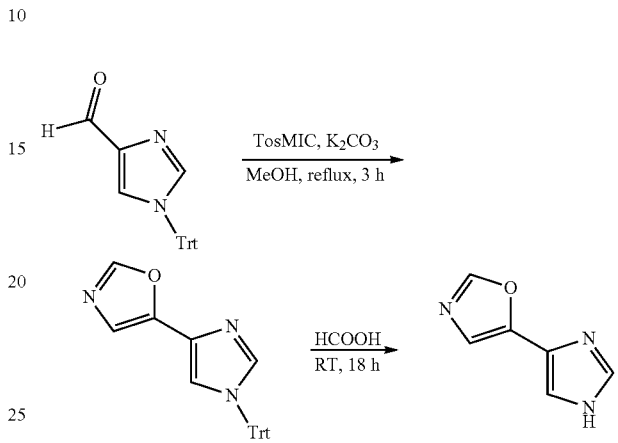

Step 1: 5-(1-trityl-1H-imidazol-4-yl)oxazole. A mixture of 1-trityl-1H-imidazole-4-carbaldehyde (25.0 g, 73.9 mmol), TosMIC (14.42 g, 73.9 mmol) and K₂CO₃ (10.21 g, 73.9 mmol) in MeOH (750 mL) was heated to reflux for 3 h. The mixture was then allowed to cool to RT, diluted with H₂O, and extracted with AcOEt. The combined org. layers were then washed with brine, dried over Na₂SO₄, filtered and concentrated in vacuo. Purification by flash chromatography (SiO2, heptane/AcOEt 100:0 to 0:100) gave the title compound (14.6 g). UPLC (2 min) rt 1.415 min.

Step 2: 5-(1H-imidazol-4-yl)oxazole. A solution of 5-(1-trityl-1H-imidazol-4-yl)oxazole (14.5 g, 38.4 mmol) was treated with a 90% aq. solution of formic acid (90 mL) and the mixture was stirred at RT for 18 h. The mixture was then diluted with DCM, and washed with H2O and sat. aq. solution of NaHCO₃. The combined aqueous layers were washed with DCM and then concentrated in vacuo. The residue obtained was placed in a Soxlet apparatus and continuously extracted with DCM for 12 h. The organic phase was then concentrated and the crude product was crystallized in DCM to give the title compound (2.68 g). UPLC-MS: MS 136.1 (M+H+); UPLC rt 0.25 min.

Preparation 30

5-(1H-imidazol-4-yl)isoxazole

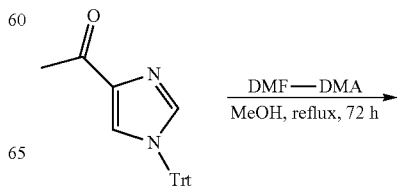

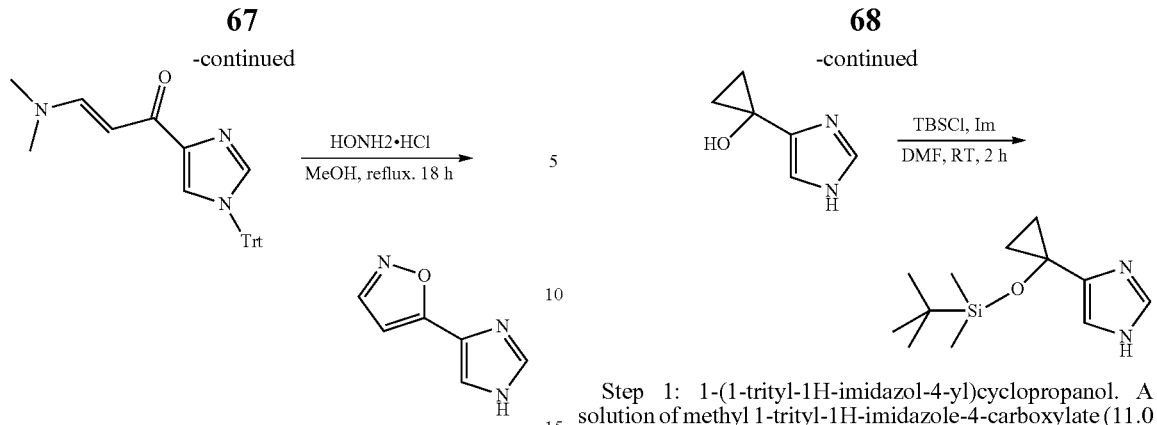

Step 1: (E)-3-(dimethylamino)-1-(1-trityl-1H-imidazol-4-yl)prop-2-en-1-one. A mixture of 1-(1-trityl-1H-imidazol-4-yl)ethanone (81.0 g, 230 mmol) and DMF-DMA (77.0 mL, 575 mmol) in MeOH (500 mL) was heated to reflux for 72 h. The mixture was then allowed to cool to RT and was then cooled to 0° C. the suspension was filtered and the filter cake was dried in vacuo at 40° C. to give the title compound (72.7 g) that was used as it is in the next step. UPLC-MS: MS 408.3 (M+H+); UPLC rt 1.08 min.

Step 2: 5-(1H-imidazol-4-yl)isoxazole. A mixture of (E)-3-(dimethylamino)-1-(1-trityl-1H-imidazol-4-yl)prop-2-en-1-one (54.0 g, 133 mmol) and HONH2*HCl (10.13 g, 146 mmol) in MeOH (800 mL) was heated to reflux for 18 h. The mixture was then allowed to cool to RT and was concentrated in vacuo. The residue obtained was taken up in DCM and washed with H₂O. The org. phase was then dried over Na₂SO₄, filtered and concentrated in vacuo. The residue obtained was stirred in Et₂O, and the suspension was filtered. The filter cake was dried in vacuo at 40° C. The aqueous phase was then concentrated in vacuo and the residue obtained was placed in a Soxlet apparatus and continuously extracted with DCM for 36 h. The organic phase was then concentrated in vacuo and the residue obtained was stirred in DCM. The suspension was then filtered and the filter cake was dried in vacuo at 40° C. The two filter cakes were then crystallized in AcOEt to give the title compound (5.44 g). UPLC-MS: MS 136.1 (M+H+); UPLC rt 0.33 min.

Preparation 31

4-(1-((tert-butyldimethylsilyl)oxy)cyclopropyl)-1H-imidazole

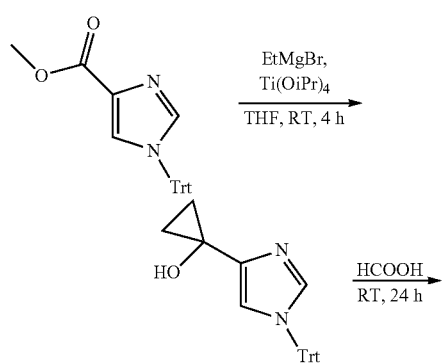

Step 1: 1-(1-trityl-1H-imidazol-4-yl)cyclopropanol. A solution of methyl 1-trityl-1H-imidazole-4-carboxylate (11.0 g, 29.9 mmol) and Ti(OiPr)₄ (12.37 mL, 41.8 mmol) in THF (3 mL) was treated dropwise with a 1M solution of EtMgBr (76 mL, 76 mmol) to maintain the temperature below 35° C. The mixture was then stirred at RT for 4 h, and then poured onto H₂O. The precipitate was filtered off, and the filtrate was extracted with AcOEt. The combined org. layers were dried over Na₂O₄, filtered and concentrated in vacuo. Purification by flash chromatography (SiO₂, AcOEt/heptane 30:70 to 100:0) gave the title compound (440 mg). UPLC-MS: MS 367.3 (M+H+); UPLC rt 1.01 min.

Step 2: 1-(1H-imidazol-4-yl)cyclopropanol. A mixture of 1-(1-trityl-1H-imidazol-4-yl)cyclopropanol (2.4 g, 6.55 mol) was treated with a 90% aq. solution of formic acid (50 mL) and the mixture was stirred at RT for 24 h. The mixture was then concentrated in vacuo, diluted in a small volume of MeOH, and the solution was rendered basic with a 7M solution of NH3 in MeOH. The white precipitate was filtered off and the filtrate was concentrated in vacuo. Purification by flash chromatography (SiO₂, DCM/MeOH 100:0 to 85:15) afforded the title compound (920 mg). UPLC-MS: MS 125.1 (M+H+).

Step 3: 4-(1-((tert-butyldimethylsilyl)oxy)cyclopropyl)-1H-imidazole. A solution of 1-(1H-imidazol-4-yl)cyclopropanol (700 mg, 5.64 mmol) in DMF (1 mL) was treated with imidazole (768 mg, 11.28 mmol) and TBSCl (935 mg, 6.20 mmol) and the mixture was stirred at RT for 2 h. The mixture was then poured onto H₂O, and extracted with AcOEt. The combined org. layers were dried over Na₂SO₄, filtered and concentrated in vacuo to give the title compound (850 mg) that was used as it is. UPLC-MS: MS 239.2 (M+H+); UPLC rt 0.82 min.

Preparation 32

4-(2-((tert-butyldiphenylsilyl)oxy)ethyl)-1H-imidazole

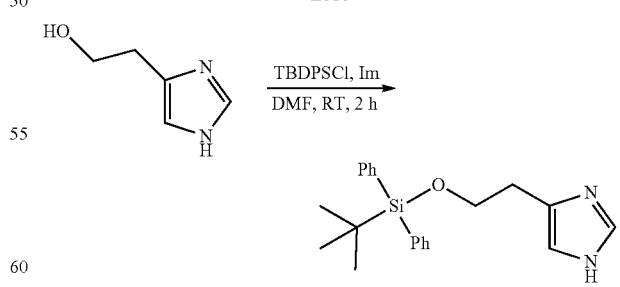

A solution of 2-(1H-imidazol-4-yl)ethanol (1.24 g, 11.1 mmol) in DMF (10 mL) was treated with imidazole (1.51 g, 22.1 mmol) and TBDPSCl (3.12 mL, 12.2 mmol) and the mixture was stirred at RT for 2 h. The mixture was then poured onto H₂O and extracted with AcOEt. The combined org. layers were dried over Na₂SO₄, filtered and concentrated in vacuo. Purification by flash chromatography (SiO$_2$, AcOEt/heptane 0:100 to 100:0) gave the title compound (1.6 g). UPLC-MS: MS 351.2 (M+H+); UPLC rt 1.02 min.

Preparation 33

3-(1H-imidazol-4-yl)oxetan-3-ol

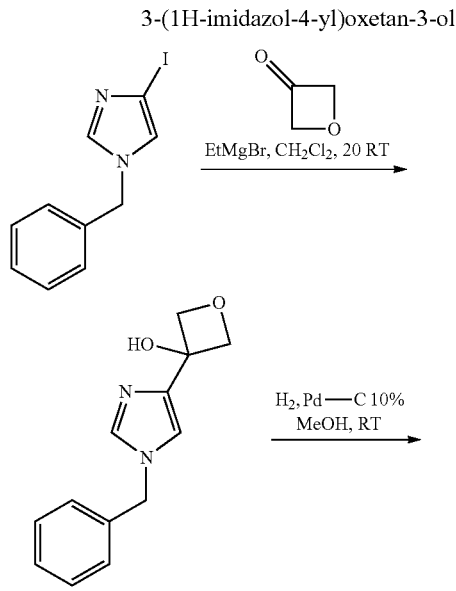

Step 1. 3-(1-benzyl-1H-imidazol-4-yl)oxetan-3-ol. A solution of 1-benzyl-4-iodo-1H-imidazole (6.0 g, 21.12 mmol) in DCM (80 mL) was treated with EtMgBr (3M in ether, 7.74 mL, 23.23 mmol) at rt and the mixture was stirred at RT overnight. The mixture was then poured onto saturated aqueous NH$_4$Cl solution and extracted with DCM. The combined org. layers were dried over Na$_2$SO$_4$, filtered and concentrated in vacuo. The crude product was purified by flash-column chromatography over silicagel (Biotage Isolera Four, eluent: 1% MeOH in DCM for 3 min, then from 1% MeOH in DCM to 5% MeOH in DCM in 25 min, followed by 5% MeOH in DCM for 6 min). The residue was crystallized from EtOAc to yield the title compound as white crystals (2.35 g). UPLC-MS: MS 231.1 (M+H$^+$); UPLC rt 0.43 min.

Step 2. 3-(1H-imidazol-4-yl)oxetan-3-ol. A solution of 3-(1-benzyl-1H-imidazol-4-yl)oxetan-3-01 (2.35 g, 10.21 mmol), 10% Pd/C (600 mg, 1.02 mmol) in MeOH (85 mL) was hydrogenated for 20 h at rt. The catalysator was filtered off and the solvent was removed in vacuo to yield the title compound as beige crystals (1.43 g). UPLC-MS: MS 141.1 (M+H$^+$); UPLC rt 0.17 min.

Example 1

9-methoxy-2-(3-methoxyphenyl)-7,8-dihydro-[1,4]diazepino[7,1-a]isoquinolin-5(4H)-one

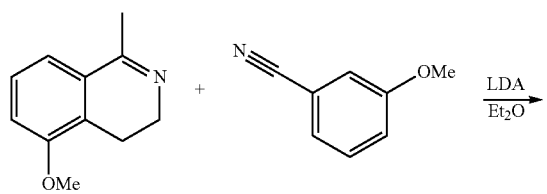

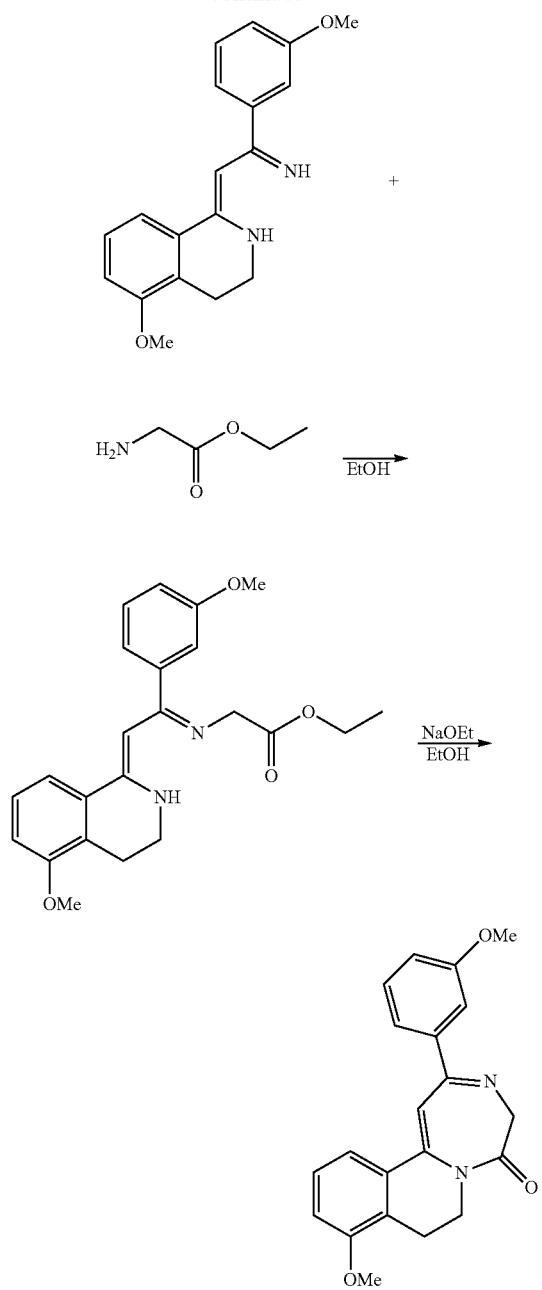

Step 1. (Z)-2-(5-methoxy-3,4-dihydroisoquinolin-1(2H)-ylidene)-1-(3-methoxyphenyl)ethanimine. 1-1. A flask was charged with 5-methoxy-1-methyl-3,4-dihydroisoquinoline (3.0 g, 17.1 mmol) and Et$_2$O (100 mL) under N$_2$ and cooled to 30° C. A 2M solution of LDA (8.56 mL, 17.1 mmol) was added dropwise. The resulting brown suspension was stirred for 30 min at this temperature, and then cooled to −78° C. A solution of 3-methoxybenzonitrile (2.28 g, 17.1 mmol) in Et$_2$O (25 mL) was added dropwise. The mixture was stirred at −78° C. for 1 h, and then allowed to warm to RT and stirred for another 18 h. the mixture was then poured onto H$_2$O and extracted with AcOEt. The org. layers were dried over Na$_2$SO$_4$, filtered and concentrated in vacuo to give the title compound (5.9 g) as a brown oil that was used as it is in the next step. UPLC-MS: MS 309.3 (M+H$^+$); UPLC rt 0.73 min.

Step 2. ethyl 2-((E)-((Z)-2-(5-methoxy-3,4-dihydroisoquinolin-1(2H)-ylidene)-1-(3-methoxyphenyl)ethylidene)amino)acetate. 1-2. A mixture of 1-1 (5.8 g, 18.81 mmol) and glycine ethyl ester hydrochloride (13.1 g, 94 mmol) in EtOH (200 mL) was heated to 100° C. and stirred for 2 h. The reaction was then cooled to RT and the mixture was concentrated in vacuo. The residue obtained was taken up in DCM and washed with a 1 M aq. solution of NaOH. The org. layer was then dried over $Na_2SO_4$, filtered and concentrated in vacuo to give the title compound (7.0 g) as a brown oil that was used as it is in the next step. UPLC-MS: MS 395.3 (M+H$^+$); UPLC rt 0.80 min.

Step 3. 9-methoxy-2-(3-methoxyphenyl)-7,8-dihydro-[1,4]diazepino[7,1-a]isoquinolin-5(4H)-one. Example 1. A solution of 1-2 (6.9 g, 17.5 mmol) in EtOH (200 mL) was treated with a solution of NaOEt in EtOH (21 wt. %, 32.7 mL, 87 mmol) and the mixture was stirred at RT for 2 h. The reaction was then concentrated in vacuo and the residue taken up in DCM. The organic phase was washed with a 1N aq. solution of NaOH, dried over $Na_2SO_4$, filtered and concentrated in vacuo. The crude product obtained was purified by flash chromatography (SiO$_2$, hexan to hexane/AcOEt 1:1) to give a red solid that was recrystallized from heptane/AcOEt to give the title compound (1.37 g) as a beige solid. MS 349.2 (M+H$^+$). UPLC (2 min) rt 1.147 min. $^1$H NMR (400 MHz, CHLOROFORM-d): δ ppm 2.87-2.97 (m, 2H); 3.86 (s, 3H); 3.88 (s, 3H); 3.90-3.96 (br s, 2H); 4.45-4.56 (br s, 2H); 6.94 (d, J=7.82 Hz, 1 H); 7.00 (dd, J=8.02, 2.93 Hz, 1 H); 7.04 (s, 1 H); 7.29-7.40 (m, 4 H); 7.42-7.52 (m, 1 H).

Following the procedure described above for Example 1 and substituting the appropriate reagents, starting materials and purification methods known to those skilled in the art, the following compounds of the present invention were prepared:

Example 2

9-chloro-2-(thiophen-2-yl)-7,8-dihydro-[1,4]diazepino[7,1-a]isoquinolin-5(4H)-one UPLC-MS: MS 329.1 (M+H$^+$); UPLC rt 1.09 min.

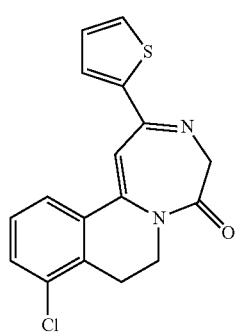

Example 3

9-chloro-2-(3-methoxyphenyl)-7,8-dihydro-[1,4]diazepino[7,1-a]isoquinolin-5(4H)-one MS 353.1 (M+H$^+$). UPLC (3.5 min) rt 1.195 min.

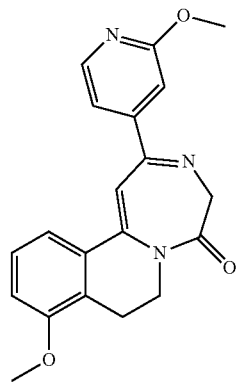 [SMILES: COc1cc(C2=NCC(=O)N3CCc4c(OC)cccc4C3=C2)ccn1]

Example 4

2-(thiophen-2-yl)-9-(trifluoromethyl)-7,8-dihydro-[1,4]diazepino[7,1-a]isoquinolin-5(4H)-one UPLC-MS: MS 363.2 (M+H$^+$); UPLC rt 1.12 min.

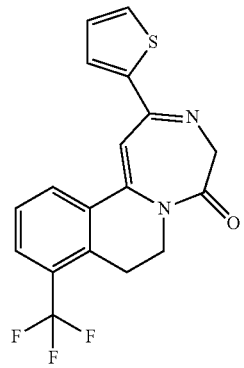 [SMILES: O=C1CN=C(c2cccs2)C=C2c3cccc(C(F)(F)F)c3CCN12]

Example 5

9-methoxy-2-(thiophen-2-yl)-7,8-dihydro-[1,4]diazepino[7,1-a]isoquinolin-5(4H)-one UPLC-MS: MS 325.2 (M+H$^+$); UPLC rt 0.95 min.

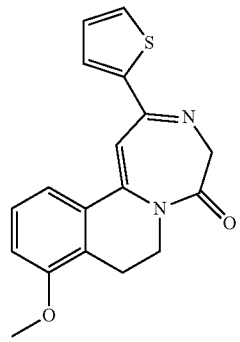 [SMILES: COc1cccc2c1CCN1C(=O)CN=C(c3cccs3)C=C21]

Example 6

9-chloro-2-(2-methoxypyridin-4-yl)-7,8-dihydro-[1,4]diazepino[7,1-a]isoquinolin-5(4H)-one UPLC-MS: MS 354.3 (M+H⁺); UPLC rt 1.11 min.

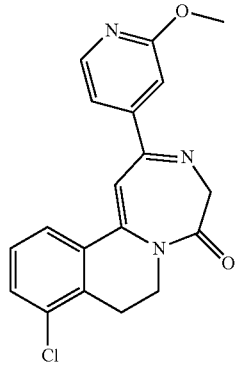 [SMILES: COc1cc(C2=NCC(=O)N3CCc4c(Cl)cccc4C3=C2)ccn1]

Example 7

9-methoxy-2-(5-methylfuran-2-yl)-7,8-dihydro-[1,4]diazepino[7,1-a]isoquinolin-5(4H)-one MS 323.2 (M+H⁺). UPLC (3.5 min) rt 0.896 min.

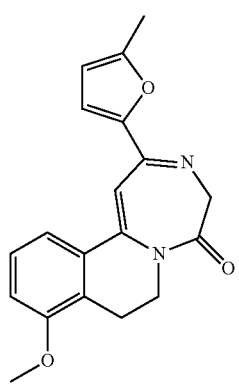 [SMILES: COc1cccc2c1CCN1C(=O)CN=C(c3ccc(C)o3)C=C21]

Example 8

9-methoxy-2-(2-methoxypyridin-4-yl)-7,8-dihydro-[1,4]diazepino[7,1-a]isoquinolin-5(4H)-one MS 350.2 (M+H⁺). UPLC (2 min) rt 1.098.

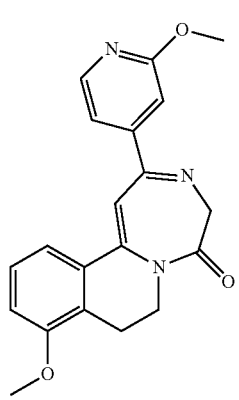 [SMILES: COc1cc(C2=NCC(=O)N3CCc4c(OC)cccc4C3=C2)ccn1]

Example 9

9-methoxy-2-(6-methoxypyridin-2-yl)-7,8-dihydro-[1,4]diazepino[7,1-a]isoquinolin-5(4H)-one UPLC-MS: MS 350.2 (M+H⁺); UPLC rt 1.12 min.

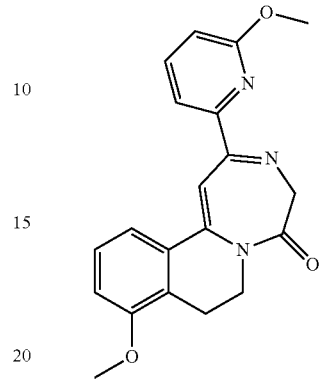

Example 10

2-(2-ethylpyridin-4-yl)-9-methoxy-7,8-dihydro-[1,4]diazepino[7,1-a]isoquinolin-5(4H)-one UPLC-MS: MS 348.5 (M+H⁺); UPLC rt 1.04 min.

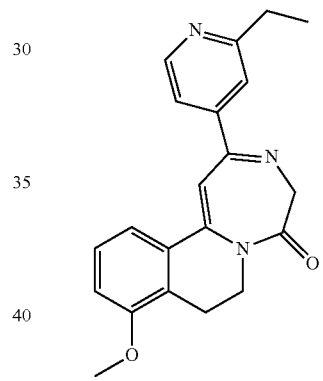

Example 11

9-methoxy-2-(1-methyl-1H-pyrazol-3-yl)-7,8-dihydro-[1,4]diazepino[7,1-a]isoquinolin-5(4H)-one UPLC-MS: MS 323.1 (M+H⁺); UPLC rt 0.77 min.

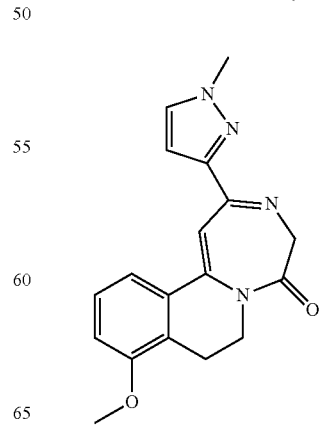

Example 12

9-methoxy-2-(3-(2-methoxyethoxy)phenyl)-7,8-dihydro-[1,4]diazepino[7,1-a]isoquinolin-5(4H)-one UPLC-MS: MS 393.5 (M+H⁺); UPLC rt 0.89 min.

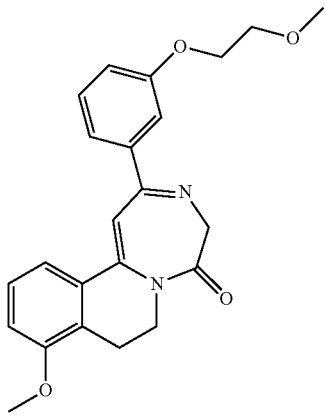 [SMILES: COCCOc1cccc(C2=NCC(=O)N3CCc4c(OC)cccc4C3=C2)c1]

Example 13

10-chloro-9-methoxy-2-(3-methoxyphenyl)-7,8-dihydro-[1,4]diazepino[7,1-a]isoquinolin-5(4H)-one UPLC-MS: MS 383.1 (M+H⁺); UPLC rt 1.06 min.

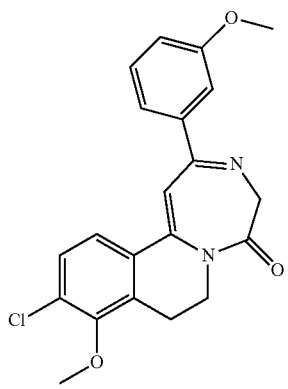 [SMILES: COc1cccc(C2=NCC(=O)N3CCc4c(ccc(Cl)c4OC)C3=C2)c1]

Example 14

11-chloro-9-methoxy-2-(3-methoxyphenyl)-7,8-dihydro-[1,4]diazepino[7,1-a]isoquinolin-5(4H)-one UPLC-MS: MS383.1 (M+H⁺); UPLC rt 1.35 min.

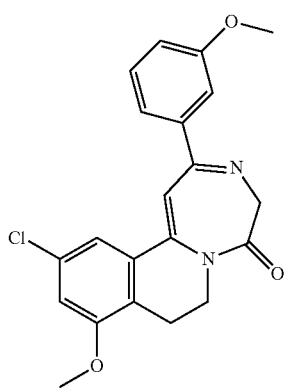 [SMILES: COc1cccc(C2=NCC(=O)N3CCc4c(OC)cc(Cl)cc4C3=C2)c1]

Example 15

2-(3-ethoxyphenyl)-9-methoxy-7-methyl-7,8-dihydro-[1,4]diazepino[7,1-a]isoquinolin-5(4H)-one UPLC-MS: MS 377.2 (M+H); UPLC rt 1.12 min.

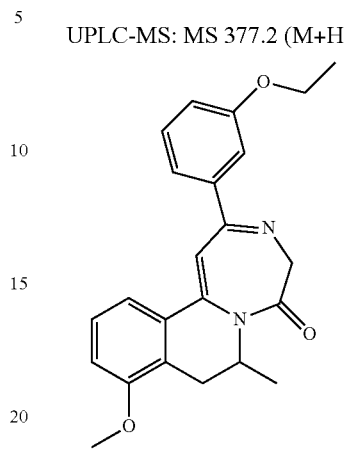

Example 16

9-methoxy-2-(3-(trifluoromethyl)phenyl)-7,8-dihydro-[1,4]diazepino[7,1-a]isoquinolin-5(4H)-one MS 387.2 (M+H⁺). UPLC (3.5 min) rt 1.477 min.

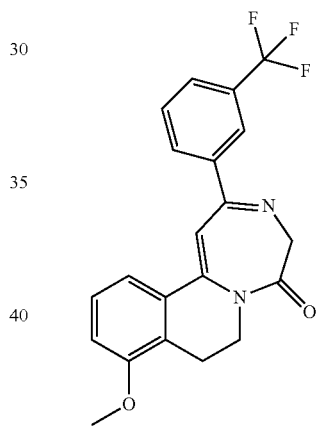

Example 17

9-methoxy-2-(4-methoxyphenyl)-7,8-dihydro-[1,4]diazepino[7,1-a]isoquinolin-5(4H)-one UPLC-MS: MS 349.2 (M+H⁺); UPLC rt 0.84 min.

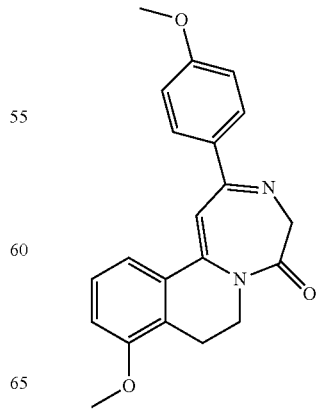

Example 18

9-methoxy-2-(5-methoxy-2-methylphenyl)-7,8-dihydro-[1,4]diazepino[7,1-a]isoquinolin-5(4H)-one MS 363.2 (M+H⁺). UPLC (3.5 min) rt 1.115 min.

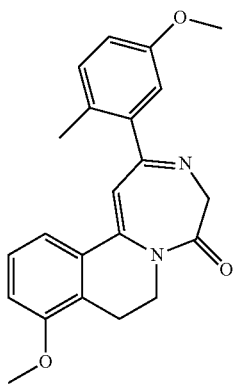 [SMILES: COc1ccc(C)c(C2=NCC(=O)N3CCc4c(OC)cccc4C3=C2)c1]

Example 19

9-fluoro-2-(thiophen-2-yl)-7,8-dihydro-[1,4]diazepino[7,1-a]isoquinolin-5(4H)-one UPLC-MS: MS 313.2 (M+H⁺); UPLC rt 0.97 min.

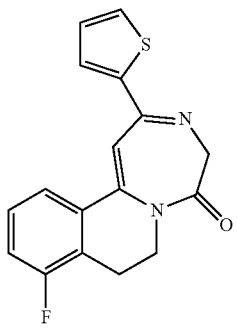 [SMILES: O=C1CN=C(c2cccs2)C=C2c3cccc(F)c3CCN12]

Example 20

9-bromo-2-(3-methoxyphenyl)-7,8-dihydro-[1,4]diazepino[7,1-a]isoquinolin-5(4H)-one UPLC-MS: MS 397.2 (M+H⁺); UPLC rt 1.09 min.

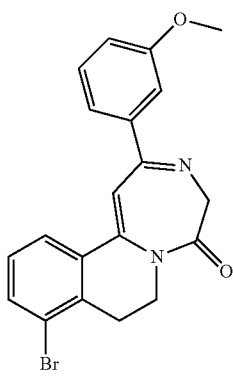

Example 21

2-(2-(dimethylamino)pyridin-4-yl)-9-methoxy-7,8-dihydro-[1,4]diazepino[7,1-a]isoquinolin-5(4H)-one UPLC-MS: MS 363.1 (M+H⁺); UPLC rt 0.85 min.

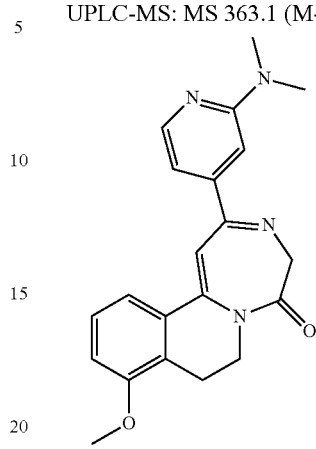

Example 22

2-(2-methoxypyridin-4-yl)-9-morpholino-7,8-dihydro-[1,4]diazepino[7,1-a]isoquinolin-5(4H)-one UPLC-MS: MS 405.1 (M+H⁺); UPLC rt 0.96 min.

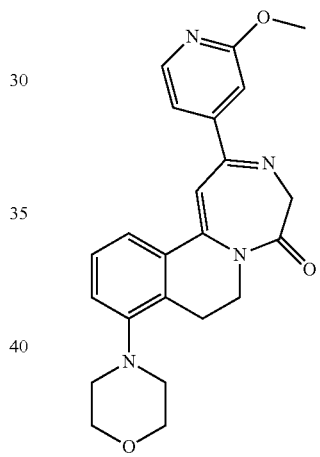

Example 23

2-(5-methylfuran-2-yl)-9-morpholino-7,8-dihydro-[1,4]diazepino[7,1-a]isoquinolin-5(4H)-one UPLC-MS: MS 378.1 (M+H⁺); UPLC rt 0.70 min.

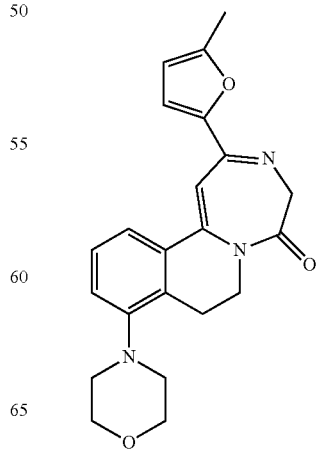

Example 24

2-(1-methyl-1H-pyrazol-3-yl)-9-morpholino-7,8-dihydro-[1,4]diazepino[7,1-a]isoquinolin-5(4H)-one UPLC-MS: MS 378.1 (M+H⁺); UPLC rt 0.64 min.

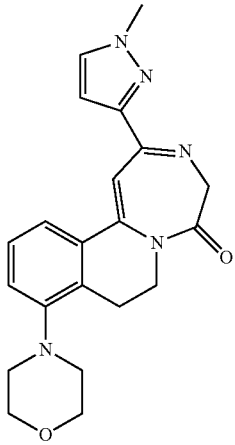 [SMILES: Cn1ccc(C2=NCC(=O)N3CCc4c(cccc4N4CCOCC4)C3=C2)n1]

Example 25

2-(1-methyl-1H-pyrazol-4-yl)-9-morpholino-7,8-dihydro-[1,4]diazepino[7,1-a]isoquinolin-5(4H)-one MS 378.2 (M+H⁺). UPLC (3.5 min) rt 0.771 min.

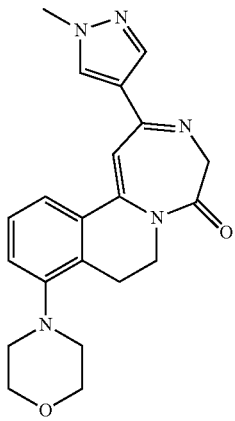 [SMILES: Cn1cc(C2=NCC(=O)N3CCc4c(cccc4N4CCOCC4)C3=C2)cn1]

Example 26

9-(2-hydroxypropan-2-yl)-2-(3-methoxyphenyl)-7,8-dihydro-[1,4]diazepino[7,1-a]isoquinolin-5(4H)-one UPLC-MS: MS 377.2 (M+H⁺); UPLC rt 0.84 min.

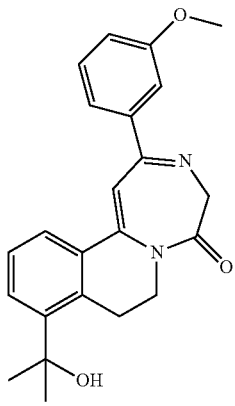 [SMILES: COc1cccc(C2=NCC(=O)N3CCc4c(cccc4C(C)(C)O)C3=C2)c1]

Example 27

9-(2-hydroxypropan-2-yl)-2-(1-methyl-1H-pyrazol-3-yl)-7,8-dihydro-[1,4]diazepino[7,1-a]isoquinolin-5(4H)-one UPLC-MS: MS 351.1 (M+H⁺); UPLC rt 0.65 min.

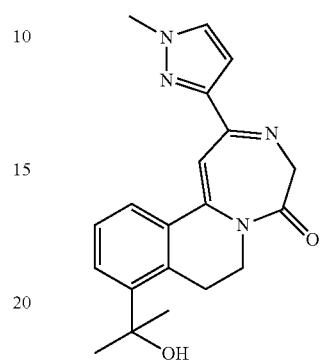

Example 28

2-(furan-2-yl)-9-(pyridin-4-yl)-7,8-dihydro-[1,4]diazepino[7,1-a]isoquinolin-5(4H)-one UPLC-MS: MS 356.0 (M+H⁺); UPLC rt 0.65 min.

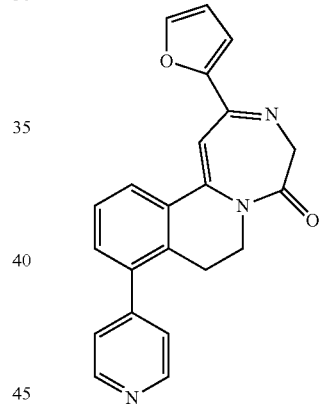

Example 29

9-bromo-2-(thiophen-2-yl)-7,8-dihydro-[1,4]diazepino[7,1-a]isoquinolin-5(4H)-one UPLC-MS: MS 373.1 (M+H⁺); UPLC rt 1.09 min.

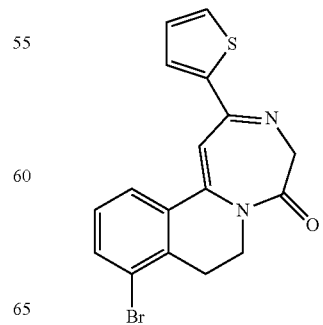

Example 30

9-iodo-2-(3-methoxyphenyl)-7,8-dihydro-[1,4]diaz-epino[7,1-a]isoquinolin-5(4H)-one UPLC-MS: MS 445.4 (M+H⁺); UPLC rt 1.32 min.

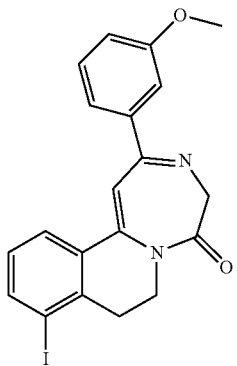 [SMILES: COc1cccc(C2=NCC(=O)N3CCc4c(I)cccc4C3=C2)c1]

Example 31

9-iodo-2-(1-methyl-1H-pyrazol-3-yl)-7,8-dihydro-[1,4]diazepino[7,1-a]isoquinolin-5(4H)-one UPLC-MS: MS 419.0 (M+H⁺); UPLC rt 1.01 min.

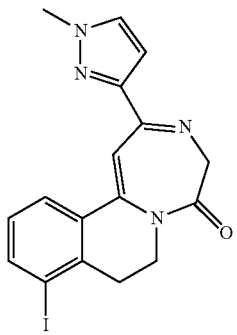 [SMILES: Cn1ccc(C2=NCC(=O)N3CCc4c(I)cccc4C3=C2)n1]

Example 32

9-iodo-2-(1-methyl-1H-pyrazol-4-yl)-7,8-dihydro-[1,4]diazepino[7,1-a]isoquinolin-5(4H)-one UPLC-MS: MS 419.1 (M+H⁺); UPLC rt 0.75 min.

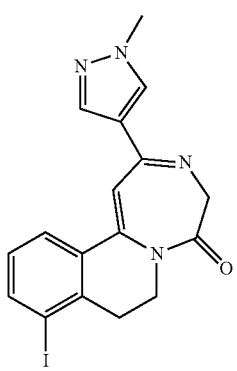 [SMILES: Cn1cc(C2=NCC(=O)N3CCc4c(I)cccc4C3=C2)cn1]

Example 33

9-iodo-2-(2-methoxypyridin-4-yl)-7,8-dihydro-[1,4]diazepino[7,1-a]isoquinolin-5(4H)-one UPLC-MS: MS 446.2 (M+H⁺); UPLC rt 1.13 min.

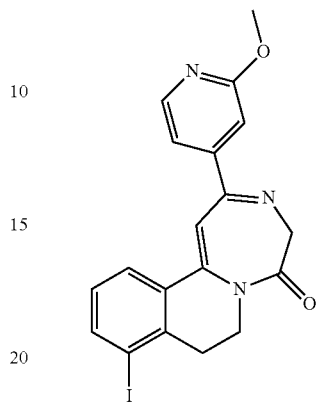

Example 34

2-(furan-3-yl)-9-iodo-7,8-dihydro-[1,4]diazepino[7,1-a]isoquinolin-5(4H)-one

UPLC-MS: MS 405.0 (M+H⁺); UPLC rt 0.94 min.

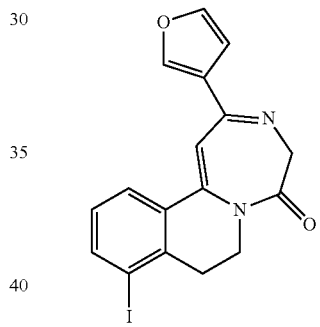

Example 35

9-iodo-2-(1-isopropyl-1H-pyrazol-4-yl)-7,8-dihydro-[1,4]diazepino[7,1-a]isoquinolin-5(4H)-one UPLC-MS: MS 447.2 (M+H⁺); UPLC rt 0.86 min.

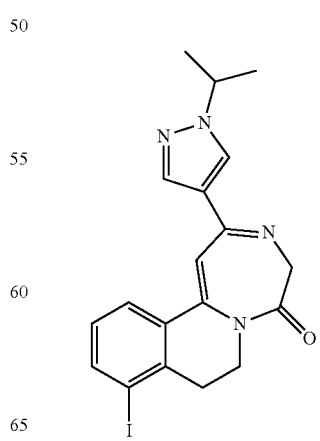

Example 36

9-iodo-2-(1-methyl-1H-imidazol-4-yl)-7,8-dihydro-[1,4]diazepino[7,1-a]isoquinolin-5(4H)-one UPLC-MS: MS 419.0 (M+H⁺); UPLC rt 0.69 min.

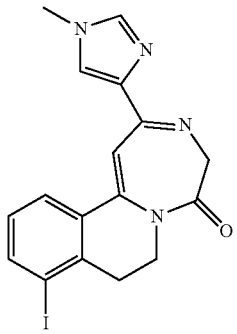 [SMILES: Cn1cnc(C2=NCC(=O)N3CCc4c(I)cccc4C3=C2)c1]

Example 36a 9-methoxy-2-(4-methyl-3,4-dihydro-2H-pyrido[3,2-b][1,4]oxazin-7-yl)-7,8-dihydro-[1,4]diazepino[7,1-a]isoquinolin-5(4H)-one UPLC-MS: MS 391.1 (M+H⁺); UPLC rt 0.95 min.

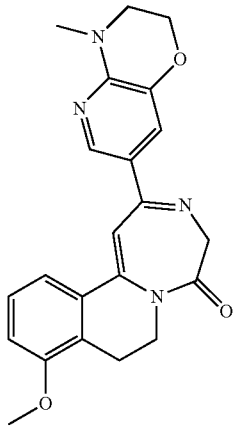 [SMILES: COc1cccc2c1CCN1C(=O)CN=C(c3cnc4c(c3)OCCN4C)C=C21]

Example 37

9-ethyl-2-(3-methoxyphenyl)-7,8-dihydro-[1,4]diazepino[7,1-a]isoquinolin-5(4H)-one

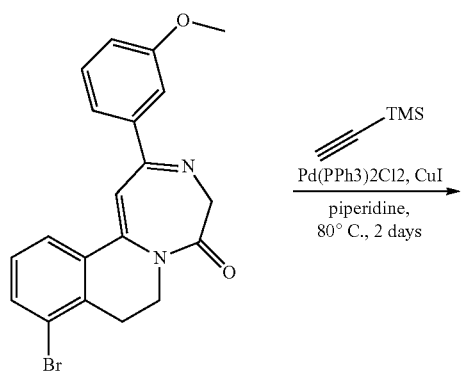

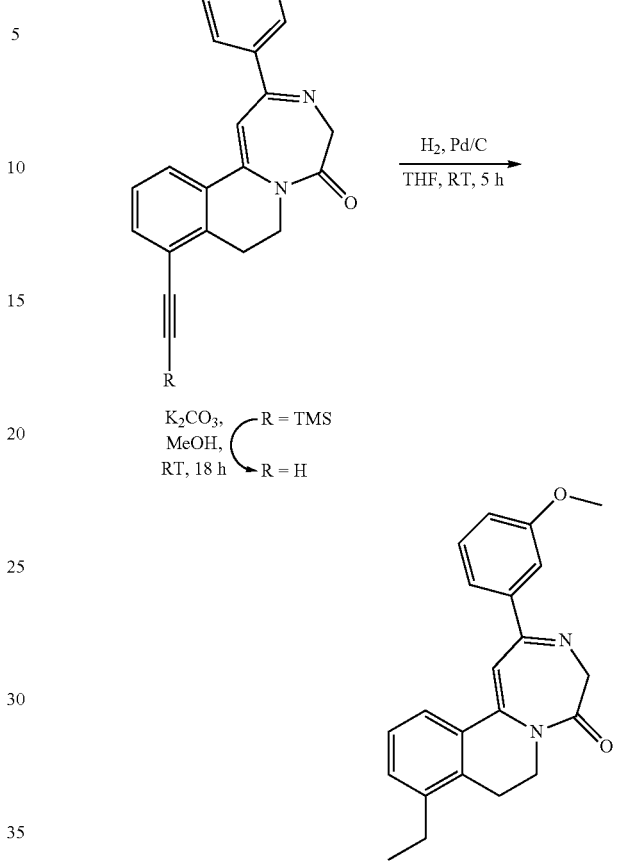

Step 1. 2-(3-methoxyphenyl)-9-((trimethylsilyl)ethynyl)-7,8-dihydro-[1,4]diazepino[7,1-a]isoquinolin-5(4H)-one. 37-1. A mixture of 9-bromo-2-(3-methoxyphenyl)-7,8-dihydro-[1,4]diazepino[7,1-a]isoquinolin-5(4H)-one (Example 20) (1.0 g, 2.52 mmol), Pd(PPh$_3$)$_2$Cl$_2$ (88 mg, 0.13 mmol) and CuI (48 mg, 0.25 mmol) in piperidine (15 mL) was degassed (sonication) with a flux of Ar, and trimethylsilylacetylene (1.06 mL, 7.55 mmol) was then added. The mixture was heated to 80° C. for 18 h. Additional trimethylsilylacetylene (1.00 mL, 7.12 mmol) and Pd(PPh$_3$)$_2$Cl$_2$ (88 mg, 0.13 mmol) were added and the mixture was heated to 80° C. for another 24 h. After cooling to RT, the reaction was diluted with AcOEt, and washed with H$_2$O. The organic layer was dried over Na$_2$SO$_4$, filtered and concentrated in vacuo. Purification by flash chromatography (SiO$_2$, hexane to hexane/AcOEt 1:1) afforded the title compound (700 mg) as a brown solid UPLC-MS: MS 415.3 (M+H⁺); UPLC rt 1.43 min.

Step 2. 9-ethynyl-2-(3-methoxyphenyl)-7,8-dihydro-[1,4]diazepino[7,1-a]isoquinolin-5(4H)-one. 40-2. A solution of 37-1 (700 mg, 1.69 mmol) in MeOH (20 mL) was treated with K$_2$CO$_3$ (467 mg, 3.38 mmol) and the mixture was stirred at RT for 18 h. The mixture was concentrated in vacuo, and the residue taken up in AcOEt and washed with H$_2$O. The organic layer was then dried over Na$_2$SO$_4$, filtered and concentrated in vacuo. The crude product was re-crystallized from heptane/AcOEt to provide the title compound (410 mg) as brown crystals. UPLC-MS: MS 343.3 (M+H+); UPLC rt 1.03 min.

Step 3. 9-ethyl-2-(3-methoxyphenyl)-7,8-dihydro-[1,4]diazepino[7,1-a]isoquinolin-5(4H)-one. Example 37. A mixture of 37-2 (200 mg, 0.58 mmol), Pd/C (10%, 100 mg, 0.94 mmol) in THF (20 mL) was stirred at RT for 5 h under an atmosphere of H₂. The mixture was then filtered and concentrated in vacuo. Purification by flash chromatography (SiO₂, hexane to hexane/AcOEt 1:1) gave the title compound (160 mg) as a yellow solid. MS 347.2 (M+H+). UPLC (2 min) rt 1.263 min. ¹H NMR (400 MHz, CHLOROFORM-d): δ ppm 2.87-2.97 (m, 2H); 3.86 (s, 3H); 3.88 (s, 3H); 3.90-3.96 (br s, 2H); 4.45-4.56 (br s, 2H); 6.94 (d, J=7.82 Hz, 1 H); 7.00 (dd, J=8.02, 2.93 Hz, 1 H); 7.04 (s, 1 H); 7.29-7.40 (m, 4 H); 7.42-7.52 (m, 1 H).

Following the procedure described above for Example 37 and substituting the appropriate reagents, starting materials and purification methods known to those skilled in the art, the following compounds of the present invention were prepared:

Example 38

9-ethynyl-2-(thiophen-2-yl)-7,8-dihydro-[1,4]diazepino[7,1-a]isoquinolin-5(4H)-one MS 319.0 (M+H+). UPLC (2 min) rt 1.086 min.

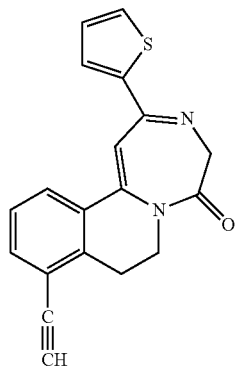 [SMILES: C#Cc1cccc2c1CCN1C(=O)CN=C(c3cccs3)C=C21]

Example 39

5-oxo-2-(thiophen-2-yl)-4,5,7,8-tetrahydro-[1,4]diazepino[7,1-a]isoquinoline-9-carbonitrile

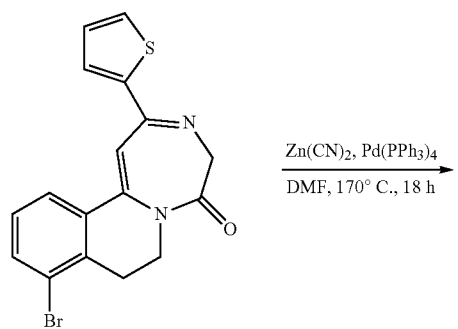

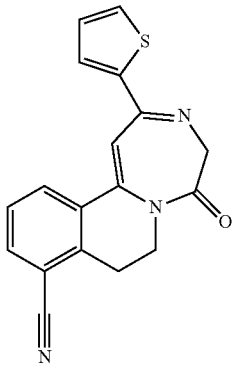

A microwave flask was charged with 9-bromo-2-(thiophen-2-yl)-7,8-dihydro-[1,4]diazepino[7,1-a]isoquinolin-5(4H)-one (Example 29) (145 mg, 0.39 mmol), Zn(CN)₂ (191 mg, 1.63 mmol) and Pd(PPh₃)₄ (47 mg, 0.041 mmol) in DMF (4 mL) was heated to 170° C. for 18 h. The reaction was allowed to cool to RT, taken up in AcOEt and washed with H₂O. The org. layer was dried over Na₂SO₄, filtered and concentrated in vacuo. The crude product was purified by flash chromatography (SiO₂, hexane to hexan/AcOEt 1:1) and prep. HPLC (column: RP-C18 sunfire, 5 μm, 100×300 mm; solvent A: H₂O+0.1% TFA; solvent B CH₃CN; gradient (% B): 10-30% in 16 min; 50 mL/min). The product obtained was passed onto a SPE cartridge to release the free base, and the residue obtained was triturated in heptane/AcOEt to give the title compound (8 mg) as a yellow solid. UPLC-MS: MS 320.2 (M+H⁺); UPLC rt 0.87 min. ¹H NMR (600 MHz, DMSO-d₆): δ ppm 3.07 (t, J=5.55 Hz, 2 H); 3.87 (br. s., 2 H); 4.29 (br. s., 2 H); 7.11 (t, J=4.14 Hz, 1 H); 7.51 (s, 1 H); 7.56 (t, J=7.87 Hz, 1 H); 7.66 (d, J=4.24 Hz, 2 H); 7.93 (d, J=7.47 Hz, 1 H); 8.42 (d, J=8.07 Hz, 1 H).

Following the procedure described above for Example 39 and substituting the appropriate reagents, starting materials and purification methods known to those skilled in the art, the following compounds of the present invention were prepared:

Example 40

2-(1-methyl-1H-pyrazol-3-yl)-5-oxo-4,5,7,8-tetrahydro-[1,4]diazepino[7,1-a]isoquinoline-9-carbonitrile UPLC-MS: MS 318.2 (M+H⁺); UPLC rt 0.66 min.

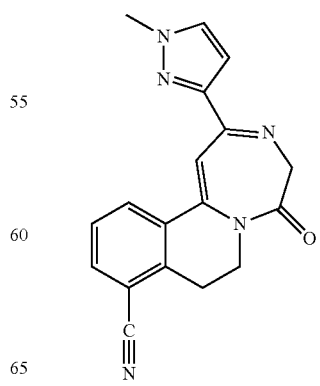

Example 41

2-(3-methoxyphenyl)-9-morpholino-7,8-dihydro-[1,4]diazepino[7,1-a]isoquinolin-5(4H)-one

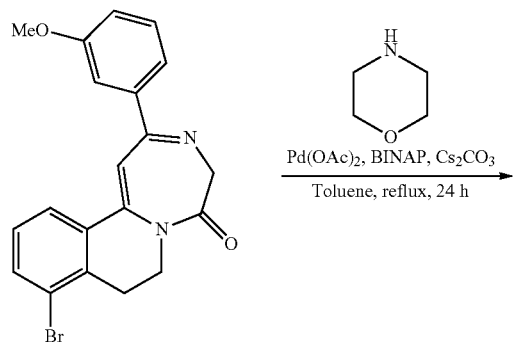

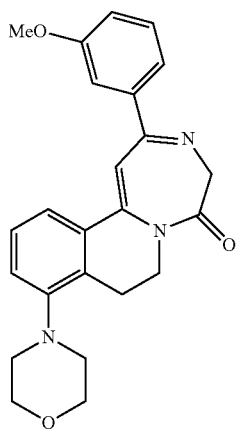

A solution of Pd(OAc)₂ (4.0 mg, 0.017 mmol), and BINAP (10.5 mg, 0.017 mmol) in toluene (5 mL) was stirred at RT under N₂ for 10 min, and then transferred to a mixture of 9-iodo-2-(3-methoxyphenyl)-7,8-dihydro-[1,4]diazepino[7,1-a]isoquinolin-5(4H)-one (Example 30) (150 mg, 0.34 mmol), morpholine (35 µL, 0.41 mmol) and Cs₂CO₃ (550 mg, 1.69 mmol) in toluene (5 mL). The reaction was stirred at RT under N₂ for 5 min, and then heated to reflux for 24 h. The mixture was allowed to cool to RT, and then filtered and concentrated in vacuo. The crude product was purified by flash chromatography (SiO₂, hexane to hexane/AcOEt 1:1) and the brown solid obtained was recrystallized from hexane to give the title compound (83 mg) as a beige solid. UPLC-MS: MS 404.5 (M+H⁺); UPLC rt 1.09 min. ¹H NMR (400 MHz, CHLOROFORM-d): δ ppm 2.84-3.03 (m, 6 H); 3.76-3.95 (m, 6 H); 3.87 (s, 3H); 4.51 (br. s., 2 H); 6.92 (s, 1 H); 7.00 (dd, J=8.21, 2.74 Hz, 1 H); 7.14 (d, J=7.82 Hz, 1 H); 7.28-7.51 (m, 5 H).

Following the procedure described above for Example 41 and substituting the appropriate reagents, starting materials and purification methods known to those skilled in the art, the following compounds of the present invention were prepared:

Example 42

2-(1-isopropyl-1H-pyrazol-4-yl)-9-(1H-pyrazol-1-yl)-7,8-dihydro-[1,4]diazepino[7,1-a]isoquinolin-5(4H)-one UPLC-MS: MS 387.1 (M+H⁺); UPLC rt 0.70 min.

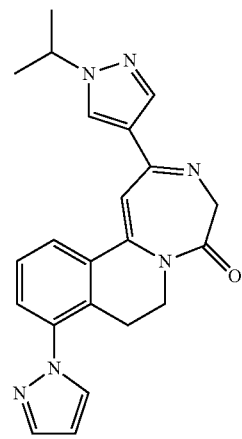 [SMILES: CC(C)n1cc(C2=NCC(=O)N3CCc4c(cccc4-n4cccn4)C3=C2)cn1]

Example 43

9-((dimethylamino)methyl)-2-(3-methoxyphenyl)-7,8-dihydro-[1,4]diazepino[7,1-a]isoquinolin-5(4H)-one

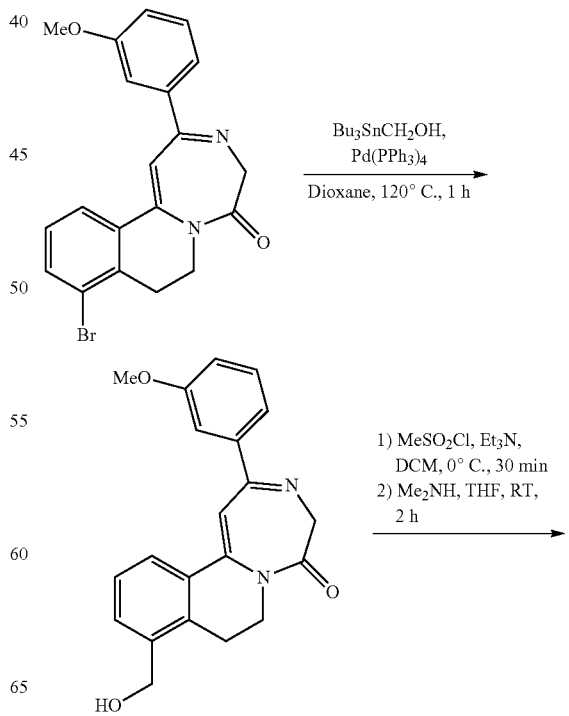

-continued

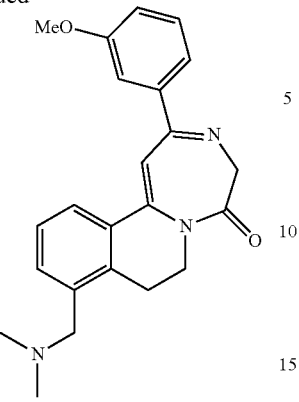

Step 1. 9-(hydroxymethyl)-2-(3-methoxyphenyl)-7,8-dihydro-[1,4]diazepino[7,1-a]isoquinolin-5(4H)-one. 43-1. A mixture of -bromo-2-(3-methoxyphenyl)-7,8-dihydro-[1,4]diazepino[7,1-a]isoquinolin-5(4H)-one (Example 20) (1.50 g, 3.78 mmol), (tributylstannyl)methanol (1.52 g, 4.72 mmol) and Pd(PPh$_3$)$_4$ (436 mg, 0.38 mmol) in dioxane (15 mL) was heated to 120° C. for 1 h in a microwave reactor. The reaction was then filtered and the filtrate concentrated in vacuo. The residue obtained was purified by flash chromatography (SiO$_2$, DCM to DCM/MeOH 95:5) to give a beige solid, which was then triturated in Et$_2$O. The suspension was filtered and the filter cake was dried in vacuo to give the title compound (652 mg) as a beige solid. UPLC-MS: MS 349.4 (M+H$^+$); UPLC rt 0.83 min. $^1$H NMR (400 MHz, CHLOROFORM-d): δ ppm 2.06 (br s, 1 H); 3.01 (t, J=6.06 Hz, 2 H); 3.85 (s, 3 H); 3.92 (t, J=6.26 Hz, 2 H); 4.49 (br. s., 2 H); 4.76 (s, 2 H); 6.96 (s, 1 H); 7.00 (dd, J=8.02, 2.54 Hz, 1 H); 7.27-7.41 (m, 3 H); 7.41-7.52 (m, 2 H); 7.66 (d, J=7.82 Hz, 1 H).

Step 2: 9-((dimethylamino)methyl)-2-(3-methoxyphenyl)-7,8-dihydro-[1,4]diazepino[7,1-a]isoquinolin-5(4H)-one. Example 43. A solution of 43-1 (200 mg, 0.57 mmol) and Et$_3$N (0.12 mL, 0.86 mmol) in DCM (10 mL) under N$_2$ was cooled to 0° C. and methanesulfonyl chloride (54 μL, 0.69 mmol) was added dropwise. The mixture was stirred at 0° C. for 30 min and then diluted with DCM and washed with H$_2$O. The org. layer was dried over Na$_2$SO$_4$, filtered and concentrated in vacuo to afford a yellow oil that as diluted in THF (5 mL). A 2M solution of Me$_2$NH in THF (0.29 mL, 0.58 mmol) was then added dropwise and the mixture was stirred at RT for 2 h. The mixture was then concentrated in vacuo and the residue obtained was purified by flash chromatography (SiO$_2$, hexane to hexane/AcOEt 1:1, followed by DCM to DCM/MeOH 95:5) to give a brown oil that solidify upon standing. Recrystallization from heptane afforded the title compound (49 mg) as a beige solid. UPLC-MS: MS 376.5 (M+H$^+$); UPLC rt 0.66 min. $^1$H NMR (400 MHz, CHLOROFORM-d): δ ppm 2.24 (s, 6 H); 3.06 (t, J=5.87 Hz, 2 H); 3.43 (s, 2 H); 3.85 (s, 3 H); 3.90 (t, J=6.26 Hz, 2 H); 4.50 (br. s., 2 H); 6.96 (s, 1 H); 6.99 (dd, J=8.02, 2.54 Hz, 1 H); 7.27-7.46 (m, 5 H); 7.62 (d, J=7.43 Hz, 1 H).

Following the procedure described above for Example 43 and substituting the appropriate reagents, starting materials and purification methods known to those skilled in the art, the following compounds of the present invention were prepared:

Example 44

9-((2-methoxyethoxy)methyl)-2-(3-methoxyphenyl)-7,8-dihydro-[1,4]diazepino[7,1-a]isoquinolin-5(4H)-one UPLC-MS: MS 407.1 (M+H$^+$); UPLC rt 0.86 min.

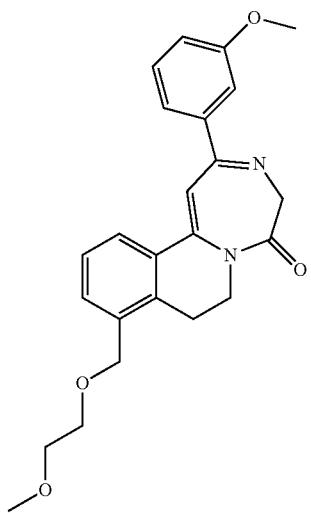 [SMILES: COCCOCc1cccc2c1CCN1C(=O)CN=C(c3cccc(OC)c3)C=C21]

Example 45

9-(hydroxymethyl)-2-(1-methyl-1H-pyrazol-3-yl)-7,8-dihydro-[1,4]diazepino[7,1-a]isoquinolin-5(4H)-one UPLC-MS: MS 323.1 (M+H$^+$); UPLC rt 0.52 min.

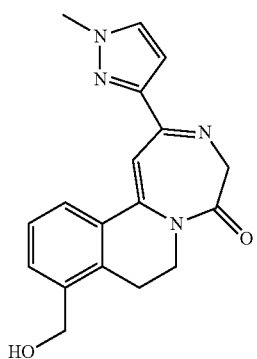 [SMILES: Cn1ccc(C2=NCC(=O)N3CCc4c(CO)cccc4C3=C2)n1]

Example 46

9-(hydroxymethyl)-2-(1-methyl-1H-pyrazol-4-yl)-7,8-dihydro-[1,4]diazepino[7,1-a]isoquinolin-5(4H)-one UPLC-MS: MS 323.1 (M+H+); UPLC rt 0.49 min.

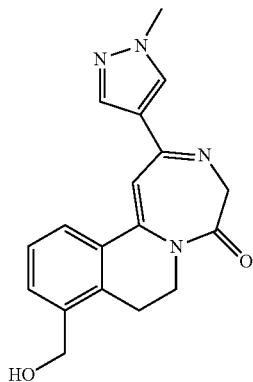 [SMILES: Cn1cc(C2=NCC(=O)N3CCc4c(CO)cccc4C3=C2)cn1]

Example 47

9-(1-methoxyethyl)-2-(1-methyl-1H-pyrazol-3-yl)-7,8-dihydro-[1,4]diazepino[7,1-a]isoquinolin-5(4H)-one

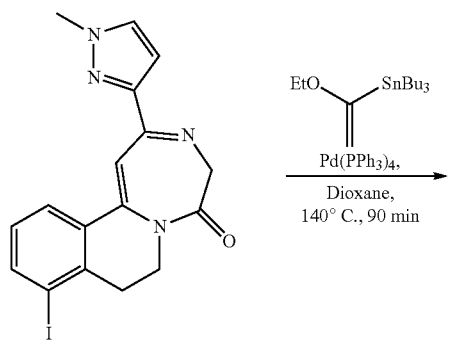

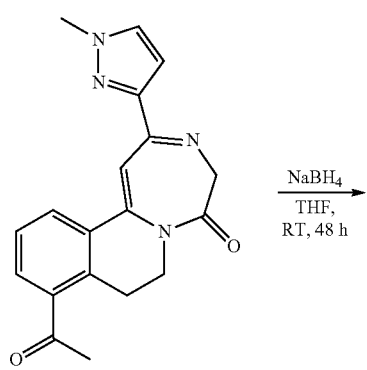

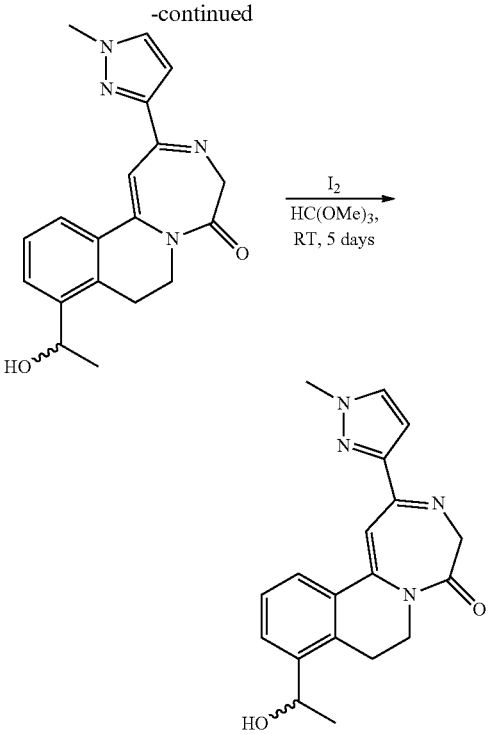

Step 1. 9-acetyl-2-(1-methyl-1H-pyrazol-3-yl)-7,8-dihydro-[1,4]diazepino[7,1-a]isoquinolin-5(4H)-one. 47-1. A mixture of 9-iodo-2-(1-methyl-1H-pyrazol-3-yl)-7,8-dihydro-[1,4]diazepino[7,1-a]isoquinolin-5(4H)-one (Example 31) (2.0 g, 4.78 mmol), tributyl(1-ethoxyvinyl)stannane (2.02 mL, 5.98 mmol) and Pd(PPh$_3$)$_4$ (276 mg, 0.24 mmol) in 1,4-dioxane (15 mL) was heated to 140° C. for 90 min. The mixture was then filtered and concentrated in vacuo and the residue obtained was purified by flash chromatography (SiO$_2$, DCM to DCM/MeOH 95:5). The brown oil obtained was taken up in THF (100 mL) and treated with a 0.1 N aq. solution of HCl (48 mL, 4.78 mmol). The mixture was stirred at RT for 90 min. The mixture was then diluted with AcOEt and washed with a saturated aq. solution of NaHCO$_3$. The organic layer was dried over Na$_2$SO$_4$, filtered and concentrated in vacuo. The residue obtained was purified by flash chromatography (SiO$_2$, DCM to DCM/MeOH 95:5) to give a brown oil that was suspended in Et$_2$O. The suspension was filtered and the filter cake was dried in vacuo to give the title compound (912 mg) as a yellow solid. UPLC-MS: MS 335.0 (M+H+); UPLC rt 0.62 min. $^1$H NMR (400 MHz, CHLOROFORM-d): δ ppm 2.62 (s, 3 H); 3.24 (t, J=6.06 Hz, 2 H); 3.81 (t, J=6.45 Hz, 2 H); 3.92 (s, 3 H); 4.49 (br. s., 2 H); 6.81 (br. s., 1 H); 7.17 (s, 1 H); 7.34-7.45 (m, 2 H); 7.77 (d, J=7.82 Hz, 1 H); 7.84 (d, J=7.82 Hz, 1 H).

Step 2. 9-(1-hydroxyethyl)-2-(1-methyl-1H-pyrazol-3-yl)-7,8-dihydro-[1,4]diazepino[7,1-a]isoquinolin-5(4H)-one. 47-2. A solution of 47-1 (400 mg, 1.20 mmol) in THF (30 mL) was treated with NaBH$_4$ (23 mg, 0.60 mmol) and the mixture was stirred at RT for 48 h. The mixture was then diluted with AcOEt, and washed with H$_2$O. The org. phase was dried over Na$_2$SO$_4$, filtered and concentrated in vacuo. The residue obtained was purified by flash chromatography (SiO$_2$, DCM to DCM/MeOH 95:5) to afford a yellow oil that was suspended in Et$_2$O. The suspension was filtered and the filter cake was dried on vacuo to give the title compound (145 mg) as a light yellow solid. UPLC-MS: MS 337.3 (M+H+); UPLC rt 0.60 min. $^1$H NMR (400 MHz, CHLOROFORM-d): δ ppm 1.49 (d, J=6.26 Hz, 3 H); 1.82-1.96 (m, 1 H); 2.86-3.09 (m, 2 H); 3.75-3.99 (m, 2 H); 3.92 (s, 3 H); 4.48 (d, J=12.12

Hz, 2 H); 5.17 (d, J=3.52 Hz, 1 H); 6.82 (br. s., 1 H); 7.19 (s, 1 H); 7.32-7.40 (m, 2 H); 7.61 (d, J=7.82 Hz, 1 H); 7.64 (d, J=7.82 Hz, 1 H).

Step 3. 9-(1-methoxyethyl)-2-(1-methyl-1H-pyrazol-3-yl)-7,8-dihydro-[1,4]diazepino[7,1-a]isoquinolin-5(4H)-one. Example 47. A solution of 47-2 (120 mg, 0.36 mmol) in trimethylorthoformate (2.0 mL, 18.1 mmol) was treated with I₂ (55 mg, 0.22 mmol) and the mixture was stirred at RT for 5 days. The mixture was then taken up in DCM and washed with an aq. saturated solution of Na₂S₂O₃. The org. phase was then dried over Na₂SO₄, filtered and concentrated in vacuo. Purification by flash chromatography (SiO₂, DCM to DCM/MeOH 9:1) gave a yellow oil that re-crystallized from heptane to give the title compound (79 mg) as a white solid. UPLC-MS: MS 351.4 (M+H⁺); UPLC rt 0.73 min. ¹H NMR (400 MHz, CHLOROFORM-d): δ ppm 1.42 (d, J=6.65 Hz, 3 H); 2.91-3.05 (m, 2 H); 3.25 (s, 3 H); 3.87 (t, J=6.26 Hz, 2 H); 3.92 (s, 3 H); 4.48 (br. s., 2 H); 4.56 (q, J=6.65 Hz, 1 H); 6.81 (br. s., 1 H); 7.19 (s, 1 H); 7.31-7.39 (m, 2 H); 7.47 (d, J=7.82 Hz, 1 H); 7.63 (d, J=7.82 Hz, 1 H).

Following the procedure described above for Example 47 and substituting the appropriate reagents, starting materials and purification methods known to those skilled in the art, the following compounds of the present invention were prepared:

Example 48

9-acetyl-2-(3-methoxyphenyl)-7,8-dihydro-[1,4]diazepino[7,1-a]isoquinolin-5(4H)-one UPLC-MS: MS 361.1 (M+H⁺); UPLC rt 0.90 min.

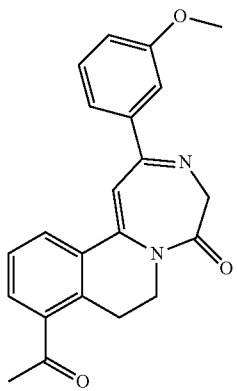 [SMILES: COc1cccc(C2=NCC(=O)N3CCc4c(C(C)=O)cccc4C3=C2)c1]

Example 49

2-(3-methoxyphenyl)-9-phenyl-7,8-dihydro-[1,4]diazepino[7,1-a]isoquinolin-5(4H)-one

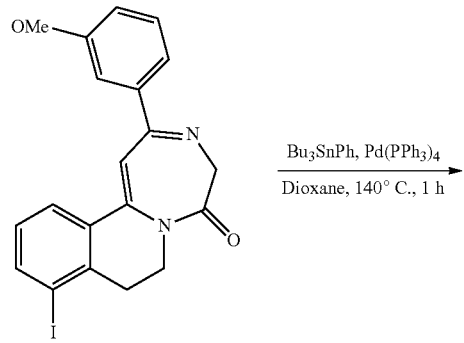

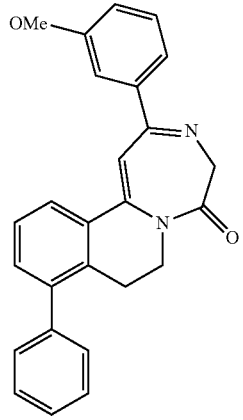

A mixture of 9-iodo-2-(3-methoxyphenyl)-7,8-dihydro-[1,4]diazepino[7,1-a]isoquinolin-5(4H)-one (Example 30) (250 mg, 0.56 mmol), tributyl(phenyl)stannane (202 μL, 1.10 mmol) and Pd(PPh₃)₄ (33 mg, 0.03 mmol) in 1,4-dioxane (4 mL) was heated in a microwave reactor at 140° C. for 1 h. The mixture was then filtered and concentrated in vacuo. The crude product obtained was purified by flash chromatography (SiO₂, hexane to hexane/AcOEt 3:1) to give a yellow oil that was recrystallized from heptane to afford the title compound (144 mg) as white solid. UPLC-MS: MS 395.1 (M+H⁺); UPLC rt 1.20 min. ¹H NMR (400 MHz, CHLOROFORM-d): δ ppm 2.90 (t, J=6.06 Hz, 2 H); 3.79 (t, J=6.26 Hz, 2 H); 3.86 (s, 3 H); 4.53 (br. s., 2 H); 6.97 (s, 1 H); 6.97-7.04 (m, 1 H); 7.28-7.37 (m, 3 H); 7.37-7.51 (m, 7 H); 7.68 (t, J=4.50 Hz, 1 H).

Following the procedure described above for Example 49 and substituting the appropriate reagents, starting materials and purification methods known to those skilled in the art, the following compounds of the present invention were prepared:

Example 50

2-(2-methoxypyridin-4-yl)-9-(pyridin-2-yl)-7,8-dihydro-[1,4]diazepino[7,1-a]isoquinolin-5(4H)-one UPLC-MS: MS 397.1 (M+H⁺); UPLC rt 0.95 min.

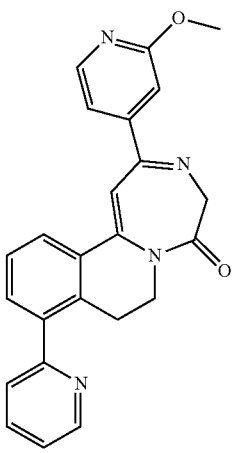 [SMILES: COc1cc(C2=NCC(=O)N3CCc4c(cccc4-c4ccccn4)C3=C2)ccn1]

Example 51

2-(furan-3-yl)-9-(pyridin-4-yl)-7,8-dihydro-[1,4]diazepino[7,1-a]isoquinolin-5(4H)-one UPLC-MS: MS 356.1 (M+H$^+$); UPLC rt 0.65 min.

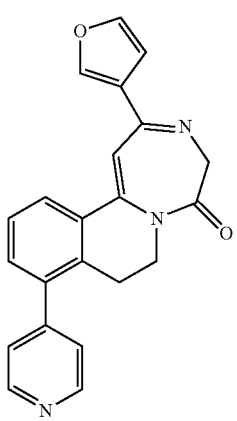 [SMILES: O=C1CN=C(c2ccoc2)C=C2c3cccc(-c4ccncc4)c3CCN12]

Example 52

2-(2-methoxypyridin-4-yl)-9-(pyrazin-2-yl)-7,8-dihydro-[1,4]diazepino[7,1-a]isoquinolin-5(4H)-one UPLC-MS: MS 398.2 (M+H$^+$); UPLC rt 0.91 min.

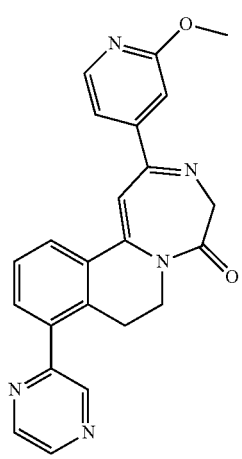 [SMILES: COc1cc(C2=NCC(=O)N3CCc4c(cccc4-c4cnccn4)C3=C2)ccn1]

Example 53

9-(6-fluoropyridin-3-yl)-2-(2-methoxypyridin-4-yl)-7,8-dihydro-[1,4]diazepino[7,1-a]isoquinolin-5(4H)-one UPLC-MS: MS 415.2 (M+H$^+$); UPLC rt 1.06 min.

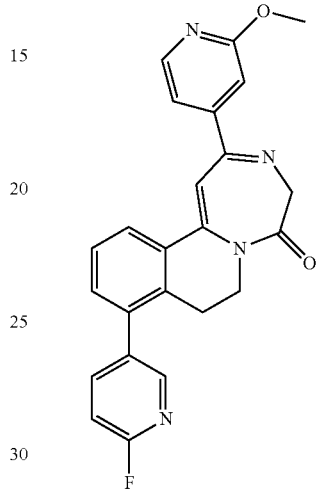

Example 54

9-(3-fluoropyridin-4-yl)-2-(2-methoxypyridin-4-yl)-7,8-dihydro-[1,4]diazepino[7,1-a]isoquinolin-5(4H)-one UPLC-MS: MS 415.2 (M+H$^+$); UPLC rt 0.98 min.

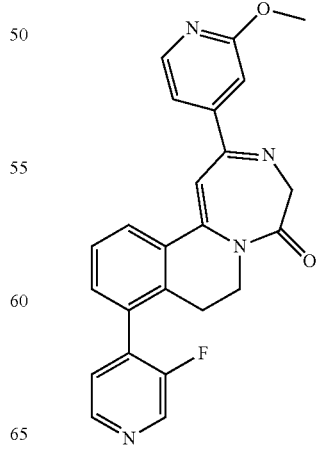

Example 55

2-(1-methyl-1H-imidazol-4-yl)-9-(pyridin-4-yl)-7,8-dihydro-[1,4]diazepino[7,1-a]isoquinolin-5(4H)-one UPLC-MS: MS 370.1 (M+H⁺); UPLC rt 0.48 min.

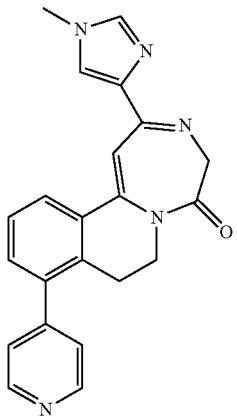 [SMILES: Cn1cnc(C2=NCC(=O)N3CCc4c(cccc4-c4ccncc4)C3=C2)c1]

Example 56

2-(1-methyl-1H-pyrazol-3-yl)-9-(2-methylpyridin-4-yl)-7,8-dihydro-[1,4]diazepino[7,1-a]isoquinolin-5(4H)-one UPLC-MS: MS 384.4 (M+H⁺); UPLC rt 0.60 min.

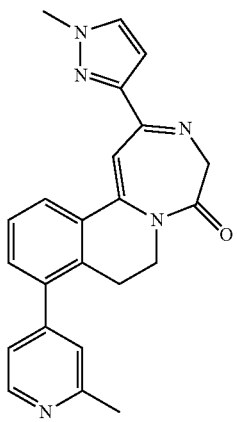 [SMILES: Cc1cc(-c2cccc3c2CCN2C(=O)CN=C(c4ccn(C)n4)C=C32)ccn1]

Example 57

2-(3-methoxyphenyl)-9-(tetrahydrofuran-2-yl)-7,8-dihydro-[1,4]diazepino[7,1-a]isoquinolin-5(4H)-one

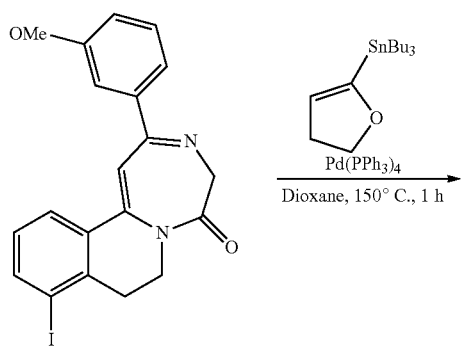

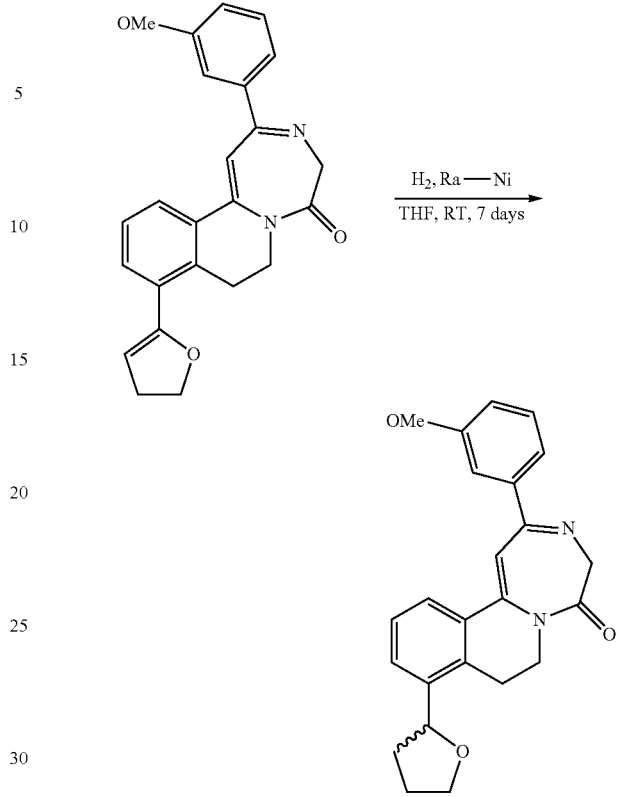

Step 1. 9-(4,5-dihydrofuran-2-yl)-2-(3-methoxyphenyl)-7,8-dihydro-[1,4]diazepino[7,1-a]isoquinolin-5(4H)-one.

57-1. A mixture of 9-iodo-2-(3-methoxyphenyl)-7,8-dihydro-[1,4]diazepino[7,1-a]isoquinolin-5(4H)-one (Example 30) (1.0 g, 2.25 mmol), tributyl(4,5-dihydrofuran-2-yl)stannane (1.21 g, 3.38 mmol) and Pd(PPh₃)₄ (0.13 g, 0.11 mmol) in 1,4-dioxane (10 mL) was heated in a microwave reactor at 150° C. for 90 min. The mixture was then diluted with AcOEt and filtered. The filtrate was concentrated in vacuo and the crude product obtained was purified by flash chromatography (SiO₂, heptane to heptane/AcOEt 1:1) to give a brown solid, which was suspended in heptane and heated to reflux. The suspension was then allowed to cool to RT and then filtered. The filter cake was then dried in vacuo to afford the title compound (543 mg) as a beige solid. UPLC-MS: MS 387.2 (M+H⁺); UPLC rt 1.10 min.

Step 2. 2-(3-methoxyphenyl)-9-(tetrahydrofuran-2-yl)-7,8-dihydro-[1,4]diazepino[7,1-a]isoquinolin-5(4H)-one.

Example 57. A mixture of 57-1 (300 mg, 0.78 mmol) and Raney-Nickel (50 mg, 1.32 mmol) in THF was evacuated in vacuo and placed under an atmosphere of H₂. The process was repeated and the mixture was then stirred at RT for 7 days under H₂. The reaction mixture was then filtered and concentrated in vacuo. The residue obtained was purified by flash chromatography (SiO₂, heptane to AcOEt) to afford the title compound (12 mg) as beige solid. UPLC-MS: MS 389.3 (M+H⁺); UPLC rt 0.97 min. ¹H NMR (400 MHz, CHLOROFORM-d): δ ppm 1.72 (dq, J=12.27, 7.64 Hz, 1 H); 2.05 (quin, J=7.14 Hz, 2 H); 2.32-2.44 (m, 1 H); 2.82-3.06 (m, 2 H); 3.71-3.84 (m, 1 H); 3.86 (s, 3 H); 3.92-4.09 (m, 2 H); 4.11-4.21 (m, 1 H); 4.51 (br. s., 2 H); 5.09 (t, J=7.23 Hz, 1 H);

6.94 (s, 1 H); 7.00 (dd, J=8.21, 2.35 Hz, 1 H); 7.28-7.41 (m, 3 H); 7.42-7.50 (m, 1 H); 7.60 (dd, J=7.62, 3.71 Hz, 2 H).

Example 58

9-methoxy-2-(6-oxo-1,6-dihydropyridin-2-yl)-7,8-dihydro-[1,4]diazepino[7,1-a]isoquinolin-5(4H)-one

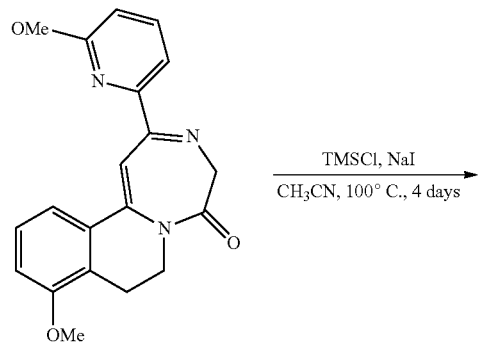

A mixture of 9-methoxy-2-(6-methoxypyridin-2-yl)-7,8-dihydro-[1,4]diazepino[7,1-a]isoquinolin-5(4H)-one Example 9 (140 mg, 0.40 mmol), NaI (156 mg, 1.04 mmol), TMSCl (768 μL, 6.01 mmol) in acetonitrile (10 mL) was heated to 100° C. for 4 days. The mixture was then diluted with AcOEt, washed with an aq. solution of $Na_2S_2O_3$ (10%) and $H_2O$. The org. layer was then dried over $Na_2SO_4$, filtered and concentrated in vacuo. The residue obtained was suspended in a small volume of DMF and the precipitate was filtered and washed with $Et_2O$. The filter cake was dried in vacuo to afford Example 58 (16 mg) as a beige solid. UPLC-MS: MS 336.4 (M+H$^+$); UPLC rt 0.94 min. $^1$H NMR (600 MHz, DMSO-d$_6$): δ ppm 2.92 (t, J=6.06 Hz, 2 H); 3.86 (s, 3 H); 3.93 (t, J=6.26 Hz, 2 H); 4.52 (s, 2 H); 7.05 (d, J=8.27 Hz, 1 H); 7.27 (d, J=8.28 Hz, 1 H); 7.45 (t, J=8.07 Hz, 1 H); 7.49 (s, 1 H); 7.75 (d, J=8.07 Hz, 1 H); 7.79 (d, J=7.27 Hz, 1 H); 7.88-7.94 (m, 1 H).

Following the procedures described above and substituting the appropriate reagents, starting materials and purification methods known to those skilled in the art, the following compounds of the present invention were prepared:

Example 59

9,10-dimethoxy-2-(3-methoxyphenyl)-7,8-dihydro-[1,4]diazepino[7,1-a]isoquinolin-5(4H)-one UPLC-MS: MS 379.5 (M+H$^+$); UPLC rt 0.87 min.

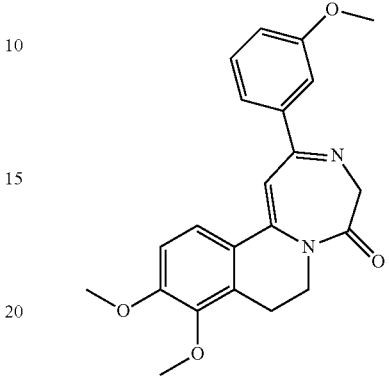

Example 60

9-methoxy-2-(2-oxo-1,2-dihydropyridin-4-yl)-7,8-dihydro-[1,4]diazepino[7,1-a]isoquinolin-5(4H)-one UPLC-MS: MS 336.0 (M+H$^+$); UPLC rt 0.84 min.

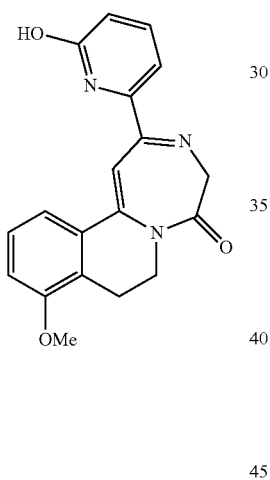

Example 61

2-(4-isopropyl-1H-imidazol-1-yl)-9-methoxy-7,8-dihydro-[1,4]diazepino[7,1-a]isoquinolin-5(4H)-one

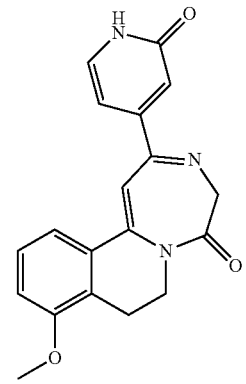 [SMILES: COc1cccc2c1CCN1C(=O)CN=C(c3cc[nH]c(=O)c3)C=C21]

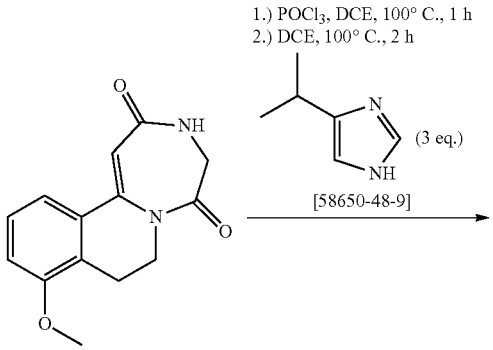

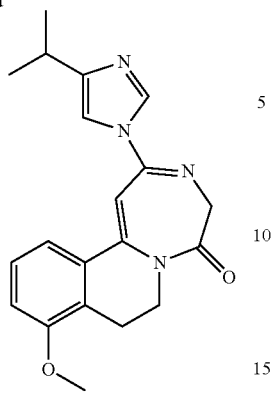

To a stirred solution of 9-methoxy-3,4,7,8-tetrahydro-[1,4]diazepino[7,1-a]isoquinoline-2,5-dione (80 mg, 0.31 mmol) in 1,2-dichloroethane (8 mL) was added POCl$_3$ (0.058 mL, 0.62 mmol) and the resulting yellow suspension was stirred at 100° C. for 1 h. The reaction mixture was cooled to RT and concentrated under reduced pressure to dryness. The resulting crude chloro compound was dissolved in 1,2-dichloroethane (8 mL), 4-isopropyl-1H-imidazole (102 mg, 0.93 mmol) was added and the mixture was stirred at 100° C. for 2 h. The reaction mixture was allowed to warm to RT. Saturated aqueous NaHCO$_3$ solution was added and the mixture was extracted twice with DCM. The combined organic layers were dried with sodium sulfate, filtered and the solvent was removed under reduced pressure. The crude product was purified by flash-column chromatography over silicagel (eluent: gradient 0% to 100% ethyl acetate/cyclohexane in 30 min) to yield 15 mg of a brown solid. Further purification by SFC (column: Diol 5 μm, 250×30 mm, 60 A, Princeton; eluent: 13% MeOH/CO$_2$ for 0.5 min, then from 13% MeOH/CO$_2$ to 18% MeOH/CO$_2$ in 6 min; then from 18% MeOH/CO$_2$ to 50% MeOH/CO$_2$ in 1 min; flow 100 mL/min; UV detection at 220 nm) yielded the title compound (9 mg). UPLC-MS: MS 351.3 (M+H$^+$); UPLC rt 0.90 min. $^1$H NMR (400 MHz, CHLOROFORM-d): δ ppm 1.35 (d, J=6.8 Hz, 6 H), 2.95 (t, J=6.2 Hz, 2 H), 3.03-3.19 (m, 1 H), 3.88 (s, 3 H), 3.92-4.05 (m, 2 H), 4.40 (s, 2 H), 6.87-7.05 (m, 2 H), 7.19-7.58 (m, 4 H).

Following the procedure described above for Example 61 and substituting the appropriate reagents, starting materials and purification methods known to those skilled in the art, the following compounds of the present invention were prepared:

Example 62

9-chloro-2-(4-methyl-1H-imidazol-1-yl)-7,8-dihydro-[1,4]diazepino[7,1-a]isoquinolin-5(4H)-one UPLC-MS: MS 326.9 (M+H$^+$); UPLC rt 0.81 min.

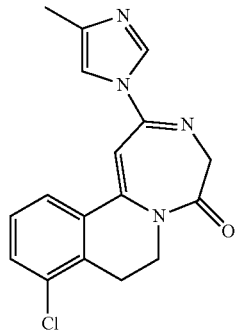 [SMILES: Cc1cn(C2=NCC(=O)N3CCc4c(Cl)cccc4C3=C2)cn1]

Example 63

9-iodo-2-(4-(trifluoromethyl)-1H-imidazol-1-yl)-7,8-dihydro-[1,4]diazepino[7,1-a]isoquinolin-5(4H)-one UPLC-MS: MS 473.1 (M+H$^+$); UPLC rt 1.14 min.

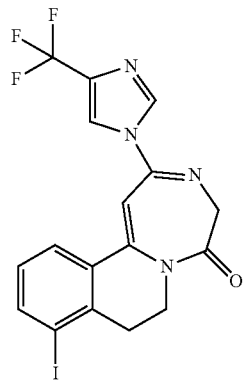 [SMILES: O=C1CN=C(n2cnc(C(F)(F)F)c2)C=C2c3cccc(I)c3CCN12]

Example 64

1-(9-iodo-5-oxo-4,5,7,8-tetrahydro-[1,4]diazepino[7,1-a]isoquinolin-2-yl)-1H-imidazole-4-carbonitrile UPLC-MS: MS 430.0 (M+H$^+$); UPLC rt 1.01 min.

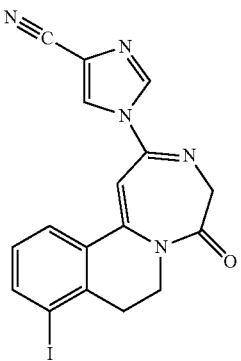 [SMILES: N#Cc1cn(C2=NCC(=O)N3CCc4c(I)cccc4C3=C2)cn1]

Example 65

2-(4-(hydroxymethyl)-1H-imidazol-1-yl)-9-iodo-7,8-dihydro-[1,4]diazepino[7,1-a]isoquinolin-5(4H)-one UPLC-MS: MS 435.2 (M+H$^+$); UPLC rt 0.80 min.

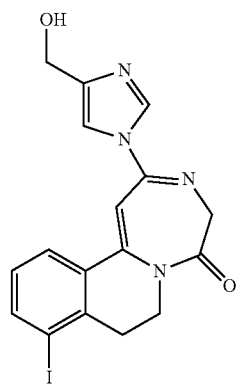 [SMILES: O=C1CN=C(n2cnc(CO)c2)C=C2c3cccc(I)c3CCN12]

Example 66 methyl 1-(9-iodo-5-oxo-4,5,7,8-tetrahydro-[1,4]diaz-epino[7,1-a]isoquinolin-2-yl)-1H-imidazole-4-carboxylate UPLC-MS: MS 463.1 (M+H⁺); UPLC rt 0.97 min.

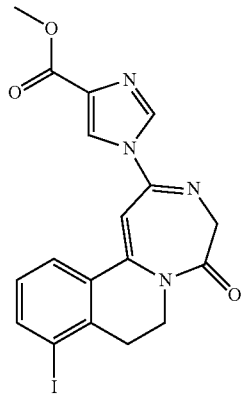 [SMILES: COC(=O)c1cn(C2=NCC(=O)N3CCc4c(I)cccc4C3=C2)cn1]

Example 67

2-(2,4-dimethyl-1H-imidazol-1-yl)-9-iodo-7,8-dihydro-[1,4]diazepino[7,1-a]isoquinolin-5(4H)-one UPLC-MS: MS 433.1 (M+H⁺); UPLC rt 0.78 min.

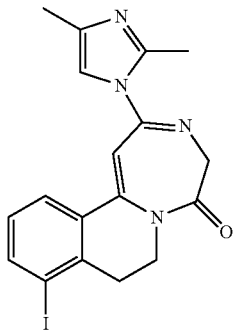 [SMILES: Cc1cn(C2=NCC(=O)N3CCc4c(I)cccc4C3=C2)c(C)n1]

Example 68 ethyl 1-(9-iodo-5-oxo-4,5,7,8-tetrahydro-[1,4]diaz-epino[7,1-a]isoquinolin-2-yl)-1H-imidazole-4-carboxylate UPLC-MS: MS 477.1 (M+H⁺); UPLC rt 1.02 min.

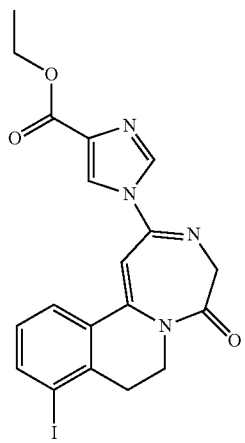 [SMILES: CCOC(=O)c1cn(C2=NCC(=O)N3CCc4c(I)cccc4C3=C2)cn1]

Example 69

2-(4-cyclobutyl-1H-imidazol-1-yl)-9-(1H-pyrazol-1-yl)-7,8-dihydro-[1,4]diazepino[7,1-a]isoquinolin-5(4H)-one UPLC-MS: MS 399.2 (M+H⁺); UPLC rt 0.85 min.

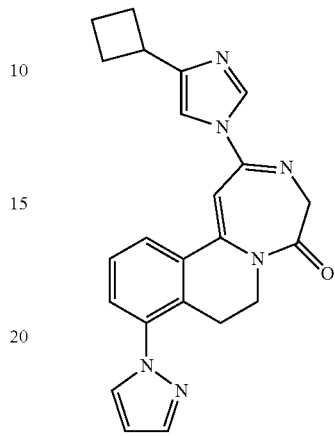

Example 70

2-(4-cyclobutyl-1H-imidazol-1-yl)-9-morpholino-7,8-dihydro-[1,4]diazepino[7,1-a]isoquinolin-5(4H)-one UPLC-MS: MS 418.2 (M+H⁺); UPLC rt 0.94 min.

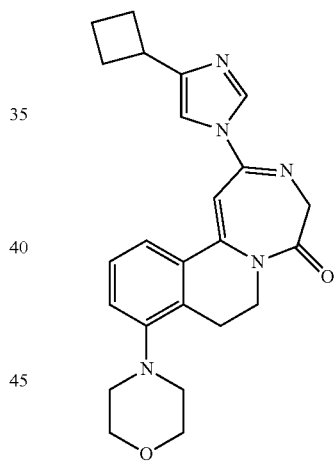

Example 71

2-(4-(methoxymethyl)-1H-imidazol-1-yl)-9-(thiazol-2-yl)-7,8-dihydro-[1,4]diazepino[7,1-a]isoquinolin-5(4H)-one

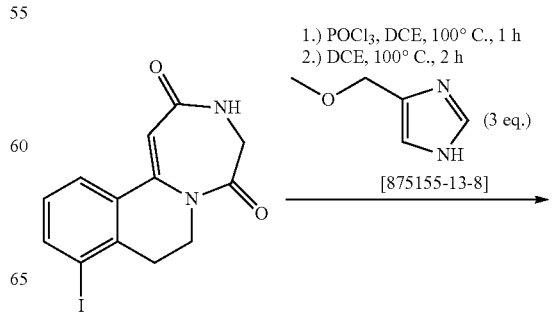

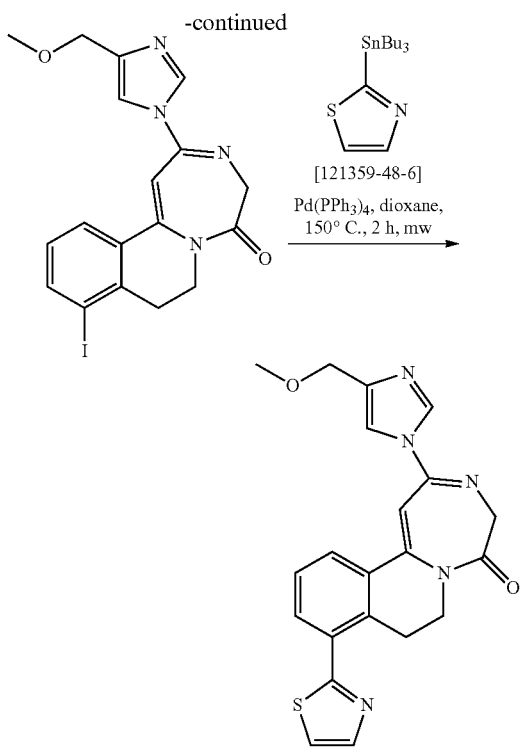

Step 1: 9-iodo-2-(4-(methoxymethyl)-1H-imidazol-1-yl)-7,8-dihydro-[1,4]diazepino[7,1-a]isoquinolin-5(4H)-one.
71-1. To a stirred solution of 9-iodo-3,4,7,8-tetrahydro-[1,4]diazepino[7,1-a]isoquinoline-2,5-dione (1.78 g, 5.03 mmol) in 1,2-dichloroethane (50 mL) was added POCl₃ (0.94 mL, 10.1 mmol) and the resulting suspension was stirred at 100° C. for 1 h. The reaction mixture was cooled to rt and concentrated under reduced pressure to dryness. For complete removal of POCl₃ the residue was taken up in toluene and evaporated twice again and dried under high vacuo.

The resulting crude chloro compound was dissolved in 1,2-dichloroethane (50 mL), 4-(methoxymethyl)-1H-imidazole (2.24 g, 20.0 mmol) was added and the mixture was stirred at 100° C. for 2 h. The reaction mixture was allowed to warm to rt and diluted with DCM.

Saturated aqueous NaHCO₃ solution was added and the mixture was extracted twice with DCM. The combined organic layers were dried with sodium sulfate, filtered and the solvent was removed under reduced pressure. The crude product was purified by flash-column chromatography over silicagel (Biotage Isolera Four, eluent: AcOEt/DCM 9:1 isocratic for 10 min, then from 1% MeOH in DCM to 2.5% MeOH in DCM in 12 min) to yield 1.44 g of a redbrown foam. Further purification by SFC (column: PPU 5 µm, 250×30 mm, 60 Å, Princeton; eluent: isocratic 5% MeOH/CO₂ for 23 min; flow 100 mL/min; UV detection at 220 nm) gave the title compound (739 mg). UPLC-MS: MS 403.2 (M+H⁺); UPLC rt 0.98 min.

Step 2: 2-(4-(methoxymethyl)-1H-imidazol-1-yl)-9-(thiazol-2-yl)-7,8-dihydro-[1,4]diazepino[7,1-a]isoquinolin-5(4H)-one. Example 71. To a degassed solution of 9-iodo-2-(4-(methoxymethyl)-1H-imidazol-1-yl)-7,8-dihydro-[1,4]diazepino[7,1-a]isoquinolin-5(4H)-one (191 mg, 0.43 mmol) and 2-(tributylstannyl)thiazole (239 mg, 0.64 mmol) in dioxane (4 mL) was added Pd(PPh₃)₄ (25 mg, 0.021 mmol) and the mixture was heated in the microwave at 150° C. for 2 h. The solvent was removed under reduced pressure. The crude product was purified by flash-column chromatography over silicagel (Biotage Isolera Four, eluent: from 1% MeOH in DCM to 5% MeOH in DCM in 18 min) to yield the title compound (64 mg). UPLC-MS: MS 406.1 (M+H⁺); UPLC rt 0.81 min. ¹H NMR (600 MHz, DMSO-d₆): δ ppm 3.18-3.31 (m, 5 H), 3.78 (t, J=6.0 Hz, 2 H), 4.30 (s, 4 H), 7.18 (s, 1 H), 7.55 (t, J=7.9 Hz, 1 H), 7.67 (s, 1 H), 7.86 (d, J=7.7 Hz, 1 H), 7.93 (d, J=3.3 Hz, 1 H), 8.04 (d, J=3.3 Hz, 1 H), 8.13 (d, J=8.1 Hz, 1 H), 8.24 (s, 1 H).

Following the procedure described above for Example 71 and substituting the appropriate reagents, starting materials and purification methods known to those skilled in the art, the following compounds of the present invention were prepared:

Example 72

2-(4-isopropyl-1H-imidazol-1-yl)-9-(1-methyl-1H-pyrazol-4-yl)-7,8-dihydro-[1,4]diazepino[7,1-a]isoquinolin-5(4H)-one UPLC-MS: MS 401.4 (M+H⁺); UPLC rt 0.82 min.

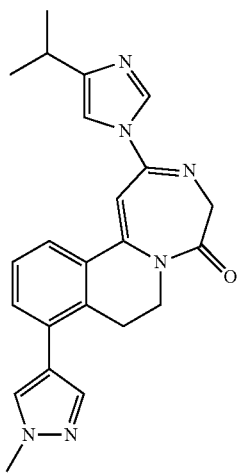 [SMILES: CC(C)c1cn(C2=NCC(=O)N3CCc4c(cccc4-c4cnn(C)c4)C3=C2)cn1]

Example 73

2-(4-isopropyl-1H-imidazol-1-yl)-9-(1-methyl-1H-imidazol-2-yl)-7,8-dihydro-[1,4]diazepino[7,1-a]isoquinolin-5(4H)-one UPLC-MS: MS 401.3 (M+H⁺); UPLC rt 0.55 min.

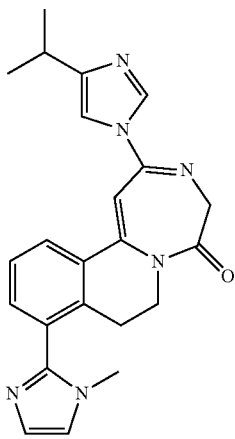 [SMILES: CC(C)c1cn(C2=NCC(=O)N3CCc4c(cccc4-c4nccn4C)C3=C2)cn1]

Example 74

2-(4-ethyl-1H-imidazol-1-yl)-9-(oxazol-2-yl)-7,8-dihydro-[1,4]diazepino[7,1-a]isoquinolin-5(4H)-one UPLC-MS: MS 374.1 (M+H⁺); UPLC rt 0.75 min.

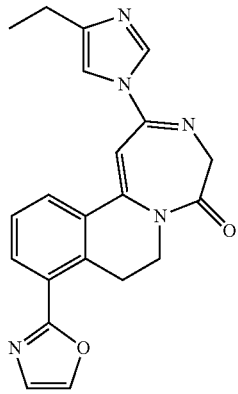 [SMILES: CCc1cn(C2=NCC(=O)N3CCc4c(cccc4-c4ncco4)C3=C2)cn1]

Example 75

2-(4-ethyl-1H-imidazol-1-yl)-9-(furan-2-yl)-7,8-dihydro-[1,4]diazepino[7,1-a]isoquinolin-5(4H)-one UPLC-MS: MS 373.2 (M+H⁺); UPLC rt 0.92 min.

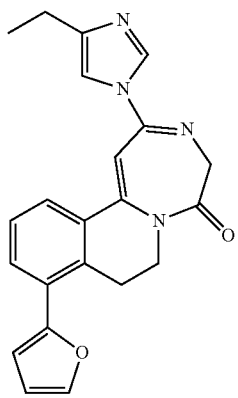 [SMILES: CCc1cn(C2=NCC(=O)N3CCc4c(cccc4-c4ccco4)C3=C2)cn1]

Example 76

2-(4-(2-methoxyethyl)-1H-imidazol-1-yl)-9-(thiazol-4-yl)-7,8-dihydro-[1,4]diazepino[7,1-a]isoquinolin-5(4H)-one UPLC-MS: MS 420.2 (M+H⁺); UPLC rt 0.75 min.

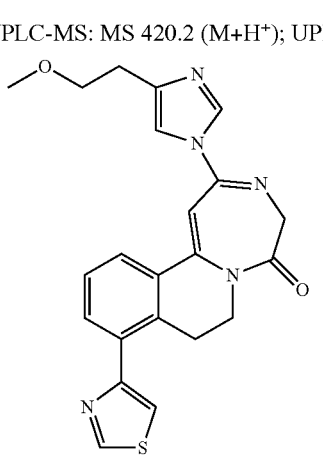

Example 77

2-(4-methoxymethyl)-1H-imidazol-1-yl)-9-(5-methylthiazol-2-yl)-7,8-dihydro-[1,4]diazepino[7,1-a]isoquinolin-5(4H)-one UPLC-MS: MS 420.2 (M+H⁺); UPLC rt 0.92 min.

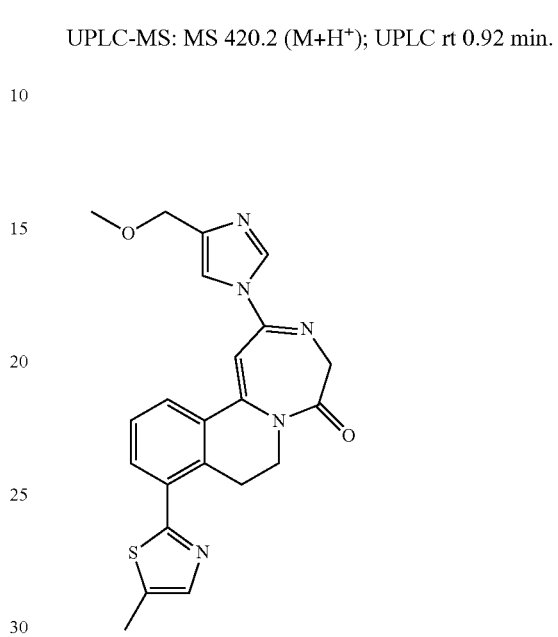

Example 78

2-(4-methyl-1H-imidazol-1-yl)-9-(pyrimidin-5-yl)-7,8-dihydro-[1,4]diazepino[7,1-a]isoquinolin-5(4H)-one UPLC-MS: MS 371.2 (M+H⁺); UPLC rt 0.61 min.

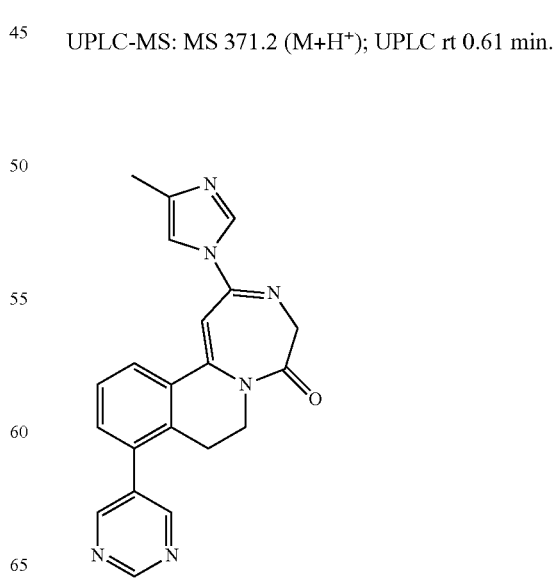

Example 79

2-(4-methyl-1H-imidazol-1-yl)-9-(pyridin-3-yl)-7,8-dihydro-[1,4]diazepino[7,1-a]isoquinolin-5(4H)-one UPLC-MS: MS 370.2 (M+H$^+$); UPLC rt 0.64 min.

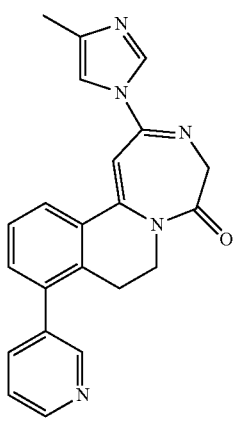 [SMILES: Cc1cn(C2=NCC(=O)N3CCc4c(cccc4-c4cccnc4)C3=C2)cn1]

Example 80

2-(4-methyl-1H-imidazol-1-yl)-9-(pyridin-4-yl)-7,8-dihydro-[1,4]diazepino[7,1-a]isoquinolin-5(4H)-one UPLC-MS: MS 370.2 (M+H$^+$); UPLC rt 0.60 min.

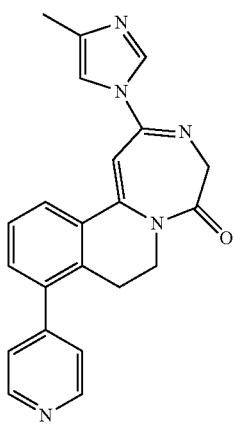 [SMILES: Cc1cn(C2=NCC(=O)N3CCc4c(cccc4-c4ccncc4)C3=C2)cn1]

Example 81

9-(6-fluoropyridin-3-yl)-2-(4-methyl-1H-imidazol-1-yl)-7,8-dihydro-[1,4]diazepino[7,1-a]isoquinolin-5(4H)-one UPLC-MS: MS 388.2 (M+H$^+$); UPLC rt 0.76 min.

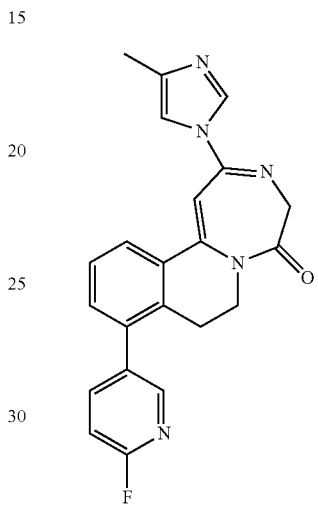

Example 82

2-(4-methyl-1H-imidazol-1-yl)-9-(thiazol-5-yl)-7,8-dihydro-[1,4]diazepino[7,1-a]isoquinolin-5(4H)-one UPLC-MS: MS 376.2 (M+H$^+$); UPLC rt 0.70 min.

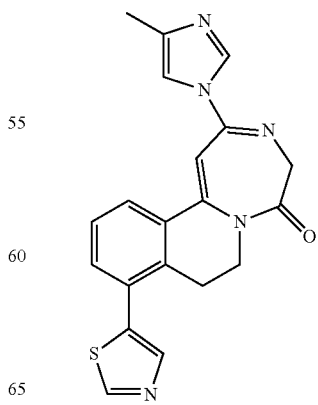

Example 83

2-(4-chloro-1H-imidazol-1-yl)-9-(5-fluoropyridin-3-yl)-7,8-dihydro-[1,4]diazepino[7,1-a]isoquinolin-5(4H)-one UPLC-MS: MS 408.3 (M+H$^+$); UPLC rt 0.94 min.

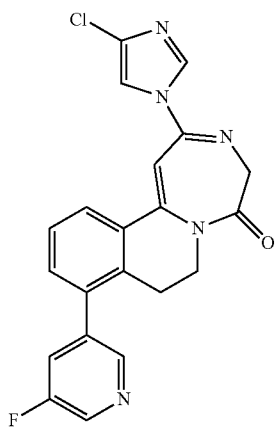 [SMILES: O=C1CN=C(n2cnc(Cl)c2)C=C2c3cccc(-c4cncc(F)c4)c3CCN12]

Example 84

9-(6-fluoropyridin-3-yl)-2-(4-(2-methoxyethyl)-1H-imidazol-1-yl)-7,8-dihydro-[1,4]diazepino[7,1-a]isoquinolin-5(4H)-one UPLC-MS: MS 432.3 (M+H$^+$); UPLC rt 0.83 min.

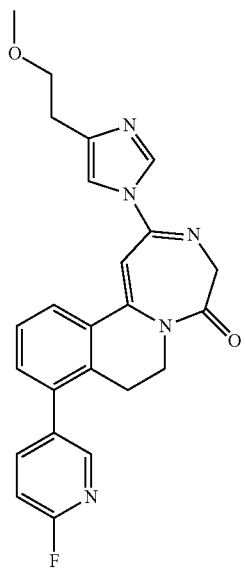 [SMILES: COCCc1cn(C2=NCC(=O)N3CCc4c(cccc4-c4ccc(F)nc4)C3=C2)cn1]

Example 85

2-(4-(methoxymethyl)-1H-imidazol-1-yl)-9-vinyl-7,8-dihydro-[1,4]diazepino[7,1-a]isoquinolin-5(4H)-one UPLC-MS: MS 349.2 (M+H$^+$); UPLC rt 0.86 min.

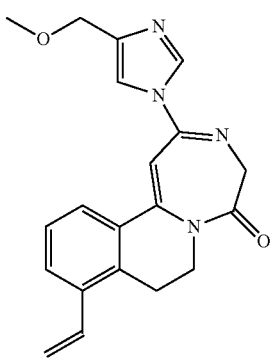 [SMILES: C=Cc1cccc2c1CCN1C(=O)CN=C(n3cnc(COC)c3)C=C21]

Example 86

2-(4-ethyl-1H-imidazol-1-yl)-9-(4-fluorophenyl)-7,8-dihydro-[1,4]diazepino[7,1-a]isoquinolin-5(4H)-one UPLC-MS: MS 401.2 (M+H$^+$); UPLC rt 1.03 min.

Example 87

2-(4-cyclopropyl-1H-imidazol-1-yl)-9-(4-methyloxazol-2-yl)-7,8-dihydro-[1,4]diazepino[7,1-a]isoquinolin-5(4H)-one UPLC-MS: MS 400.2 (M+H⁺); UPLC rt 0.95 min.

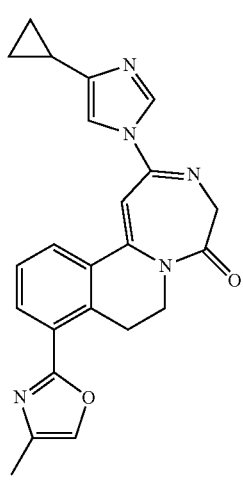 [SMILES: Cc1coc(-c2cccc3c2CCN2C(=O)CN=C(n4cnc(C5CC5)c4)C=C32)n1]

Example 88

2-(4-cyclopropyl-1H-imidazol-1-yl)-9-(5-methyloxazol-2-yl)-7,8-dihydro-[1,4]diazepino[7,1-a]isoquinolin-5(4H)-one UPLC-MS: MS 400.2 (M+H⁺); UPLC rt 0.94 min.

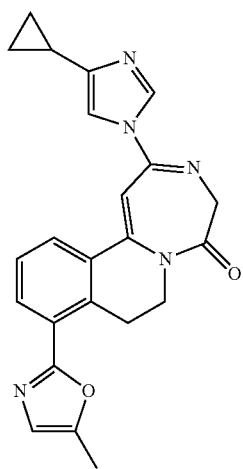 [SMILES: Cc1cnc(-c2cccc3c2CCN2C(=O)CN=C(n4cnc(C5CC5)c4)C=C32)o1]

Example 88a 2-(4-(oxazol-2-yl)-1H-imidazol-1-yl)-9-propyl-7,8-dihydro-[1,4]diazepino[7,1-a]isoquinolin-5(4H)-one UPLC-MS: MS 388.1 (M+H+); UPLC rt 1.00 min.

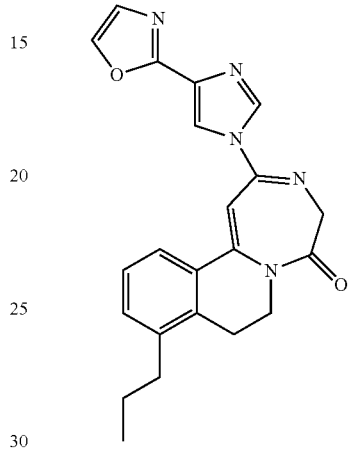

Starting from bromo-[O]-intermediate, instead of iodo-[O]-intermediate

Example 88b 2-(3-cyclopropyl-1H-1,2,4-triazol-1-yl)-9-(3-fluoropyrazin-2-yl)-7,8-dihydro-[1,4]diazepino[7,1-a]isoquinolin-5(4H)-one UPLC-MS: MS 416.2 (M+H⁺); UPLC rt 0.96 min.

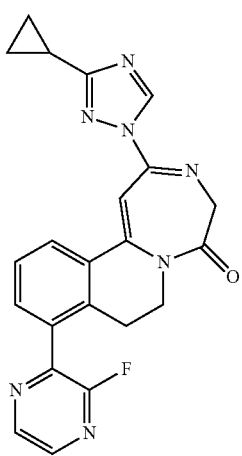 [SMILES: O=C1CN=C(n2cnc(C3CC3)n2)C=C2c3cccc(-c4nccnc4F)c3CCN12]

Example 88c 2-(3-cyclopropyl-1H-1,2,4-triazol-1-yl)-9-(3-fluoro-pyridin-2-yl)-7,8-dihydro-[1,4]diazepino[7,1-a]iso-quinolin-5(4H)-one UPLC-MS: MS 415.2 (M+H$^+$); UPLC rt 0.98 min.

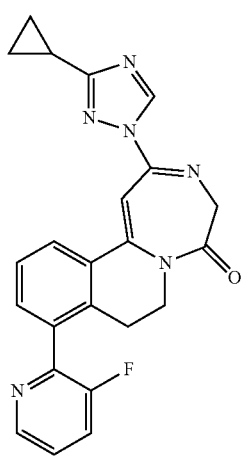 [SMILES: O=C1CN=C(n2cnc(C3CC3)n2)C=C2c3cccc(-c4ncccc4F)c3CCN12]

Example 88e 2-(4-cyclopropyl-1H-imidazol-1-yl)-9-(2-methylthi-azol-5-yl)-7,8-dihydro-[1,4]diazepino[7,1-a]iso-quinolin-5(4H)-one UPLC-MS: MS 416.1 (M+H$^+$); UPLC rt 0.96 min.

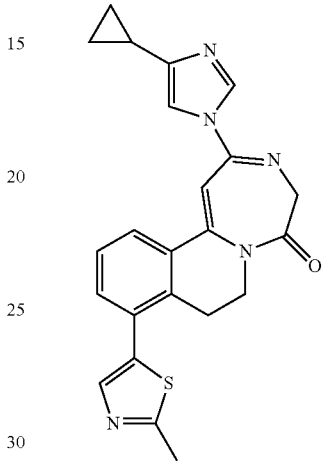

Example 88d 2-(4-cyclopropyl-1H-imidazol-1-yl)-9-(thiazol-5-yl)-7,8-dihydro-[1,4]diazepino[7,1-a]isoquinolin-5(4H)-one UPLC-MS: MS 402.1 (M+H$^+$); UPLC rt 0.89 min.

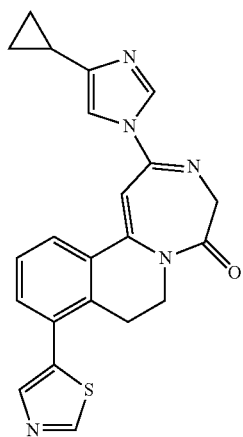 [SMILES: O=C1CN=C(n2cnc(C3CC3)c2)C=C2c3cccc(-c4cncs4)c3CCN12]

Example 88f (from Precursor Described in Preparation 17)

2-(4-cyclopropyl-1H-imidazol-1-yl)-9-(pyrazin-2-yl)-7,8-dihydro-[1,4]diazepino[7,1-a]isoquinolin-5(4H)-one UPLC-MS: MS 397.3 (M+H$^+$); UPLC rt 0.79 min.

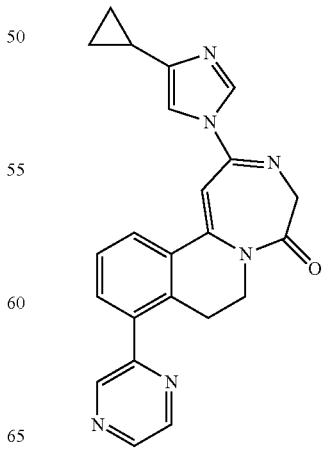

Example 88g (from Precursor Described in Preparation 17)

2-(3-cyclopropyl-1H-1,2,4-triazol-1-yl)-9-(thiazol-2-yl)-7,8-dihydro-[1,4]diazepino[7,1-a]isoquinolin-5(4H)-one UPLC-MS: MS 403.3 (M+H$^+$); UPLC rt 1.01 min.

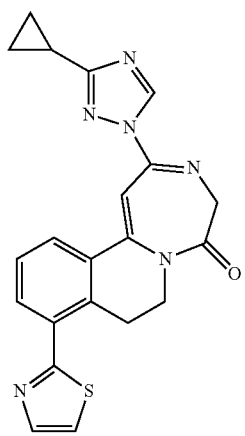 [SMILES: O=C1CN=C(n2cnc(C3CC3)n2)C=C2c3cccc(-c4nccs4)c3CCN12]

Example 88h (from Precursor Described in Preparation 17)

2-(4-(2-methoxyethyl)-1H-imidazol-1-yl)-9-(thiazol-2-yl)-7,8-dihydro-[1,4]diazepino[7,1-a]isoquinolin-5(4H)-one UPLC-MS: MS 420.2 (M+H$^+$); UPLC rt 0.83 min.

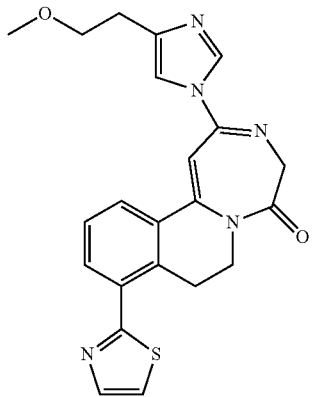 [SMILES: COCCc1cn(C2=NCC(=O)N3CCc4c(cccc4-c4nccs4)C3=C2)cn1]

Example 88i (from Precursor Described in Preparation 17)

2-(4-(ethoxymethyl)-1H-imidazol-1-yl)-9-(4-methylthiazol-2-yl)-7,8-dihydro-[1,4]diazepino[7,1-a]isoquinolin-5(4H)-one UPLC-MS: MS 434.2 (M+H$^+$); UPLC rt 0.98 min.

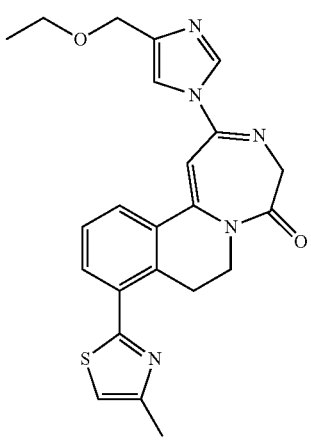 [SMILES: CCOCc1cn(C2=NCC(=O)N3CCc4c(cccc4-c4nc(C)cs4)C3=C2)cn1]

Example 88j (from Precursor Described in Preparation 17)

2-(4-(ethoxymethyl)-1H-imidazol-1-yl)-9-(thiazol-2-yl)-7,8-dihydro-[1,4]diazepino[7,1-a]isoquinolin-5(4H)-one UPLC-MS: MS 420.2 (M+H$^+$); UPLC rt 0.88 min.

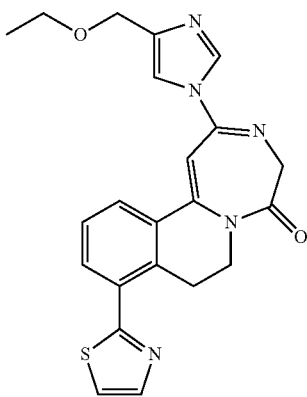 [SMILES: CCOCc1cn(C2=NCC(=O)N3CCc4c(cccc4-c4nccs4)C3=C2)cn1]

Example 88k (from Precursor Described in Preparation 17)

2-(4-cyclopropyl-1H-imidazol-1-yl)-9-(4-fluoropyridin-3-yl)-7,8-dihydro-[1,4]diazepino[7,1-a]isoquinolin-5(4H)-one UPLC-MS: MS 414.3 (M+H⁺); UPLC rt 0.83 min.

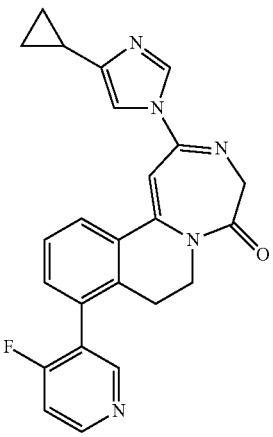 [SMILES: O=C1CN=C(n2cnc(C3CC3)c2)C=C2c3cccc(-c4cnccc4F)c3CCN12]

Example 89

9-ethyl-2-(4-isopropyl-1H-imidazol-1-yl)-7,8-dihydro-[1,4]diazepino[7,1-a]isoquinolin-5(4H)-one

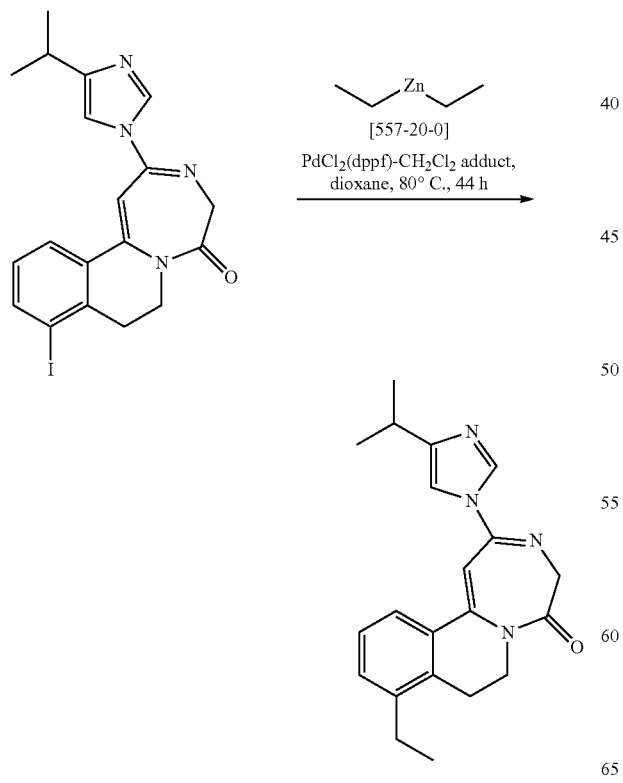

To a degassed solution of 9-iodo-2-(4-isopropyl-1H-imidazol-1-yl)-7,8-dihydro-[1,4]diazepino[7,1-a]isoquinolin-5(4H)-one (20 mg, 0.045 mmol) and PdCl$_2$(dppf)-CH$_2$Cl$_2$ adduct (2 mg, 2.24 µmol) in dioxane (1 mL) was added diethylzinc (135 µL, 0.135 mmol, 1M in hexane) and the mixture was heated in the microwave at 80° C. for 44 h. The reaction mixture was allowed to warm to rt and then diluted with AcOEt and 2M aqueous HCl. The organic phase was separated, dried over sodium sulfate and concentrated under reduced pressure. The crude product was purified by SFC (column: Diol 5 µm, 250×30 mm, 60 A, Princeton; eluent: 7% MeOH/CO$_2$ for 1 min, then from 7% MeOH/CO$_2$ to 12% MeOH/CO$_2$ in 6 min; flow 100 mL/min; UV detection at 220 nm) to yield the title compound (5 mg). UPLC-MS: MS 349.2 (M+H⁺); UPLC rt 1.01 min. ¹H NMR (400 MHz, CHLOROFORM-d): δ ppm 1.21-1.28 (m, 9 H) 2.72 (q, J=7.4 Hz, 2 H) 2.85-2.92 (m, 1 H) 2.96 (t, J=6.2 Hz, 2 H) 3.91 (t, J=6.3 Hz, 2 H) 4.35 (br. s., 2 H) 6.61 (s, 1 H) 7.18 (s, 1 H) 7.27-7.38 (m, 2 H) 7.52 (d, J=7.3 Hz, 1 H) 7.93 (s, 1 H).

Example 90

2-(4-methyl-1H-imidazol-1-yl)-9-propyl-7,8-dihydro-[1,4]diazepino[7,1-a]isoquinolin-5(4H)-one

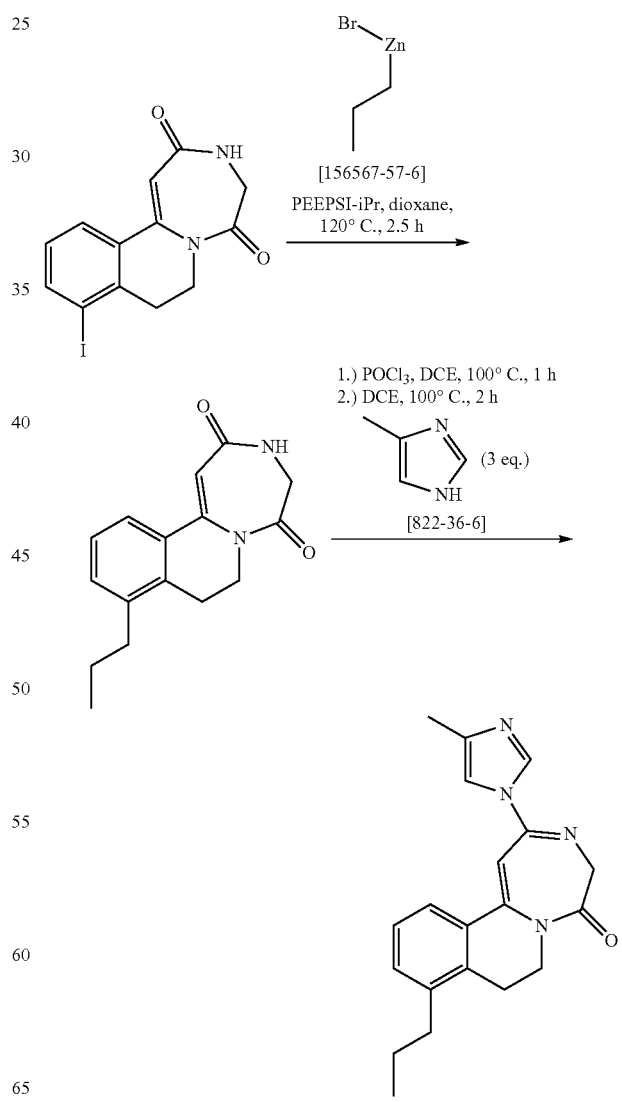

Step 1: 9-propyl-3,4,7,8-tetrahydro-[1,4]diazepino[7,1-a]isoquinoline-2,5-dione. 90-1. To a degassed solution of 9-iodo-3,4,7,8-tetrahydro-[1,4]diazepino[7,1-a]isoquinoline-2,5-dione (1.0 g, 2.82 mmol) and propylzinc(II)-bromide (14.1 mL, 7.05 mmol, 0.5M in THF) in dioxane (28 mL) was added PEPPSI-iPr (0.29 g, 0.424 mmol) under argon and the mixture was heated in a pressure vessel at 120° C. for 2.5 h. The reaction mixture was allowed to warm to rt and the solvent was removed under reduced pressure. The residue was suspended in DCM/MeOH (9:1, v/v), filtrated through a pad of celite and the filtrate was evaporated under reduced pressure. The crude product was purified by flash-column chromatography over silicagel (Biotage Isolera Four, eluent: from 1% MeOH in DCM to 10% MeOH in DCM in 35 min) to yield the product as an oil. The title compound was crystallized from diethyl ether to afford yellow crystals (370 mg). UPLC-MS: MS 271.2 (M+H$^+$); UPLC rt 0.86 min.

Step 2: 2-(4-methyl-1H-imidazol-1-yl)-9-propyl-7,8-dihydro-[1,4]diazepino[7,1-a]isoquinolin-5(4H)-one. Example 90. To a stirred solution of 9-propyl-3,4,7,8-tetrahydro-[1,4]diazepino[7,1-a]isoquinoline-2,5-dione (370 mg, 1.36 mmol) in 1,2-dichloroethane (14 mL) was added POCl$_3$ (0.25 mL, 2.73 mmol) and the resulting suspension was stirred at 100° C. for 1 h. The reaction mixture was cooled to RT and concentrated under reduced pressure to dryness. For complete removal of POCl$_3$ the residue was taken up in toluene and evaporated twice again and dried under high vacuo.

The resulting crude chloro compound was dissolved in 1,2-dichloroethane (14 mL), 4-methyl-1H-imidazole (335 mg, 4.08 mmol) was added and the mixture was stirred at 100° C. for 2 h. The reaction mixture was allowed to warm to RT and diluted with DCM. Saturated aqueous NaHCO$_3$ solution was added and the mixture was extracted twice with DCM. The combined organic layers were dried with sodium sulfate, filtered and the solvent was removed under reduced pressure. The crude product was purified by flash-column chromatography over silicagel (Biotage Isolera Four, eluent: 1% MeOH in DCM for 5 min, then to 5% MeOH in DCM in 25 min, then 5% MeOH in DCM for 3 min) to yield 153 mg of a red foam. Further purification by SFC (column: Diol 5 µm, 250×30 mm, 60 A, Princeton; eluent: 11% MeOH/CO$_2$ for 1 min, then from 11% MeOH/CO$_2$ to 16% MeOH/CO$_2$ in 6 min; flow 100 mL/min; UV detection at 220 nm) gave the title compound which was crystallized from diethyl ether (55 mg). UPLC-MS: MS 335.2 (M+H$^+$); UPLC rt 0.92 min. $^1$H NMR (600 MHz, DMSO-d$_6$) δ ppm 0.92 (t, J=7.2 Hz, 3 H), 1.52 (sxt, J=7.3 Hz, 2 H), 2.11 (s, 3 H), 2.61 (t, J=7.6 Hz, 2 H), 2.90 (br. s., 2 H), 3.79 (br. s., 2 H), 4.21 (br. s., 2 H), 7.10 (s, 1 H), 7.22-7.33 (m, 2 H), 7.38 (s, 1 H), 7.84 (d, J=7.3 Hz, 1 H), 8.11 (s, 1 H).

Following the procedure described above for Example 90 and substituting the appropriate reagents, starting materials and purification methods known to those skilled in the art, the following compounds of the present invention were prepared:

Example 91

9-cyclobutyl-2-(4-(methoxymethyl)-1H-imidazol-1-yl)-7,8-dihydro-[1,4]diazepino[7,1-a]isoquinolin-5(4H)-one UPLC-MS: 377.3 (M+H$^+$); UPLC rt 1.01 min.

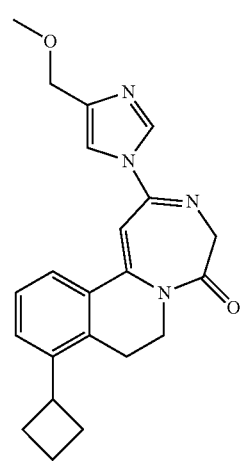 [SMILES: COCc1cn(C2=NCC(=O)N3CCc4c(cccc4C4CCC4)C3=C2)cn1]

Example 92

9-cyclobutyl-2-(3-methyl-1H-1,2,4-triazol-1-yl)-7,8-dihydro-[1,4]diazepino[7,1-a]isoquinolin-5(4H)-one UPLC-MS: MS 348.2 (M+H$^+$); UPLC rt 1.08 min.

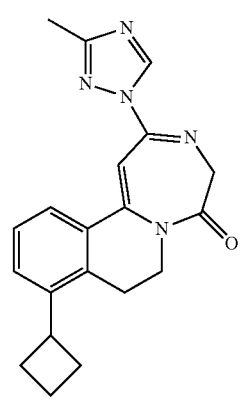 [SMILES: Cc1ncn(C2=NCC(=O)N3CCc4c(cccc4C4CCC4)C3=C2)n1]

Example 93
9-cyclopropyl-2-(3-(methoxymethyl)-1H-1,2,4-triazol-1-yl)-7,8-dihydro-[1,4]diazepino[7,1-a]isoquinolin-5(4H)-one
UPLC-MS: MS 364.2 (M+H⁺); UPLC rt 0.98 min.
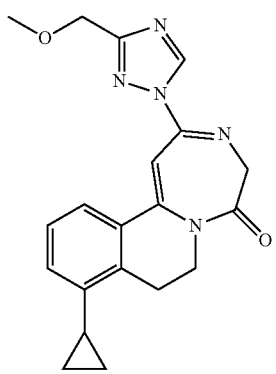 [SMILES: COCc1ncn(C2=NCC(=O)N3CCc4c(cccc4C4CC4)C3=C2)n1]
Example 94
4-(6-fluoropyridin-3-yl)-11-(4-isopropyl-1H-imidazol-1-yl)-5,6-dihydro-[1,4]diazepino[1,7-h][1,7]naphthyridin-8(9H)-one
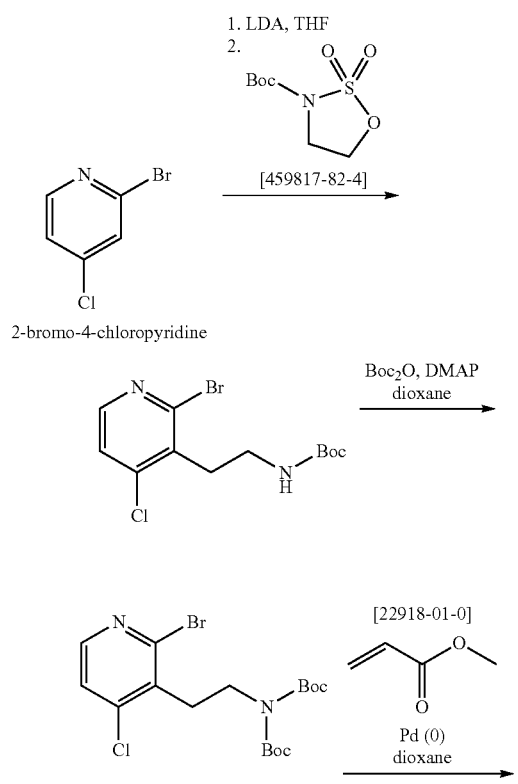
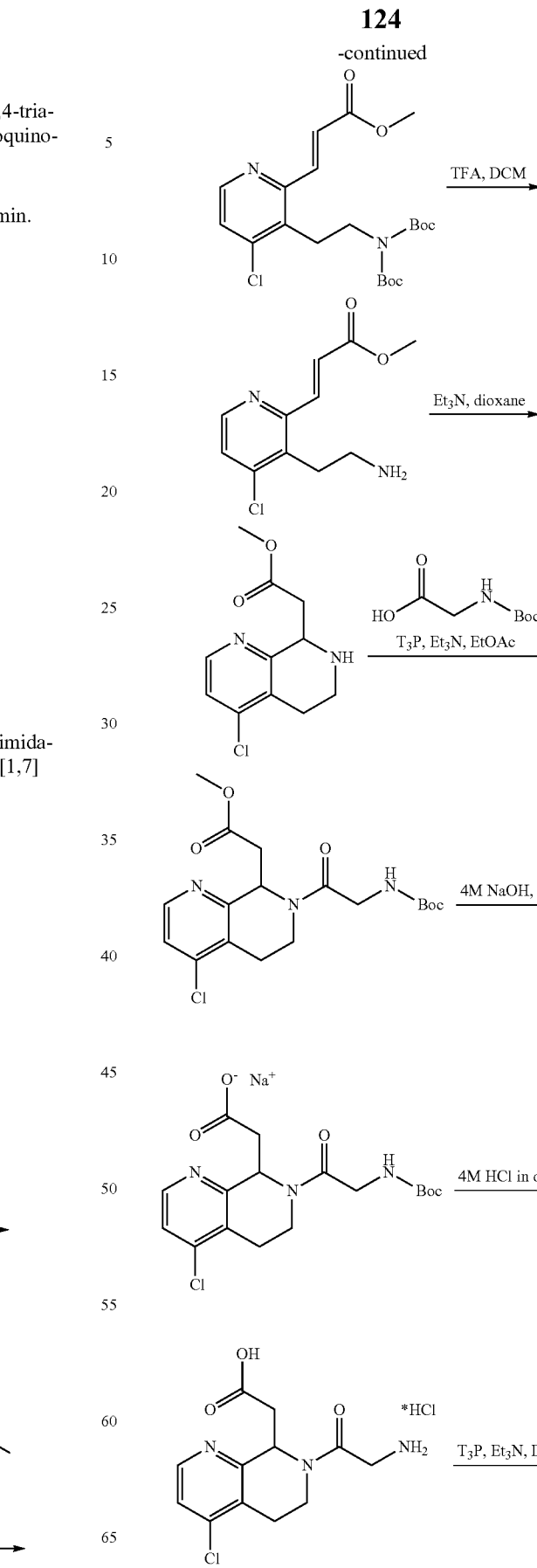

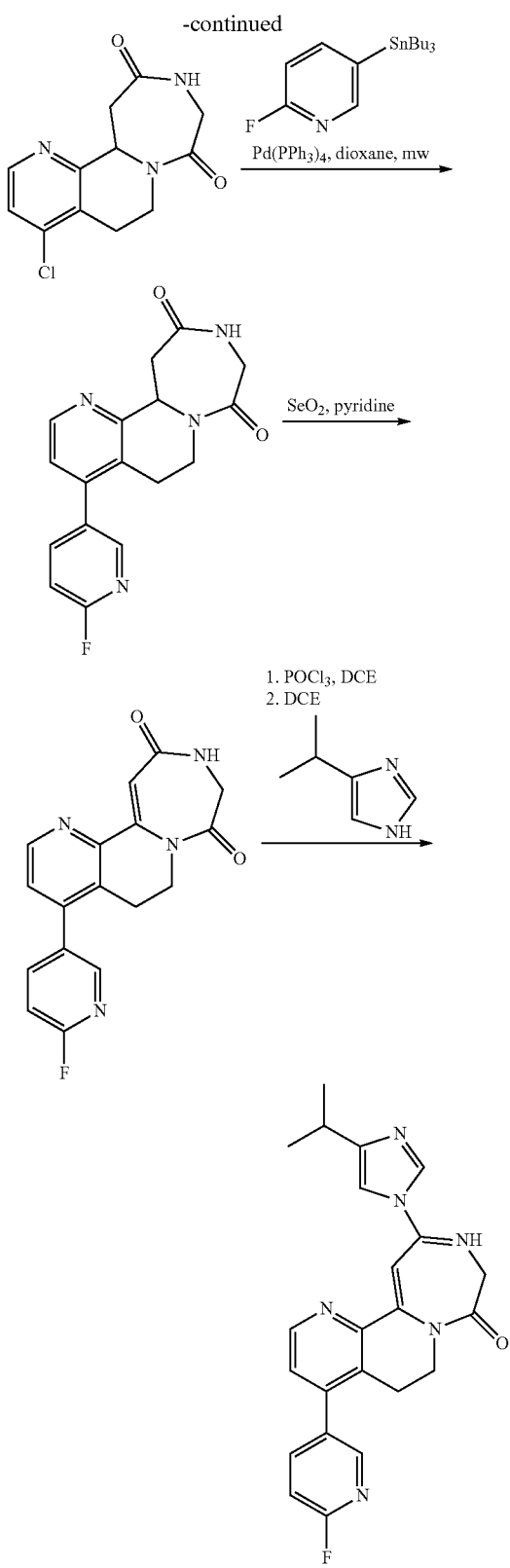

Step 1: tert-butyl (2-(2-bromo-4-chloropyridin-3-yl)ethyl) carbamate. 94-1. To a stirred solution of LDA (5.98 mmol) in THF (50 mL) 2-bromo-4-chloropyridine (1.0 g, 5.20 mmol) was added at −70° C. and the resulting solution was stirred at −70° C. for 1 h. Then a solution of tert-butyl 1,2,3-oxathiazolidine-3-carboxylate 2,2-dioxide (1.39 g, 6.24 mmol) in THF (20 mL) was added at −70° C. and the reaction mixture was stirred for 3 h. Saturated aqueous NH$_4$Cl solution was added at −70° C. and the mixture was allowed to warm to RT. The mixture was extracted with AcOEt (2×). The combined organic layers were washed with brine, dried with sodium sulfate, filtered and the solvent was removed under reduced pressure. The crude product was purified by flash-column chromatography over silicagel (Biotage Isolera One, eluent: gradient from 2% MeOH in DCM to 13% MeOH in DCM in 12 min) to yield the title compound as a white solid (1.36 g). UPLC-MS: MS 335.1 (M+H$^+$); UPLC rt 1.06 min.

Step 2: di-tert-butyl (2-(2-bromo-4-chloropyridin-3-yl) ethyl)imidodicarbonate. 94-2. To a stirred solution of tert-butyl (2-(2-bromo-4-chloropyridin-3-yl)ethyl)carbamate (1.15 g, 3.43 mmol) in dioxane (50 mL) Boc$_2$O (3.0 g, 13.7 mmol) and DMAP (42 mg, 0.34 mmol) was added and the resulting yellow solution was stirred at reflux for 72 h. The reaction mixture was allowed to warm to rt and saturated aqueous NaHCO$_3$ solution was added. The mixture was extracted with AcOEt (2×). The combined organic layers were washed with brine, dried with sodium sulfate, filtered and the solvent was removed under reduced pressure. The crude product was purified by flash-column chromatography over silicagel (Biotage Isolera One, eluent: gradient from 6% AcOEt in cyclohexane to 40% AcOEt in cyclohexane in 18 min) to yield the title compound as a white solid (1.42 g). UPLC-MS: MS 435.1 (M+H$^+$); UPLC rt 1.36 min.

Step 3: (E)-methyl 3-(3-(2-((di-tert-butoxycarbonyl) amino)ethyl)-4-chloropyridin-2-yl)acrylate. 94-3. A mixture of 94-2 (700 mg, 1.61 mmol), methyl acrylate (290 mg, 3.37 mmol), bis(tri-tert-butylphosphine)palladium(0) (25 mg, 0.048 mmol) and N,N-dicyclohexyl-methylamine (690 mg, 3.53 mmol) in dioxane (10 mL) was stirred under Argon at 150° C. for 2 h in the microwave. The solvent was removed under reduced pressure. The crude product was purified by flash-column chromatography over silicagel (Biotage Isolera One, eluent: gradient from 7% AcOEt in cyclohexane to 100% AcOEt in cyclohexane in 18 min) to yield the title compound as a clear oil (520 mg). UPLC-MS: MS 441.2 (M+H$^+$); UPLC rt 1.37 min.

Step 4: (E)-methyl 3-(3-(2-aminoethyl)-4-chloropyridin-2-yl)acrylate. 94-4. To a stirred solution of 94-3 (520 mg, 1.18 mmol) in DCM (10 mL), TFA (0.91 mL, 11.79 mmol) was added and the reaction mixture was stirred at RT for 64 h. The reaction mixture was evaporated under reduced pressure and the residue was suspended in diethyl ether. The white precipitate was filtered off and washed with a small amount of diethyl ether (2×). The HCl salt was dried under high vacuo overnight to yield the title compound as white solid (380 mg). UPLC-MS: MS 241.1 (M+H$^+$); UPLC rt 0.50 min.

Step 5: methyl 2-(4-chloro-5,6,7,8-tetrahydro-1,7-naphthyridin-8-yl)acetate. 94-5. A yellow solution of (E)-methyl 3-(3-(2-aminoethyl)-4-chloropyridin-2-yl)acrylate (530 mg, 1.49 mmol) and triethylamine (1.04 mL, 7.47 mmol) in dioxane (10 mL) was stirred at 50° C. for 1 h. The solvent was removed under reduced pressure. The crude product was purified by flash-column chromatography over silicagel (Biotage Isolera One, eluent: gradient from 2% MeOH in DCM to 20% MeOH in DCM in 14 min) to yield the title compound as a clear oil (308 mg). UPLC-MS: MS 241.1 (M+H$^+$); UPLC rt 0.43 min.

Step 6: methyl 2-(7-(2-((tert-butoxycarbonyl)amino) acetyl)-4-chloro-5,6,7,8-tetrahydro-1,7-naphthyridin-8-yl) acetate. 94-6. To a stirred solution of methyl 2-(4-chloro-5,6,7,8-tetrahydro-1,7-naphthyridin-8-yl)acetate (320 mg, 1.33 mmol), Boc-glycine (233 mg, 1.33 mmol) and triethylamine (0.37 mL, 2.66 mmol) in AcOEt (7 mL), T3P (0.93 mL, 1.59 mmol, 50% m/m in DMF) was added and the solution was stirred at RT for 16 h. Water was added and the mixture was extracted with AcOEt (2×). The combined organic layers were dried with sodium sulfate, filtered and the solvent was removed under reduced pressure. The crude product was purified by flash-column chromatography over silicagel (Biotage Isolera One, eluent: gradient from 0% AcOEt in cyclohexane to 100% AcOEt in cyclohexane in 21 min) to yield the title compound as a clear oil (510 mg). UPLC-MS: MS 398.1 (M+H$^+$); UPLC rt 0.95 min.

Step 7: sodium 2-(7-(2-(((tert-butoxycarbonyl)amino)acetyl)-4-chloro-5,6,7,8-tetrahydro-1,7-naphthyridin-8-yl)acetate. 94-7. To a stirred solution of methyl 2-(7-(2-(((tert-butoxycarbonyl)amino)acetyl)-4-chloro-5,6,7,8-tetrahydro-1,7-naphthyridin-8-yl)acetate (540 mg, 1.36 mmol) in MeOH (10 mL), 4N aqueous NaOH (0.39 mL, 1.56 mmol) was added and the solution was stirred at RT for 5 days. The solvent was evaporated under reduced pressure. The residue was dried under high vacuo overnight to yield the title compound as a beige powder (540 mg) which was used without further purification in the next step. UPLC-MS: MS 384.1 (M+H$^+$); UPLC rt 0.81 min.

Step 8: 2-(8-(carboxymethyl)-4-chloro-5,6-dihydro-1,7-naphthyridin-7(8H)-yl)-2-oxoethanaminium chloride. 94-8. To a stirred suspension of sodium 2-(7-(2-(((tert-butoxycarbonyl)amino)acetyl)-4-chloro-5,6,7,8-tetrahydro-1,7-naphthyridin-8-yl)acetate (540 mg, 1.41 mmol) in dioxane (10 mL), 4N HCl in dioxane (1.76 mL, 7.03 mmol) was added and the reaction mixture was stirred at RT for 48 h. The beige precipitate was filtered off washed with a small amount of diethyl ether (2×). The HCl salt was dried under high vacuo overnight to yield the title compound as beige solid (590 mg) containing a residual amount of NaCl. UPLC-MS: MS 284.1 (M+H$^+$); UPLC rt 0.45 min.

Step 9: 4-chloro-5,6,9,10,12,12a-hexahydro-[1,4]diazepino[1,7-h][1,7]naphthyridine-8,11-dione. 94-9. To a stirred solution of 2-(7-(2-aminoacetyl)-4-chloro-5,6,7,8-tetrahydro-1,7-naphthyridin-8-yl)acetic acid (HCl-salt) (450 mg, 1.41 mmol) and triethylamine (1.17 mL, 8.43 mmol) in DCM (20 mL), T3P (1.25 mL, 2.11 mmol, 50% m/m in AcOEt) was added slowly and the suspension was stirred at RT for 1 h. Saturated aqueous NaHCO$_3$ solution was added and the mixture was extracted with DCM (2×). The combined organic layers were dried with sodium sulfate, filtered and the solvent was removed under reduced pressure. The crude product was purified by flash-column chromatography over silicagel (Biotage Isolera One, eluent: gradient from 2% MeOH in AcOEt to 15% MeOH in AcOEt in 18 min) to yield the title compound as a beige solid (66 mg). UPLC-MS: MS 266.1 (M+H$^+$); UPLC rt 0.57 min.

Step 10: 4-(6-fluoropyridin-3-yl)-5,6,9,10,12,12a-hexahydro-[1,4]diazepino[1,7-h][1,7]naphthyridine-8,11-dione. 94-10. To a degassed solution of 4-chloro-5,6,9,10,12,12a-hexahydro-[1,4]diazepino[1,7-h][1,7]naphthyridine-8,11-dione (66 mg, 0.25 mmol) and 2-fluoro-5-(tributylstannyl)pyridine (120 mg, 0.31 mmol) in dioxane (2 mL) Pd(PPh$_3$)$_4$ (15 mg, 0.012 mmol) was added and the mixture was heated in the microwave at 150° C. for 5 h. The solvent was removed under reduced pressure. The crude product was purified by flash-column chromatography over silicagel (Biotage Isolera Four, eluent: from 2% MeOH in AcOEt to 20% MeOH in AcOEt in 21 min) to yield the title compound as a beige solid (32 mg). UPLC-MS: MS 327.2 (M+H$^+$); UPLC rt 0.58 min.

Step 11: 4-(6-fluoropyridin-3-yl)-5,6,9,10-tetrahydro-[1,4]diazepino[1,7-h][1,7]naphthyridine-8,11-dione. 94-11. A mixture of 4-(6-fluoropyridin-3-yl)-5,6,9,10,12,12a-hexahydro-[1,4]diazepino[1,7-h][1,7]naphthyridine-8,11-dione (32 mg, 0.098 mmol) and SeO$_2$ (19 mg, 0.17 mmol) in pyridine (1.5 mL) was stirred at 160° C. for 30 min under microwave conditions. The reaction mixture was allowed to warm to rt and poured into saturated aqueous NaHCO$_3$ solution. The mixture was extracted with AcOEt (3×). The combined organic layers were dried with sodium sulfate, filtered and the solvent was removed under reduced pressure. The crude product was dried under high vacuo overnight to yield the title compound as a beige solid (32 mg) which was used without further purification in the next step. UPLC-MS: MS 325.2 (M+H$^+$); UPLC rt 0.65 min.

Step 12: 4-(6-fluoropyridin-3-yl)-11-(4-isopropyl-1H-imidazol-1-yl)-5,6-dihydro-[1,4]diazepino[1,7-h][1,7]naphthyridin-8(9H)-one. Example 94. To a stirred solution of 4-(6-fluoropyridin-3-yl)-5,6,9,10-tetrahydro-[1,4]diazepino[1,7-h][1,7]naphthyridine-8,11-dione (31 mg, 0.096 mmol) in 1,2-dichloroethane (2 mL) POCl$_3$ (29.3 mg, 0.19 mmol) was added and the resulting suspension was stirred at 100° C. for 1 h. The reaction mixture was cooled to rt and concentrated under reduced pressure to dryness. For complete removal of POCl$_3$ the residue was taken up in toluene and evaporated twice again and dried under high vacuo. The resulting crude chloro compound was dissolved in 1,2-dichloroethane (5 mL), 4-isopropyl-1H-imidazole (53 mg, 0.48 mmol) was added and the mixture was stirred at 100° C. for 1 h. The reaction mixture was allowed to warm to rt and diluted with DCM. Saturated aqueous NaHCO$_3$ solution was added and the mixture was extracted twice with DCM. The combined organic layers were dried with sodium sulfate, filtered and the solvent was removed under reduced pressure. The crude product was purified by SFC (column: DEAP 5 μm, 250×30 mm, 60 A, Princeton; eluent: from 6% MeOH/CO$_2$ to 11% MeOH/CO$_2$ in 11 min; flow 100 mL/min; UV detection at 220 nm) and yielded the title compound as beige powder (11 mg). UPLC-MS: MS 417.2 (M+H$^+$); UPLC rt 0.87 min. $^1$H NMR (400 MHz, CHLOROFORM-d) δ ppm 1.17-1.34 (m, 6 H), 2.81-2.98 (m, 3 H), 4.05 (br. s., 2 H), 4.40 (s, 2 H), 7.09 (dd, J=8.3, 2.8 Hz, 1 H), 7.22-7.36 (m, 2 H), 7.77 (td, J=7.9, 2.1 Hz, 1 H), 7.96 (s, 1 H), 8.03 (s, 1 H), 8.23 (d, J=1.5 Hz, 1 H), 8.68 (d, J=4.8 Hz, 1 H).

Example 95-1

2-(4-cyclopropyl-1H-imidazol-1-yl)-9-(6-fluoropyridin-3-yl)-7,8-dihydro-[1,4]diazepino[7,1-a]isoquinolin-5(4H)-one

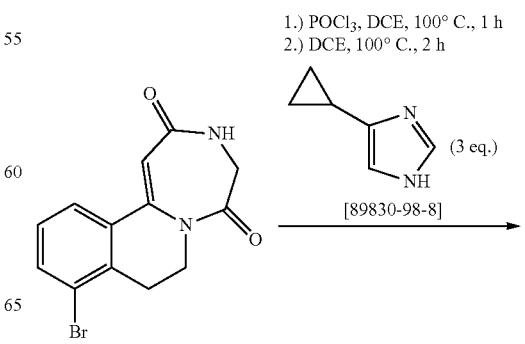

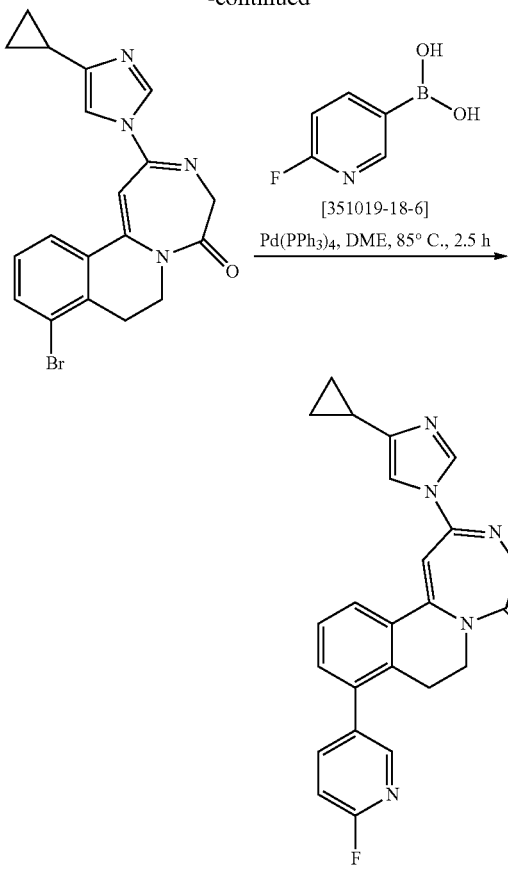

Step 1: 9-bromo-2-(4-cyclopropyl-1H-imidazol-1-yl)-7,8-dihydro-[1,4]diazepino[7,1-a]isoquinolin-5(4H)-one. 95-1-1. To a stirred solution of 9-bromo-3,4,7,8-tetrahydro-[1,4]diazepino[7,1-a]isoquinoline-2,5-dione (2.0 g, 6.51 mmol) in 1,2-dichloroethane (65 mL) was added POCl$_3$ (1.21 mL, 13.02 mmol) at RT and the resulting suspension was stirred at 100° C. for 1 h. The reaction mixture was cooled to rt and concentrated under reduced pressure to dryness. For complete removal of POCl$_3$ the residue was taken up in toluene and the solvent was evaporated under reduced pressure. The residue was dried under high vacuo at RT.

The resulting crude chloro intermediate was dissolved in 1,2-dichloroethane (50 mL), a solution of 4-cyclopropyl-1H-imidazole (2.11 g, 19.53 mmol) in 1,2-dichloroethane (15 mL) was added and the mixture was stirred at 100° C. for 2 h. The reaction mixture was allowed to warm to rt and diluted with DCM. Saturated aqueous NaHCO$_3$ solution was added and the mixture was extracted twice with DCM. The combined organic layers were washed with brine, dried with sodium sulfate, filtered and the solvent was removed under reduced pressure. The crude product was purified by flash-column chromatography over silicagel (Biotage Isolera Four, eluent: 1% MeOH in DCM for 5 min, then from 1% MeOH in DCM to 4% MeOH in DCM in 25 min, 4% MeOH in DCM for 5 min) to yield 1.72 g of a redbrown foam. A second flash-column chromatography over silicagel was done (Biotage Isolera Four, eluent: 20% AcOEt in DCM for 3 min, then from 20% AcOEt in DCM to 80% AcOEt in DCM in 25 min, followed by 80% AcOEt in DCM for 10 min) to yield the title compound as a yellow solid (1.48 g). UPLC-MS: MS 397.1/399.1 (M+H$^+$); UPLC rt 1.00 min.

Step 2: 2-(4-cyclopropyl-1H-imidazol-1-yl)-9-(6-fluoropyridin-3-yl)-7,8-dihydro-[1,4]diazepino[7,1-a]isoquinolin-5(4H)-one. Example 95-1. 9-bromo-2-(4-cyclopropyl-1H-imidazol-1-yl)-7,8-dihydro-[1,4]diazepino[7,1-a]isoquinolin-5(4H)-one (1.48 g, 3.73 mmol), (6-fluoropyridin-3-yl)boronic acid (1.05 g, 7.45 mmol) and a solution of Na$_2$CO$_3$ (1.97 g, 18.63 mmol) in water (14.5 mL) was treated with DME (58 mL). The suspension was degassed, Pd(PPh$_3$)$_4$ (646 mg, 0.56 mmol) was added and the mixture was heated at 85° C. for 2 h. The mixture was allowed to warm to RT and the solvent was removed under reduced pressure. The residue was dissolved in DCM and extracted with water, saturated aqueous NaHCO$_3$ solution and brine. The combined organic layers were dried with sodium sulfate, filtered and the solvent was removed under reduced pressure. The crude product was purified by flash-column chromatography over silicagel (Biotage Isolera Four, eluent: 1% MeOH in DCM for 3 min, then from 1% MeOH in DCM to 4% MeOH in DCM in 25 min, 4% MeOH in DCM for 5 min) to yield a beige foam (1.04 g). The residue was crystallized from AcOEt to afford the title compound as white crystals (720 mg). UPLC-MS: MS 414.2 (M+H$^+$); UPLC rt 0.95 min. $^1$H NMR (600 MHz, DMSO-d$_6$) δ ppm 0.66 (d, J=3.4 Hz, 2 H), 0.72-0.84 (m, 2 H), 1.70-1.88 (m, 1 H), 2.84 (br. s., 2 H), 3.72 (br. s., 2 H), 4.24 (br. s., 2 H), 7.18 (s, 1 H), 7.31 (d, J=8.5 Hz, 1 H), 7.43 (s, 1 H), 7.47-7.57 (m, 2 H), 7.97-8.14 (m, 3 H), 8.27 (s, 1 H).

Example 95-2

2-(3-cyclopropyl-1H-1,2,4-triazol-1-yl)-9-(6-fluoropyridin-3-yl)-7,8-dihydro-[1,4]diazepino[7,1-a]isoquinolin-5(4H)-one

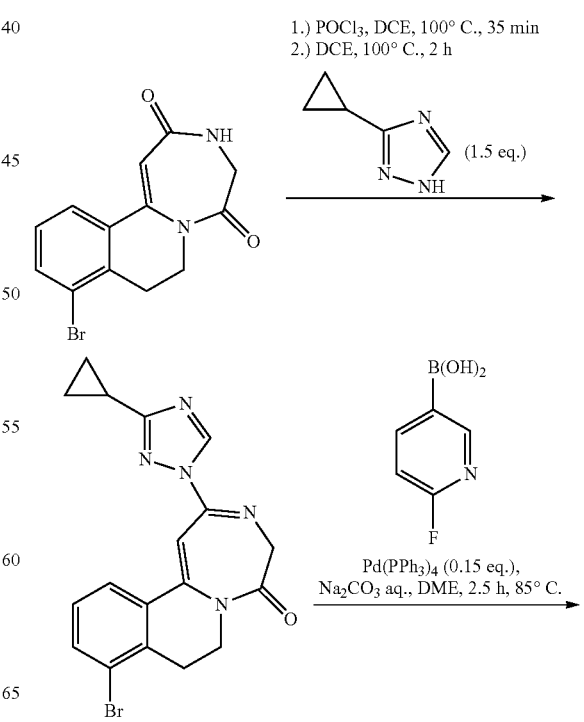

-continued

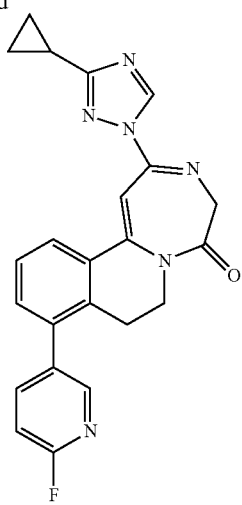

Step 1: 9-bromo-2-(3-cyclopropyl-1H-1,2,4-triazol-1-yl)-7,8-dihydro-[1,4]diazepino[7,1-a]isoquinolin-5(4H)-one.
95-2-1. To a stirred solution of 9-bromo-3,4,7,8-tetrahydro-[1,4]diazepino[7,1-a]isoquinoline-2,5-dione (5.0 g, 16.28 mmol) in 1,2-dichloroethane (203 mL) was added POCl$_3$ (3.03 mL, 32.6 mmol) at rt and the resulting suspension was stirred at 100° C. for 35 min. The reaction mixture was cooled to rt and concentrated under reduced pressure to dryness. For complete removal of POCl$_3$ the residue was taken up in toluene and the solvent was evaporated under reduced pressure. The residue was dried under high vacuo at rt.

The resulting crude chloro intermediate was dissolved in 1,2-dichloroethane (190 mL), a solution of 3-cyclopropyl-1H-1,2,4-triazole (2.66 g, 24.37 mmol) in 1,2-dichloroethane (15 mL) was added and the mixture was stirred at 100° C. for 2 h. The reaction mixture was allowed to warm to rt and diluted with DCM. Saturated aqueous NaHCO$_3$ solution was added and the mixture was extracted twice with DCM. The combined organic layers were washed with brine, dried with sodium sulfate, filtered and the solvent was removed under reduced pressure. The crude product was purified by flash-column chromatography over silicagel (Biotage Isolera Four, eluent: 0.5% MeOH in DCM for 3 min, then from 0.5% MeOH in DCM to 2.5% MeOH in DCM in 50 min, 2.5% MeOH in DCM for 5 min) to yield slightly red foam. The residue was triturated with AcOEt to yield the title compound as a slightly red solid (3.92 g). UPLC-MS: MS 398.2/400.2 (M+H$^+$); UPLC rt 1.08 min.

Step 2: 2-(3-cyclopropyl-1H-1,2,4-triazol-1-yl)-9-(6-fluoropyridin-3-yl)-7,8-dihydro-[1,4]diazepino[7,1-a]isoquinolin-5(4H)-one. Example 95-2. 9-bromo-2-(3-cyclopropyl-1H-1,2,4-triazol-1-yl)-7,8-dihydro-[1,4]diazepino[7,1-a]isoquinolin-5(4H)-one (5.7 g, 14.31 mmol), (6-fluoropyridin-3-yl)boronic acid (4.03 g, 28.6 mmol) and a solution of Na$_2$CO$_3$ (7.58 g, 71.6 mmol) in water (28 mL) was treated with DME (114 mL). The suspension was degassed, Pd(PPh$_3$)$_4$ (2.48 g, 2.15 mmol) was added and the mixture was heated at 85° C. for 2 h. The mixture was allowed to warm to RT and the solvent was removed under reduced pressure. The residue was dissolved in DCM and extracted with water, saturated aqueous NaHCO$_3$ solution and brine. The combined organic layers were dried with sodium sulfate, filtered and the solvent was removed under reduced pressure. The crude product was purified by flash-column chromatography over silicagel (Biotage Isolera Four, eluent: 70% AcOEt in heptane for 3 min, then from 70% AcOEt in heptane to 100% AcOEt in heptane in 50 min, 100% AcOEt in heptane for 10 min) to yield a beige foam (5.91 g). The residue was dissolved in DCM (100 mL) and MP-TMT resin (4.0 g, 0.71 mmol/g) was added and the mixture was stirred for 2.5 h. The resin was filtered off and the solvent was removed under reduced pressure to yield a yellow foam. The foam was crystallized from hot n-butanol (50 mL) to afford the title compound as white crystals (4.8 g). UPLC-MS: MS 415.4 (M+H$^+$); UPLC rt 1.02 min. $^1$H NMR (400 MHz, DMSO-d$_6$) δ ppm 0.79-0.87 (m, 2 H), 0.89-0.99 (m, 2 H), 1.98-2.07 (m, 1 H), 2.87 (t, J=6.11 Hz, 2 H), 3.72 (t, J=6.11 Hz, 2 H), 4.30 (s, 2 H), 7.05 (s, 1 H), 7.31 (dd, J=8.44, 2.57 Hz, 1 H), 7.47-7.56 (m, 2 H), 7.89-7.97 (m, 1 H), 8.07 (td, J=8.13, 2.57 Hz, 1 H), 8.30 (d, J=2.45 Hz, 1 H), 9.00 (s, 1 H).

Example 96-1

9-cyclopropyl-2-(4-(methoxymethyl)-1H-imidazol-1-yl)-7,8-dihydro-[1,4]diazepino[7,1-a]isoquinolin-5(4H)-one

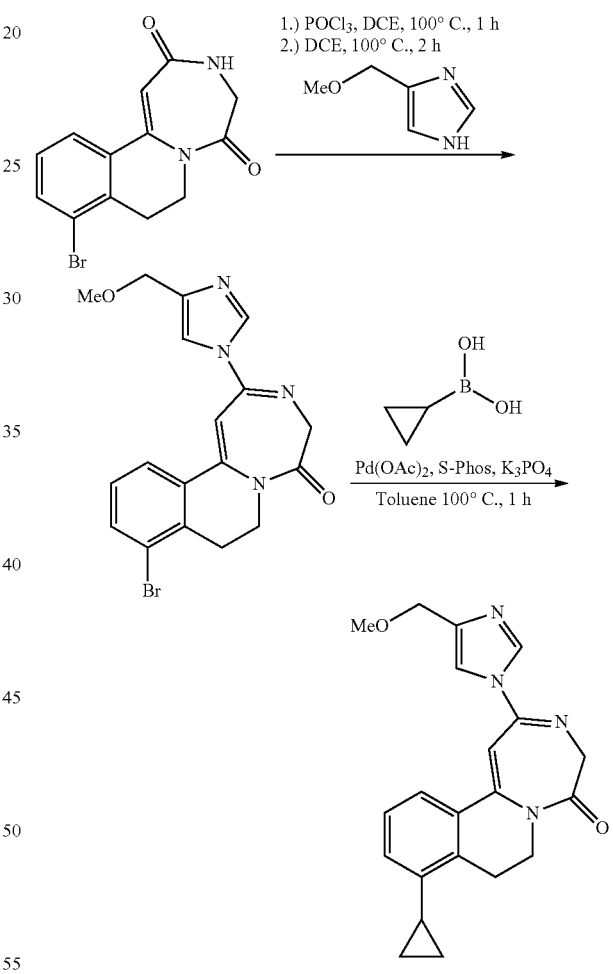

Step 1: 9-bromo-2-(4-(methoxymethyl)-1H-imidazol-1-yl)-7,8-dihydro-[1,4]diazepino[7,1-a]isoquinolin-5(4H)-one. 96-1-1. To a stirred solution of 9-bromo-3,4,7,8-tetrahydro-[1,4]diazepino[7,1-a]isoquinoline-2,5-dione (10.0 g, 32.6 mmol) in 1,2-dichloroethane (500 mL) was added POCl$_3$ (6.07 mL, 65.1 mmol) at RT and the resulting suspension was stirred at 100° C. for 1 h. The reaction mixture was cooled to rt and concentrated under reduced pressure to dryness. For complete removal of POCl$_3$ the residue was taken up in toluene and the solvent was evaporated under reduced pressure. The residue was dried under high vacuo at RT.

The resulting crude chloro intermediate (14.85 g) was dissolved in 1,2-dichloroethane (400 mL), a solution of 4-(methoxymethyl)-1H-imidazole (10.97 g, 98 mmol) in 1,2-dichloroethane (100 mL) was added and the mixture was stirred at 100° C. for 2 h. The reaction mixture was allowed to warm to RT and diluted with DCM. Saturated aqueous NaHCO$_3$ solution was added and the mixture was extracted twice with DCM. The combined organic layers were washed with brine, dried with sodium sulfate, filtered and the solvent was removed under reduced pressure. The crude product was purified by flash-column chromatography over silicagel (Biotage Isolera Four, eluent: AcOEt/DCM 9:1 for 20 min, then from 1% MeOH in DCM to 2.5% MeOH in DCM in 25 min, 2.5% MeOH in DCM for 35 min) to yield 8.35 g of a redbrown foam. The residue was dissolved in AcOEt (50 mL) and stirred overnight while the desired regioisomer crystallized. The solid was filtered of, washed with a small amount of AcOEt and dried overnight under high vacuo to yield the title compound as pale yellow crystals (2.6 g). UPLC-MS: MS 401.2/403.2 (M+H$^+$); UPLC rt 0.91 min.

Step 2: 9-cyclopropyl-2-(4-(methoxymethyl)-1H-imidazol-1-yl)-7,8-dihydro-[1,4]diazepino[7,1-a]isoquinolin-5(4H)-one. Example 96-1. 9-bromo-2-(4-(methoxymethyl)-1H-imidazol-1-yl)-7,8-dihydro-[1,4]diazepino[7,1-a]isoquinolin-5(4H)-one (7.73 g, 19.26 mmol) was dissolved in toluene (155 mL) and S-Phos (2.58 g, 6.16 mmol), cyclopropylboronic acid (3.45 g, 38.5 mmol) and K$_3$PO$_4$ (8.59 g, 40.5 mmol) were added. The suspension was degassed, Pd(OAc)$_2$ (0.87 g, 3.85 mmol) was added under Argon and the mixture was heated at 100° C. for 1 h. The mixture was allowed to warm to RT and filtered through a pad of celite. The residue was diluted with DCM and extracted with water, saturated aqueous NaHCO$_3$ solution and brine. The combined organic layers were dried with sodium sulfate, filtered and the solvent was removed under reduced pressure. The crude product was purified by flash-column chromatography over silicagel (Biotage Isolera Four, eluent: 1% MeOH in DCM for 5 min, then from 1% MeOH in DCM to 5% MeOH in DCM in 60 min, 5% MeOH in DCM for 10 min) to yield a beige foam (6.85 g). The residue was crystallized from AcOEt to afford the title compound as white crystals (5.8 g). UPLC-MS: MS 363.3 (M+H$^+$); UPLC rt 0.95 min. $^1$H NMR (400 MHz, DMSO-d$_6$): δ ppm 0.50-0.72 (m, 2 H), 0.79-1.06 (m, 2 H), 1.77-2.08 (m, 1 H), 2.93-3.14 (m, 2 H), 3.24 (s, 3 H), 3.87 (br. s, 2 H), 4.13-4.39 (m, 4 H), 7.09-7.21 (m, 2 H), 7.24-7.35 (m, 1 H), 7.62 (s, 1 H), 7.84-7.94 (m, 1 H), 8.20 (s, 1 H).

Example 96-2

9-cyclopropyl-10-fluoro-2-(4-(methoxymethyl)-1H-imidazol-1-yl)-7,8-dihydro-[1,4]diazepino[7,1-a]isoquinolin-5(4H)-one

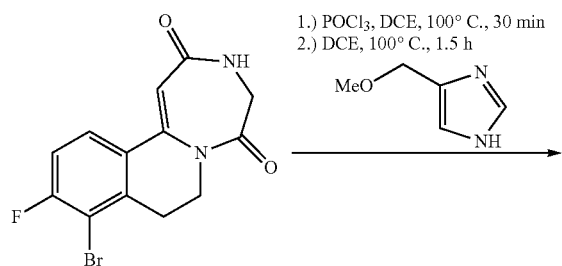

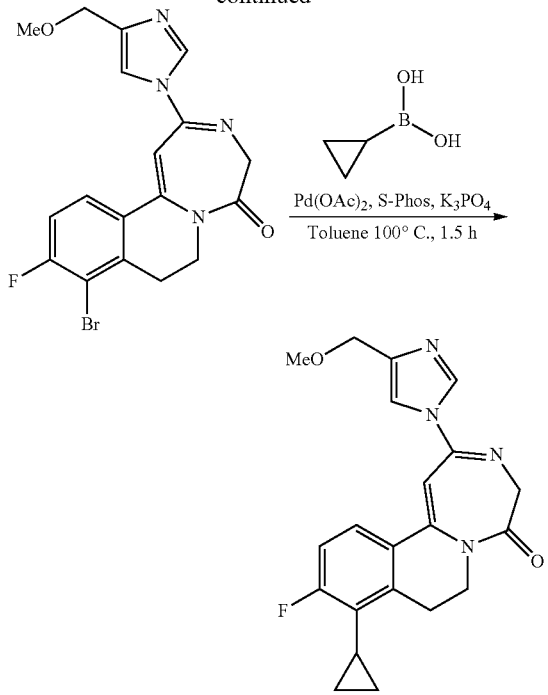

Step 1: 9-bromo-10-fluoro-2-(4-(methoxymethyl)-1H-imidazol-1-yl)-7,8-dihydro-[1,4]diazepino[7,1-a]isoquinolin-5(4H)-one. 96-2-1. To a stirred solution of 9-bromo-10-fluoro-3,4,7,8-tetrahydro-[1,4]diazepino[7,1-a]isoquinoline-2,5-dione (see preparation 17a) (4.40 g, 13.53 mmol) in 1,2-dichloroethane (135 mL) was added POCl$_3$ (2.52 mL, 27.1 mmol) at RT and the resulting suspension was stirred at 100° C. for 30 min. The reaction mixture was cooled to rt and concentrated under reduced pressure to dryness. For complete removal of POCl$_3$ the residue was taken up in toluene and the solvent was evaporated under reduced pressure. The residue was dried under high vacuo at RT.

The resulting crude chloro intermediate (4.65 g) was dissolved in 1,2-dichloroethane (135 mL), 4-(methoxymethyl)-1H-imidazole (6.07 g, 54.1 mmol) was added and the mixture was stirred at 100° C. for 1.5 h. The reaction mixture was allowed to warm to RT and diluted with DCM. Water was added and the mixture was extracted twice with DCM. The combined organic layers were washed with brine, dried with sodium sulfate, filtered and the solvent was removed under reduced pressure. The crude product was purified by flash-column chromatography over silicagel (Biotage Isolera Four, eluent: 0.5% MeOH in DCM for 5 min, then from 0.5% MeOH in DCM to 4% MeOH in DCM in 50 min, 4% MeOH in DCM for 10 min) to yield a beige foam. The residue was triturated with AcOEt to yield beige crystals. For a complete regioisomer separation the crystals were once again crystallized from AcOEt (25 mL) and stirred overnight. The solid was filtered of, washed with a small amount of AcOEt and dried overnight under high vacuo to yield the title compound as pale yellow crystals (1.5 g). UPLC-MS: MS 419.2/421.2 (M+H)$^+$; UPLC rt 3.22 min (10 min method).

Step 2: 9-cyclopropyl-10-fluoro-2-(4-(methoxymethyl)-1H-imidazol-1-yl)-7,8-dihydro-[1,4]diazepino[7,1-a]isoquinolin-5(4H)-one. Example 96-2. 9-bromo-10-fluoro-2-(4-(methoxymethyl)-1H-imidazol-1-yl)-7,8-dihydro-[1,4]diazepino[7,1-a]isoquinolin-5(4H)-one (1.5 g, 3.58 mmol) was dissolved in toluene (36 mL) and S-Phos (0.47 g, 1.14 mmol), cyclopropylboronic acid (0.615 g, 7.16 mmol) and K$_3$PO$_4$ (1.59 g, 7.51 mmol) were added. The suspension was degassed, Pd(OAc)$_2$ (0.16 g, 0.72 mmol) was added under Argon and the mixture was heated at 100° C. for 1.5 h. The mixture was allowed to warm to RT and filtered through a pad of celite. The residue was diluted with DCM and extracted with water, saturated aqueous NaHCO$_3$ solution and brine. The combined organic layers were dried with sodium sulfate, filtered and the solvent was removed under reduced pressure. The crude product was purified by flash-column chromatography over silicagel (Biotage Isolera Four, eluent: 50% AcOEt in DCM for 5 min, then from 50% AcOEt in DCM to 100% AcOEt in DCM in 40 min, followed by 100% AcOEt in DCM for 10 min)) to yield a foam. A second flash-column chromatography over silicagel was done (Biotage Isolera Four, eluent: 0.5% MeOH in DCM for 4 min, then from 0.5% MeOH in DCM to 4% MeOH in DCM in 60 min, 4% MeOH in DCM for 20) to yield the title compound as a yellow solid. The residue was dissolved in DCM and MP-TMT resin (0.71 mmol/g) was added and the mixture was stirred for 2.5 h. The resin was filtered off and the solvent was removed under reduced pressure to yield a yellow foam. The foam was crystallized from hot n-butanol to afford the title compound as white crystals (683 mg). UPLC-MS: MS 381.3 (M+H$^+$); UPLC rt 3.53 min (10 min method). $^1$H NMR (400 MHz, DMSO-d$_6$) δ ppm 0.55-0.64 (m, 2 H), 0.94-1.04 (m, 2 H), 1.67-1.78 (m, 1 H), 3.08 (t, J=5.99 Hz, 2 H), 3.23 (s, 3 H), 3.77-3.88 (m, 2 H), 4.22 (br. s., 2 H), 4.27 (s, 2 H), 7.10-7.20 (m, 2 H), 7.63 (s, 1 H), 7.98 (dd, J=8.93, 5.01 Hz, 1 H), 8.20 (d, J=1.47 Hz, 1 H).

Following the procedure described above for Example 95-1, 95-2, 96-1 and 96-2, and substituting the appropriate reagents, starting materials and purification methods known to those skilled in the art, the following compounds of the present invention were prepared:

Example 97

2-(4-cyclopropyl-1H-imidazol-1-yl)-9-(2-fluoropyridin-3-yl)-7,8-dihydro-[1,4]diazepino[7,1-a]isoquinolin-5(4H)-one UPLC-MS: MS 414.2 (M+H$^+$); 0.89 min.

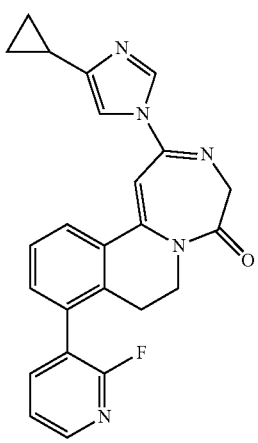 [SMILES: O=C1CN=C(n2cnc(C3CC3)c2)C=C2c3cccc(-c4cccnc4F)c3CCN12]

Example 98

2-(4-cyclobutyl-1H-imidazol-1-yl)-9-(2-fluoropyridin-3-yl)-7,8-dihydro-[1,4]diazepino[7,1-a]isoquinolin-5(4H)-one UPLC-MS: MS 428.2 (M+H$^+$); UPLC rt 0.96 min.

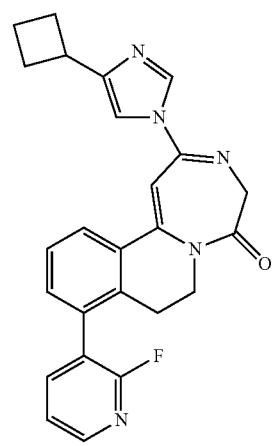 [SMILES: O=C1CN=C(n2cnc(C3CCC3)c2)C=C2c3cccc(-c4cccnc4F)c3CCN12]

Example 99

2-(4-cyclopropyl-1H-imidazol-1-yl)-9-(2,6-difluoropyridin-3-yl)-7,8-dihydro-[1,4]diazepino[7,1-a]isoquinolin-5(4H)-one UPLC-MS: MS 432.2 (M+H$^+$); UPLC rt 1.01 min.

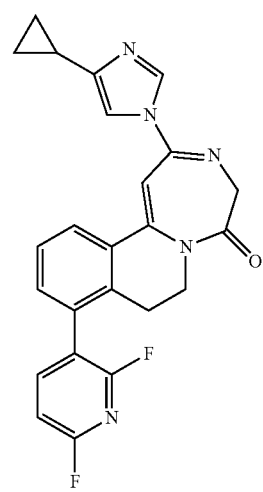 [SMILES: O=C1CN=C(n2cnc(C3CC3)c2)C=C2c3cccc(-c4ccc(F)nc4F)c3CCN12]

Example 99a 2-(4-methyl-1H-imidazol-1-yl)-9-(2-methyloxazol-5-yl)-7,8-dihydro-[1,4]diazepino[7,1-a]isoquinolin-5(4H)-one UPLC-MS: MS 374.1 (M+H$^+$); UPLC rt 0.73 min.

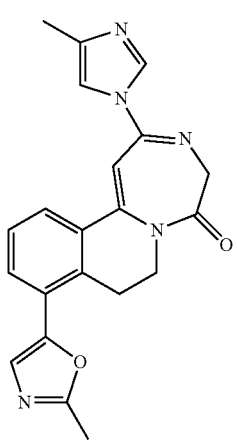 [SMILES: Cc1cn(C2=NCC(=O)N3CCc4c(cccc4-c4cnc(C)o4)C3=C2)cn1]

Example 99c 2-(4-cyclopropyl-1H-imidazol-1-yl)-9-(6-hydroxypyridin-3-yl)-7,8-dihydro-[1,4]diazepino[7,1-a]isoquinolin-5(4H)-one UPLC-MS: MS 412.4 (M+H$^+$); UPLC rt 0.71 min.

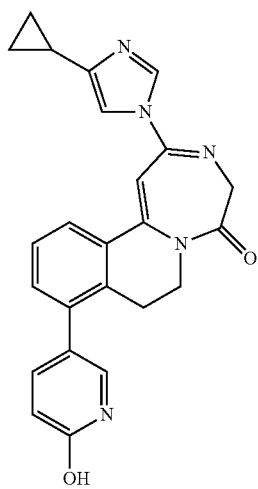

Example 99b 2-(4-cyclopropyl-1H-imidazol-1-yl)-9-(3-(trifluoromethyl)-1H-pyrazol-5-yl)-7,8-dihydro-[1,4]diazepino[7,1-a]isoquinolin-5(4H)-one UPLC-MS: MS 453.3 (M+H$^+$); UPLC rt 0.98 min.

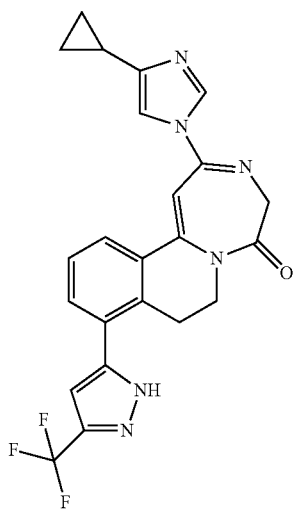 [SMILES: O=C1CN=C(n2cnc(C3CC3)c2)C=C2c3cccc(-c4cc(C(F)(F)F)n[nH]4)c3CCN12]

Example 99d 2-(4-cyclopropyl-1H-imidazol-1-yl)-9-(6-methoxypyridin-3-yl)-7,8-dihydro-[1,4]diazepino[7,1-a]isoquinolin-5(4H)-one UPLC-MS: MS 426.4 (M+H$^+$); UPLC rt 1.01 min.

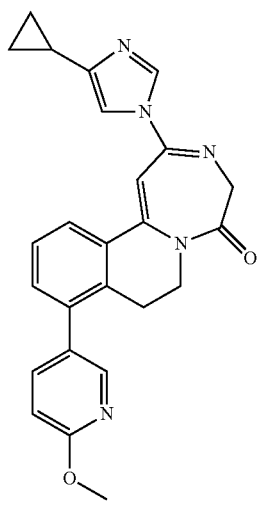 [SMILES: COc1ccc(-c2cccc3c2CCN2C(=O)CN=C(n4cnc(C5CC5)c4)C=C32)cn1]

Example 99e 2-(4-cyclopropyl-1H-imidazol-1-yl)-9-(1H-pyrazol-3-yl)-7,8-dihydro-[1,4]diazepino[7,1-a]isoquinolin-5(4H)-one UPLC-MS: MS 385.4 (M+H⁺); UPLC rt 0.78 min.

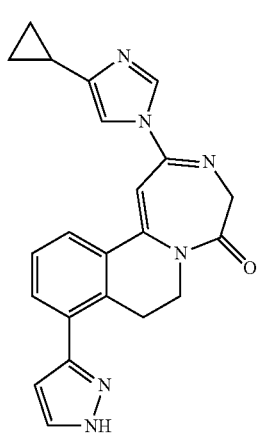 [SMILES: O=C1CN=C(n2cnc(C3CC3)c2)C=C2c3cccc(-c4cc[nH]n4)c3CCN12]

Example 99f 2-(4-cyclopropyl-1H-imidazol-1-yl)-9-(2-fluoropyrimidin-5-yl)-7,8-dihydro-[1,4]diazepino[7,1-a]isoquinolin-5(4H)-one UPLC-MS: MS 415.3 (M+H⁺); UPLC rt 0.87 min.

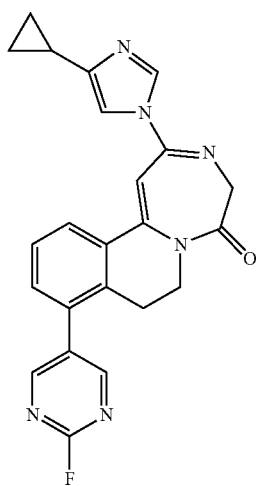 [SMILES: O=C1CN=C(n2cnc(C3CC3)c2)C=C2c3cccc(-c4cnc(F)nc4)c3CCN12]

Example 99g 2-(4-cyclopropyl-1H-imidazol-1-yl)-9-(2-fluoropyridin-4-yl)-7,8-dihydro-[1,4]diazepino[7,1-a]isoquinolin-5(4H)-one UPLC-MS: MS 414.2 (M+H⁺); UPLC rt 0.94 min.

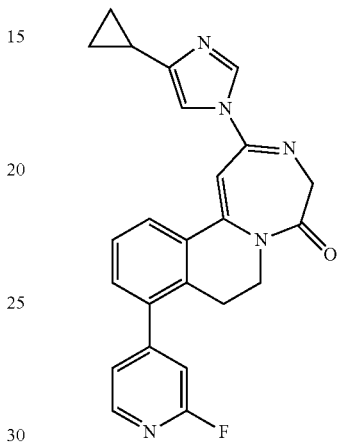

Example 99h 2-(3-cyclobutyl-1H-1,2,4-triazol-1-yl)-9-(6-fluoropyridin-3-yl)-7,8-dihydro-[1,4]diazepino[7,1-a]isoquinolin-5(4H)-one UPLC-MS: MS 429.3 (M+H⁺); UPLC rt 1.11 min.

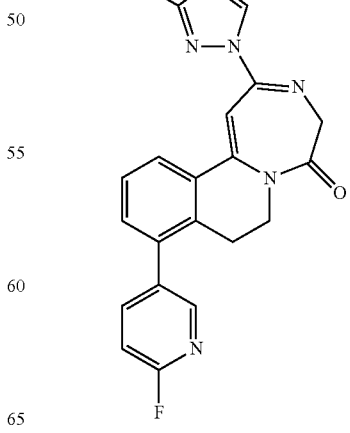

141

Example 99i (from Precursor Described in Preparation 17b)

9-cyclopropyl-12-fluoro-2-(4-(methoxymethyl)-1H-imidazol-1-yl)-7,8-dihydro-[1,4]diazepino[7,1-a]isoquinolin-5(4H)-one UPLC-MS: MS 381.3 (M+H$^+$); UPLC rt 0.96 min.

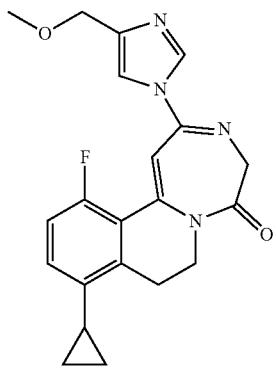 [SMILES: COCc1cn(C2=NCC(=O)N3CCc4c(C5CC5)ccc(F)c4C3=C2)cn1]

Example 99j (from Precursor Described in Preparation 17b)

(R)-9-cyclopropyl-12-fluoro-2-(4-(1-methoxyethyl)-1H-imidazol-1-yl)-7,8-dihydro-[1,4]diazepino[7,1-a]isoquinolin-5(4H)-one UPLC-MS: MS 395.3 (M+H$^+$); UPLC rt 1.00 min.

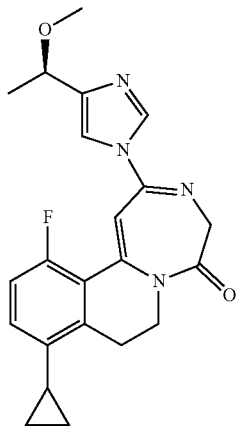 [SMILES: CO[C@H](C)c1cn(C2=NCC(=O)N3CCc4c(C5CC5)ccc(F)c4C3=C2)cn1]

142

Example 99k (from Precursor Described in Preparation 17c)

9-cyclopropyl-11-fluoro-2-(4-(methoxymethyl)-1H-imidazol-1-yl)-7,8-dihydro-[1,4]diazepino[7,1-a]isoquinolin-5(4H)-one UPLC-MS: MS 381.2 (M+H$^+$); UPLC rt 0.97 min.

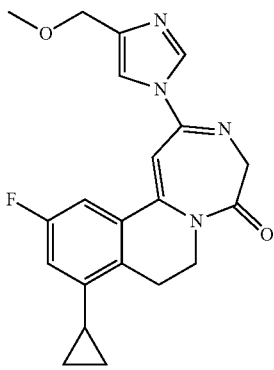

Example 99l (from Precursor Described in Preparation 17)

9-cyclopropyl-2-(4-(difluoromethyl)-1H-imidazol-1-yl)-7,8-dihydro-[1,4]diazepino[7,1-a]isoquinolin-5(4H)-one UPLC-MS: MS 369.2 (M+H$^+$); UPLC rt 1.05 min.

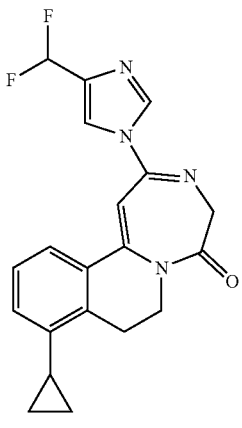 [SMILES: O=C1CN=C(n2cnc(C(F)F)c2)C=C2c3cccc(C4CC4)c3CCN12]

Example 99m (from Precursor Described in Preparation 17)

9-cyclopropyl-2-(4-(fluoromethyl)-1H-imidazol-1-yl)-7,8-dihydro-[1,4]diazepino[7,1-a]isoquinolin-5(4H)-one UPLC-MS: MS 351.2 (M+H$^+$); UPLC rt 1.00 min.

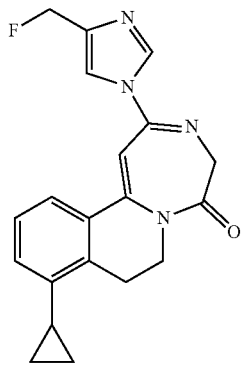 [SMILES: O=C1CN=C(n2cnc(CF)c2)C=C2c3cccc(C4CC4)c3CCN12]

Example 99n (from Precursor Described in Preparation 17a)

(R)-9-cyclopropyl-10-fluoro-2-(4-(1-methoxyethyl)-1H-imidazol-1-yl)-7,8-dihydro-[1,4]diazepino[7,1-a]isoquinolin-5(4H)-one UPLC-MS: MS 395.4 (M+H$^+$); UPLC rt 1.00 min.

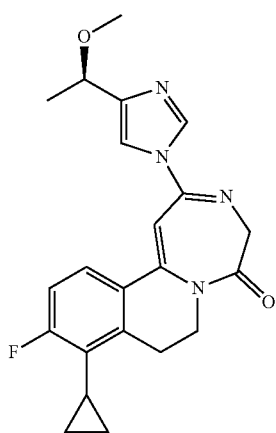 [SMILES: CO[C@H](C)c1cn(C2=NCC(=O)N3CCc4c(ccc(F)c4C4CC4)C3=C2)cn1]

Example 99o (from Precursor Described in Preparation 17a)

10-fluoro-9-(6-fluoropyridin-3-yl)-2-(3-methyl-1H-1,2,4-triazol-1-yl)-7,8-dihydro-[1,4]diazepino[7,1-a]isoquinolin-5(4H)-one UPLC-MS: MS 407.3 (M+H$^+$); UPLC rt 0.92 min.

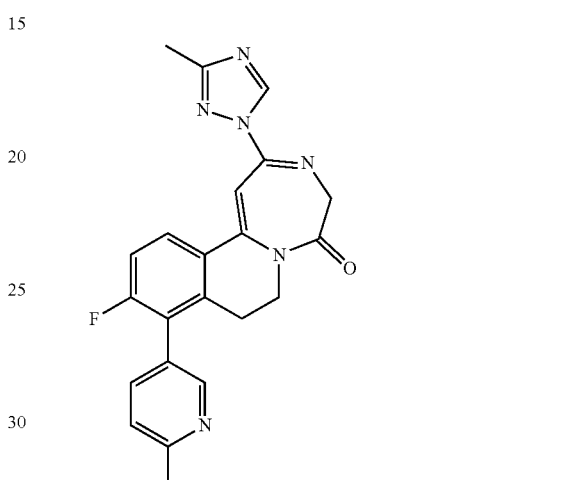

Example 99p (from Precursor Described in Preparation 17a)

9-cyclopropyl-10-fluoro-2-(3-(methoxymethyl)-1H-1,2,4-triazol-1-yl)-7,8-dihydro-[1,4]diazepino[7,1-a]isoquinolin-5(4H)-one UPLC-MS: MS 382.3 (M+H$^+$); UPLC rt 1.01 min.

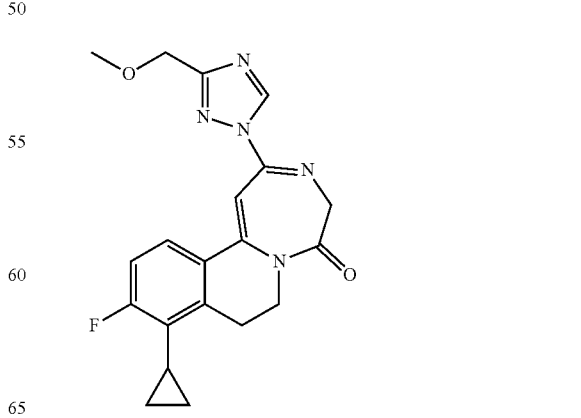

Example 99q (from Precursor Described in Preparation 17a)

2-(3-cyclopropyl-1H-1,2,4-triazol-1-yl)-10-fluoro-9-(2-fluoropyridin-3-yl)-7,8-dihydro-[1,4]diazepino[7,1-a]isoquinolin-5(4H)-one UPLC-MS: MS 433.3 (M+H$^+$); UPLC rt 1.00 min.

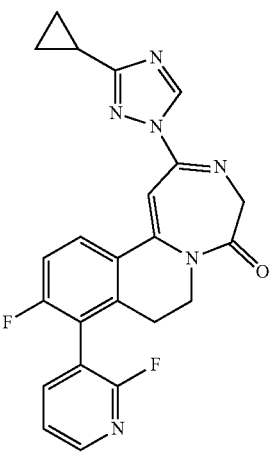 [SMILES: O=C1CN=C(n2cnc(C3CC3)n2)C=C2c3ccc(F)c(-c4cccnc4F)c3CCN12]

Example 99r (from Precursor Described in Preparation 17a)

10-fluoro-9-(2-fluoropyridin-3-yl)-2-(3-methyl-1H-1,2,4-triazol-1-yl)-7,8-dihydro-[1,4]diazepino[7,1-a]isoquinolin-5(4H)-one UPLC-MS: MS 407.3 (M+H$^+$); UPLC rt 0.89 min.

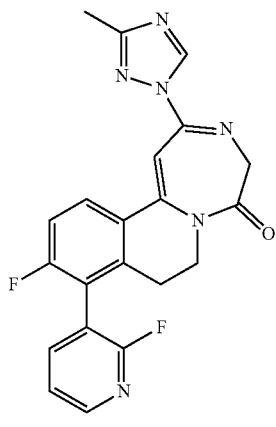 [SMILES: Cc1ncn(C2=NCC(=O)N3CCc4c(ccc(F)c4-c4cccnc4F)C3=C2)n1]

Example 99s (from Precursor Described in Preparation 17a)

10-fluoro-9-(2-fluoropyridin-3-yl)-2-(4-methyl-1H-imidazol-1-yl)-7,8-dihydro-[1,4]diazepino[7,1-a]isoquinolin-5(4H)-one UPLC-MS: MS 406.3 (M+H$^+$); UPLC rt 0.78 min.

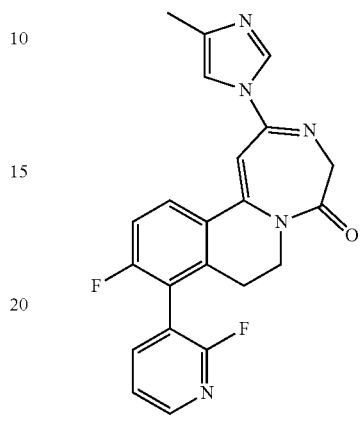

Example 100

2-(4-cyclopropyl-1H-imidazol-1-yl)-9-(isoxazol-5-yl)-7,8-dihydro-[1,4]diazepino[7,1-a]isoquinolin-5(4H)-one

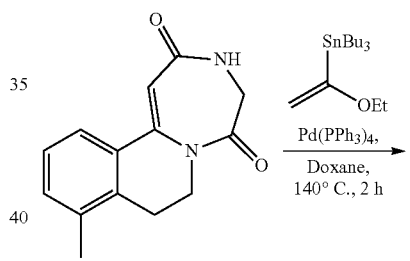

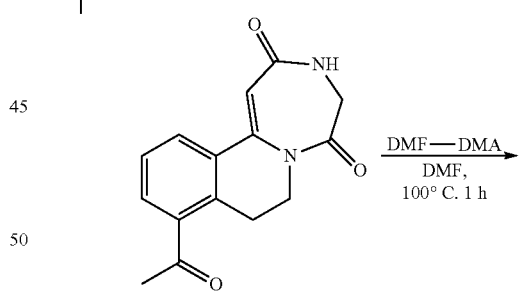

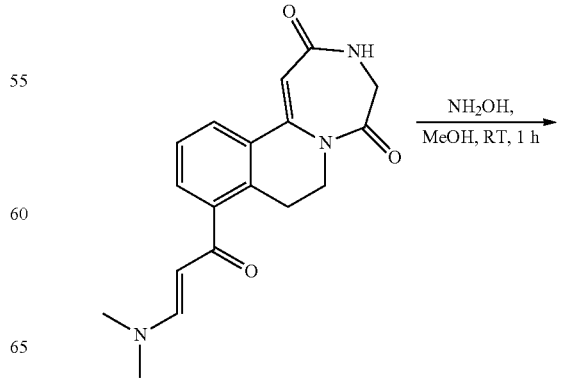

-continued

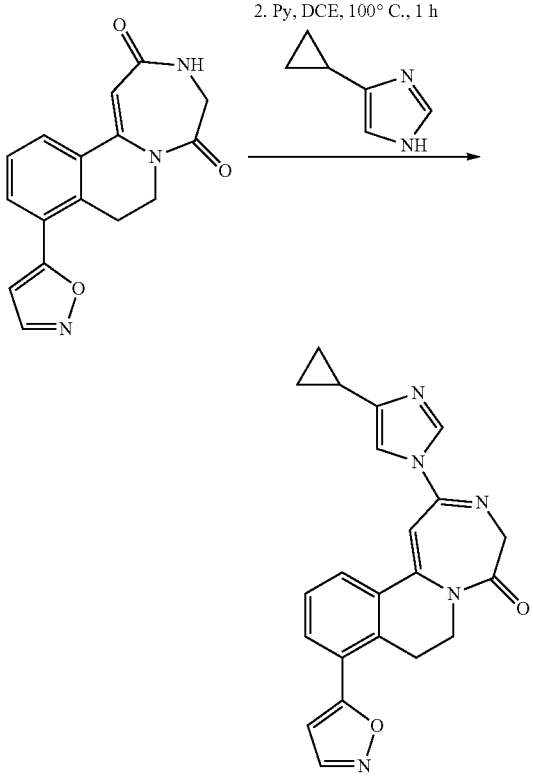

Step 1: 9-acetyl-3,4,7,8-tetrahydro-[1,4]diazepino[7,1-a]isoquinoline-2,5-dione. 100-1. A mixture of 9-iodo-3,4,7,8-tetrahydro-[1,4]diazepino[7,1-a]isoquinoline-2,5-dione (150 mg, 0.42 mmol), tributyl(1-ethoxyvinyl)stannane (153 mg, 0.42 mmol) and Pd(PPh$_3$)$_4$ (49 mg, 0.04 mmol) in dioxane (3 mL) was heated to 140° C. for 2 h in a microwave reactor. The mixture was then concentrated in vacuo and the residue obtained was purified by flash chromatography (SiO$_2$, heptane to AcOEt to AcOEt/MeOH 85:15) afforded the compound obtained was taken up in THF (20 mL) and treated with a 2M aqueous solution of HCl (0.68 mL, 1.36 mmol). The solution was stirred at RT for 1 h and then concentrated in vacuo. The residue obtained was taken up in a saturated aq. solution of NaHCO$_3$ and extracted with DCM. The combined org. layers were then dried over Na$_2$SO$_4$, filtered and concentrated in vacuo to give the title compound (79 mg). UPLC-MS: MS 271.2 (M+H$^+$); UPLC rt 0.59 min.

Step 2: (E)-9-(3-(dimethylamino)acryloyl)-3,4,7,8-tetrahydro-[1,4]diazepino[7,1-a]isoquinoline-2,5-dione. 100-2. A mixture of 9-acetyl-3,4,7,8-tetrahydro-[1,4]diazepino[7,1-a]isoquinoline-2,5-dione (200 mg, 0.74 mmol) in DMF (1.0 mL) was treated with DMF-DMA (0.12 mL, 0.89 mmol) and stirred at 100° C. for 1 h. The mixture was concentrated in vacuo and the crude product obtained was purified by flash chromatography (SiO$_2$, DCM/MeOH 98:2 to 85:15) to give the title compound (135 mg) as a beige solid. UPLC-MS: MS 236.2 (M+H$^+$), UPLC rt 0.54 min.

Step 3: 9-(isoxazol-5-yl)-3,4,7,8-tetrahydro-[1,4]diazepino[7,1-a]isoquinoline-2,5-dione. 100-3. NH$_2$OH*HCl (51 mg, 0.74 mmol) was added to a mixture of (E)-9-(3-(dimethylamino)acryloyl)-3,4,7,8-tetrahydro-[1,4]diazepino[7,1-a]isoquinoline-2,5-dione (160 mg, 0.49 mmol) in MeOH (5 mL) and the solution was heated to reflux for 1 h. The mixture was then concentrated in vacuo and the crude product was purified by flash chromatography (SiO$_2$, DCM/MeOH 99:1 to 90:10) to afford the title compound (90 mg) as a beige solid. UPLC-MS: MS 296.1 (M+H$^+$). UPLC rt 0.65 nm.

Step 4: 2-(4-cyclopropyl-1H-imidazol-1-yl)-9-(isoxazol-5-yl)-7,8-dihydro-[1,4]diazepino[7,1-a]isoquinolin-5(4H)-one. Example 100. A solution of 9-(isoxazol-5-yl)-3,4,7,8-tetrahydro-[1,4]diazepino[7,1-a]isoquinoline-2,5-dione (90 mg, 0.31 mmol) in DCE (4 mL) was treated with POCl$_3$ (57 µL, 0.61 mmol) and the mixture was heated to 100° C. for 1 h. The mixture was then allowed to cool to RT, poured onto H$_2$O and extracted with DCM. The org. phases were then dried over Na$_2$SO$_4$, filtered and concentrated in vacuo. The brown residue obtained was taken up in DCE (4 mL) and 4-cyclopropyl-1H-imidazole (50 mg, 0.46 mmol) and pyridine (74 µL, 0.91 mmol) were then added. The mixture was heated to 110° C. for 1 h, and then allowed to cool to RT, poured onto H$_2$O and extracted with DCM. The org. layers were then dried over Na$_2$SO$_4$, filtered and concentrated in vacuo. Purification by flash chromatography (SiO$_2$, cHex/AcOEt 100:0 to 0:100 and DCm/MeOH 99:1 to 90:10) afforded the title compound (42 mg) as a pale red solid. UPLC-MS: MS 386.2 (M+H$^+$); UPLC rt 0.85 min. $^1$H NMR (400 MHz, CHLOROFORM-d): δ ppm 0.67-0.79 (m, 2 H); 0.80-0.91 (m, 2 H); 1.80-1.91 (m, 1 H); 3.17 (t, J=6.06 Hz, 2 H); 3.90 (t, J=6.19 Hz, 2 H); 4.37 (s, 2 H); 6.47 (s, 1 H); 6.63 (s, 1 H); 7.18 (s, 1 H); 7.50 (t, J=7.83 Hz, 1 H); 7.70-7.83 (m, 2 H); 7.88 (s, 1 H); 8.38 (s, 1 H).

Example 101

2-(4-(methoxymethyl)-1H-imidazol-1-yl)-9-(thiazol-4-yl)-7,8-dihydro-[1,4]diazepino[7,1-a]isoquinolin-5(4H)-one

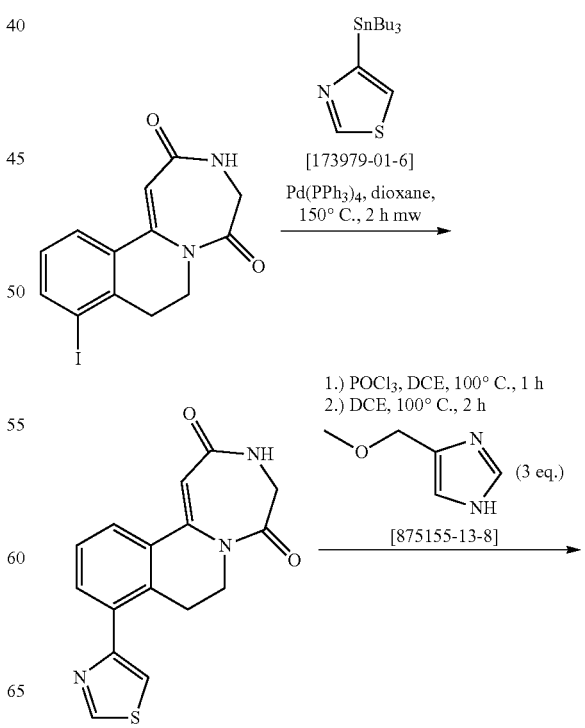

-continued

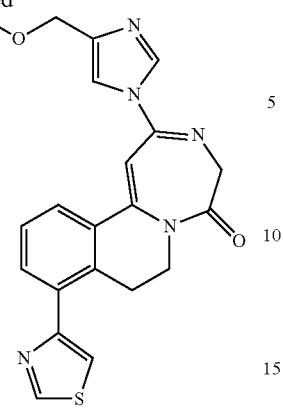

Step 1: 9-(thiazol-4-yl)-3,4,7,8-tetrahydro-[1,4]diazepino[7,1-a]isoquinoline-2,5-dione. 104-1. To a degassed solution of 9-iodo-3,4,7,8-tetrahydro-[1,4]diazepino[7,1-a]isoquinoline-2,5-dione (1 g, 2.82 mmol) and 4-(tributylstannyl)thiazole (1.48 g, 3.95 mmol) in dioxane (16 mL) was added Pd(PPh$_3$)$_4$ (130 mg, 0.11 mmol) and the mixture was heated in the microwave at 150° C. for 2 h. The solvent was removed under reduced pressure. The crude product was crystallized from DCM to yield the title compound (760 mg). UPLC-MS: MS 312.1 (M+H$^+$); UPLC rt 0.66 min.

Step 2: 2-(4-(methoxymethyl)-1H-imidazol-1-yl)-9-(thiazol-4-yl)-7,8-dihydro-[1,4]diazepino[7,1-a]isoquinolin-5(4H)-one. Example 101. To a stirred solution of 9-(thiazol-4-yl)-3,4,7,8-tetrahydro-[1,4]diazepino[7,1-a]isoquinoline-2,5-dione (160 mg, 0.51 mmol) in 1,2-dichloroethane (4 mL) POCl$_3$ (0.096 mL, 1.03 mmol) was added and the resulting suspension was stirred at 100° C. for 1 h. The reaction mixture was cooled to rt and concentrated under reduced pressure to dryness. For complete removal of POCl$_3$ the residue was taken up in toluene and evaporated twice again and dried under high vacuo. The resulting crude chloro compound was dissolved in 1,2-dichloroethane (4 mL), 4-(methoxymethyl)-1H-imidazole (172 mg, 1.53 mmol) was added and the mixture was stirred at 100° C. for 2 h. The reaction mixture was allowed to warm to rt and diluted with DCM. Saturated aqueous NaHCO$_3$ solution was added and the mixture was extracted twice with DCM. The combined organic layers were dried with sodium sulfate, filtered and the solvent was removed under reduced pressure. The crude product was purified by SFC (column: Reprosil 70 NH2, 5 μm, 250×30 mm, Dr. Maisch; eluent: 14% MeOH/CO$_2$ for 1 min, then from 14% MeOH/CO$_2$ to 19% MeOH/CO$_2$ in 6 min; flow 100 mL/min; UV detection at 220 nm) to yield the title compound as white powder (27 mg). UPLC-MS: MS 406.2 (M+H$^+$); UPLC rt 0.78 min. $^1$H NMR (400 MHz, CHLOROFORM-d) δ ppm 3.14 (t, J=5.9 Hz, 2 H), 3.42 (s, 3 H), 3.85 (t, J=6.1 Hz, 2 H), 4.39 (br. s., 2 H), 4.44 (s, 2 H), 6.61 (s, 1 H), 7.37-7.50 (m, 3 H), 7.68 (d, J=7.8 Hz, 1 H), 7.72 (d, J=7.8 Hz, 1 H), 8.04 (s, 1 H), 8.95 (s, 1 H).

Following the procedure described above for Example 101 and substituting the appropriate reagents, starting materials and purification methods known to those skilled in the art, the following compounds of the present invention were prepared:

Example 102

2-(3-ethyl-1H-1,2,4-triazol-1-yl)-9-(6-fluoropyridin-3-yl)-7,8-dihydro-[1,4]diazepino[7,1-a]isoquinolin-5(4H)-one UPLC-MS: MS 403.1 (M+H$^+$); UPLC rt 0.96 min.

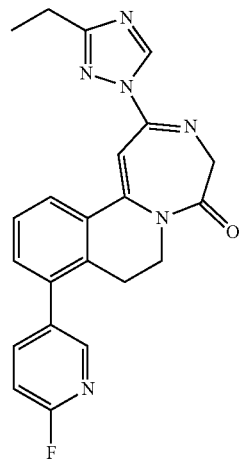 [SMILES: CCc1ncn(C2=NCC(=O)N3CCc4c(cccc4-c4ccc(F)nc4)C3=C2)n1]

Example 103

2-(4-cyclopropyl-1H-imidazol-1-yl)-9-(3-methylisothiazol-5-yl)-7,8-dihydro-[1,4]diazepino[7,1-a]isoquinolin-5(4H)-one UPLC-MS: MS 416.1 (M+H$^+$); UPLC rt 0.95 min.

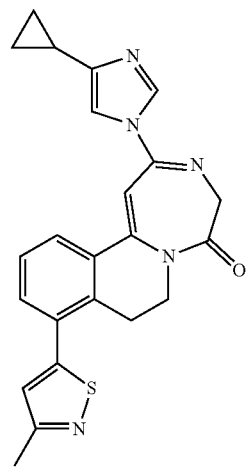 [SMILES: Cc1cc(-c2cccc3c2CCN2C(=O)CN=C(n4cnc(C5CC5)c4)C=C32)sn1]

Example 104

2-(4-cyclopropyl-1H-imidazol-1-yl)-9-(oxazol-2-yl)-7,8-dihydro-[1,4]diazepino[7,1-a]isoquinolin-5(4H)-one UPLC-MS: MS 386.2 (M+H⁺); UPLC rt 0.87 min.

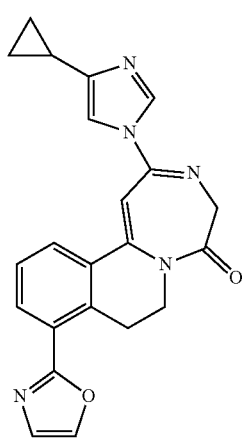 [SMILES: O=C1CN=C(n2cnc(C3CC3)c2)C=C2c3cccc(-c4ncco4)c3CCN12]

Example 105

2-(4-ethynyl-1H-imidazol-1-yl)-9-(thiazol-4-yl)-7,8-dihydro-[1,4]diazepino[7,1-a]isoquinolin-5(4H)-one UPLC-MS: MS 386.2 (M+H⁺); UPLC rt 0.88 min.

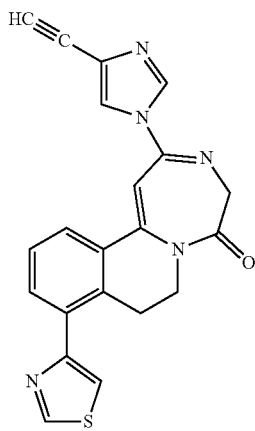 [SMILES: C#Cc1cn(C2=NCC(=O)N3CCc4c(cccc4-c4cscn4)C3=C2)cn1]

Example 106

9-(2-fluoropyridin-3-yl)-2-(4-(oxazol-2-yl)-1H-imidazol-1-yl)-7,8-dihydro-[1,4]diazepino[7,1-a]isoquinolin-5(4H)-one UPLC-MS: MS 441.1 (M+H+); UPLC rt 0.85 min.

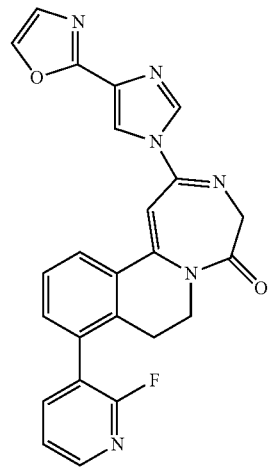 [SMILES: O=C1CN=C(n2cnc(-c3ncco3)c2)C=C2c3cccc(-c4cccnc4F)c3CCN12]

Example 106a 9-(6-fluoropyridin-3-yl)-2-(4-(1-methoxycyclopropyl)-1H-imidazol-1-yl)-7,8-dihydro-[1,4]diazepino[7,1-a]isoquinolin-5(4H)-one UPLC-MS: MS 444.2 (M+H+); UPLC rt 0.96 min.

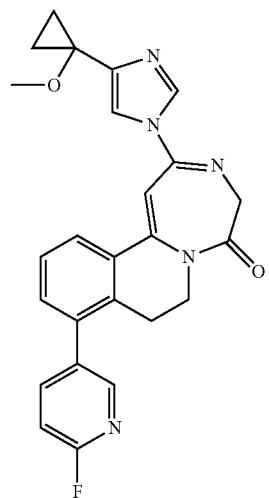 [SMILES: COC1(c2cn(C3=NCC(=O)N4CCc5c(cccc5-c5ccc(F)nc5)C4=C3)cn2)CC1]

Example 106b 2-(4-methyl-1H-imidazol-1-yl)-9-(pyrazin-2-yl)-7,8-dihydro-[1,4]diazepino[7,1-a]isoquinolin-5(4H)-one UPLC-MS: MS 371.2 (M+H+); UPLC rt 0.65 min.

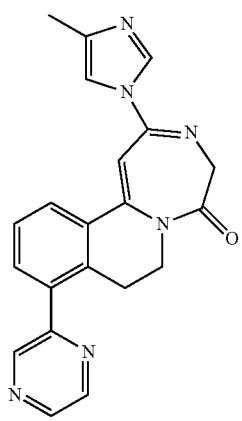 [SMILES: Cc1cn(C2=NCC(=O)N3CCc4c(cccc4-c4cnccn4)C3=C2)cn1]

Example 106c (from Precursor Described in Preparation 17)

9-(6-fluoropyridin-3-yl)-2-(4-(3-hydroxyoxetan-3-yl)-1H-imidazol-1-yl)-7,8-dihydro-[1,4]diazepino[7,1-a]isoquinolin-5(4H)-one UPLC-MS: MS 446.1 (M+H+); UPLC rt 0.80 min.

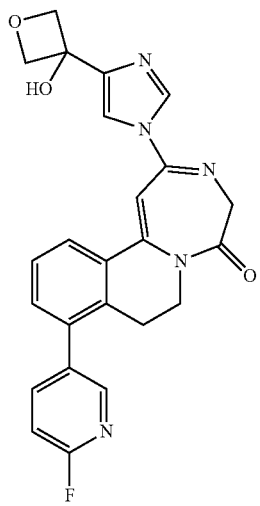 [SMILES: O=C1CN=C(n2cnc(C3(O)COC3)c2)C=C2c3cccc(-c4ccc(F)nc4)c3CCN12]

Example 107

2-(4-cyclopropyl-1H-imidazol-1-yl)-1-methyl-9-(3-methylisoxazol-5-yl)-7,8-dihydro-[1,4]diazepino[7,1-a]isoquinolin-5(4H)-one

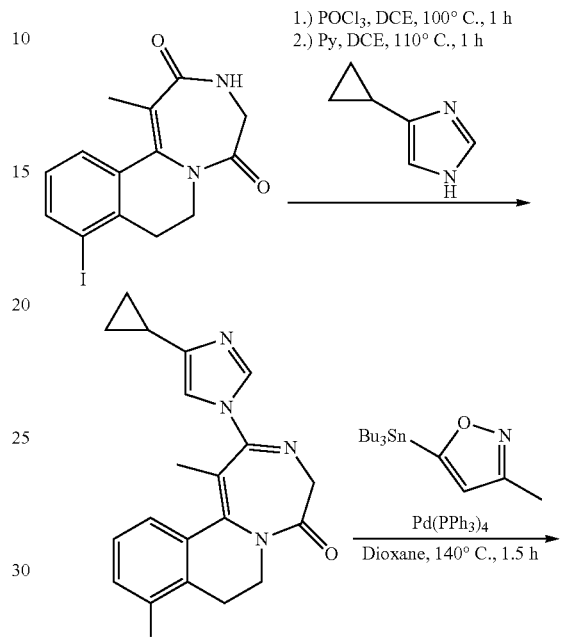

Step 1: 2-(4-cyclopropyl-1H-imidazol-1-yl)-9-iodo-1-methyl-7,8-dihydro-[1,4]diazepino[7,1-a]isoquinolin-5(4H)-one. 107-1. A mixture of 9-iodo-1-methyl-3,4,7,8-tetrahydro-[1,4]diazepino[7,1-a]isoquinoline-2,5-dione (30 mg, 81 μmol) in DCE (2 mL) is treated with POCl$_3$ (15 μL, 0.16 mmol) and heated to 100° C. for 3 h. The mixture was then allowed to cool to RT, poured onto H$_2$O and extracted with DCM. The org. phases were dried over Na$_2$SO$_4$, filtered and concentrated in vacuo. The brown residue obtained was taken up in DCE (2 mL) and 4-cyclopropyl-1H-imidazole (31 mg, 0.28 mmol) and pyridine (20 μL, 0.24 mmol) were then added. The mixture was heated to 100° C. for 4.5 h, and then allowed to cool to RT, poured onto H$_2$O and extracted with DCM. The org. layers were then dried over Na$_2$SO$_4$, filtered and concentrated in vacuo. Filtration through a pad of SiO$_2$ (AcOEt) afforded a brown solid that was purified by SFC (column: Diol 5 µm, 250×30 mm, 60 A, Princeton; eluent: 13% MeOH/CO$_2$ for 1 min, then from 13% MeOH/CO$_2$ to 18% MeOH/CO$_2$ in 6 min; then from 18% MeOH/CO$_2$ to 50% MeOH/CO$_2$ in 1 min; flow 100 mL/min; UV detection at 220 nm) to give the title compound (11 mg) as a white powder. UPLC-MS: MS 459.0 (M+H$^+$); UPLC rt 0.98 min.

Step 2: 2-(4-cyclopropyl-1H-imidazol-1-yl)-1-methyl-9-(3-methylisoxazol-5-yl)-7,8-dihydro-[1,4]diazepino[7,1-a]isoquinolin-5(4H)-one. Example 107. A mixture of 2-(4-cyclopropyl-1H-imidazol-1-yl)-9-iodo-1-methyl-7,8-dihydro-[1,4]diazepino[7,1-a]isoquinolin-5(4H)-one (8 mg, 17 µmol), 3-methyl-5-(tributylstannyl)isoxazole (10 mg, 26 µmol) and Pd(PPh$_3$)$_4$ (1.0 mg, 0.9 µmol) in dioxane (0.2 mL) is heated to 140° C. for 1.5 h under N$_2$ in a microwave reactor. The mixture was then concentrated in vacuo the residue obtained was purified by SFC (column: 2-Ethylpyridine 5 µm, 250×30 mm, 60 A, Princeton; eluent: 8% MeOH/CO$_2$ for 1 min, then from 8% MeOH/CO$_2$ to 13% MeOH/CO$_2$ in 6 min; then from 13% MeOH/CO$_2$ to 50% MeOH/CO$_2$ in 1 min; flow 100 mL/min; UV detection at 220 nm) to afford the title compound (4 mg) as a beige solid. UPLC-MS: MS 414.2 (M+H$^+$); UPLC rt 0.88 min. $^1$H NMR (400 MHz, CHLOROFORM-d): δ ppm 0.74-0.88 (m, 4 H); 1.74-1.91 (m, 1 H); 2.18 (s, 3 H); 2.42 (s, 3 H); 2.81 (td, J=14.68, 5.27 Hz, 1 H); 3.17 (td, J=13.49, 3.64 Hz, 1 H); 3.45 (m., 1 H); 3.91-4.02 (m, 2 H); 4.70 (d, J=10.79 Hz, 1 H); 6.32 (s, 1 H); 6.95 (s, 1 H); 7.45 (t, J=7.65 Hz, 1 H); 7.56 (d, J=7.78 Hz, 1 H); 7.66-7.76 (m, 2 H).

Example 108

2-(4-cyclopropyl-1H-imidazol-1-yl)-9-(2-methyloxazol-4-yl)-7,8-dihydro-[1,4]diazepino[7,1-a]isoquinolin-5(4H)-one

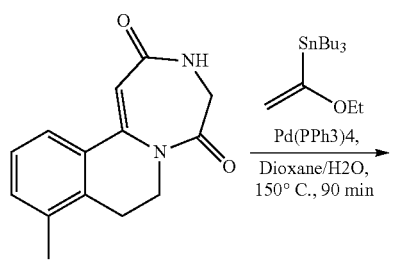

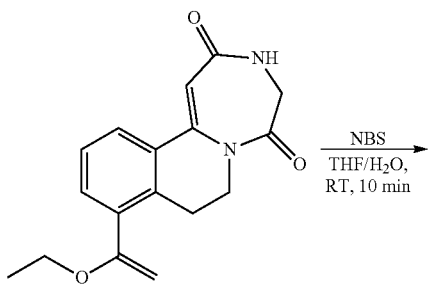

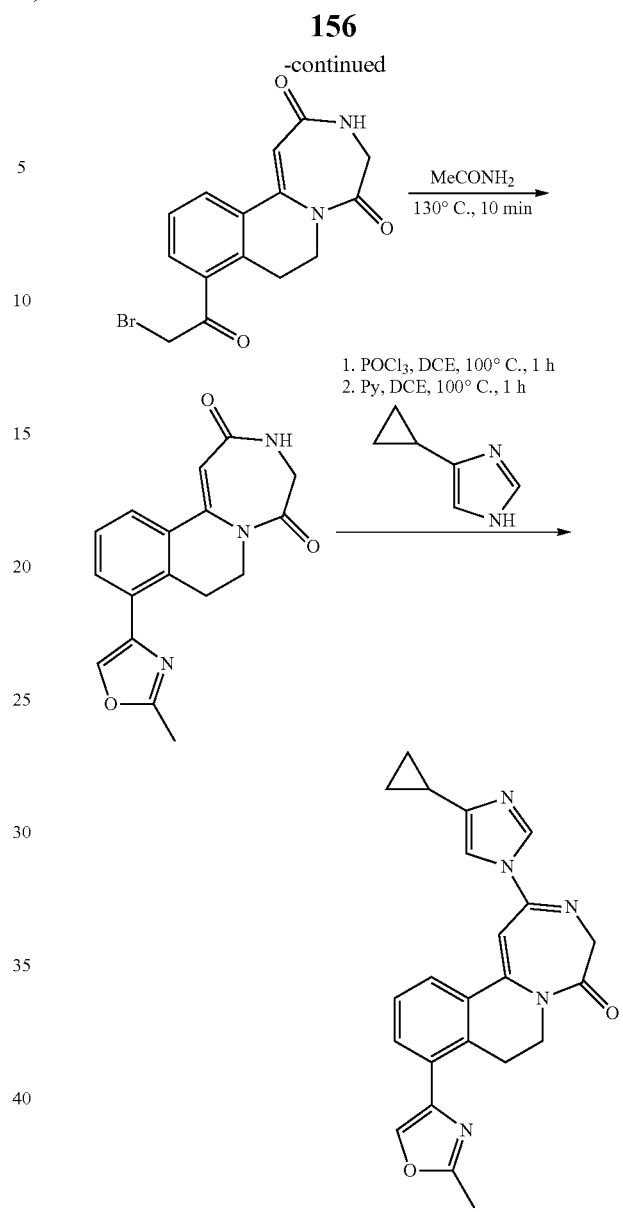

Step 1: 9-(1-ethoxyvinyl)-3,4,7,8-tetrahydro-[1,4]diazepino[7,1-a]isoquinoline-2,5-dione. 111-1. A mixture of 9-iodo-3,4,7,8-tetrahydro-[1,4]diazepino[7,1-a]isoquinoline-2,5-dione (2.5 g, 7.06 mmol) in dioxane (15 mL) was treated with tributyl(1-ethoxyvinyl)stannane (2.98 mL, 8.82 mmol) and Pd(PPh$_3$)$_4$ (408 mg, 0.35 mmol) under Ar, and the mixture was heated to 150° C. for 90 min in a microwave reactor. The mixture was then filtered and the filtrate concentrated in vacuo. Purification by flash chromatography (SiO$_2$, DCM/MeOH 99:1 to 90:10) gave the title compound (1.20 g) as a beige solid. UPLC-MS: MS 299.2 (M+H$^+$); UPLC rt 0.85 min.

Step 2: 9-(2-bromoacetyl)-3,4,7,8-tetrahydro-[1,4]diazepino[7,1-a]isoquinoline-2,5-dione. 111-2. A solution of 9-(1-ethoxyvinyl)-3,4,7,8-tetrahydro -[1,4]diazepino[7,1-a]isoquinoline-2,5-dione (1.2 g, 4.02 mmol) in a mixture of THF/H$_2$O (3:1, 40 mL) was treated with NBS (716 mg, 4.02 mmol) and the mixture was stirred at 0° C. for 10 min. The mixture was partioned between AcOEt and brine and the org. phase was separated, dried over Na$_2$SO$_4$, filtered and concentrated in vacuo to give the title compound (880 mg) that was used as it is in the next step. UPLC-MS: MS 349.0 (M+H$^+$); UPLC rt 0.69 min.

Step 3: 9-(2-methyloxazol-4-yl)-3,4,7,8-tetrahydro-[1,4]diazepino[7,1-a]isoquinoline-2,5-dione. 111-3. A flask was charged with 9-(2-bromoacetyl)-3,4,7,8-tetrahydro-[1,4]diazepino[7,1-a]isoquinoline-2,5-dione (230 mg, 0.66 mmol) and acetamide (233 mg, 3.95 mmol) and the solid mixture was heated to 130° C. for 15 min. The resulting brown liquid mass was partitioned in AcOEt and H$_2$O. The org. phase was separated, dried over Na$_2$SO$_4$, filtered and concentrated in vacuo. Purification by flash chromatography (SiO$_2$, AcOEt/MeOH (100:0 to 90:10) gave the title compound (110 mg) as a beige powder. UPLC-MS: MS 310.2 (M+H$^+$); UPLC rt 0.67 min.

Step 4: 2-(4-cyclopropyl-1H-imidazol-1-yl)-9-(2-methyloxazol-4-yl)-7,8-dihydro-[1,4]diazepino[7,1-a]isoquinolin-5(4H)-one. Example 108. A mixture of 9-(2-methyloxazol-4-yl)-3,4,7,8-tetrahydro-[1,4]diazepino[7,1-a]isoquinoline-2,5-dione (140 mg, 0.45 mmol) in DCE (10 mL) was treated with POCl$_3$ (84 μL, 0.91 mmol) and heated to 100° C. for 1 h. The mixture was then allowed to cool to RT, poured onto cold H$_2$O and extracted with DCM. The org. phases were dried over Na$_2$SO$_4$, filtered and concentrated in vacuo. The brown residue obtained was taken up in DCE (5 mL) and 4-cyclopropyl-1H-imidazole (59 mg, 0.54 mmol) and pyridine (110 μL, 1.36 mmol) were then added. The mixture was heated to 100° C. for 1 h, and then allowed to cool to RT, poured onto H$_2$O and extracted with DCM. The org. layers were then dried over Na$_2$SO$_4$, filtered and concentrated in vacuo. Purification by SFC (column: 2-Ethylpyridine 5 μm, 250×30 mm, 60 A, Princeton; eluent: 10% MeOH/CO$_2$ for 1 min, then from 10% MeOH/CO$_2$ to 15% MeOH/CO$_2$ in 6 min; then from 15% MeOH/CO$_2$ to 50% MeOH/CO$_2$ in 1 min; flow 100 mL/min; UV detection at 220 nm) afforded the title compound (42 mg) as beige powder. UPLC-MS: MS 400.2 (M+H$^+$); UPLC rt 0.86 min. $^1$H NMR (400 MHz, CHLOROFORM-d): δ ppm 0.61-0.82 (m, 2 H); 0.82-0.91 (m, 2 H); 1.78-1.96 (m, 1 H); 2.56 (s, 3 H); 3.16 (t, J=6.02 Hz, 2 H); 3.89 (t, J=6.15 Hz, 2 H); 4.37 (br. s., 2 H); 6.62 (s, 1 H); 7.19 (d, J=1.25 Hz, 1 H); 7.38-7.48 (m, 1 H); 7.63-7.70 (m, 2 H); 7.78 (dd, J=7.65, 1.13 Hz, 1 H); 7.89 (d, J=1.26 Hz, 1 H).

Following the procedure described above for Example 108 and substituting the appropriate reagents, starting materials and purification methods known to those skilled in the art, the following compounds of the present invention were prepared:

Example 108a 2-(3-cyclopropyl-1H-1,2,4-triazol-1-yl)-9-(2-methyloxazol-4-yl)-7,8-dihydro-[1,4]diazepino[7,1-a]isoquinolin-5(4H)-one UPLC-MS: MS 401.2 (M+H$^+$); UPLC rt 0.99 min.

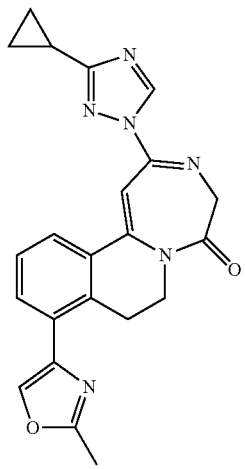 [SMILES: Cc1nc(-c2cccc3c2CCN2C(=O)CN=C(n4cnc(C5CC5)n4)C=C32)co1]

Example 108b 2-(4-cyclobutyl-1H-imidazol-1-yl)-9-(2-methyloxazol-4-yl)-7,8-dihydro-[1,4]diazepino[7,1-a]isoquinolin-5(4H)-one UPLC-MS: MS 414.2.2 (M+H$^+$); UPLC rt 0.96 min.

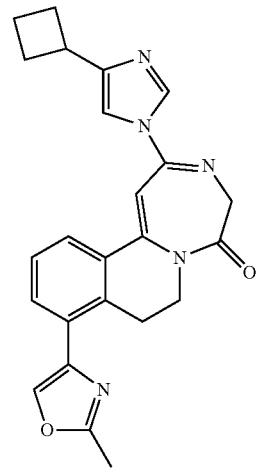 [SMILES: Cc1nc(-c2cccc3c2CCN2C(=O)CN=C(n4cnc(C5CCC5)c4)C=C32)co1]

Example 108c 2-(4-methyl-1H-imidazol-1-yl)-9-(2-methyloxazol-4-yl)-7,8-dihydro-[1,4]diazepino[7,1-a]isoquinolin-5(4H)-one UPLC-MS: MS 374.2 (M+H$^+$); UPLC rt 0.75 min.

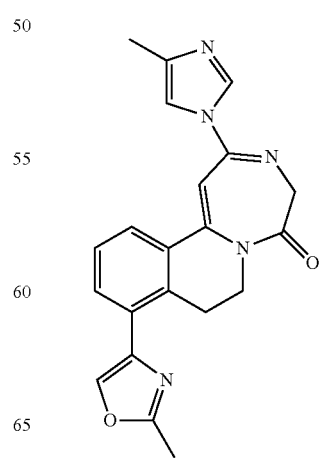

Example 109

2-(4-cyclopropyl-1H-imidazol-1-yl)-9-(oxazol-5-yl)-7,8-dihydro-[1,4]diazepino[7,1-a]isoquinolin-5(4H)-one

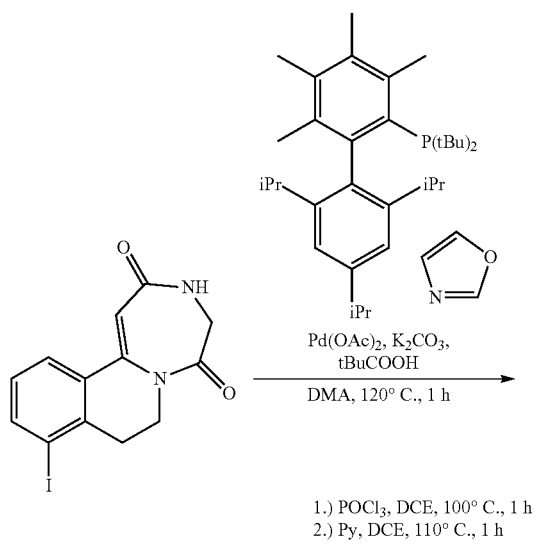

Step 1: 9-(oxazol-5-yl)-3,4,7,8-tetrahydro-[1,4]diazepino[7,1-a]isoquinoline-2,5-dione. 112-1. A mixture of 9-iodo-3,4,7,8-tetrahydro-[1,4]diazepino[7,1-a]isoquinoline-2,5-dione (520 mg, 1.47 mmol), oxazole (0.24 mL, 3.67 mmol), Pd(OAc)$_2$ (49 mg, 0.22 mmol), di-tert-butyl(2',4',6'-triisopropyl-3,4,5,6-tetramethyl-[1,1'-biphenyl]-2-yl)phosphine (141 mg, 0.29 mmol), K$_2$CO$_3$ (609 mg, 4.40 mmol) and pivalic acid (68 μL, 0.59 mmol) in DMA (4 mL) was heated to 120° C. for 1 h in a microwave reactor. The mixture was then filtered and the filtrate was concentrated in vacuo. Purification of the obtained residue by flash chromatography (SiO$_2$, AcOEt/MeOH 99:1 to 90:10) afforded the title compound (140 mg) as a beige powder. UPLC-MS: MS 296.1 (M+H$^+$); UPLC rt 0.60 min.

Step 2: 2-(4-cyclopropyl-1H-imidazol-1-yl)-9-(oxazol-5-yl)-7,8-dihydro-[1,4]diazepino[7,1-a]isoquinolin-5(4H)-one. Example 109. A mixture of 9-(oxazol-5-yl)-3,4,7,8-tetrahydro-[1,4]diazepino[7,1-a]isoquinoline-2,5-dione (180 mg, 0.61 mmol) in DCE (10 mL) was treated with POCl$_3$ (114 μL, 1.22 mmol) and heated to 100° C. for 1 h. The mixture was then allowed to cool to RT, poured onto cold H$_2$O and extracted with DCM. The org. phases were dried over Na$_2$SO$_4$, filtered and concentrated in vacuo. The brown residue obtained was taken up in DCE (5 mL) and 4-cyclopropyl-1H-imidazole (79 mg, 0.73 mmol) and pyridine (148 μL, 1.83 mmol) were then added. The mixture was heated to 100° C. for 1 h, and then allowed to cool to RT, poured onto H$_2$O and extracted with DCM. The org. layers were then dried over Na$_2$SO$_4$, filtered and concentrated in vacuo. Purification by SFC (column: 2-Ethylpyridine 5 μm, 250×30 mm, 60 A, Princeton; eluent: 9% MeOH/CO$_2$ for 1 min, then from 9% MeOH/CO$_2$ to 14% MeOH/CO$_2$ in 6 min; then from 14% MeOH/CO$_2$ to 50% MeOH/CO$_2$ in 1 min; flow 100 mL/min; UV detection at 220 nm) afforded the title compound (7 mg) as pale brown solid. UPLC-MS: MS 386.1 (M+H$^+$); UPLC rt 0.79 min. $^1$H NMR (400 MHz, CHLOROFORM-d): δ ppm 0.78 (m, 2 H); 0.81-0.87 (m, 2 H); 1.79-1.93 (m, 1 H); 3.14 (t, J=6.02 Hz, 2 H); 3.94 (t, J=6.15 Hz, 2 H); 4.38 (br. s., 2 H); 6.66 (s, 1 H); 7.20 (s, 1 H); 7.30 (s, 1 H); 7.42-7.60 (m, 1 H); 7.77 (d, J=7.78 Hz, 1 H); 7.74 (d, J=8.03 Hz, 1 H); 7.90 (s, 1 H); 8.03 (s, 1 H).

Example 110

2-(4-cyclopropyl-1H-imidazol-1-yl)-9-(6-fluoropyridin-3-yl)-7,8-dihydro-[1,4]diazepino[7,1-a][2,6]naphthyridin-5(4H)-one

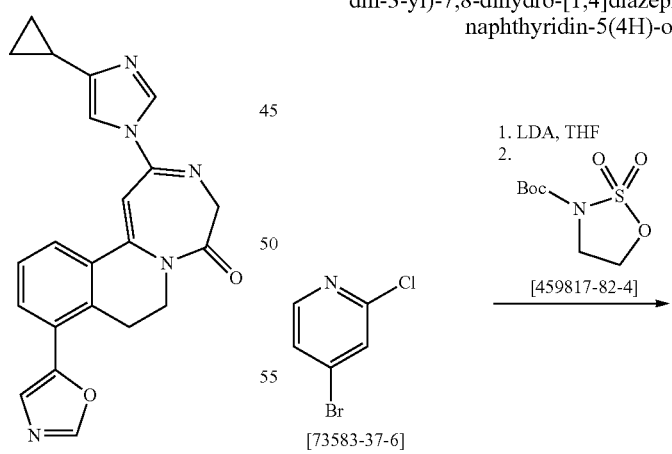

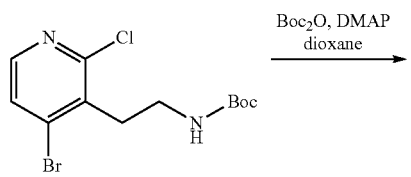

161
-continued
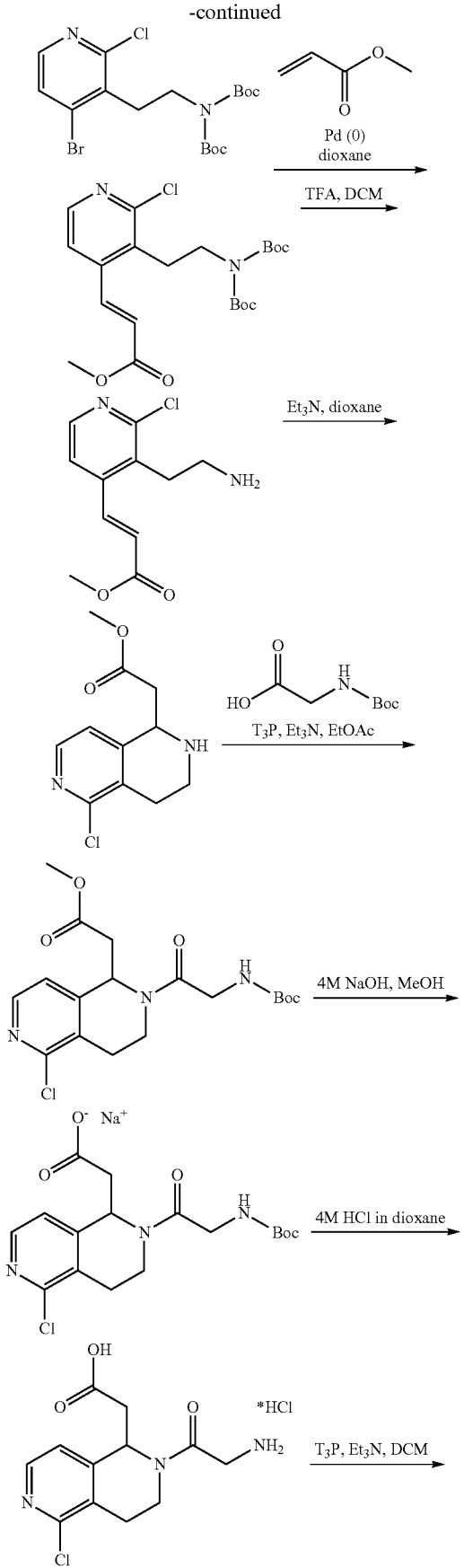
162
-continued
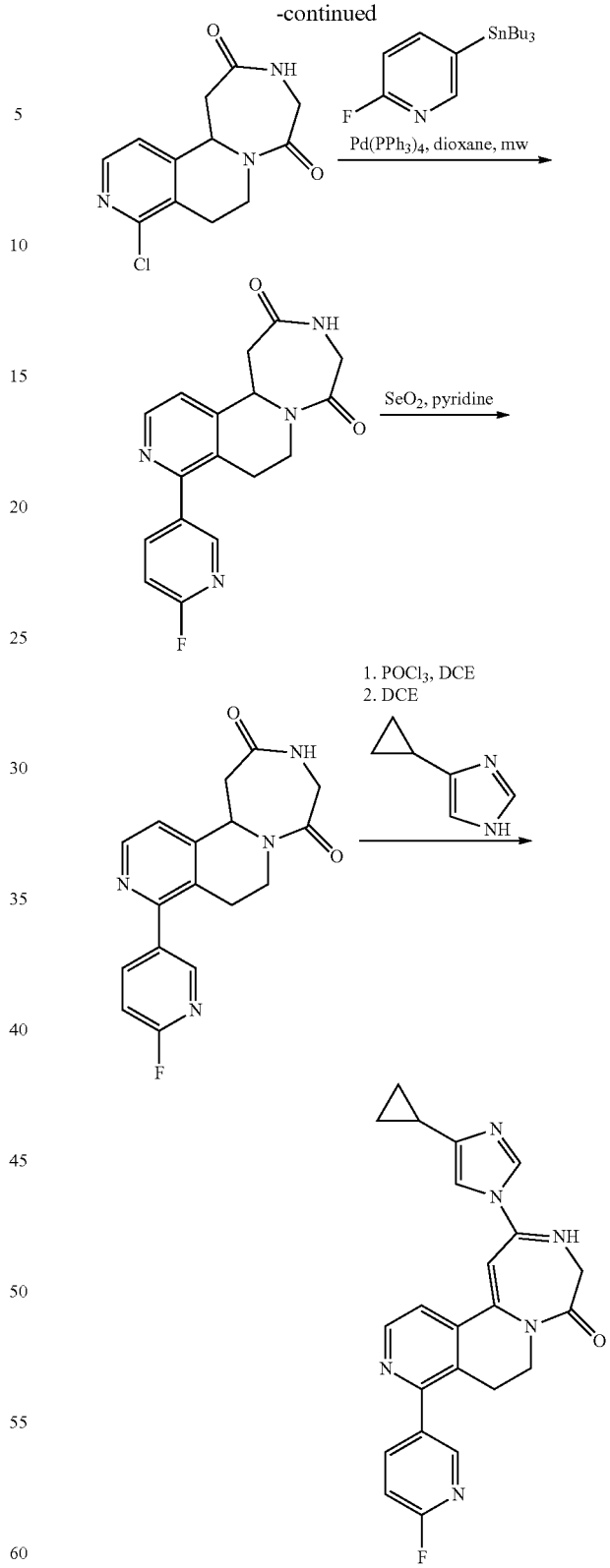
In analogy to Example 94 the title compound was synthesized from 4-bromo-2-chloropyridine and tert-butyl 1,2,3-oxathiazolidine-3-carboxylate 2,2-dioxide. UPLC-MS: MS 415.2 (M+H$^+$); UPLC rt 0.77 min. $^1$H NMR (400 MHz, CHLOROFORM-d) δ ppm 0.66-0.82 (m, 2 H), 0.84-0.99 (m, 2 H), 1.78-1.96 (m, 1 H), 3.07 (t, J=6.1 Hz, 2 H), 3.91 (t, J=6.1 Hz, 2 H), 4.41 (s, 2 H), 6.79 (s, 1 H), 7.11 (dd, J=8.3, 2.8 Hz, 1 H), 7.21 (d, J=1.0 Hz, 1 H), 7.59 (d, J=5.3 Hz, 1 H), 7.91 (d, J=1.3 Hz, 1 H), 8.07 (td, J=8.0, 2.5 Hz, 1 H), 8.45 (d, J=2.3 Hz, 1 H), 8.77 (d, J=5.3 Hz, 1 H).

Following the procedure described above for Example 110 and substituting the appropriate reagents, starting materials and purification methods known to those skilled in the art, the following compounds of the present invention were prepared:

Example 110a 9-cyclopropyl-2-(4-cyclopropyl-1H-imidazol-1-yl)-7,8-dihydro-[1,4]diazepino[7,1-a][2,6]naphthyridin-5(4H)-one UPLC-MS: MS 360.2 (M+H+); UPLC rt 0.85 min.

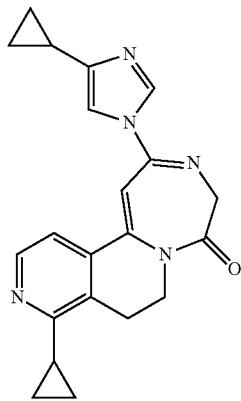 [SMILES: O=C1CN=C(n2cnc(C3CC3)c2)C=C2c3ccnc(C4CC4)c3CCN12]

Example 110b 9-cyclopropyl-2-(3-cyclopropyl-1H-1,2,4-triazol-1-yl)-7,8-dihydro-[1,4]diazepino[7,1-a][2,6]naphthyridin-5(4H)-one UPLC-MS: MS 361.2 (M+H+); UPLC rt 0.91 min.

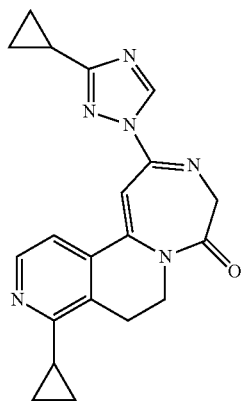 [SMILES: O=C1CN=C(n2cnc(C3CC3)n2)C=C2c3ccnc(C4CC4)c3CCN12]

Example 110c (R)-9-cyclopropyl-2-(4-(1-methoxyethyl)-1H-imidazol-1-yl)-7,8-dihydro-[1,4]diazepino[7,1-a][2,6]naphthyridin-5(4H)-one UPLC-MS: MS 378.2 (M+H+); UPLC rt 0.80 min.

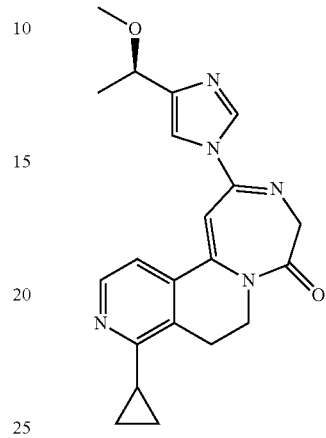

Example 110d 9-cyclopropyl-2-(4-(difluoromethyl)-1H-imidazol-1-yl)-7,8-dihydro-[1,4]diazepino[7,1-a][2,6]naphthyridin-5(4H)-one UPLC-MS: MS 370.2 (M+H+); UPLC rt 0.86 min.

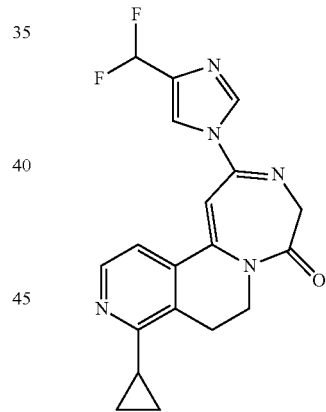

Example 111

2-(4-ethyl-1H-imidazol-1-yl)-9-(tetrahydrofuran-2-yl)-7,8-dihydro-[1,4]diazepino[7,1-a]isoquinolin-5(4H)-one

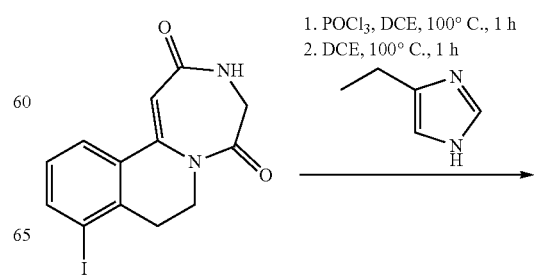

-continued

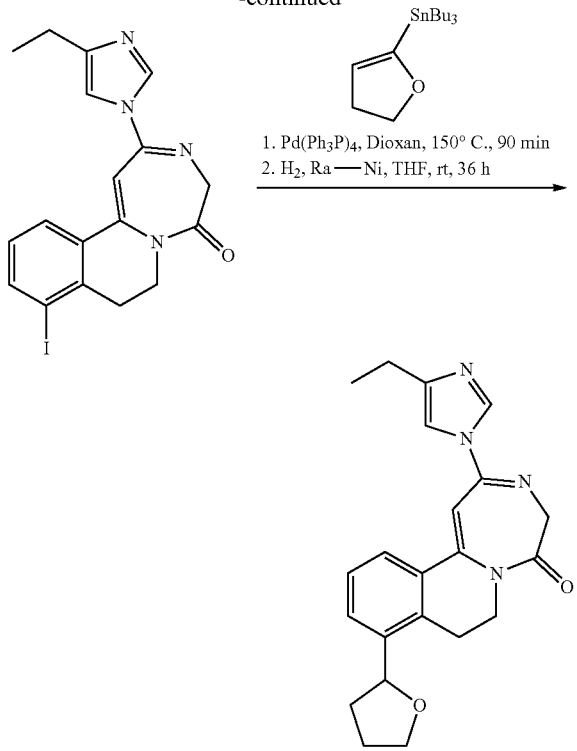

Step 1: 2-(4-ethyl-1H-imidazol-1-yl)-9-iodo-7,8-dihydro-[1,4]diazepino[7,1-a]isoquinolin-5(4H)-one. 111-1. A mixture of 9-iodo-3,4,7,8-tetrahydro-[1,4]diazepino[7,1-a]isoquinoline-2,5-dione (440 mg, 1.24 mmol) in dry DCE (10 mL) was treated with POCl$_3$ (0.23 mL, 2.49 mmol) and heated to 100° C. for 1 h. The mixture was allowed to cool to RT and then poured onto H$_2$O and extracted with DCM. The combined org. layers were then dried over Na$_2$SO$_4$, filtered and concentrated in vacuo. The residue obtained was taken up in DCE (10 mL) and 4-ethyl-1H-imidazole (597 mg, 6.21 mmol) was added. The mixture was heated to 100° C. for 1 h. The mixture was then allowed to cool to RT, poured onto H$_2$O, extracted with DCM and the combined org. layers were then dried over Na$_2$SO$_4$, filtered and concentrated in vacuo. The crude product was purified by flash chromatography (SiO$_2$, DCM to DCM/MeOH 9:1) to give the title compound (523 mg) as a brown oil. UPLC-MS: MS 433.1 (M+H$^+$); UPLC rt 0.93 min.

Step 2: 9-(4,5-dihydrofuran-2-yl)-2-(4-ethyl-1H-imidazol-1-yl)-7,8-dihydro-[1,4]diazepino[7,1-a]isoquinolin-5 (4H)-one. 111-2. A mixture of 2-(4-ethyl-1H-imidazol-1-yl)-9-iodo-7,8-dihydro-[1,4]diazepino[7,1-a]isoquinolin-5 (4H)-one (520 mg, 1.20 mmol), tributyl(4,5-dihydrofuran-2-yl)stannane (864 mg, 2.41 mmol) and Pd(PPh$_3$)$_4$ (70 mg, 0.06 mmol) in dioxane (10 mL) was heated to 150° C. for 1.5 h. The mixture was filtered and the filtrate concentrated in vacuo. Purification by flash chromatography (SiO$_2$, DCM to DCM/MeOH 95:5) afforded the title compound (254 mg) as a beige solid. UPLC-MS: MS 375.3 (M+H$^+$); UPLC rt 0.91 min.

Step 3: 2-(4-ethyl-1H-imidazol-1-yl)-9-(tetrahydrofuran-2-yl)-7,8-dihydro-[1,4]diazepino[7,1-a]isoquinolin-5(4H)-one. Example 111. A flask was charged with 9-(4,5-dihydrofuran-2-yl)-2-(4-ethyl-1H-imidazol-1-yl)-7,8-dihydro-[1,4]diazepino[7,1-a]isoquinolin-5(4H)-one (250 mg, 0.67 mmol) in 20 mL THF and Raney-Nickel (100 mg, 0.67 mmol) was added. The flask was evacuated in vacuo and then filled with H$_2$. The mixture was stirred at RT for 36 h. The reaction mixture was then filtered and the filtrate concentrated in vacuo. The residue obtained was purified by flash chromatography (SiO$_2$, DCM to DCM/MeOH 9:1) and the product obtained was recrystallized from heptane to give the title compound (63 mg; racemic) as beige solid. UPLC-MS: MS 377.3 (M+H+); UPLC rt 0.83 min. $^1$H NMR (400 MHz, DMSO-d$_6$): δ ppm 1.13 (t, J=7.62 Hz, 3H); 1.47-1.64 (m, 1 H); 1.81-2.00 (m, 2 H); 2.24-2.40 (m, 1 H); 2.40-2.55 (m, 2 H); 2.74-3.04 (m, 2 H); 3.59-3.74 (m, 1 H); 3.81 (q, J=7.56 Hz, 1 H); 3.86-3.97 (m, 1 H); 4.03 (q, J=7.17 Hz, 1 H); 4.21 (br. s., 2 H); 5.04 (t, J=7.04 Hz, 1 H); 7.06-7.17 (m, 1 H); 7.25-7.44 (m, 2 H); 7.52 (d, J=7.43 Hz, 1 H); 7.89 (d, J=8.21 Hz, 1 H); 8.12 (s, 1 H).

Following the procedure described above for Example 111 and substituting the appropriate reagents, starting materials and purification methods known to those skilled in the art, the following compounds of the present invention were prepared:

Example 112

2-(4-(tert-butyl)-1H-imidazol-1-yl)-9-(tetrahydrofuran-2-yl)-7,8-dihydro-[1,4]diazepino[7,1-a]isoquinolin-5(4H)-one UPLC-MS: MS 405.3 (M+H$^+$); UPLC rt 0.97 min.

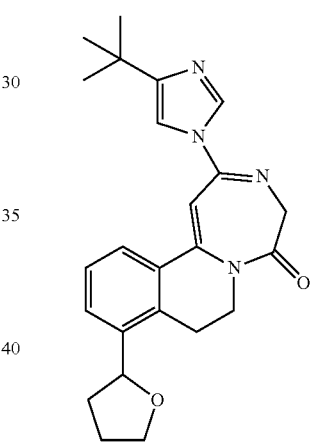

Example 113

2-(4-ethyl-1H-imidazol-1-yl)-9-(1-fluorocyclobutyl)-7,8-dihydro-[1,4]diazepino[7,1-a]isoquinolin-5(4H)-one

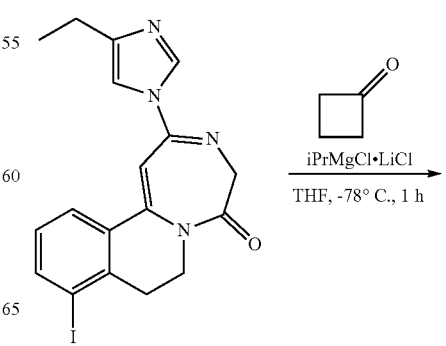

-continued

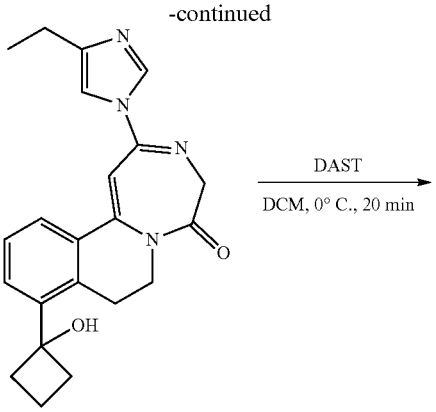

Step 1: 2-(4-ethyl-1H-imidazol-1-yl)-9-(1-hydroxycyclobutyl)-7,8-dihydro-[1,4]diazepino[7,1-a]isoquinolin-5(4H)-one. 113-1. A solution of 2-(4-ethyl-1H-imidazol-1-yl)-9-iodo-7,8-dihydro-[1,4]diazepino[7,1-a]isoquinolin-5(4H)-one (250 mg, 0.58 mmol) in dry THF was cooled to −78° C. under Ar and a solution of iPrMgCl*LiCl (1.78 mL, 2.31 mmol) was added dropwise. The mixture was stirred at −78° C. for 30 min and cyclobutanone (0.22 mL, 2.90 mmol) was then added dropwise. The mixture was stirred at −78° C. for another 30 min and then at RT for 4 h. The mixture was poured onto a saturated aq. solution of NH₄Cl and the mixture was extracted with AcOEt. The combined org. phases were then dried over Na₂SO₄, filtered and concentrated in vacuo. The residue obtained was purified by flash chromatography (SiO₂, heptane to AcOEt to AcOEt/MeOH 9:1) gave the title compound (129 mg) as a red solid. UPLC-MS: MS 377.3 (M+H+); UPLC rt 0.76 min.

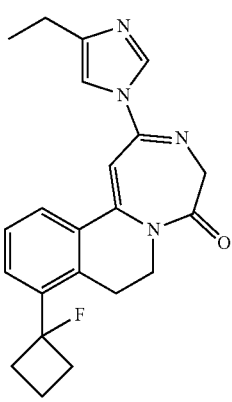

Step 2: 2-(4-ethyl-1H-imidazol-1-yl)-9-(1-fluorocyclobutyl)-7,8-dihydro-[1,4]diazepino[7,1-a]isoquinolin-5(4H)-one. Example 113. A solution of 2-(4-ethyl-1H-imidazol-1-yl)-9-(1-hydroxycyclobutyl)-7,8-dihydro-[1,4]diazepino[7,1-a]isoquinolin-5(4H)-one (120 mg, 0.32 mmol) in DCM was cooled to 0° C. under N₂ and treated with DAST (0.42 mL, 3.19 mmol) dropwise. The mixture was stirred for 20 min at 0° C., and the allowed to warm to RT. The reaction mixture was then slowly poured onto a cooled saturated aq. solution of NaHCO₃ and extracted with DCM. The combined org layers were then dried over Na₂SO₄, filtered and concentrated in vacuo. The crude product obtained was purified by flash chromatography (SiO₂, heptane to AcOEt to AcOEt/MeOH 9:1) and SFC (column: 2-Ethylpyridine 5 µm, 250×30 mm, 60 A, Princeton; eluent: isocratic 6% MeOH/CO₂ for 11 min; flow 100 mL/min; UV detection at 220 nm) to afford the title compound (42 mg) as a beige solid. UPLC-MS: MS 379.2 (M+H+); UPLC rt 0.95 min. ¹H NMR (400 MHz, DMSO-d₆): δ ppm 1.10-1.19 (m, 3 H); 1.46-1.64 (m, 1 H); 1.88-2.09 (m, 1 H); 2.47 (m, 2 H); 2.51-2.79 (m, 4 H); 2.95 (t, J=5.28 Hz, 2 H); 3.73 (t, J=6.06 Hz, 2 H); 4.22 (br. s., 2 H); 7.07 (s, 1 H); 7.33-7.48 (m, 2 H); 7.58-7.67 (m, 1 H); 7.95 (d, J=8.21 Hz, 1 H); 8.13 (s, 1 H).

Following the procedure described above for Example 113 and substituting the appropriate reagents, starting materials and purification methods known to those skilled in the art, the following compounds of the present invention were prepared:

Example 114

2-(4-ethyl-1H-imidazol-1-yl)-9-(3-fluorooxetan-3-yl)-7,8-dihydro-[1,4]diazepino[7,1-a]isoquinolin-5(4H)-one UPLC-MS: MS 381.2 (M+H+); UPLC rt 0.73 min.

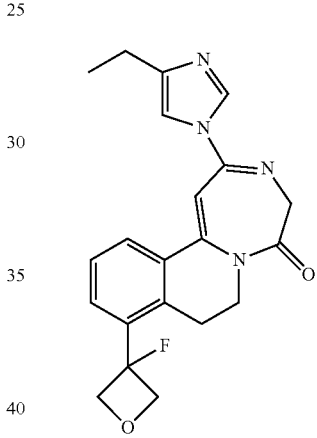

Example 115

2-(4-ethyl-1H-imidazol-1-yl)-9-(1-hydroxyethyl)-7,8-dihydro-[1,4]diazepino[7,1-a]isoquinolin-5(4H)-one 1. POCl3, DCE, 110° C., 1 h
2. DCE, 110° C., 1 h

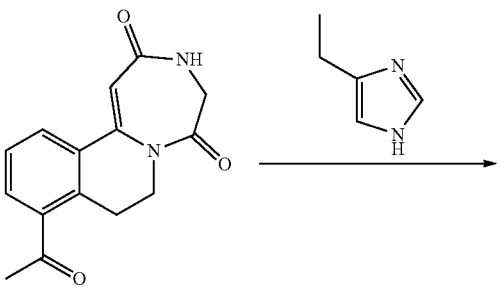

-continued

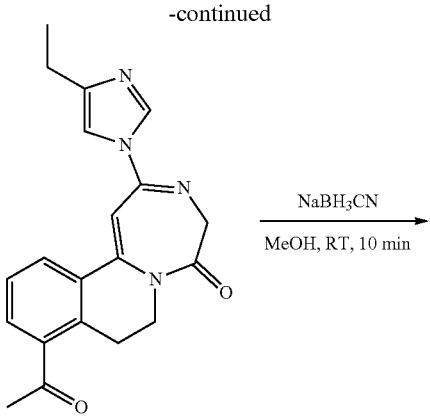

Step 1: 9-acetyl-2-(4-ethyl-1H-imidazol-1-yl)-7,8-dihydro-[1,4]diazepino[7,1-a]isoquinolin-5(4H)-one. 115-1. A mixture of 9-acetyl-3,4,7,8-tetrahydro-[1,4]diazepino[7,1-a]isoquinoline-2,5-dione [example 100-1] (128 mg, 0.47 mmol) in DCE (4 mL) was treated with POCl₃ (0.053 mL, 0.57 mmol) and heated to 110° C. for 1 h. The mixture was then allowed to cool to RT and then poured onto cooled H₂O. The mixture was extracted with DCM and the combined org. phases were dried over Na₂SO₄, filtered and concentrated in vacuo. The residue obtained was taken up in DCE (4 mL) and 4-ethyl-1H-imidazole (182 mg, 1.89 mmol) was added. The mixture was heated to 110° C. for 1 h, then allowed to cool to rt and poured onto a saturated aq. solution of NaHCO₃. The mixture was extracted with DCM and the combined org. layers were dried over Na₂SO₄, filtered and concentrated in vacuo to give the title compound (210 mg) that was used as it is in the next step. UPLC-MS: MS 349.2 (M+H⁺); UPLC rt 0.71 min.

Step 2: rac-2-(4-ethyl-1H-imidazol-1-yl)-9-(1-hydroxyethyl)-7,8-dihydro-[1,4]diazepino[7,1-a]isoquinolin-5(4H)-one. Example 115. A solution of 9-acetyl-2-(4-ethyl-1H-imidazol-1-yl)-7,8-dihydro-[1,4]diazepino[7,1-a]isoquinolin-5(4H)-one (210 mg, 0.36 mmol) in MeOH (20 mL) was treated with NaBH₃CN (23 mg, 0.36 mmol) and the mixture was stirred at RT for 10 min. The mixture was then concentrated in vacuo and the residue obtained was taken up in DCM and washed with H₂O. The org layer was then dried over Na₂SO₄, filtered and concentrated in vacuo. Purification by flash chromatography (SiO₂, heptane to AcOEt to AcOEt/MeOH 85:15) and preparative TLC (SiO₂, DCM/MeOH 95:5) afforded the title compound (6 mg). UPLC-MS: MS 351.2 (M+H⁺); UPLC rt 0.65 min. ¹H NMR (400 MHz, CD₃OD): δ ppm 1.16-1.27 (m, 3 H); 1.44 (d, J=6.26 Hz, 3 H); 2.58 (q, J=7.56 Hz, 2 H); 2.97-3.17 (m, 2 H); 3.80 (m, 1 H); 3.88-4.00 (m, 2 H); 4.31-4.36 (m, 2 H); 5.14 (d, J=6.65 Hz, 1 H); 6.95 (s, 1 H); 7.34 (s, 1 H); 7.37-7.49 (m, 1 H); 7.67 (d, J=7.43 Hz, 1 H); 7.77 (d, J=7.82 Hz, 1 H); 8.11 (s, 1 H).

Following the procedure described above for Example 115 and substituting the appropriate reagents, starting materials and purification methods known to those skilled in the art, the following compounds of the present invention were prepared:

Example 116

9-acetyl-2-(4-methyl-1H-imidazol-1-yl)-7,8-dihydro-[1,4]diazepino[7,1-a]isoquinolin-5(4H)-one UPLC-MS: MS 335.2 (M+H⁺); UPLC rt 0.63 min.

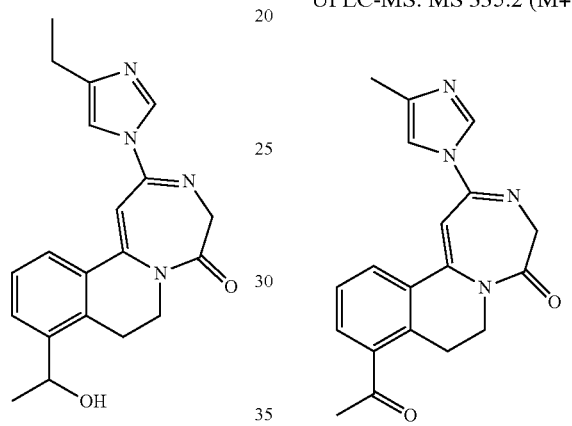

Example 117

9-acetyl-2-(4-cyclobutyl-1H-imidazol-1-yl)-7,8-dihydro-[1,4]diazepino[7,1-a]isoquinolin-5(4H)-one UPLC-MS: MS 375.2 (M+H⁺); UPLC rt 0.83 min.

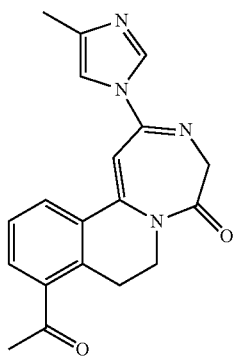 [SMILES: CC(=O)c1cccc2c1CCN1C(=O)CN=C(n3cnc(C)c3)C=C21]

Example 118

(R)-2-(4-(1-methoxyethyl)-1H-imidazol-1-yl)-9-(prop-1-en-2-yl)-7,8-dihydro-[1,4]diazepino[7,1-a]isoquinolin-5(4H)-one

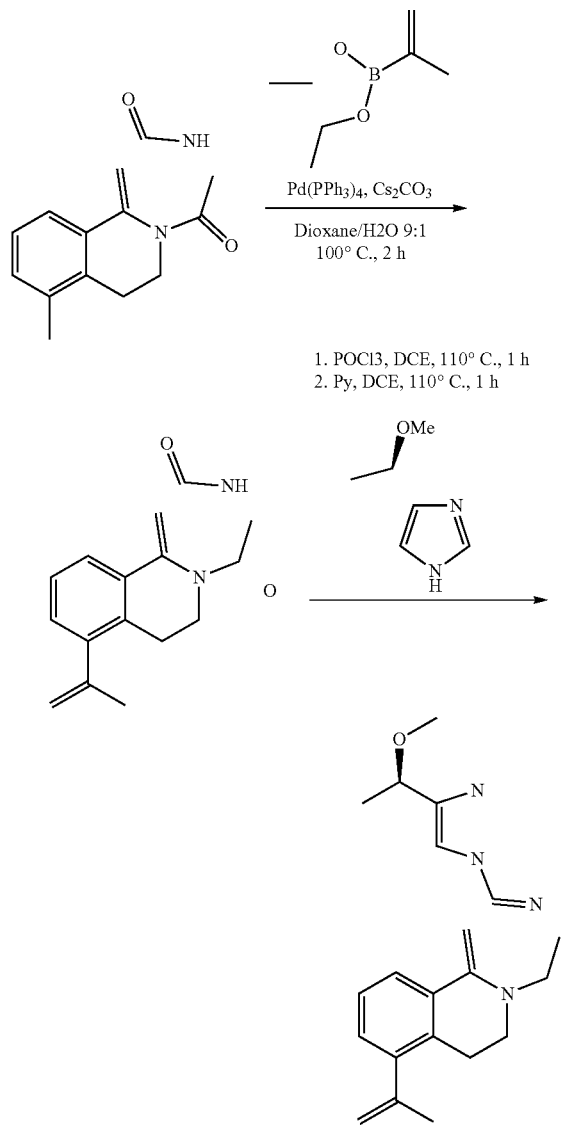

Step 1: 9-(prop-1-en-2-yl)-3,4,7,8-tetrahydro-[1,4]diazepino[7,1-a]isoquinoline-2,5-dione. 118-1. A mixture of 9-iodo-3,4,7,8-tetrahydro-[1,4]diazepino[7,1-a]isoquinoline-2,5-dione (750 mg, 2.12 mmol), 4,4,5,5-tetramethyl-2-(prop-1-en-2-yl)-1,3,2-dioxaborolane (712 mg, 4.24 mmol), $Cs_2CO_3$ (1.72 g, 5.29 mmol) and $Pd(PPh_3)_4$ (122 mg, 0.11 mmol) in dioxane/$H_2O$ (9:1, 20 mL) was heated to 100° C. for 2 h in a microwave reactor. The mixture was then concentrated in vacuo and the residue purified by flash chromatography ($SiO_2$, heptane to AcOEt to AcOEt/MeOH 85:15) to give the title compound (550 mg). UPLC-MS: MS 269.2 (M+H$^+$); UPLC rt 0.83 min.

Step 2: (R)-2-(4-(1-methoxyethyl)-1H-imidazol-1-yl)-9-(prop-1-en-2-yl)-7,8-dihydro-[1,4]diazepino[7,1-a]isoquinolin-5(4H)-one. Example 118. A solution of 9-(prop-1-en-2-yl)-3,4,7,8-tetrahydro-[1,4]diazepino[7,1-a]isoquinoline-2,5-dione (275 mg, 1.03 mmol) in DCE (20 mL) was treated with $POCl_3$ (0.29 mL, 3.07 mmol) and the mixture was heated to 100° C. for 1 h. The mixture was then allowed to cool to RT, diluted with DCM and washed with $H_2O$. The org. phase was then dried over $Na_2SO_4$, filtered and concentrated in vacuo. The residue obtained was taken up in DCE (20 mL) and (R)-4-(1-methoxyethyl)-1H-imidazole (200 mg, 1.59 mmol) and pyridine (0.17 mL, 2.05 mmol) were then added. The mixture was heated to 110° C. for 1 h, and then allowed to cool to RT, diluted with DCM and washed with $H_2O$. The org. layer was then dried over $Na_2SO_4$, filtered and concentrated in vacuo. Purification by flash chromatography ($SiO_2$, heptane to AcOEt to AcOEt/MeOH 85:15) and SFC (column: 4-Ethylpyridine 5 μm, 250×30 mm, 60 A, Princeton; eluent: 6% MeOH/$CO_2$ for 1 min, then from 6% MeOH/$CO_2$ to 11% MeOH/$CO_2$ in 6 min; then from 11% MeOH/$CO_2$ to 50% MeOH/$CO_2$ in 1 min; flow 100 mL/min; UV detection at 220 nm) gave the title compound (60 mg). UPLC-MS: MS 377.2 (M+H$^+$); UPLC rt 1.02 min. $^1$H NMR (400 MHz, DMSO-$d_6$): δ ppm 1.35 (d, J=5.87 Hz, 3 H); 2.01 (s, 3 H); 2.90 (t, J=5.87 Hz, 2 H); 3.14 (s, 3 H); 3.75 (t, J=6.06 Hz, 2 H); 4.16-4.33 (m, 3 H); 4.85 (s, 1 H); 5.29 (s, 1 H); 7.12 (s, 1 H); 7.27-7.40 (m, 2 H); 7.57 (s, 1 H); 7.90 (d, J=7.82 Hz, 1 H); 8.18 (s, 1 H).

Following the procedure described above for Example 118 and substituting the appropriate reagents, starting materials and purification methods known to those skilled in the art, the following compounds of the present invention were prepared:

Example 119

(S)-2-(4-(1-methoxyethyl)-1H-imidazol-1-yl)-9-(prop-1-en-2-yl)-7,8-dihydro-[1,4]diazepino[7,1-a]isoquinolin-5(4H)-one UPLC-MS: MS 377.2 (M+H$^+$); UPLC rt 1.01 min.

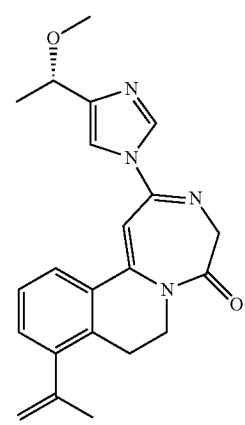 [SMILES: C=C(C)c1cccc2c1CCN1C(=O)CN=C(n3cnc([C@H](C)OC)c3)C=C21]

Example 120

9-(cyclopent-1-en-1-yl)-2-(4-(methoxymethyl)-1H-imidazol-1-yl)-7,8-dihydro-[1,4]diazepino[7,1-a]isoquinolin-5(4H)-one UPLC-MS: MS 389.2 (M+H+); UPLC rt 1.05 min.

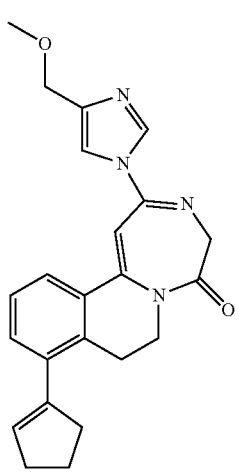 [SMILES: COCc1cn(C2=NCC(=O)N3CCc4c(C5=CCCC5)cccc4C3=C2)cn1]

Example 121

2-(4-(methoxymethyl)-1H-imidazol-1-yl)-9-(prop-1-en-2-yl)-7,8-dihydro-[1,4]diazepino[7,1-a]isoquinolin-5(4H)-one UPLC-MS: MS 363.0 (M+H+); UPLC rt 0.93 min.

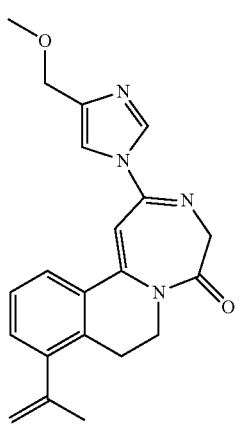 [SMILES: C=C(C)c1cccc2c1CCN1C(=O)CN=C(n3cnc(COC)c3)C=C21]

Example 122

(S)-9-cyclopropyl-2-(4-(1-methoxyethyl)-1H-imidazol-1-yl)-7,8-dihydro-[1,4]diazepino[7,1-a]isoquinolin-5(4H)-one UPLC-MS: MS 377.2 (M+H+); UPLC rt 0.95 min.

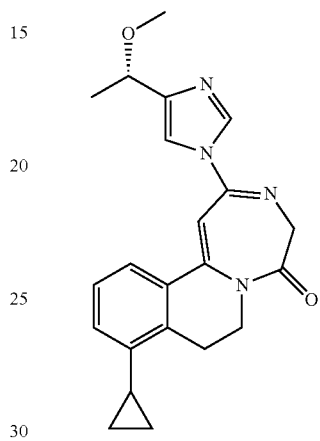

Example 123

(R)-9-cyclopropyl-2-(4-(1-methoxyethyl)-1H-imidazol-1-yl)-7,8-dihydro-[1,4]diazepino[7,1-a]isoquinolin-5(4H)-one UPLC-MS: MS 377.2 (M+H+); UPLC rt 0.96 min.

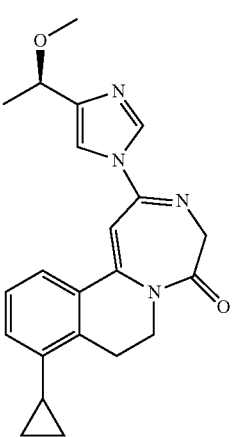 [SMILES: CO[C@H](C)c1cn(C2=NCC(=O)N3CCc4c(cccc4C4CC4)C3=C2)cn1]

Starting from bromo-[O]-intermediate instead of iodo-[O]-intermediate

Example 123a 9-cyclopropyl-2-(4-(oxazol-5-yl)-1H-imidazol-1-yl)-7,8-dihydro-[1,4]diazepino[7,1-a]isoquinolin-5(4H)-one UPLC-MS: MS 386.3 (M+H$^+$); UPLC rt 0.99 min.

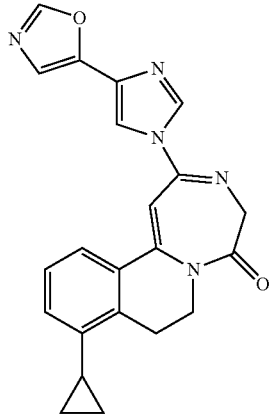 [SMILES: O=C1CN=C(n2cnc(-c3cnco3)c2)C=C2c3cccc(C4CC4)c3CCN12]

Example 123b 9-cyclopropyl-2-(4-(isoxazol-5-yl)-1H-imidazol-1-yl)-7,8-dihydro-[1,4]diazepino[7,1-a]isoquinolin-5(4H)-one UPLC-MS: MS 386.3 (M+H$^+$); UPLC rt 1.04 min.

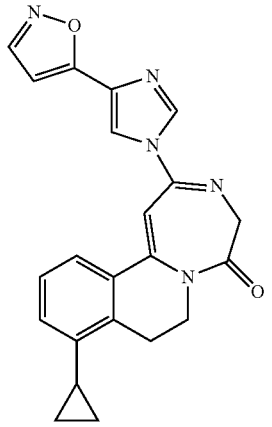 [SMILES: O=C1CN=C(n2cnc(-c3ccno3)c2)C=C2c3cccc(C4CC4)c3CCN12]

Example 123c 9-cyclopropyl-2-(3-cyclopropyl-1H-1,2,4-triazol-1-yl)-7,8-dihydro-[1,4]diazepino[7,1-a]isoquinolin-5(4H)-one UPLC-MS: MS 360.3 (M+H$^+$); UPLC rt 1.13 min.

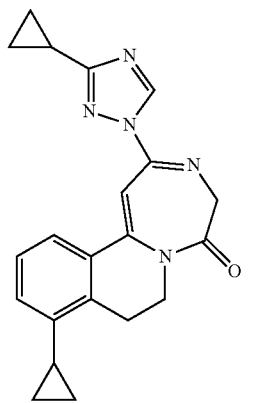

Example 123d 9-cyclopropyl-2-(4-methoxy-1H-imidazol-1-yl)-7,8-dihydro-[1,4]diazepino[7,1-a]isoquinolin-5(4H)-one UPLC-MS: MS 349.2 (M+H$^+$); UPLC rt 0.99 min.

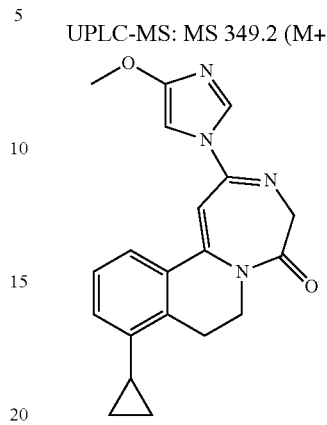

Example 123e 9-cyclopropyl-2-(4-(trifluoromethyl)-1H-imidazol-1-yl)-7,8-dihydro-[1,4]diazepino[7,1-a]isoquinolin-5(4H)-one. UPLC-MS: MS 387.2 (M+H$^+$); UPLC rt 1.16 min.

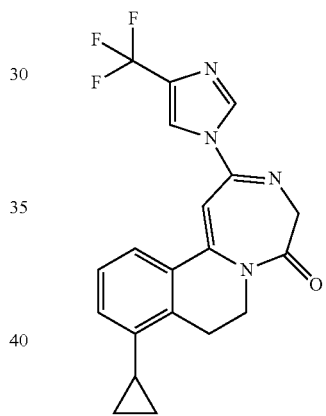

Example 123f 9-cyclopropyl-2-(4-(pyridin-4-yl)-1H-imidazol-1-yl)-7,8-dihydro-[1,4]diazepino[7,1-a]isoquinolin-5(4H)-one UPLC-MS: MS 396.3 (M+H$^+$); UPLC rt 0.87 min.

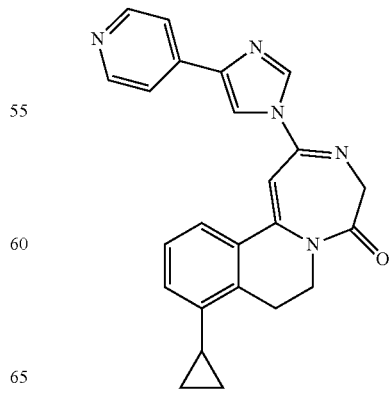

Example 124

2-(4-cyclobutyl-1H-imidazol-1-yl)-9-propionyl-7,8-dihydro-[1,4]diazepino[7,1-a]isoquinolin-5(4H)-one

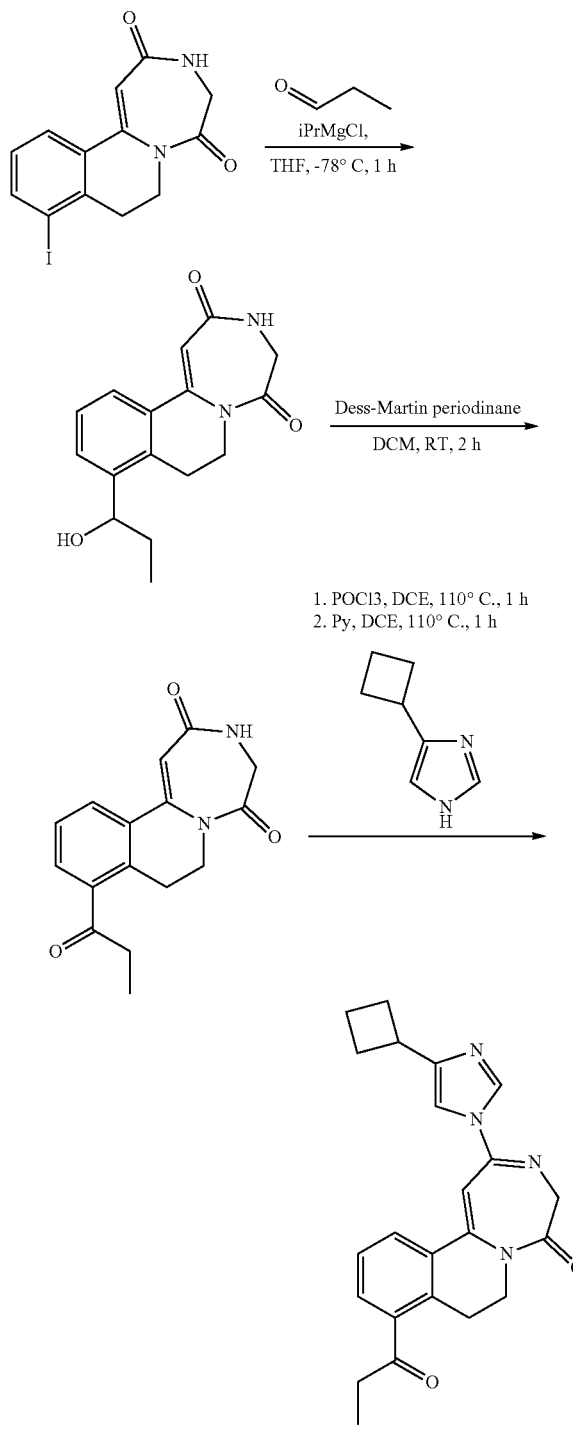

Step 1: rac-9-(1-hydroxypropyl)-3,4,7,8-tetrahydro-[1,4]diazepino[7,1-a]isoquinoline-2,5-dione. 124-1. A mixture of 9-iodo-3,4,7,8-tetrahydro-[1,4]diazepino[7,1-a]isoquinoline-2,5-dione (2.2 g, 6.21 mmol) in dry THF (150 mL) was cooled to −78° C. under Ar, and a 2M solution of iPrMgCl in THF (18.6 mL, 37.3 mmol) was added dropwise. The mixture was stirred at −78° C. for 30 min and propionaldehyde (3.61 g, 62.1 mmol) was then added. The mixture was stirred at −78° C. for another 30 min and then allowed to warm to RT overnight. The reaction mixture was poured onto a saturated aq. solution of NH$_4$Cl and extracted with AcOEt. The combined org. layers were then dried over Na$_2$SO$_4$, filtered and concentrated in vacuo. The crude product was purified by flash chromatography (SiO$_2$, heptane to AcOEt/MeOH 9:1) to give the title compound (231 mg). UPLC-MS: MS 287.2 (M+H$^+$); UPLC rt 0.59 min.

Step 2: 9-propionyl-3,4,7,8-tetrahydro-[1,4]diazepino[7,1-a]isoquinoline-2,5-dione. 124-2. A solution of 9-(1-hydroxypropyl)-3,4,7,8-tetrahydro-[1,4]diazepino[7,1-a]isoquinoline-2,5-dione (231 mg, 0.78 mmol) in DCM (40 mL) was treated with Dess-Martin periodinane (365 mg, 0.86 mmol) and the mixture was stirred at RT for 2 h. The reaction mixture was then poured onto a saturated aq. solution of NaHCO$_3$ and extracted with DCM. The combined org. layers were then dried over Na$_2$SO$_4$, filtered and concentrated in vacuo. Purification by flash chromatography (SiO$_2$, AcOEt/MeOH 95:5) gave the title compound (225 mg). UPLC-MS: MS 285.2 (M+H$^+$); UPLC rt 0.68 min.

Step 3: 2-(4-cyclobutyl-1H-imidazol-1-yl)-9-propionyl-7,8-dihydro-[1,4]diazepino[7,1-a]isoquinolin-5(4H)-one. Example 124. A solution of 9-propionyl-3,4,7,8-tetrahydro-[1,4]diazepino[7,1-a]isoquinoline-2,5-dione (225 mg, 0.77 mmol) in DCE (20 mL) was treated with POCl$_3$ (0.22 mL, 2.30 mmol) and the mixture was heated to 110° C. for 1 h. The mixture was then allowed to cool to RT, diluted with DCM and washed with H$_2$O. The org. phase was then dried over Na$_2$SO$_4$, filtered and concentrated in vacuo. The residue obtained was taken up in DCE (20 mL) and 4-cyclobutyl-1H-imidazole (188 mg, 1.54 mmol) and pyridine (0.12 mL, 1.54 mmol) were then added. The mixture was heated to 110° C. for 1 h, and then allowed to cool to RT, poured onto H$_2$O and extracted with DCM. The org. layer was then dried over Na$_2$SO$_4$, filtered and concentrated in vacuo. Purification by flash chromatography (SiO$_2$, heptane to AcOEt to AcOEt/MeOH 85:15) and SFC (column: 2-Ethylpyridine 5 µm, 250× 30 mm, 60 A, Princeton; eluent: 7% MeOH/CO$_2$ for 1 min, then from 7% MeOH/CO$_2$ to 12% MeOH/CO$_2$ in 6 min; then from 12% MeOH/CO$_2$ to 50% MeOH/CO$_2$ in 1 min; flow 100 mL/min; UV detection at 220 nm) afforded the title compound (36 mg). UPLC-MS: MS 389.2 (M+H+); UPLC rt 0.95 min. $^1$H NMR (400 MHz, DMSO-d$_6$): δ ppm 1.06 (t, J=7.23 Hz, 3 H); 1.55-1.90 (m, 2 H); 1.99-2.27 (m, 4 H); 2.91-3.05 (m, 4 H); 3.36 (m, 1 H); 3.70 (t, J=6.06 Hz, 2 H); 4.22 (s, 2 H); 7.10 (s, 1 H); 7.41 (s, 1 H); 7.49 (t, J=8.02 Hz, 1 H); 7.88 (d, J=7.43 Hz, 1 H); 8.05-8.20 (m, 2 H).

Example 125

9-(tert-butyl)-2-(4-(methoxymethyl)-1H-imidazol-1-yl)-7,8-dihydro-[1,4]diazepino[7,1-a]isoquinolin-5(4H)-one

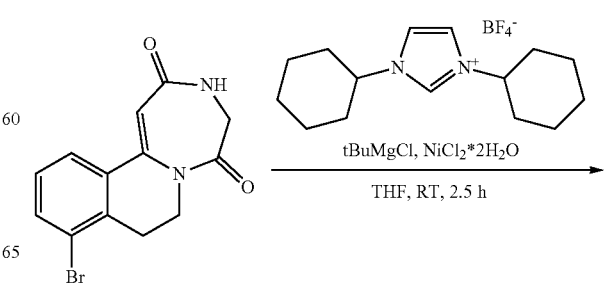

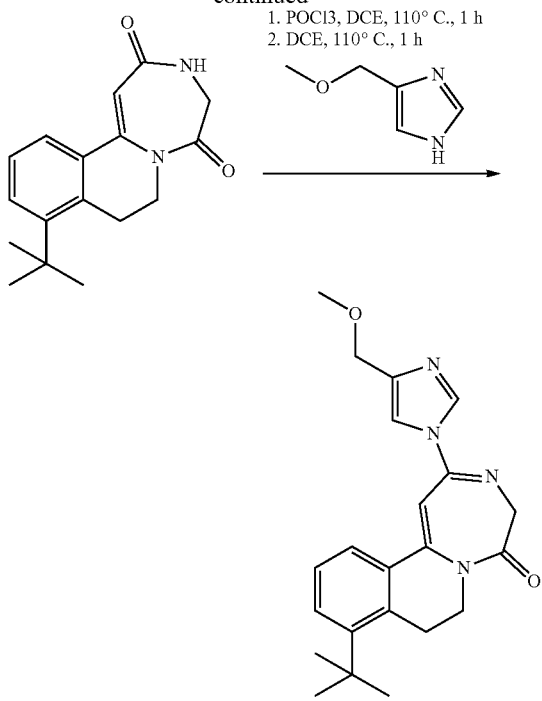

Step 1: 9-(tert-butyl)-3,4,7,8-tetrahydro-[1,4]diazepino[7,1-a]isoquinoline-2,5-dione. 125-1. A mixture of 9-bromo-3,4,7,8-tetrahydro-[1,4]diazepino[7,1-a]isoquinoline-2,5-dione (2.0 g, 6.51 mmol), NiCl$_2$*2H$_2$O (0.43 g, 2.60 mmol) and dicyclohexylimidazolium tetrafluoroborate (0.83 g, 2.60 mmol) in THF (80 mL) was cooled to −20° C. and then treated with a 1M solution of tBuMgCl (39.0 mL, 39.0 mmol) dropwise. The mixture was allowed to slowly warm to RT, then poured onto a saturated aq. solution of NH$_4$Cl and extracted with AcOEt. The combined org. layers were then dried over Na$_2$SO$_4$, filtered and concentrated in vacuo. Purification by flash chromatography (SiO$_2$, heptane to AcOEt to AcOEt/MeOH 95:5) afforded the title compound (370 mg). UPLC-MS: MS 285.2 (M+H$^+$); UPLC rt 0.91 min.

Step 2: 9-(tert-butyl)-2-(4-(methoxymethyl)-1H-imidazol-1-yl)-7,8-dihydro-[1,4]diazepino[7,1-a]isoquinolin-5(4H)-one. Example 125. A solution of -(tert-butyl)-3,4,7,8-tetrahydro-[1,4]diazepino[7,1-a]isoquinoline-2,5-dione (370 mg, 1.30 mmol) in DCE (20 mL) was treated with POCl$_3$ (0.24 mL, 2.60 mmol) and the mixture was heated to 110° C. for 1 h. The mixture was then allowed to cool to RT, diluted with DCM and washed with H$_2$O. The org. phase was then dried over Na$_2$SO$_4$, filtered and concentrated in vacuo. The residue obtained was taken up in DCE (20 mL) and 4-(methoxymethyl)-1H-imidazole (438 mg, 3.90 mmol) was then added. The mixture was heated to 110° C. for 1 h, and then allowed to cool to RT, diluted with DCM and washed with H$_2$O. The org. layer was then dried over Na$_2$SO$_4$, filtered and concentrated in vacuo. Purification by flash chromatography (SiO$_2$, heptane to AcOEt to AcOEt/MeOH 85:15) and SFC (column: PPU 5 μm, 250×30 mm, 60 A, Princeton; eluent: isocratic 5% MeOH/CO$_2$ for 11 min; flow 100 mL/min; UV detection at 220 nm) gave the title compound (83 mg). UPLC-MS: MS 379.2 (M+H$^+$); UPLC rt 1.04 min. $^1$H NMR (400 MHz, DMSO-d6): δ ppm 1.38 (s, 9 H); 3.10-3.20 (m, 2 H); 3.22 (br s, 3 H); 3.63 (m, 2 H); 4.25 (m, 4 H); 6.86 (d, J=1.96 Hz, 1 H); 7.31 (s, 1 H); 7.49 (d, J=8.21 Hz, 1 H); 7.54-7.69 (m, 2 H); 8.17 (d, J=1.56 Hz, 1 H).

Example 126

9-cyclopropyl-2-(4-(((trifluoromethoxy)methyl)-1H-imidazol-1-yl)-7,8-dihydro-[1,4]diazepino[7,1-a]isoquinolin-5(4H)-one

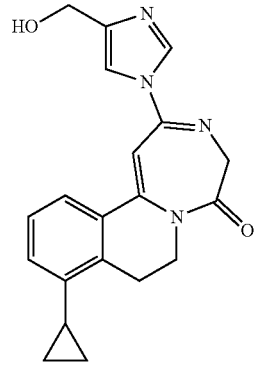

A solution of 2-(4-(((tert-butyldiphenylsilyl)oxy)methyl)-1H-imidazol-1-yl)-9-cyclopropyl-7,8-dihydro-[1,4]diazepino[7,1-a]isoquinolin-5(4H)-one (130 mg, 0.21 mmol, it can be obtained by analogy to example 118) in THF (15 mL) was treated with a solution of TBAF in THF (0.25 mL, 0.25 mmol) and the mixture was stirred at RT for 15 min. It was then diluted with DCM and H$_2$O. The aqueous phase was extracted twice with DCM and the combined org. layers were over Na$_2$SO$_4$, filtered and concentrated in vacuo. The crude product was purified by SFC (column: PPU 5 m, 250×30 mm, 60 A, Princeton; eluent: 13-18% MeOH/CO2 over 11 min; flow 100 mL/min; UV detection at 220 nm) and crystallization in Et$_2$O gave the title compound as a solid (28 mg). UPLC-MS: MS 349.3 (M+H$^+$); UPLC rt 0.82 min. $^1$H NMR (400 MHz, DMSO-d6): δ ppm 0.54-0.75 (m, 2H); 0.89-1.04 (m, 2H); 1.90-2.11 (m, 1H); 2.96-3.20 (m, 2H); 3.80-3.98 (m, 2H); 4.29-4.46 (br s, 2H); 4.55 (s, 2H); 7.08-7.27 (m, 2H); 7.27-7.41 (m, 1H); 7.79-7.90 (m, 1H); 8.05 (br s, 1H); 9.65 (br s, 1H).

Following the procedure described above for Example 126 and substituting the appropriate reagents, starting materials and purification methods known to those skilled in the art, the following compounds of the present invention were prepared:

Example 127

9-cyclopropyl-2-(4-(1-hydroxycyclopropyl)-1H-imidazol-1-yl)-7,8-dihydro-[1,4]diazepino[7,1-a]isoquinolin-5(4H)-one UPLC-MS: MS 375.2 (M+H⁺); UPLC rt 0.90 min.

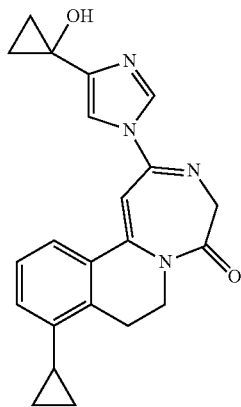 [SMILES: O=C1CN=C(n2cnc(C3(O)CC3)c2)C=C2c3cccc(C4CC4)c3CCN12]

Example 128

9-cyclopropyl-2-(4-(2-hydroxyethyl)-1H-imidazol-1-yl)-7,8-dihydro-[1,4]diazepino[7,1-a]isoquinolin-5(4H)-one UPLC-MS: MS 363.2 (M+H⁺); UPLC rt 0.81 min.

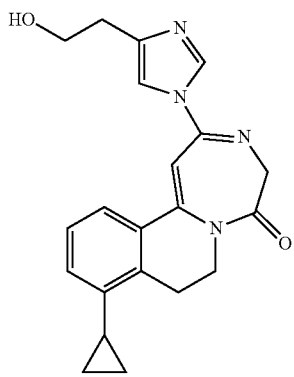 [SMILES: O=C1CN=C(n2cnc(CCO)c2)C=C2c3cccc(C4CC4)c3CCN12]

Example 129

9-cyclopropyl-2-(4-(1-hydroxyethyl)-1H-imidazol-1-yl)-7,8-dihydro-[1,4]diazepino[7,1-a]isoquinolin-5(4H)-one

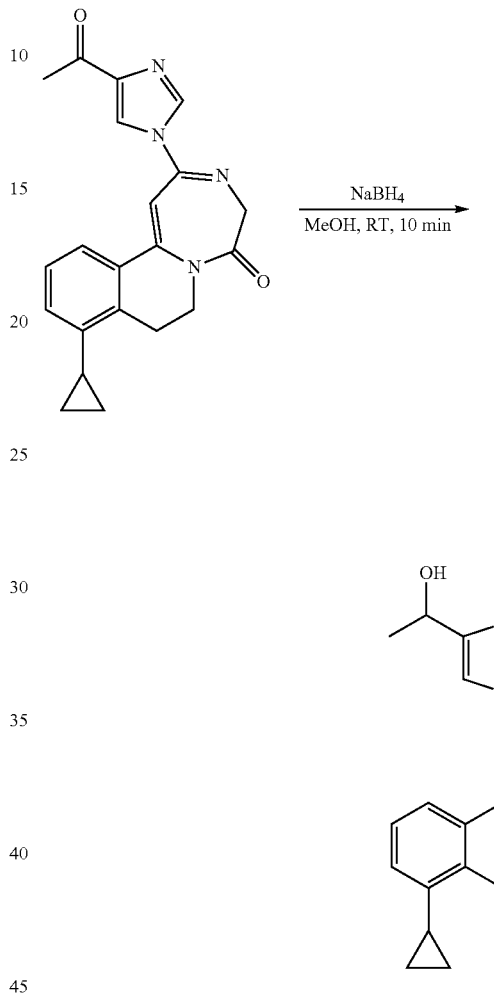

A solution of 2-(4-acetyl-1H-imidazol-1-yl)-9-cyclopropyl-7,8-dihydro-[1,4]diazepino[7,1-a]isoquinolin-5(4H)-one (202 mg, 0.35 mmol, it can be obtained by analogy to example 118) in MeOH (8 mL) was treated with NaBH₄ (27 mg, 0.71 mmol) and the mixture was stirred at RT for 10 min. The mixture was then diluted with DCM and H₂O, and the aqueous phase was extracte with DCM. The combined org. layers were dried over Na₂SO₄, filtered and concentrated in vacuo. The crude product was purified by SFC (column: PPU 5 m, 250×30 mm, 60 A, Princeton; eluent: 12-17% MeOH/CO2 over 14 min; flow 100 mL/min; UV detection at 220 nm) and crystallization in Et₂O gave the title compound as a solid (41 mg). UPLC-MS: MS 363.2 (M+H⁺); UPLC rt 0.86 min. ¹H NMR (600 MHz, DMSO-d6): δ ppm 0.55-0.71 (m, 2H); 0.88-1.02 (m, 2H); 1.35 (d, J=6.40 Hz, 3H); 1.87-2.05 (m, 1H); 2.99-3.17 (m, 2H); 3.79-3.97 (m, 2H); 4.17-4.31 (m, 2H); 4.55-4.71 (m, 1H); 5.01 (d, J=4.89 Hz, 1H); 7.09-7.25 (m, 2H); 7.25-7.39 (m, 1H); 7.46 (s, 1H); 7.84-7.98 (m, 1H); 8.16 (br s, 1H).

Example 130

9-cyclopropyl-2-(4-(cyclopropyl(hydroxy)methyl)-1H-imidazol-1-yl)-7,8-dihydro-[1,4]diazepino[7,1-a]isoquinolin-5(4H)-one

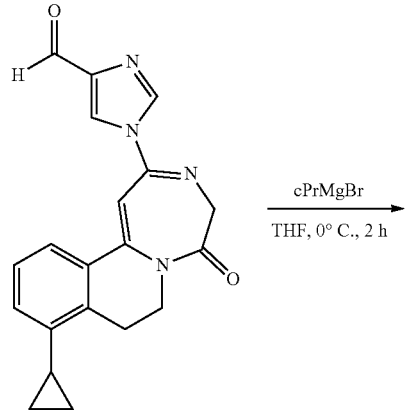

A solution of 1-(9-cyclopropyl-5-oxo-4,5,7,8-tetrahydro-[1,4]diazepino[7,1-a]isoquinolin-2-yl)-1H-imidazole-4-carbaldehyde (230 mg, 0.66 mmol, it can be obtained by analogy to example 118) in THF (35 mL) was cooled to 0° C. and then treated with a solution of cPrMgBr in THF (1.39 mL, 0.70 mmol) dropwise. The mixture was stirred at 0° C. for 1 h, and an aq. solution of saturated NH$_4$Cl was then added. The mixture was extracted with AcOEt, and the combined org. layers were dried over Na$_2$SO$_4$, filtered and concentrated in vacuo. Purification by flash chromatography (SiO$_2$, AcOEt:MeOH 100:0 to 90:10) and crystallization in AcOEt gave the tile compound (66 mg). UPLC-MS: MS 389.2 (M+H$^+$); UPLC rt 0.92 min. $^1$H NMR (600 MHz, DMSO-d6): δ ppm 0.21-0.46 (m, 4H); 0.58-0.70 (m, 2H); 0.91-1.00 (m, 2H); 1.08-1.25 (m, 1H); 1.91-2.04 (m, 1H); 3.01-3.17 (m, 2H); 3.88 (br s, 2H); 3.93-4.03 (m, 1H); 4.24 (br s, 2H); 4.96 (d, J=5.27 Hz, 1H); 7.12-7.25 (m, 2H); 7.25-7.35 (m, 1H); 7.49 (s, 1H); 7.91 (d, J=8.03 Hz, 1H); 8.17 (s, 1H).

Example 131

9-cyclopropyl-2-(4-((trifluoromethoxy)methyl)-1H-imidazol-1-yl)-7,8-dihydro-[1,4]diazepino[7,1-a]isoquinolin-5(4H)-one

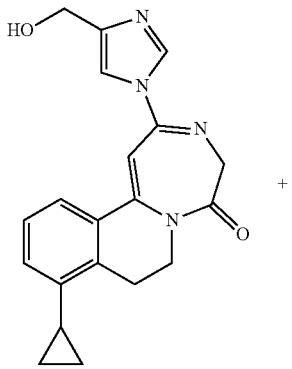

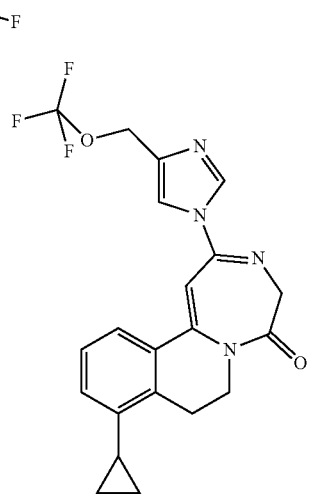

A solution of 9-cyclopropyl-2-(4-(hydroxymethyl)-1H-imidazol-1-yl)-7,8-dihydro-[1,4]diazepino[7,1-a]isoquinolin-5(4H)-one (135 mg, 0.38 mmol) in CHCl$_3$ (50 mL) under Ar, was treated with 3,3-Dimethyl-1-(trifluoromethyl)-1,2-benziodoxole (245 mg, 0.78 mmol) and Zn(NTf$_2$)$_2$ (242 mg, 0.39 mmol). The mixture was stirred at RT for 16 h, and then treated again with 3,3-Dimethyl-1-(trifluoromethyl)-1,2-benziodoxole (245 mg, 0.78 mmol) and Zn(NTf$_2$)$_2$ (242 mg, 0.39 mmol). After 24 h, the mixture was poured onto H$_2$O and extracted with DCM. The combined org. layers were then dried over Na$_2$SO$_4$, filtered and concentrated in vacuo. The crude product was purified by flash chromatography (SiO$_2$, DCM/MeOH 100:0 to 95:5) and by SFC (column: PPU 5 m, 250×30 mm, 60 A, Princeton; eluent: isocratic 20% MeOH/CO2 for 11 min; flow 100 mL/min; UV detection at 220 nm) to give the title compound (3 mg). UPLC-MS: MS 417.2

(M+H⁺); UPLC rt 1.15 min. ¹H NMR (400 MHz, DMSO-d6): δ ppm 0.56-0.71 (m, 2H); 0.93-1.05 (m, 2H); 1.91-2.04 (m, 1H); 3.14-3.20 (m, 2H); 3.89-4.01 (m, 2H); 4.34 (br s, 2H); 5.00 (s, 2H); 7.03 (s, 1H); 7.18-7.26 (m, 1H); 7.26-7.34 (m, 1H); 7.69-7.85 (m, 2H); 8.25 (s, 1H).

Example 132 methyl 2-(4-cyclopropyl-1H-imidazol-1-yl)-5-oxo-4,5,7,8-tetrahydro-[1,4]diazepino[7,1-a]isoquinoline-9-carboxylate

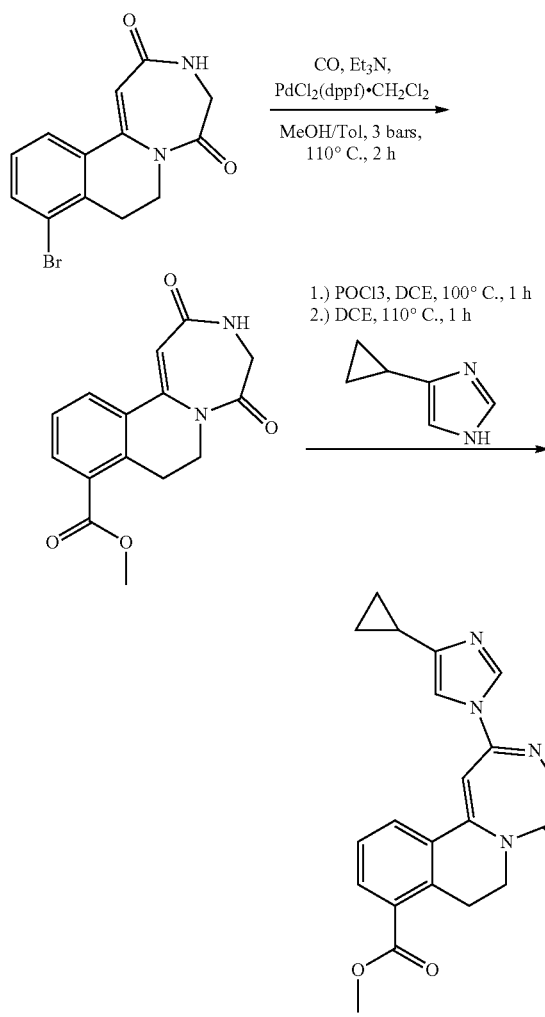

Step 1: methyl 2,5-dioxo-2,3,4,5,7,8-hexahydro-[1,4]diazepino[7,1-a]isoquinoline-9-carboxylate. 132-1. A solution of 9-bromo-3,4,7,8-tetrahydro-[1,4]diazepino[7,1-a]isoquinoline-2,5-dione (600 mg, 1.95 mmol), PdCl₂(dppf)*CH₂CL₂ (319 mg, 0.39 mmol) and Et₃N (1.4 mL, 9.77 mmol) in MeOH/Toluene (30 mL, 1:1) was flushed with CO, and then placed under CO atmosphere at RT (3.0 bar). The mixture was then stirred and heated to 110° C. for 2 h. The mixture was then filter over celite and the filtrate concentrated in vacuo. Purification by flash chromatography (SiO2, AcOEt/MeOH 100:0 to 90:10) gave the title compound (255 mg). UPLC-MS: MS 287.1 (M+H⁺); UPLC rt 0.65 min.

Step 2: methyl 2-(4-cyclopropyl-1H-imidazol-1-yl)-5-oxo-4,5,7,8-tetrahydro-[1,4]diazepino[7,1-a]isoquinoline-9-carboxylate. Example 132. A solution of methyl 2,5-dioxo-2,3,4,5,7,8-hexahydro-[1,4]diazepino[7,1-a]isoquinoline-9-carboxylate (225 mg, 0.79 mmol) in DCE (20 mL) was treated with POCl3 (0.37 mL, 3.93 mmol) and the mixture was heated to 100° C. for 1 h. The mixture was then allowed to cool to RT, and then concentrated in vacuo, and dried azeotropically with toluene. The residue obtained was taken up in DCE (40 mL) and 4-cyclopropyl-1H-imidazole (261 mg, 2.41 mmol) were added. The mixture was heated to to 100° C. for 1 h and then allowed to cool to RT, diluted with DCM and washed with a saturated aq. solution of NaHCO₃. The org. layer was dried over Na₂SO₄, filtered and concentrated in vacuo. Purification by flash chromatography (SiO₂, AcOEt/MeOH 100:0 to 90:10) and crystallization in Et₂O/petroleum ether gave the title compound (116 mg). UPLC-MS: MS 377.2 (M+H⁺); UPLC rt 0.88 min. ¹H NMR (600 MHz, DMSO-d6): δ ppm 0.54-0.73 (m, 2H); 0.73-0.88 (m, 2H); 1.74-1.89 (m, 1H); 3.25 (br s, 2H); 3.67-3.82 (m, 2H); 3.88 (s, 3H); 4.25 (br s, 2H); 7.13 (s, 1H); 7.44 (s, 1H); 7.48-7.57 (m, 1H); 7.96 (d, J=7.65 Hz, 1H); 8.09 (s, 1H); 8.19 (d, J=7.91, 1H).

Example 133

2-(3-cyclopropyl-1H-1,2,4-triazol-1-yl)-9-(5-fluoropyridin-2-yl)-7,8-dihydro-[1,4]diazepino[7,1-a]isoquinolin-5(4H)-one

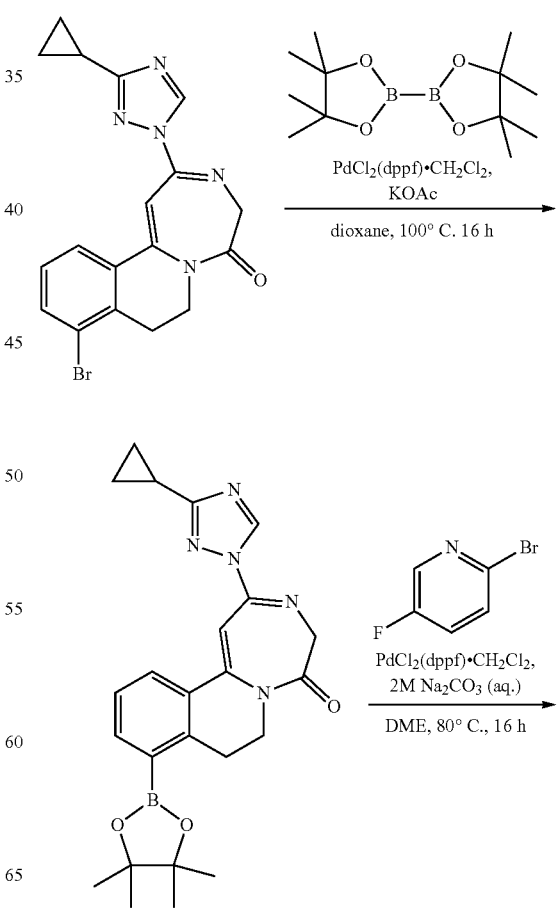

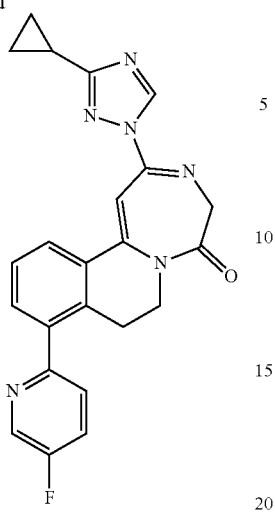

Step 1: 2-(3-cyclopropyl-1H-1,2,4-triazol-1-yl)-9-(4,4,5,5-tetramethyl-1,3,2-dioxaborolan-2-yl)-7,8-dihydro-[1,4]diazepino[7,1-a]isoquinolin-5(4H)-one. 133-3. A solution of 9-bromo-2-(3-cyclopropyl-1H-1,2,4-triazol-1-yl)-7,8-dihydro-[1,4]diazepino[7,1-a]isoquinolin-5(4H)-one (120 mg, 0.30 mmol), bis pinacol ester (153 mg, 0.60 mmol) and KOAc (89 mg, 0.90 mmol) in dioxane (3 mL) was treated with $PdCl_2(dppf)*CH_2Cl_2$ (37 mg, 0.045 mmol). The mixture was stirred under $N_2$ at 100° C. for 90 min, and then allowed to cool to RT. The mixture was filtered on Hyflo, and the filtrate concentrated in vacuo. Purification by flash chromatography (SiO2, AcOEt/heptane 88:12 to 100:0) afforded the title compound (97 mg). UPLC-MS: MS 446.3 (M+H$^+$); UPLC rt 1.27 min.

Step 2: 2-(3-cyclopropyl-1H-1,2,4-triazol-1-yl)-9-(5-fluoropyridin-2-yl)-7,8-dihydro-[1,4]diazepino[7,1-a]isoquinolin-5(4H)-one. Example 133. A suspension of 2-(3-cyclopropyl-1H-1,2,4-triazol-1-yl)-9-(4,4,5,5-tetramethyl-1,3,2-dioxaborolan-2-yl)-7,8-dihydro-[1,4]diazepino[7,1-a]isoquinolin-5(4H)-one (95 mg, 0.21 mmol), 2-bromo-5-fluoropyridine (79 mg, 0.45 mmol) and $PdCl_2(dppf)*CH_2Cl_2$ (17 mg, 0.021 mmol) in DME (2.1 mL) was treated with a 2M aq. solution of $Na_2CO_3$ (0.5 mL, 1.06 mmol). The mixture was heated to 80° C. for 13 h, the allowed to cool to RT and poured onto $H_2O$. The mixture was extracted with DCM and the combined org. layers were washed with brine, dried over over $Na_2SO_4$, filtered and concentrated in vacuo. Purification by SFC (Column: Silica 5 μm, 250×30 mm, Princeton; isocratic 5% MeOH/$CO_2$ for 20 min; flow 100 mL/min) gave the title compound (19 mg). UPLC-MS: MS 415.2 (M+H$^+$); UPLC rt 1.02 min. $^1$H NMR (600 MHz, DMSO-d6): δ ppm 0.71-0.90 (m, 2H); 0.90-1.00 (m, 2H); 1.91-2.09 (m, 1H); 2.91-3.09 (m, 2H); 3.73 (t, J=6.24 Hz, 2H); 4.33 (s, 2H); 7.06 (s, 1H); 7.40-7.56 (m, 1H); 7.66 (d, J=7.70 Hz, 1H); 7.73 (dd, J=8.71, 4.68 Hz, 1H); 7.83-8.01 (m, 2H); 8.73 (d, J=2.75 Hz, 1H); 9.03 (s, 1H).

Following the procedure described above for Example 133 and substituting the appropriate reagents, starting materials and purification methods known to those skilled in the art, the following compounds of the present invention were prepared:

Example 134

2-(3-cyclopropyl-1H-1,2,4-triazol-1-yl)-9-(6-fluoropyridin-2-yl)-7,8-dihydro-[1,4]diazepino[7,1-a]isoquinolin-5(4H)-one UPLC-MS: MS 415.2 (M+H$^+$); UPLC rt 1.05 min.

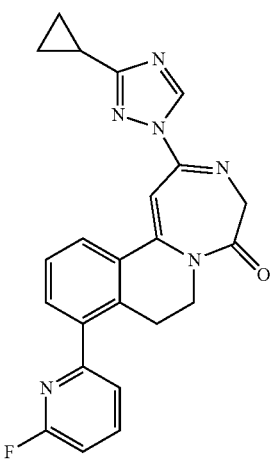 [SMILES: O=C1CN=C(n2cnc(C3CC3)n2)C=C2c3cccc(-c4cccc(F)n4)c3CCN12]

Example 135

2-(3-cyclopropyl-1H-1,2,4-triazol-1-yl)-9-(4-fluoropyridin-2-yl)-7,8-dihydro-[1,4]diazepino[7,1-a]isoquinolin-5(4H)-one UPLC-MS: MS 415.2 (M+H$^+$); UPLC rt 1.00 min.

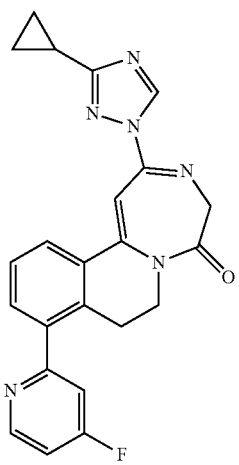 [SMILES: O=C1CN=C(n2cnc(C3CC3)n2)C=C2c3cccc(-c4cc(F)ccn4)c3CCN12]

Example 136

2-(3-cyclopropyl-1H-1,2,4-triazol-1-yl)-9-(5-fluoropyrazin-2-yl)-7,8-dihydro-[1,4]diazepino[7,1-a]isoquinolin-5(4H)-one UPLC-MS: MS 416.2 (M+H$^+$); UPLC rt 0.99 min.

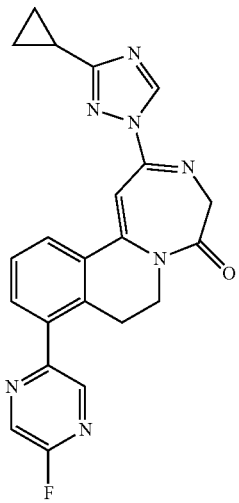 [SMILES: O=C1CN=C(n2cnc(C3CC3)n2)C=C2c3cccc(-c4cnc(F)cn4)c3CCN12]

Example 137

9-(5-fluoropyrazin-2-yl)-2-(3-methyl-1H-1,2,4-triazol-1-yl)-7,8-dihydro-[1,4]diazepino[7,1-a]isoquinolin-5(4H)-one UPLC-MS: MS 390.2 (M+H$^+$); UPLC rt 0.87 min.

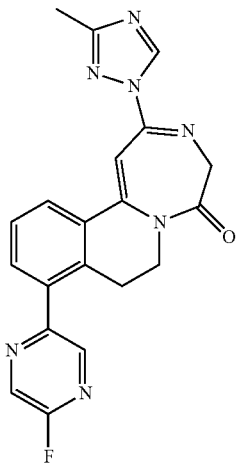 [SMILES: Cc1ncn(C2=NCC(=O)N3CCc4c(cccc4-c4cnc(F)cn4)C3=C2)n1]

Example 138

2-(4-cyclopropyl-1H-imidazol-1-yl)-9-(2H-1,2,3-triazol-2-yl)-7,8-dihydro-[1,4]diazepino[7,1-a]isoquinolin-5(4H)-one

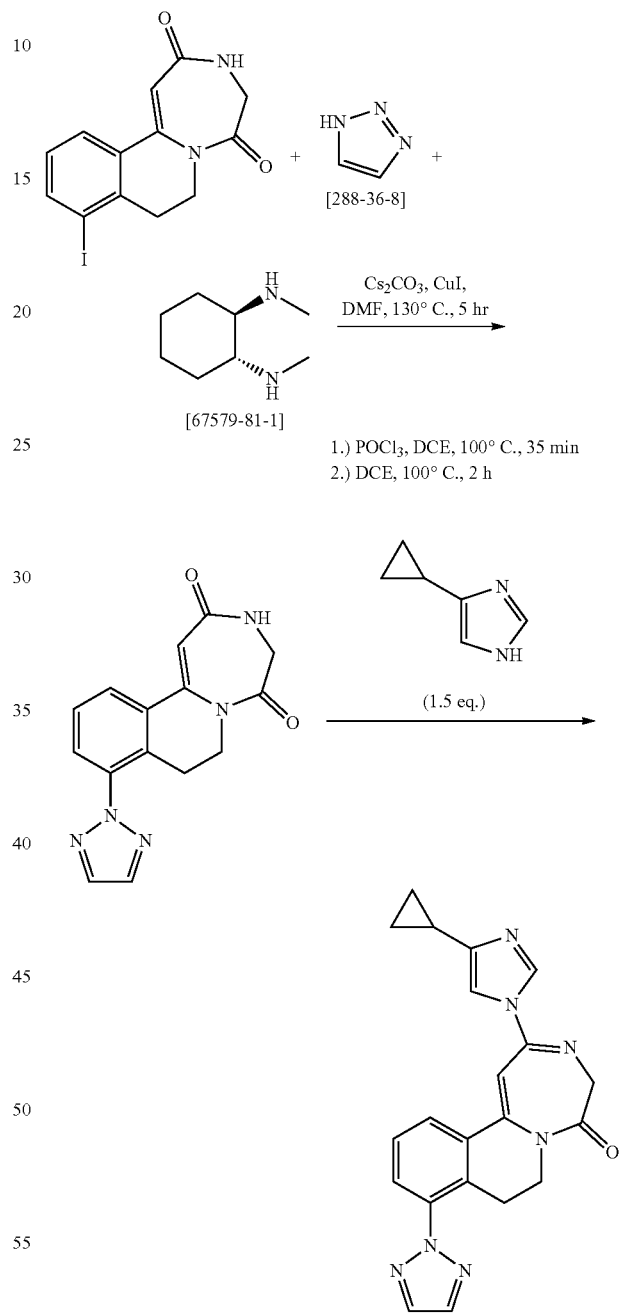

Step 1: 9-(2H-1,2,3-triazol-2-yl)-3,4,7,8-tetrahydro-[1,4]diazepino[7,1-a]isoquinoline-2,5-dione. 136-1. A mixture of 9-iodo-3,4,7,8-tetrahydro-[1,4]diazepino[7,1-a]isoquinoline-2,5-dione (600 mg, 1.69 mmol), 1H-1,2,3-triazole (421 mg, 6.10 mmol), trans-N,N-dimethylcyclohexane-1,2-diamine (87 mg, 0.61 mmol), cesium carbonate (1987 mg, 6.10 mmol) and CuI (323 mg, 1.69 mmol) in DMF (6 mL) were heated under Ar at 130° C. in the microwave for 5 hr. The mixture was cooled to rt. Water was added and the mixture was extracted with CH₂Cl₂ (2×). The combined organic layers were dried with sodium sulfate and evaporated under reduced pressure. The crude product was purified by flash-column chromatography over silicagel (Biotage Isolera Four, eluent: DCM for 4 min, then from 0% MeOH in DCM to 5% MeOH in DCM in 26 min, followed by 5% MeOH in DCM for 5 min) to yield the title compound as yellow oil (97 mg). UPLC-MS: MS 296.2 (M+H⁺); UPLC rt 0.63 min.

Step 2: 2-(4-cyclopropyl-1H-imidazol-1-yl)-9-(2H-1,2,3-triazol-2-yl)-7,8-dihydro-[1,4]diazepino[7,1-a]isoquinolin-5(4H)-one. Example 136. To a stirred solution of 9-(2H-1,2,3-triazol-2-yl)-3,4,7,8-tetrahydro-[1,4]diazepino[7,1-a]isoquinoline-2,5-dione (97 mg, 0.328 mmol) in 1,2-dichloroethane (3 mL) was added POCl₃ (0.061 mL, 0.657 mmol) at rt and the resulting suspension was stirred at 100° C. for 35 min. The reaction mixture was cooled to rt and concentrated under reduced pressure to dryness. For complete removal of POCl₃ the residue was taken up in toluene and the solvent was evaporated under reduced pressure. The residue was dried under high vacuo at rt.

The resulting crude chloro intermediate was dissolved in 1,2-dichloroethane (3 mL), 4-cyclopropyl-1H-imidazole (107 mg, 0.985 mmol) was added and the mixture was stirred at 100° C. for 2 h. The reaction mixture was allowed to warm to rt and diluted with DCM. Saturated aqueous NaHCO₃ solution was added and the mixture was extracted twice with DCM. The combined organic layers were washed with brine, dried with sodium sulfate, filtered and the solvent was removed under reduced pressure. The crude product was purified by flash-column chromatography over silicagel (Biotage Isolera Four, eluent: pure DCM for 3 min, then from 0% MeOH in DCM to 5% MeOH in DCM in 14 min, 5% MeOH in DCM for 3 min) to yield a yellow foam. Further purification by SFC (column: 2-Ethylpyridine 5 μm, 250×30 mm, 60 A, Princeton; eluent: 8% MeOH/CO₂ for 1 min, then from 8% MeOH/CO₂ to 13% MeOH/CO₂ in 6 min; flow 100 mL/min; UV detection at 220 nm) gave the title compound as slightly yellow foam (21 mg). UPLC-MS: MS 386.2 (M+H⁺); UPLC rt 0.86 min. ¹H NMR (400 MHz, DMSO-d₆) δ ppm 0.58-0.70 (m, 2 H), 0.74-0.82 (m, 2 H), 1.74-1.86 (m, 1 H), 2.91 (t, J=5.75 Hz, 2 H), 3.75 (t, J=5.87 Hz, 2 H), 4.25 (s, 2 H), 7.22 (s, 1 H), 7.43 (s, 1 H), 7.54-7.63 (m, 1 H), 7.76 (d, J=8.80 Hz, 1 H), 8.10 (s, 1 H), 8.14-8.21 (m, 3 H).

Example 139

2-(4-cyclopropyl-1H-imidazol-1-yl)-9-(5-fluoropyrazin-2-yl)-7,8-dihydro-[1,4]diazepino[7,1-a]isoquinolin-5(4H)-one

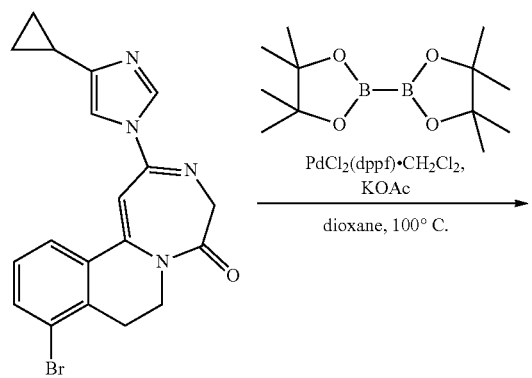

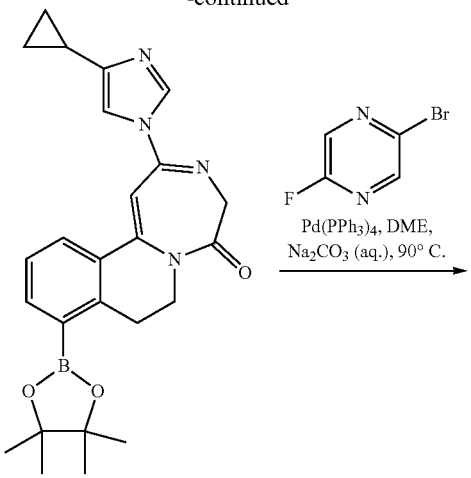

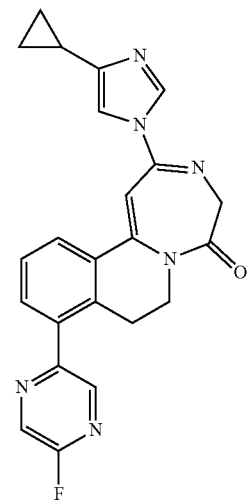

Step 1: 2-(4-cyclopropyl-1H-imidazol-1-yl)-9-(4,4,5,5-tetramethyl-1,3,2-dioxaborolan-2-yl)-7,8-dihydro-[1,4]diazepino[7,1-a]isoquinolin-5(4H)-one. 137-1. A solution of 9-bromo-2-(4-cyclopropyl-1H-imidazol-1-yl)-7,8-dihydro-[1,4]diazepino[7,1-a]isoquinolin-5(4H)-one (500 mg, 1.259 mmol), bis pinacol ester (484 mg, 1.888 mmol) and KOAc (371 mg, 3.78 mmol) in dioxane (8 mL) was treated with PdCl₂(dppf)*CH₂Cl₂ (103 mg, 0.126 mmol). The mixture was stirred under N₂ at 100° C. for 90 min, and then allowed to cool to RT. The mixture was filtered on Hyflo, and the filtrate concentrated in vacuo. The crude product was purified by flash-column chromatography over silicagel (Biotage Isolera Four, eluent: 10% EtOAc in heptane for 2 min, then from 10% EtOAc in heptane to 75% EtOAc in heptane in 13 min, 75% EtOAc in heptane for 3 min) to yield the title compound (232 mg). UPLC-MS: MS 445.4 (M+H⁺); UPLC rt 1.18 min.

Step 2: 2-(4-cyclopropyl-1H-imidazol-1-yl)-9-(5-fluoropyrazin-2-yl)-7,8-dihydro-[1,4]diazepino[7,1-a]isoquinolin-5(4H)-one. Example 137. A suspension of 2-(4-cyclopropyl- 1H-imidazol-1-yl)-9-(4,4,5,5-tetramethyl-1,3,2-dioxaborolan-2-yl)-7,8-dihydro-[1,4]diazepino[7,1-a]isoquinolin-5(4H)-one (100 mg, 0.225 mmol), 2-bromo-5-fluoropyrazine (90 mg, 0.51 mmol) and Pd(PPh$_3$)$_4$ (39 mg, 0.034 mmol) in DME (2.8 mL) was treated with a 2M aq. solution of Na$_2$CO$_3$ (0.6 mL, 1.12 mmol). The mixture was heated to 90° C. for 2 h, allowed to cool to RT and poured onto H$_2$O. The mixture was extracted with DCM and the combined org. layers were washed with brine, dried over Na$_2$SO$_4$, filtered and concentrated in vacuo. The crude product was purified by flash-column chromatography over silicagel (Biotage Isolera Four, eluent: 25% EtOAc in heptane for 2 min, then from 25% EtOAc in heptane to 100% EtOAc in heptane in 10 min, 100% EtOAc in heptane for 5 min) to yield a solid which was crystallized from diethyl ether and afforded the title compound (57 mg). UPLC-MS: MS 415.2 (M+H$^+$); UPLC rt 0.92 min. $^1$H NMR (400 MHz, DMSO-d$_6$) δ ppm 0.59-0.69 (m, 2 H), 0.72-0.82 (m, 2 H), 1.75-1.86 (m, 1 H), 2.97 (t, J=5.62 Hz, 2 H), 3.70 (t, J=6.11 Hz, 2 H), 4.24 (br. s., 2 H), 7.15 (s, 1 H), 7.43 (s, 1 H), 7.54 (t, J=7.82 Hz, 1 H), 7.69 (d, J=7.58 Hz, 1 H), 8.01-8.16 (m, 2 H), 8.58 (s, 1 H), 8.83 (d, J=8.31 Hz, 1 H).

Following the procedure described above for Example 139 and substituting the appropriate reagents, starting materials and purification methods known to those skilled in the art, the following compounds of the present invention were prepared:

Example 140 (from Precursor Described in Preparation 17a)

9-cyclopropyl-2-(4-(1-fluorocyclopropyl)-1H-imidazol-1-yl)-7,8-dihydro-[1,4]diazepino[7,1-a][2,6]naphthyridin-5(4H)-one UPLC-MS: MS 433.3 (M+H$^+$); UPLC rt 0.91 min.

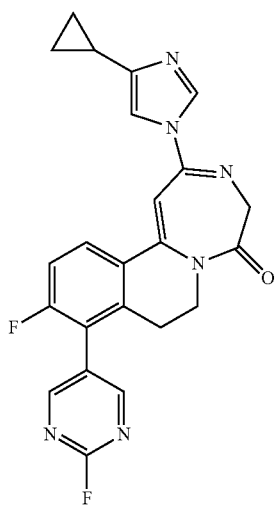 [SMILES: O=C1CN=C(n2cnc(C3CC3)c2)C=C2c3ccc(F)c(-c4cnc(F)nc4)c3CCN12]

Example 141 (from Precursor Described in Preparation 17)

2-(4-cyclopropyl-1H-imidazol-1-yl)-9-(6-fluoropyrazin-2-yl)-7,8-dihydro-[1,4]diazepino[7,1-a]isoquinolin-5(4H)-one UPLC-MS: MS 415.3 (M+H$^+$); UPLC rt 0.89 min.

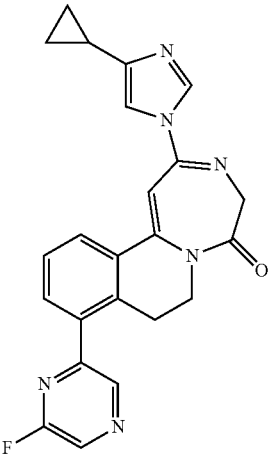 [SMILES: O=C1CN=C(n2cnc(C3CC3)c2)C=C2c3cccc(-c4cncc(F)n4)c3CCN12]

Example 142

9-isopropoxy-2-(4-(methoxymethyl)-1H-imidazol-1-yl)-7,8-dihydro-[1,4]diazepino[7,1-a]isoquinolin-5(4H)-one

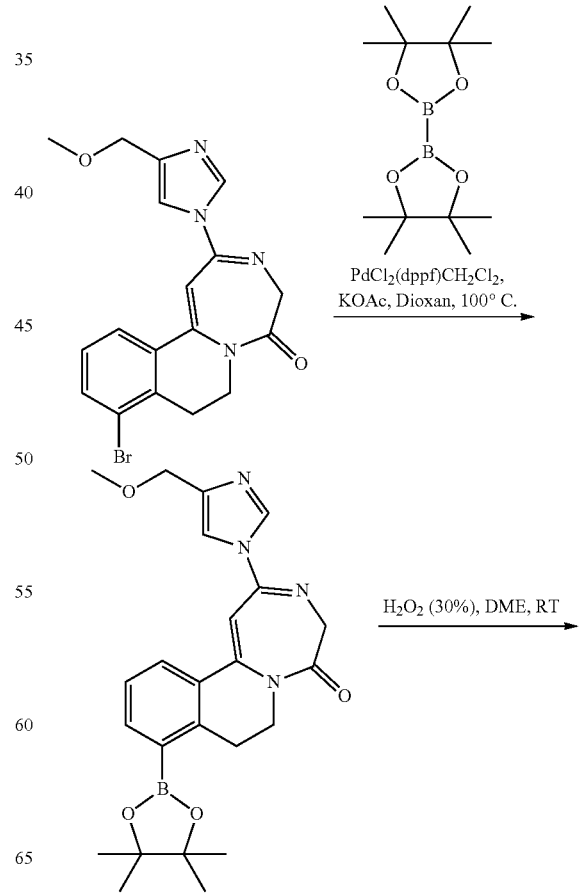

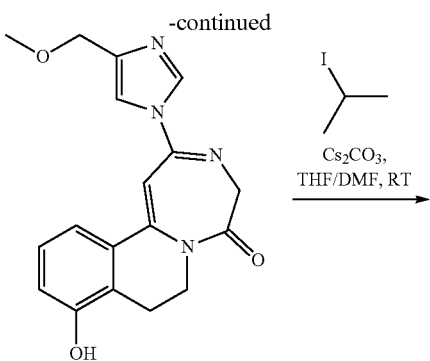

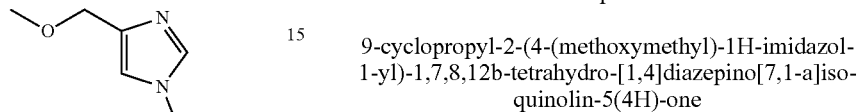

Step 1: 2-(4-(methoxymethyl)-1H-imidazol-1-yl)-9-(4,4,5,5-tetramethyl-1,3,2-dioxaborolan-2-yl)-7,8-dihydro-[1,4]diazepino[7,1-a]isoquinolin-5(4H)-one. 142-1. A solution of 9-bromo-2-(4-(methoxymethyl)-1H-imidazol-1-yl)-7,8-dihydro-[1,4]diazepino[7,1-a]isoquinolin-5(4H)-one (369 mg, 0.92 mmol), bis pinacol ester (354 mg, 1.38 mmol) and KOAc (271 mg, 2.76 mmol) in dioxane (5.3 mL) was treated with PdCl$_2$(dppf)*CH$_2$Cl$_2$ (75 mg, 0.092 mmol). The mixture was stirred under N$_2$ at 100° C. for 5 h, and then allowed to cool to RT. The mixture was filtered on Hyflo, and the filtrate concentrated in vacuo. The crude product was purified by flash-column chromatography over silicagel (Biotage Isolera Four, eluent: 1% MeOH in DCM for 3 min, then from 1% MeOH in DCM to 5% MeOH in DCM in 27 min, 5% MeOH in DCM for 5 min) to yield the title compound (418 mg). UPLC-MS: MS 449.3 (M+H$^+$); UPLC rt 1.10 min.

Step 2: 9-hydroxy-2-(4-(methoxymethyl)-1H-imidazol-1-yl)-7,8-dihydro-[1,4]diazepino[7,1-a]isoquinolin-5(4H)-one. Example 142-2. 2-(4-(methoxymethyl)-1H-imidazol-1-yl)-9-(4,4,5,5-tetramethyl-1,3,2-dioxaborolan-2-yl)-7,8-dihydro-[1,4]diazepino[7,1-a]isoquinolin-5(4H)-one (413 mg, 0.737 mmol) was dissolved in DME (10 mL) and hydrogen peroxide (30%, 3.40 mL, 33.3 mmol) was added at rt. The mixture was stirred overnight and the resulting crystals were filtered off (62 mg). UPLC-MS: MS 339.2 (M+H$^+$); UPLC rt 0.63 min.

Step 3: 9-isopropoxy-2-(4-(methoxymethyl)-1H-imidazol-1-yl)-7,8-dihydro-[1,4]diazepino[7,1-a]isoquinolin-5(4H)-one. Example 142. To a stirred suspension of 9-hydroxy-2-(4-(methoxymethyl)-1H-imidazol-1-yl)-7,8-dihydro-[1,4]diazepino[7,1-a]isoquinolin-5(4H)-one (50 mg, 0.148 mmol) and cesium carbonate (120 mg, 0.369 mmol) in THF (1 mL) and DMF (0.35 mL), isopropyl iodide (55 mg, 0.325 mmol) was added. The mixture was stirred at rt for 17 h and poured onto H$_2$O. The mixture was extracted with DCM and the combined org. layers were washed with brine, dried over Na$_2$SO$_4$, filtered and concentrated in vacuo.

The crude product was purified by by SFC (column: PPU 5 μm, 250×30 mm, 60 A, Princeton; eluent: 5% MeOH/CO$_2$ isocratic run for 20 min; flow 100 mL/min; UV detection at 220 nm). The residue was crystallized from diethyl ether and gave the title compound as white crystals (27 mg). UPLC-MS: MS 381.2 (M+H$^+$); UPLC rt 0.98 min. $^1$H NMR (400 MHz, DMSO-d$_6$) δ ppm 1.27 (d, J=6.11 Hz, 6 H), 2.80 (t, J=6.11 Hz, 2 H), 3.23 (s, 3 H), 3.82 (br. s., 2 H), 4.22 (br. s., 2 H), 4.27 (s, 2 H), 4.64 (dt, J=12.04, 6.08 Hz, 1 H), 7.14 (d, J=8.07 Hz, 1 H), 7.22 (s, 1 H), 7.31 (t, J=8.19 Hz, 1 H), 7.63 (s, 1 H), 7.66 (d, J=7.82 Hz, 1 H), 8.20 (s, 1 H).

Example 143

9-cyclopropyl-2-(4-(methoxymethyl)-1H-imidazol-1-yl)-1,7,8,12b-tetrahydro-[1,4]diazepino[7,1-a]isoquinolin-5(4H)-one

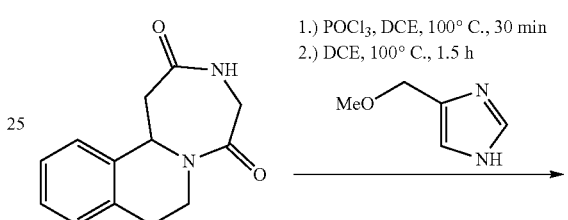

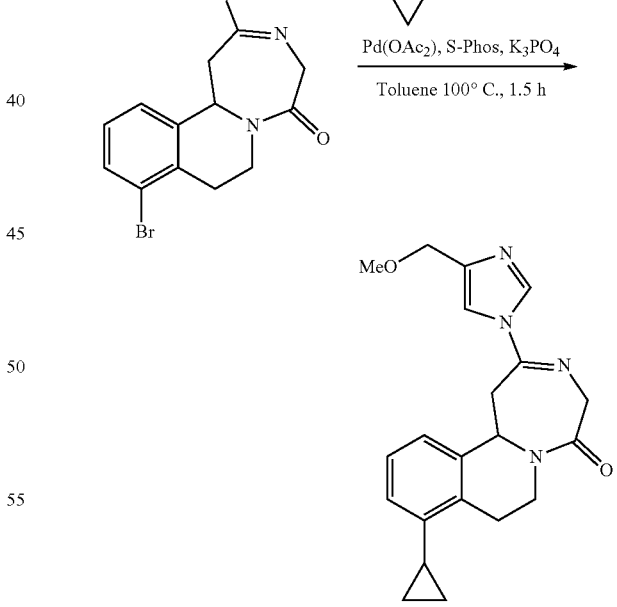

Step 1: 9-bromo-2-(4-(methoxymethyl)-1H-imidazol-1-yl)-1,7,8,12b-tetrahydro-[1,4]diazepino[7,1-a]isoquinolin-5(4H)-one. 143-1. To a stirred solution of 9-bromo-1,3,4,7,8,12b-hexahydro-[1,4]diazepino[7,1-a]isoquinoline-2,5-dione (0.464 g, 1.5 mmol) in 1,2-dichloroethane (15 mL) was added POCl$_3$ (0.28 mL, 3.0 mmol) at RT and the resulting suspension was stirred at 100° C. for 60 min. The reaction mixture was cooled to rt and concentrated under reduced pressure to dryness. For complete removal of POCl₃ the residue was taken up in toluene and the solvent was evaporated under reduced pressure. The residue was dried under high vacuo at RT.

The resulting crude chloro intermediate (0.491 g) was dissolved in 1,2-dichloroethane (15 mL), 4-(methoxymethyl)-1H-imidazole (0.841 g, 7.5 mmol) was added and the mixture was stirred at 100° C. for 1.5 h. The reaction mixture was allowed to warm to RT and diluted with DCM. Water and saturated aqueous NaHCO₃ solution was added and the mixture was extracted twice with DCM. The combined organic layers were washed with brine, dried with sodium sulfate, filtered and the solvent was removed under reduced pressure. The crude product was purified by flash-column chromatography over silicagel (Biotage Isolera Four, eluent: 1% MeOH in DCM for 3 min, then from 1% MeOH in DCM to 4% MeOH in DCM in 25 min, 4% MeOH in DCM for 5 min) to yield a yellow foam (149 mg). UPLC-MS: MS 403.1/405.1 (M+H⁺); UPLC rt 0.82 min.

Step 2: 9-cyclopropyl-2-(4-(methoxymethyl)-1H-imidazol-1-yl)-1,7,8,12b-tetrahydro-[1,4]diazepino[7,1-a]isoquinolin-5(4H)-one. Example 143. 9-bromo-2-(4-(methoxymethyl)-1H-imidazol-1-yl)-1,7,8,12b-tetrahydro-[1,4]diazepino[7,1-a]isoquinolin-5(4H)-one (148 mg, 0.367 mmol) was dissolved in toluene (3.6 mL) and S-Phos (49 mg, 0.117 mmol), cyclopropylboronic acid (66 mg, 0.734 mmol) and K₃PO₄ (164 mg, 0.771 mmol) were added. The suspension was degassed, Pd(OAc)₂ (17 mg, 0.073 mmol) was added under Argon and the mixture was heated at 100° C. for 1.5 h. The mixture was allowed to warm to RT and filtered through a pad of celite and the solvent was removed under reduced pressure. The crude product was purified by flash-column chromatography over silicagel (Biotage Isolera Four, eluent: 1% MeOH in DCM for 3 min, then from 1% MeOH in DCM to 4% MeOH in DCM in 12 min, 4% MeOH in DCM for 3 min) to yield a yellow foam. Further purification by SFC (column: 2-Ethylpyridine 5 μm, 250×30 mm, 60 A, Princeton; eluent: 11% MeOH/CO₂ for 1 min, then from 11% MeOH/CO₂ to 16% MeOH/CO₂ in 6 min; flow 100 mL/min; UV detection at 220 nm) gave the title compound as white foam (30 mg). UPLC-MS: MS 365.3 (M+H⁺); UPLC rt 0.85 min. ¹H NMR (400 MHz, DMSO-d₆) δ ppm 0.51-0.66 (m, 2 H), 0.86-0.98 (m, 2 H), 1.86-2.00 (m, 1 H), 2.97-3.09 (m, 2 H), 3.21 (s, 3 H), 3.54-3.66 (m, 1 H), 3.67-3.77 (m, 1 H), 4.11-4.30 (m, 3 H), 5.26 (d, J=15.31 Hz, 1 H), 5.73 (dd, J=9.91, 4.89 Hz, 1 H), 6.95 (d, J=7.28 Hz, 1 H), 7.12-7.21 (m, 1 H), 7.21-7.27 (m, 1 H), 7.57 (s, 1 H), 8.10 (s, 1 H).

Biological Testing 1.1 In-vitro Testing

Activity of compounds of the present invention was examined by determination to what extent the glutamate-induced elevation of the intracellular calcium concentration in L(tk-) cells expressing human mGluR5a receptors (see L. P. Daggett et al., Neuropharm. Vol. 34, pages 871-886, 1995) is inhibited by utilizing methods as described e.g. by L. P. Daggett et al., Neuropharm. Vol. 34, pages 871-886 (1995) and P. J. Flor et al., J. Neurochem. Vol. 67, pages 58-63 (1996).

Activity of compounds of the present invention with respect to mGluR1 antagonism was examined by an assay based on measurements of L-glutamate induced intracellular calcium increases using a 96 well plate-based Fluorometric Imaging Plate Reader (FLIPR), and CHO cells stably expressing human mGluR1. L-glutamate induced robust calcium responses via human mGluR1 in a concentration-dependent manner and in the low micromolar range. The table below represents $IC_{50}$ values of the inhibition of the glutamate-induced elevation of the intracellular calcium concentration.

| Example | mGluR5 $IC_{50}$ (μM) | mGluR1 $IC_{50}$ (μM) |
|---|---|---|
| 1 | 0.327 | 6.4 |
| 2 | 0.09 | 0.027 |
| 3 | 0.22 | 0.585 |
| 4 | 0.18 | 0.15 |
| 5 | 0.044 | 0.015 |
| 6 | 0.075 | 3.05 |
| 7 | 0.024 | 0.21 |
| 8 | 0.022 | 4.9 |
| 9 | 0.6 | >10 |
| 10 | 0.345 | 0.94 |
| 11 | 0.17 | 0.69 |
| 12 | 0.046 | 1.3 |
| 13 | 0.082 | 0.53 |
| 14 | 0.55 | >10 |
| 15 | 42% [a] | 44% [a] |
| 16 | 2.2 | 3.5 |
| 17 | 2.2 | >10 |
| 18 | 4.1 | >10 |
| 19 | 4.5 | 0.8 |
| 20 | 1.2 | 2.8 |
| 21 | 3.9 | 5.2 |
| 22 | 0.071 | >10 |
| 23 | 0.022 | >10 |
| 24 | 0.035 | >10 |
| 25 | 0.066 | >10 |
| 26 | 0.235 | >10 |
| 27 | 0.437 | >10 |
| 28 | 0.08 | 4.8 |
| 29 | 0.09 | 0.008 |
| 30 | 0.15 | 1.4 |
| 31 | 0.167 | 1.3 |
| 32 | 0.01 | 0.035 |
| 33 | 0.013 | 1.4 |
| 34 | 0.041 | 0.093 |
| 35 | 0.014 | 0.015 |
| 36 | 3.8 | 6.9 |
| 36a | 5.5 | 1% [a] |
| 37 | 0.077 | 2.2 |
| 38 | 0.05 | 0.022 |
| 39 | 0.61 | 1.6 |
| 40 | 5.2 | >10 |
| 41 | 0.032 | >10 |
| 42 | 0.032 | 3.4 |
| 43 | 0.685 | >10 |
| 44 | 1.6 | >10 |
| 45 | 0.7 | >10 |
| 46 | 0.27 | 2.2 |
| 47 | 0.071 | 3.4 |
| 48 | 0.035 | 2.3 |
| 49 | 1.3 | >10 |
| 50 | 0.046 | >10 |
| 51 | 0.035 | >10 |
| 52 | 0.066 | >10 |
| 53 | 0.007 | >10 |
| 54 | 0.011 | >10 |
| 55 | 4.9 | >10 |
| 56 | 24% [a] | 0% [a] |
| 57 | 0.014 | 4.5 |
| 58 | 26% [a] | 8.9 |
| 59 | 23% [a] | 6.5 |
| 60 | 27% [a] | 15% [a] |
| 61 | 0.345 | 3.1 |
| 62 | 0.595 | 1.6 |
| 63 | 0.535 | 3.2 |
| 64 | 4.3 | >10 |
| 65 | 0.21 | 1.5 |
| 66 | 0.78 | >10 |
| 67 | 0.715 | 1.4 |
| 68 | 1.7 | >10 |
| 69 | 0.02 | >10 |
| 70 | 0.049 | >10 |
| 71 | 0.027 | 6.4 |

| Example | mGluR5 IC$_{50}$ (μM) | mGluR1 IC$_{50}$ (μM) |
|---|---|---|
| 72 | 0.275 | >10 |
| 73 | 3.5 | >10 |
| 74 | 0.022 | 1.2 |
| 75 | 0.009 | 0.17 |
| 76 | 0.034 | 4.2 |
| 77 | 0.032 | 73% [a] |
| 78 | 0.54 | >10 |
| 79 | 0.13 | >10 |
| 80 | 0.145 | >10 |
| 81 | 0.036 | >10 |
| 82 | 0.072 | >10 |
| 83 | 0.205 | >10 |
| 84 | 0.028 | >10 |
| 85 | 0.039 | 1.6 |
| 86 | 0.012 | 5.9 |
| 87 | 0.148 | 56% [a] |
| 88 | 0.131 | 47% [a] |
| 88a | 0.005 | 24% [a] |
| 88b | 0.020 | >2 |
| 88c | 0.271 | >10 |
| 88d | 0.031 | >2 |
| 88e | 0.034 | 3.881 |
| 88f | 0.100 | 1.953 |
| 88g | 0.017 | 0.761 |
| 88h | 0.046 | 1.053 |
| 88i | 0.340 | >10 |
| 88j | 0.056 | 1.857 |
| 88k | 0.069 | 5.86 |
| 89 | 0.028 | 0.65 |
| 90 | 0.01 | 1.5 |
| 91 | 0.009 | 0.22 |
| 92 | <0.001 | 0.636 |
| 93 | 0.003 | 1.5 |
| 94 | 2.7 | >10 |
| 95-1 | 0.02 | 10 |
| 95-2 | 0.011 | >10 |
| 96-1 | 0.006 | 0.54 |
| 96-2 | 0.002 | 0.289 |
| 97 | 0.037 | 5.9 |
| 98 | 0.014 | 2.4 |
| 99 | 0.083 | >2 |
| 99a | 0.077 | >10 |
| 99b | 41% [b] | >10 |
| 99c | 31% [b] | >10 |
| 99d | 0.347 | >2 |
| 99e | 0.127 | 8.261 |
| 99f | 0.102 | 11.993 |
| 99g | 0.220 | 18.193 |
| 99h | 0.038 | not tested |
| 99i | 0.016 | 0.687 |
| 99j | 0.007 | 3.206 |
| 99k | 0.003 | 0.561 |
| 99l | 0.002 | 0.702 |
| 99m | 0.002 | 0.672 |
| 99n | 0.006 | 2.079 |
| 99o | 0.050 | >10 |
| 99p | 0.002 | 0.814 |
| 99q | 0.088 | >6 |
| 99r | 0.136 | >10 |
| 99s | 0.153 | >10 |
| 100 | 0.019 | 0.56 |
| 101 | 0.026 | >10 |
| 102 | 0.016 | >10 |
| 103 | 0.018 | >10 |
| 104 | 0.007 | 1.3 |
| 105 | 0.122 | >10 |
| 106 | 0.182 | >10 |
| 106a | 0.068 | >10 |
| 106b | 0.168 | 7.333 |
| 106c | 1.090 | >10 |
| 107 | 0.835 | >10 |
| 108 | 0.018 | 3.3 |
| 108a | 0.091 | >10 |
| 108b | 0.023 | 1.919 |
| 108c | 0.115 | >10 |
| 109 | 0.01 | 1.8 |
| 110 | 0.27 | >10 |
| 110a | 0.328 | >2 |
| 110b | 0.758 | >10 |
| 110c | 72% [b] | >10 |
| 110d | 57% [b] | >10 |
| 111 | 0.053 | 9.3 |
| 112 | 0.515 | >10 |
| 113 | 0.12 | 2.3 |
| 114 | 1.6 | >10 |
| 115 | 0.495 | >10 |
| 116 | 0.41 | >10 |
| 117 | 0.035 | 0.66 |
| 118 | 0.018 | >10 |
| 119 | 0.024 | 2.6 |
| 120 | 0.007 | 0.89 |
| 121 | 0.014 | 0.49 |
| 122 | 0.005 | 1.1 |
| 123 | 0.003 | 7 |
| 123a | 0.012 | >2 |
| 123b | 0.001 | 2.342 |
| 123c | 0.008 | 0.226 |
| 123d | 0.011 | 0.511 |
| 123e | 0.056 | 1.644 |
| 123f | 0.108 | >2 |
| 124 | 0.005 | 3.3 |
| 125 | 0.18 | >2 |
| 126 | 0.006 | 0.712 |
| 127 | 0.007 | 1.195 |
| 128 | 0.001 | 0.041 |
| 129 | 0.002 | 1.5 |
| 130 | 0.027 | 3.312 |
| 131 | 0.046 | >2 |
| 132 | 0.061 | 2.068 |
| 133 | 0.215 | >10 |
| 134 | 0.198 | >10 |
| 135 | 0.829 | >10 |
| 136 | 0.019 | >2 |
| 137 | 0.048 | >10 |
| 138 | 0.079 | 1.485 |
| 139 | 0.017 | 1.103 |
| 140 | 0.093 | >10 |
| 141 | 0.026 | 0.402 |
| 142 | 0.273 | >2 |
| 143 | 0.282 | >10 |

[a] % inhibition at 10 μM;
[b] % inhibition at 2 μM

The following two compounds of formula (I) were tested at 10 μM in the above described mGluR5a antagonism test and less than 20% inhibition was seen:

9-chloro-2-(5-methyl-1H-pyrazol-1-yl)-7,8-dihydro-[1,4]diazepino[7,1-a]isoquinolin-5(4H)-one; and 2-(4-ethyl-1H-imidazol-1-yl)-9-(3-hydroxyoxetan-3-yl)-7,8-dihydro-[1,4]diazepino[7,1-a]isoquinolin-5(4H)-one.

The invention claimed is:

1. A method for the treatment of a substance-related disorder through mGluR5 antagonism comprising administration of a therapeutically effective amount of a compound of formula (I) or a pharmaceutically acceptable salt thereof to a patient in need of treatment thereof

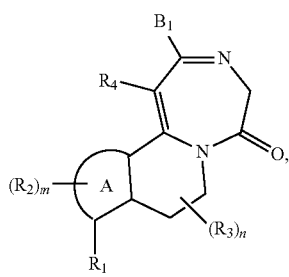

(I)

wherein
A is a fused five- to seven-membered monocyclic ring system which may be aromatic, saturated or unsaturated non-aromatic and which may contain from 1 to 4 hetero atoms selected from nitrogen, oxygen and sulfur;
$R_1$ is —$X_2$—$B_2$;
$X_2$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;
$B_2$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_6$;
each $R_6$ independently is halogen, hydroxy, cyano, $C_{1-4}$alkyl, $C_{1-4}$halogenalkyl, $C_{1-4}$alkoxy, or $C_{1-4}$halogenalkoxy; or two $R_6$ at the same ring atom together are oxo;
m is 0, 1, 2, 3 or 4;
each $R_2$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;
n is 0, 1, 2, 3 or 4;
each $R_3$ independently is halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;
$R_4$ is hydrogen, halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;
$B_1$ is a five- to six-membered aromatic ring system, which may contain from 1 to 4 hetero atoms selected from nitrogen, oxygen and sulfur, wherein the ring system may in turn be substituted once or more than once by $R_7$;
each $R_7$ independently is
halogen, cyano, hydroxy, amino,
$C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl;
$C_{2-4}$alkenyl; $C_{2-4}$halogenalkenyl; $C_{2-4}$alkinyl; $C_{2-4}$halogenalkinyl;
$C_{1-4}$alkoxy; $C_{1-4}$alkoxy-$C_{1-4}$alkoxy $C_{1-4}$halogenalkoxy; $C_{1-4}$alkyl-amino; di-($C_{1-4}$alkyl)amino;
$C_{1-4}$alkoxycarbonyl;
or a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_8$;
each $R_8$ independently is halogen, hydroxy, cyano, $C_{1-4}$alkyl, $C_{1-4}$halogenalkyl, $C_{1-4}$alkoxy, or $C_{1-4}$halogenalkoxy; or two $R_8$ at the same ring atom together are oxo;
or two $R_7$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_9$;
each $R_9$ independently is halogen, hydroxy, cyano, $C_{1-4}$alkyl, $C_{1-4}$halogenalkyl, $C_{1-4}$alkoxy, or $C_{1-4}$halogenalkoxy; or two $R_9$ at the same ring atom together are oxo.

2. The method according to claim 1, wherein A is phenyl.

3. The method according to claim 1, wherein $R_1$ is —$X_2$—$B_2$, wherein $X_2$ is bond; $B_2$ is $C_{3-6}$cycloalkyl which may be substituted once or more than once by $R_6$;
or $B_2$ is a five- to six-membered aromatic ring system which may contain from 1 to 4 hetero atoms selected from nitrogen, oxygen and sulfur, wherein the ring system may in turn be substituted once or more than once by $R_6$; each $R_6$ independently is halogen, hydroxy, cyano, $C_{1-4}$alkyl, $C_{1-4}$halogenalkyl, $C_{1-4}$alkoxy, or $C_{1-4}$halogenalkoxy.

4. The method according to claim 1, wherein
m is 0, 1 or 2;
each $R_2$ independently is halogen, $C_{1-4}$alkyl; $C_{1-4}$halogenalkyl; $C_{1-4}$alkoxy; $C_{1-4}$halogenalkoxy or $C_{3-6}$cycloalkyl;
n is 0; and
$R_4$ is hydrogen.

5. The method according to claim 1, wherein $B_1$ is a five- to six-membered aromatic ring system, which contains from 1 to 4 hetero atoms selected from nitrogen, oxygen and sulfur, wherein the ring system may in turn be substituted once or more than once by $R_7$; and wherein each $R_7$ independently is halogen, $C_{1-4}$alkyl; $C_{1-4}$halogenalkyl; $C_{1-4}$alkoxy-$C_{1-4}$alkyl, $C_{1-4}$alkoxy, $C_{1-4}$alkoxy-$C_{1-4}$alkoxy or $C_{3-6}$cycloalkyl.

6. The method according to claim 1, wherein
A is phenyl;
$R_1$ is —$X_2$—$B_2$, wherein $X_2$ is bond;

B₂ is C₃₋₆cycloalkyl which may be substituted once or more than once by R₆;

or B₂ is a five- to six-membered aromatic ring system which may contain from 1 to 4 hetero atoms selected from nitrogen, oxygen and sulfur, wherein the ring system may in turn be substituted once or more than once by R₆;

each R₆ independently is halogen, hydroxy, cyano, C₁₋₄alkyl, C₁₋₄halogenalkyl, C₁₋₄alkoxy, or C₁₋₄halogenalkoxy;

m is 0, 1 or 2;

each R₂ independently is halogen, C₁₋₄alkyl; C₁₋₄halogenalkyl; C₁₋₄alkoxy; C₁₋₄halogenalkoxy or C₃₋₆cycloalkyl;

n is 0, 1 or 2;

each R₃ independently is halogen, C₁₋₄alkyl; C₁₋₄halogenalkyl; C₁₋₄alkoxy; C₁₋₄halogenalkoxy or C₃₋₆cycloalkyl;

R₄ is hydrogen, halogen, C₁₋₄alkyl; C₁₋₄halogenalkyl; C₁₋₄alkoxy; C₁₋₄halogenalkoxy or C₃₋₆cycloalkyl;

B₁ is a five- to six-membered aromatic ring system, which contains from 1 to 4 hetero atoms selected from nitrogen, oxygen and sulfur, wherein the ring system may in turn be substituted once or more than once by R₇;

and wherein each R₇ independently is halogen, C₁₋₄alkyl; C₁₋₄halogenalkyl; C₁₋₄alkoxy-C₁₋₄alkyl, C₁₋₄alkoxy, C₁₋₄alkoxy-C₁₋₄alkoxy or C₃₋₆cycloalkyl.

7. The method according to claim 1, wherein said compound of formula (I) is selected from the group consisting of 2-(2-methoxypyridin-4-yl)-9-morpholino-7,8-dihydro-[1,4]diazepino[7,1-a]isoquinolin-5(4H)-one;

2-(5-methylfuran-2-yl)-9-morpholino-7,8-dihydro-[1,4]diazepino[7,1-a]isoquinolin-5(4H)-one;

2-(1-methyl-1H-pyrazol-3-yl)-9-morpholino-7,8-dihydro-[1,4]diazepino[7,1-a]isoquinolin-5(4H)-one;

2-(1-methyl-1H-pyrazol-4-yl)-9-morpholino-7,8-dihydro-[1,4]diazepino[7,1-a]isoquinolin-5(4H)-one;

2-(furan-2-yl)-9-(pyridin-4-yl)-7,8-dihydro-[1,4]diazepino[7,1-a]isoquinolin-5(4H)-one;

2-(3-methoxyphenyl)-9-morpholino-7,8-dihydro-[1,4]diazepino[7,1-a]isoquinolin-5(4H)-one;

2-(1-isopropyl-1H-pyrazol-4-yl)-9-(1H-pyrazol-1-yl)-7,8-dihydro-[1,4]diazepino[7,1-a]isoquinolin-5(4H)-one;

2-(3-methoxyphenyl)-9-phenyl-7,8-dihydro-[1,4]diazepino[7,1-a]isoquinolin-5(4H)-one;

2-(2-methoxypyridin-4-yl)-9-(pyridin-2-yl)-7,8-dihydro-[1,4]diazepino[7,1-a]isoquinolin-5(4H)-one;

2-(furan-3-yl)-9-(pyridin-4-yl)-7,8-dihydro-[1,4]diazepino[7,1-a]isoquinolin-5(4H)-one;

2-(2-methoxypyridin-4-yl)-9-(pyrazin-2-yl)-7,8-dihydro-[1,4]diazepino[7,1-a]isoquinolin-5(4H)-one;

9-(6-fluoropyridin-3-yl)-2-(2-methoxypyridin-4-yl)-7,8-dihydro-[1,4]diazepino[7,1-a]isoquinolin-5(4H)-one;

9-(3-fluoropyridin-4-yl)-2-(2-methoxypyridin-4-yl)-7,8-dihydro-[1,4]diazepino[7,1-a]isoquinolin-5(4H)-one;

2-(1-methyl-1H-imidazol-4-yl)-9-(pyridin-4-yl)-7,8-dihydro-[1,4]diazepino[7,1-a]isoquinolin-5(4H)-one;

2-(1-methyl-1H-pyrazol-3-yl)-9-(2-methylpyridin-4-yl)-7,8-dihydro-[1,4]diazepino[7,1-a]isoquinolin-5(4H)-one;

2-(3-methoxyphenyl)-9-(tetrahydrofuran-2-yl)-7,8-dihydro-[1,4]diazepino[7,1-a]isoquinolin-5(4H)-one, (R)-2-(3-methoxyphenyl)-9-(tetrahydrofuran-2-yl)-7,8-dihydro-[1,4]diazepino[7,1-a]isoquinolin-5(4H)-one;

(S)-2-(3-methoxyphenyl)-9-(tetrahydrofuran-2-yl)-7,8-dihydro-[1,4]diazepino[7,1-a]isoquinolin-5(4H)-one;

2-(4-cyclobutyl-1H-imidazol-1-yl)-9-(1H-pyrazol-1-yl)-7,8-dihydro-[1,4]diazepino[7,1-a]isoquinolin-5(4H)-one;

2-(4-cyclobutyl-1H-imidazol-1-yl)-9-morpholino-7,8-dihydro-[1,4]diazepino[7,1-a]isoquinolin-5(4H)-one;

2-(4-(methoxymethyl)-1H-imidazol-1-yl)-9-(thiazol-2-yl)-7,8-dihydro-[1,4]diazepino[7,1-a]isoquinolin-5(4H)-one;

2-(4-isopropyl-1H-imidazol-1-yl)-9-(1-methyl-1H-pyrazol-4-yl)-7,8-dihydro-[1,4]diazepino[7,1-a]isoquinolin-5(4H)-one;

2-(4-isopropyl-1H-imidazol-1-yl)-9-(1-methyl-1H-imidazol-2-yl)-7,8-dihydro-[1,4]diazepino[7,1-a]isoquinolin-5(4H)-one;

2-(4-ethyl-1H-imidazol-1-yl)-9-(oxazol-2-yl)-7,8-dihydro-[1,4]diazepino[7,1-a]isoquinolin-5(4H)-one;

2-(4-ethyl-1H-imidazol-1-yl)-9-(furan-2-yl)-7,8-dihydro-[1,4]diazepino[7,1-a]isoquinolin-5(4H)-one;

2-(4-(2-methoxyethyl)-1H-imidazol-1-yl)-9-(thiazol-4-yl)-7,8-dihydro-[1,4]diazepino[7,1-a]isoquinolin-5(4H)-one;

2-(4-(methoxymethyl)-1H-imidazol-1-yl)-9-(5-methylthiazol-2-yl)-7,8-dihydro-[1,4]diazepino[7,1-a]isoquinolin-5(4H)-one;

2-(4-methyl-1H-imidazol-1-yl)-9-(pyrimidin-5-yl)-7,8-dihydro-[1,4]diazepino[7,1-a]isoquinolin-5(4H)-one;

2-(4-methyl-1H-imidazol-1-yl)-9-(pyridin-3-yl)-7,8-dihydro-[1,4]diazepino[7,1-a]isoquinolin-5(4H)-one;

2-(4-methyl-1H-imidazol-1-yl)-9-(pyridin-4-yl)-7,8-dihydro-[1,4]diazepino[7,1-a]isoquinolin-5(4H)-one;

9-(6-fluoropyridin-3-yl)-2-(4-methyl-1H-imidazol-1-yl)-7,8-dihydro-[1,4]diazepino[7,1-a]isoquinolin-5(4H)-one;

2-(4-methyl-1H-imidazol-1-yl)-9-(thiazol-5-yl)-7,8-dihydro-[1,4]diazepino[7,1-a]isoquinolin-5(4H)-one;

2-(4-chloro-1H-imidazol-1-yl)-9-(5-fluoropyridin-3-yl)-7,8-dihydro-[1,4]diazepino[7,1-a]isoquinolin-5(4H)-one;

9-(6-fluoropyridin-3-yl)-2-(4-(2-methoxyethyl)-1H-imidazol-1-yl)-7,8-dihydro-[1,4]diazepino[7,1-a]isoquinolin-5(4H)-one;

2-(4-ethyl-1H-imidazol-1-yl)-9-(4-fluorophenyl)-7,8-dihydro-[1,4]diazepino[7,1-a]isoquinolin-5(4H)-one;

2-(4-cyclopropyl-1H-imidazol-1-yl)-9-(4-methyloxazol-2-yl)-7,8-dihydro-[1,4]diazepino[7,1-a]isoquinolin-5(4H)-one;

2-(4-cyclopropyl-1H-imidazol-1-yl)-9-(5-methyloxazol-2-yl)-7,8-dihydro-[1,4]diazepino[7,1-a]isoquinolin-5(4H)-one;

9-cyclobutyl-2-(4-(methoxymethyl)-1H-imidazol-1-yl)-7,8-dihydro-[1,4]diazepino[7,1-a]isoquinolin-5(4H)-one;

9-cyclobutyl-2-(3-methyl-1H-1,2,4-triazol-1-yl)-7,8-dihydro-[1,4]diazepino[7,1-a]isoquinolin-5(4H)-one;

9-cyclopropyl-2-(3-(methoxymethyl)-1H-1,2,4-triazol-1-yl)-7,8-dihydro-[1,4]diazepino[7,1-a]isoquinolin-5(4H)-one;

4-(6-fluoropyridin-3-yl)-11-(4-isopropyl-1H-imidazol-1-yl)-5,6-dihydro-[1,4]diazepino[1,7-h][1,7]naphthyridin-8(9H)-one;

2-(4-cyclopropyl-1H-imidazol-1-yl)-9-(2-fluoropyridin-3-yl)-7,8-dihydro-[1,4]diazepino[7,1-a]isoquinolin-5(4H)-one;

2-(4-cyclobutyl-1H-imidazol-1-yl)-9-(2-fluoropyridin-3-yl)-7,8-dihydro-[1,4]diazepino[7,1-a]isoquinolin-5(4H)-one;

2-(4-cyclopropyl-1H-imidazol-1-yl)-9-(2,6-difluoropyridin-3-yl)-7,8-dihydro-[1,4]diazepino[7,1-a]isoquinolin-5(4H)-one;

2-(4-cyclopropyl-1H-imidazol-1-yl)-9-(isoxazol-5-yl)-7,8-dihydro-[1,4]diazepino[7,1-a]isoquinolin-5(4H)-one;

2-(4-(methoxymethyl)-1H-imidazol-1-yl)-9-(thiazol-4-yl)-7,8-dihydro-[1,4]diazepino[7,1-a]isoquinolin-5(4H)-one;

2-(3-ethyl-1H-1,2,4-triazol-1-yl)-9-(6-fluoropyridin-3-yl)-7,8-dihydro-[1,4]diazepino[7,1-a]isoquinolin-5(4H)-one;

2-(4-cyclopropyl-1H-imidazol-1-yl)-9-(3-methylisothiazol-5-yl)-7,8-dihydro-[1,4]diazepino[7,1-a]isoquinolin-5(4H)-one;

2-(4-cyclopropyl-1H-imidazol-1-yl)-9-(oxazol-2-yl)-7,8-dihydro-[1,4]diazepino[7,1-a]isoquinolin-5(4H)-one;

2-(4-ethynyl-1H-imidazol-1-yl)-9-(thiazol-4-yl)-7,8-dihydro-[1,4]diazepino[7,1-a]isoquinolin-5(4H)-one;

9-(2-fluoropyridin-3-yl)-2-(4-(oxazol-2-yl)-1H-imidazol-1-yl)-7,8-dihydro-[1,4]diazepino[7,1-a]isoquinolin-5(4H)-one;

2-(4-cyclopropyl-1H-imidazol-1-yl)-1-methyl-9-(3-methylis oxazol-5-yl)-7,8-dihydro-[1,4]diazepino[7,1-a]isoquinolin-5(4H)-one;

2-(4-cyclopropyl-1H-imidazol-1-yl)-9-(oxazol-5-yl)-7,8-dihydro-[1,4]diazepino[7,1-a]isoquinolin-5(4H)-one;

2-(4-cyclopropyl-1H-imidazol-1-yl)-9-(6-fluoropyridin-3-yl)-7,8-dihydro-[1,4]diazepino[7,1-a][2,6]naphthyridin-5(4H)-one;

2-(4-ethyl-1H-imidazol-1-yl)-9-(tetrahydrofuran-2-yl)-7,8-dihydro-[1,4]diazepino[7,1-a]isoquinolin-5(4H)-one;

(R)-2-(4-ethyl-1H-imidazol-1-yl)-9-(tetrahydrofuran-2-yl)-7,8-dihydro-[1,4]diazepino[7,1-a]isoquinolin-5(4H)-one;

(S)-2-(4-ethyl-1H-imidazol-1-yl)-9-(tetrahydrofuran-2-yl)-7,8-dihydro-[1,4]diazepino[7,1-a]isoquinolin-5(4H)-one;

2-(4-(tert-butyl)-1H-imidazol-1-yl)-9-(tetrahydrofuran-2-yl)-7,8-dihydro-[1,4]diazepino[7,1-a]isoquinolin-5(4H)-one;

(R)-2-(4-(tert-butyl)-1 H-imidazol-1-yl)-9-(tetrahydrofuran-2-yl)-7,8-dihydro-[1,4]diazepino[7,1-a]isoquinolin-5(4H)-one;

(S)-2-(4-(tert-butyl)-1H-imidazol-1-yl)-9-(tetrahydrofuran-2-yl)-7,8-dihydro-[1,4]diazepino[7,1-a]isoquinolin-5(4H)-one;

2-(4-ethyl-1H-imidazol-1-yl)-9-(1-fluorocyclobutyl)-7,8-dihydro-[1,4]diazepino[7,1-a]isoquinolin-5(4H)-one;

2-(4-ethyl-1H-imidazol-1-yl)-9-(3-fluorooxetan-3-yl)-7,8-dihydro-[1,4]diazepino[7,1-a]isoquinolin-5(4H)-one;

9-(cyclopent-1-en-1-yl)-2-(4-(methoxymethyl)-1H-imidazol-1-yl)-7,8-dihydro-[1,4]diazepino[7,1-a]isoquinolin-5(4H)-one;

9-cyclopropyl-2-(4-(1-methoxyethyl)-1H-imidazol-1-yl)-7,8-dihydro-[1,4]diazepino[7,1-a]isoquinolin-5(4H)-one;

(S)-9-cyclopropyl-2-(4-(1-methoxyethyl)-1H-imidazol-1-yl)-7,8-dihydro-[1,4]diazepino[7,1-a]isoquinolin-5(4H)-one;

(R)-9-cyclopropyl-2-(4-(1-methoxyethyl)-1H-imidazol-1-yl)-7,8-dihydro-[1,4]diazepino[7,1-a]isoquinolin-5(4H)-one;

2-(3-cyclopropyl-1H-1,2,4-triazol-1-yl)-9-(3-fluoropyrazin-2-yl)-7,8-dihydro-[1,4]diazepino[7,1-a]isoquinolin-5(4H)-one;

2-(3-cyclopropyl-1H-1,2,4-triazol-1-yl)-9-(3-fluoropyridin-2-yl)-7,8-dihydro-[1,4]diazepino[7,1-a]isoquinolin-5(4H)-one;

2-(4-cyclopropyl-1H-imidazol-1-yl)-9-(thiazol-5-yl)-7,8-dihydro-[1,4]diazepino[7,1-a]isoquinolin-5(4H)-one;

2-(4-cyclopropyl-1H-imidazol-1-yl)-9-(2-methylthiazol-5-yl)-7,8-dihydro-[1,4]diazepino[7,1-a]isoquinolin-5(4H)-one;

2-(4-cyclopropyl-1H-imidazol-1-yl)-9-(pyrazin-2-yl)-7,8-dihydro-[1,4]diazepino[7,1-a]isoquinolin-5(4H)-one;

2-(4-(2-methoxyethyl)-1H-imidazol-1-yl)-9-(thiazol-2-yl)-7,8-dihydro-[1,4]diazepino[7,1-a]isoquinolin-5(4H)-one;

2-(4-(ethoxymethyl)-1H-imidazol-1-yl)-9-(4-methylthiazol-2-yl)-7,8-dihydro-[1,4]diazepino[7,1-a]isoquinolin-5(4H)-one;

2-(4-(ethoxymethyl)-1H-imidazol-1-yl)-9-(thiazol-2-yl)-7,8-dihydro-[1,4]diazepino[7,1-a]isoquinolin-5(4H)-one;

2-(4-cyclopropyl-1H-imidazol-1-yl)-9-(4-fluoropyridin-3-yl)-7,8-dihydro-[1,4]diazepino[7,1-a]isoquinolin-5(4H)-one;

2-(4-methyl-1H-imidazol-1-yl)-9-(2-methyloxazol-5-yl)-7,8-dihydro-[1,4]diazepino[7,1-a]isoquinolin-5(4H)-one;

2-(4-cyclopropyl-1H-imidazol-1-yl)-9-(3-(trifluoromethyl)-1H-pyrazol-5-yl)-7,8-dihydro-[1,4]diazepino[7,1-a]isoquinolin-5(4H)-one;

2-(4-cyclopropyl-1H-imidazol-1-yl)-9-(6-hydroxypyridin-3-yl)-7,8-dihydro-[1,4]diazepino[7,1-a]isoquinolin-5(4H)-one;

2-(4-cyclopropyl-1H-imidazol-1-yl)-9-(6-methoxypyridin-3-yl)-7,8-dihydro-[1,4]diazepino[7,1-a]isoquinolin-5(4H)-one;

2-(4-cyclopropyl-1H-imidazol-1-yl)-9-(1H-pyrazol-3-yl)-7,8-dihydro-[1,4]diazepino[7,1-a]isoquinolin-5(4H)-one;

2-(4-cyclopropyl-1H-imidazol-1-yl)-9-(2-fluoropyrimidin-5-yl)-7,8-dihydro-[1,4]diazepino[7,1-a]isoquinolin-5(4H)-one;

2-(4-cyclopropyl-1H-imidazol-1-yl)-9-(2-fluoropyridin-4-yl)-7,8-dihydro-[1,4]diazepino[7,1-a]isoquinolin-5(4H)-one;

2-(3-cyclobutyl-1H-1,2,4-triazol-1-yl)-9-(6-fluoropyridin-3-yl)-7,8-dihydro-[1,4]diazepino[7,1-a]isoquinolin-5(4H)-one;

9-cyclopropyl-12-fluoro-2-(4-(methoxymethyl)-1H-imidazol-1-yl)-7,8-dihydro-[1,4]diazepino[7,1-a]isoquinolin-5(4H)-one;

(R)-9-cyclopropyl-12-fluoro-2-(4-(1-methoxyethyl)-1H-imidazol-1-yl)-7,8-dihydro-[1,4]diazepino[7,1-a]isoquinolin-5(4H)-one;

9-cyclopropyl-1 1-fluoro-2-(4-(methoxymethyl)-1H-imidazol-1-yl)-7,8-dihydro-[1,4]diazepino[7,1-a]isoquinolin-5(4H)-one;

9-cyclopropyl-2-(4-(difluoromethyl)-1H-imidazol-1-yl)-7,8-dihydro-[1,4]diazepino[7,1-a]isoquinolin-5(4H)-one;

9-cyclopropyl-2-(4-(fluoromethyl)-1H-imidazol-1-yl)-7,8-dihydro-[1,4]diazepino[7,1-a]isoquinolin-5(4H)-one;

10-fluoro-9-(6-fluoropyridin-3-yl)-2-(3-methyl-1H-1,2, 4-triazol-1-yl)-7,8-dihydro-[1,4]diazepino[7,1-a]iso-quinolin-5(4H)-one;
2-(3-cyclopropyl-1H-1,2,4-triazol-1-yl)-10-fluoro-9-(2-fluoropyridin-3-yl)-7,8-dihydro-[1,4]diazepino[7,1-a]isoquinolin-5(4H)-one;
10-fluoro-9-(2-fluoropyridin-3-yl)-2-(3-methyl-1H-1,2, 4-triazol-1-yl)-7,8-dihydro-[1,4]diazepino[7,1-a]iso-quinolin-5(4H)-one;
10-fluoro-9-(2-fluoropyridin-3-yl)-2-(4-methyl-1H-imidazol-1-yl)-7,8-dihydro-[1,4]diazepino[7,1-a]iso-quinolin-5(4H)-one;
9-(6-fluoropyridin-3-yl)-2-(4-(1-methoxycyclopropyl)-1H-imidazol-1-yl)-7,8-dihydro-[1,4]diazepino[7,1-a]isoquinolin-5(4H)-one;
2-(4-methyl-1H-imidazol-1-yl)-9-(pyrazin-2-yl)-7,8-dihydro-[1,4]diazepino[7,1-a]isoquinolin-5(4H)-one;
9-(6-fluoropyridin-3-yl)-2-(4-(3-hydroxyoxetan-3-yl)-1H-imidazol-1-yl)-7,8-dihydro-[1,4]diazepino[7,1-a]isoquinolin-5(4H)-one;
2-(3-cyclopropyl-1H-1,2,4-triazol-1-yl)-9-(2-methyloxazol-4-yl)-7,8-dihydro-[1,4]diazepino[7,1-a]isoquinolin-5(4H)-one;
2-(4-cyclobutyl-1H-imidazol-1-yl)-9-(2-methyloxazol-4-yl)-7,8-dihydro-[1,4]diazepino[7,1-a]isoquinolin-5 (4H)-one;
2-(4-methyl-1H-imidazol-1-yl)-9-(2-methyloxazol-4-yl)-7,8-dihydro-[1,4]diazepino[7,1-a]isoquinolin-5(4H)-one;
9-cyclopropyl-2-(4-cyclopropyl-1H-imidazol-1-yl)-7,8-dihydro-[1,4]diazepino[7,1-a][2,6]naphthyridin-5 (4H)-one;
9-cyclopropyl-2-(3-cyclopropyl-1H-1,2,4-triazol-1-yl)-7, 8-dihydro-[1,4]diazepino[7,1-a][2,6]naphthyridin-5 (4H)-one;
(R)-9-cyclopropyl-2-(4-(1-methoxyethyl)-1H-imidazol-1-yl)-7,8-dihydro-[1,4]diazepino[7,1-a][2,6]naphthyridin-5(4H)-one;
9-cyclopropyl-2-(4-(difluoromethyl)-1H-imidazol-1-yl)-7,8-dihydro-[1,4]diazepino[7,1-a][2,6]naphthyridin-5 (4H)-one;
9-cyclopropyl-2-(4-(oxazol-5-yl)-1H-imidazol-1-yl)-7,8-dihydro-[1,4]diazepino[7,1-a]isoquinolin-5(4H)-one;
9-cyclopropyl-2-(4-(isoxazol-5-yl)-1H-imidazol-1-yl)-7, 8-dihydro-[1,4]diazepino[7,1-a]isoquinolin-5(4H)-one;
9-cyclopropyl-2-(3-cyclopropyl-1H-1,2,4-triazol-1-yl)-7, 8-dihydro-[1,4]diazepino[7,1-a]isoquinolin-5(4H)-one;
9-cyclopropyl-2-(4-methoxy-1H-imidazol-1-yl)-7,8-dihydro-[1,4]diazepino[7,1-a]isoquinolin-5(4H)-one;
9-cyclopropyl-2-(4-(trifluoromethyl)-1H-imidazol-1-yl)-7,8-dihydro-[1,4]diazepino[7,1-a]isoquinolin-5(4H)-one;
9-cyclopropyl-2-(4-(pyridin-4-yl)-1H-imidazol-1-yl)-7,8-dihydro-[1,4]diazepino[7,1-a]isoquinolin-5(4H)-one;
9-cyclopropyl-2-(4-(1-hydroxycyclopropyl)-1H-imidazol-1-yl)-7,8-dihydro-[1,4]diazepino[7,1-a]isoquinolin-5(4H)-one;
9-cyclopropyl-2-(4-(2-hydroxyethyl)-1H-imidazol-1-yl)-7,8-dihydro-[1,4]diazepino[7,1-a]isoquinolin-5(4H)-one;
9-cyclopropyl-2-(4-(1-hydroxyethyl)-1H-imidazol-1-yl)-7,8-dihydro-[1,4]diazepino[7,1-a]isoquinolin-5(4H)-one;
9-cyclopropyl-2-(4-(cyclopropyl(hydroxy)methyl)-1H-imidazol-1-yl)-7,8-dihydro-[1,4]diazepino[7,1-a]isoquinolin-5(4H)-one;
9-cyclopropyl-2-(4-((trifluoromethoxy)methyl)-1H-imidazol-1-yl)-7,8-dihydro-[1,4]diazepino[7,1-a]iso-quinolin-5(4H)-one;
2-(3-cyclopropyl-1H-1,2,4-triazol-1-yl)-9-(5-fluoropyridin-2-yl)-7,8-dihydro-[1,4]diazepino[7,1-a]isoquinolin-5(4H)-one;
2-(3-cyclopropyl-1H-1,2,4-triazol-1-yl)-9-(6-fluoropyridin-2-yl)-7,8-dihydro-[1,4]diazepino[7,1-a]isoquinolin-5(4H)-one;
2-(3-cyclopropyl-1H-1,2,4-triazol-1-yl)-9-(4-fluoropyridin-2-yl)-7,8-dihydro-[1,4]diazepino[7,1-a]isoquinolin-5(4H)-one;
2-(3-cyclopropyl-1H-1,2,4-triazol-1-yl)-9-(5-fluoropyrazin-2-yl)-7,8-dihydro-[1,4]diazepino[7,1-a]isoquinolin-5(4H)-one;
2-(4-cyclopropyl-1H-imidazol-1-yl)-9-(2H-1,2,3-triazol-2-yl)-7,8-dihydro-[1,4]diazepino[7,1-a]isoquinolin-5 (4H)-one;
2-(4-cyclopropyl-1H-imidazol-1-yl)-9-(5-fluoropyrazin-2-yl)-7,8-dihydro-[1,4]diazepino[7,1-a]isoquinolin-5 (4H)-one;
2-(4-cyclopropyl-1H-imidazol-1-yl)-9-(6-fluoropyrazin-2-yl)-7,8-dihydro-[1,4]diazepino[7,1-a]isoquinolin-5 (4H)-one;
9-isopropoxy-2-(4-(methoxymethyl)-1H-imidazol-1-yl)-7,8-dihydro-[1,4]diazepino[7,1-a]isoquinolin-5(4H)-one;

or a pharmaceutically acceptable salt thereof.

8. The method according to claim 1 wherein the compound of formula (I) is 2-(3-Cyclopropyl-1H-1,2,4-triazol-1-yl)-9-(6-fluoropyridin-3-yl)-7,8-dihydro-[1,4]diazepino[7,1-a]isoquinolin-5(4H)-one having the following formula:

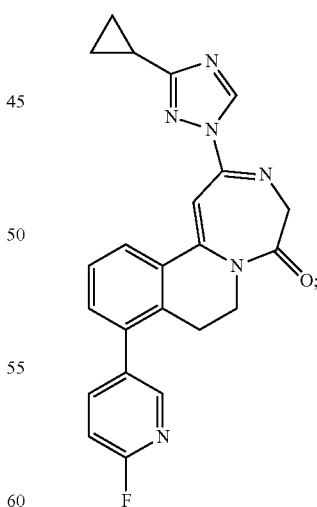

or a pharmaceutically acceptable salt thereof.

9. The method according to claim 1 wherein the compound of formula (I) is 9-Cyclopropyl-10-fluoro-2-(4-(methoxymethyl)-1H-imidazol-1-yl)-7,8-dihydro-[1,4]diazepino[7,1-a]isoquinolin-5(4H)-one having the following formula

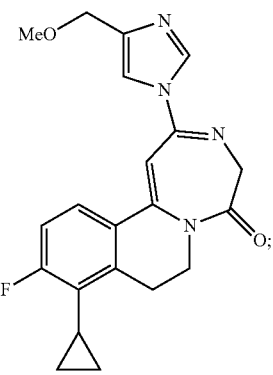 [SMILES: COCc1cn(C2=NCC(=O)N3CCc4c(ccc(F)c4C4CC4)C3=C2)cn1]

or a pharmaceutically acceptable salt thereof.

10. The method according to claim 1 wherein the compound of formula (I) is 2-(4-Cyclopropyl-1H-imidazol-1-yl)-9-(6-fluoropyridin-3-yl)-7,8-dihydro-[1,4]diazepino[7,1-a]isoquinolin-5(4H)-one having the following formula

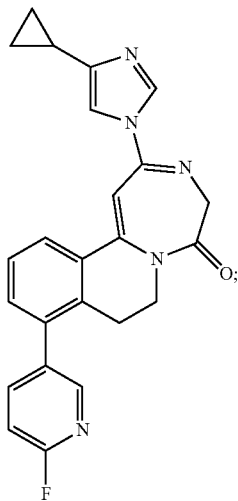 [SMILES: O=C1CN=C(n2cnc(C3CC3)c2)C=C2c3cccc(-c4ccc(F)nc4)c3CCN12]

or a pharmaceutically acceptable salt thereof.

11. The method according to claim 1 wherein the compound of formula (I) is 9-Cyclopropyl-2-(4-(methoxymethyl)-1H-imidazol-1-yl)-7,8-dihydro-[1,4]diazepino[7,1-a]isoquinolin-5(4H)-one having the following formula

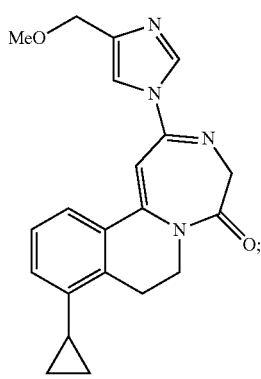 [SMILES: COCc1cn(C2=NCC(=O)N3CCc4c(cccc4C4CC4)C3=C2)cn1]

or a pharmaceutically acceptable salt thereof.

12. The method according to claim 1 wherein the compound of formula (I) is 2-(4-Cyclopropyl-1H-imidazol-1-yl)-9-(2-methyloxazol-4-yl)-7,8-dihydro-[1,4]diazepino[7,1-a]isoquinolin-5(4H)-one having the following formula

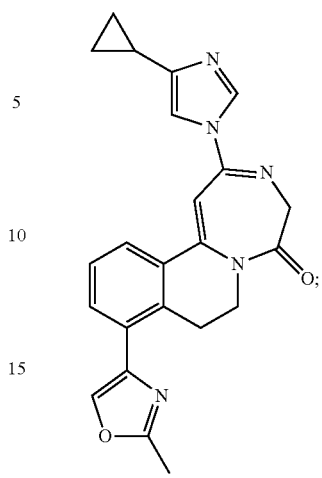

or a pharmaceutically acceptable salt thereof.

13. The method according to claim 1 wherein the compound of formula (I) is 2-(3-Cyclopropyl-1H-1,2,4-triazol-1-yl)-9-(thiazol-2-yl)-7,8-dihydro-[1,4]diazepino[7,1-a]isoquinolin-5(4H)-one having the following formula

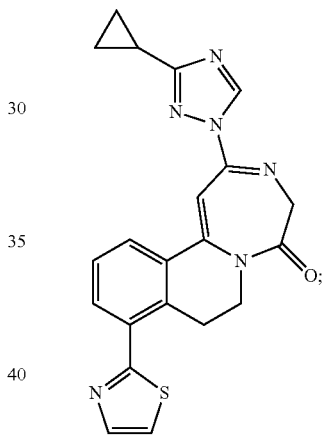

or a pharmaceutically acceptable salt thereof.

14. The method according to claim 1 wherein the compound of formula (I) is 9-(5-fluoropyrazin-2-yl)-2-(3-methyl-1H-1,2,4-triazol-1-yl)-7,8-dihydro-[1,4]diazepino[7,1-a]isoquinolin-5(4H)-one having the following formula

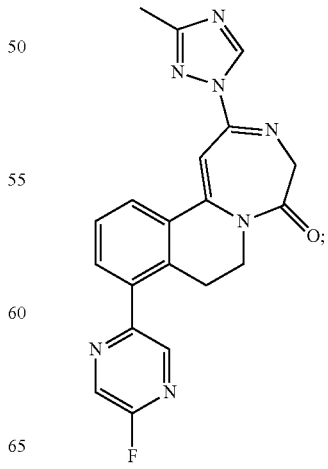

or a pharmaceutically acceptable salt thereof.

15. The method according to claim 1 wherein the compound of formula (I) is (R)-9-cyclopropyl-10-fluoro-2-(4-(1-methoxyethyl)-1H-imidazol-1-yl)-7,8-dihydro-[1,4]diazepino[7,1-a]isoquinolin-5(4H)-one having the following formula

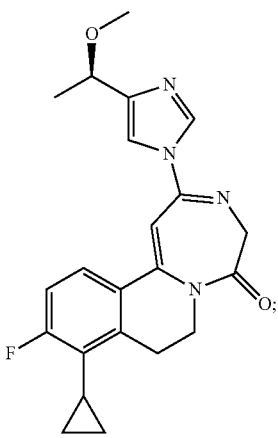 [SMILES: CO[C@H](C)c1cn(C2=NCC(=O)N3CCc4c(ccc(F)c4C4CC4)C3=C2)cn1]

or a pharmaceutically acceptable salt thereof.

16. The method according to claim 1 wherein the compound of formula (I) is 9-Cyclopropyl-10-fluoro-2-(3-(methoxymethyl)-1H-1,2,4-triazol-1-yl)-7,8-dihydro-[1,4]diazepino[7,1-a]isoquinolin-5(4H)-one having the following formula

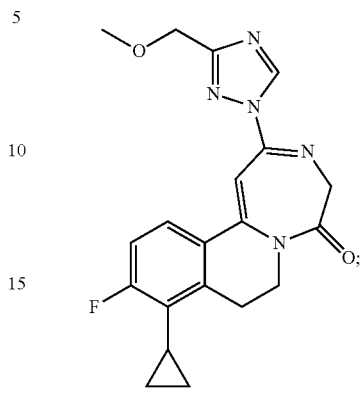

or a pharmaceutically acceptable salt thereof.

17. The method according to claim 1 wherein the substance-related disorder is substance abuse.

18. The method according to claim 1 wherein the substance-related disorder is substance dependence.

19. The method according to claim 1 wherein the substance-related disorder is substance withdrawal.

* * * * *